(12) United States Patent
Oh et al.

(10) Patent No.: US 12,084,446 B2
(45) Date of Patent: Sep. 10, 2024

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Hong-Se Oh, Gyeonggi-do (KR); Sung-Woo Jang, Gyeonggi-do (KR); Joon-Hyung Kil, Gyeonggi-do (KR); Seon-Jin Hwang, Gyeonggi-do (KR); Seung-Ae Kim, Gyeonggi-do (KR); Hee-Ryong Kang, Gyeonggi-do (KR); Sang-Hee Cho, Gyeonggi-do (KR); Hyo-Soon Park, Gyeonggi-do (KR)

(73) Assignee: Rohm and Haas Electronic Materials Korea (KR)

( * ) Notice: Subject to any disclaimer, the term of this patent is extended or adjusted under 35 U.S.C. 154(b) by 535 days.

(21) Appl. No.: 17/442,469

(22) PCT Filed: Mar. 24, 2020

(86) PCT No.: PCT/KR2020/003997
§ 371 (c)(1),
(2) Date: Sep. 23, 2021

(87) PCT Pub. No.: WO2020/197240
PCT Pub. Date: Oct. 1, 2020

(65) Prior Publication Data
US 2022/0162210 A1   May 26, 2022

(30) Foreign Application Priority Data

Mar. 25, 2019 (KR) .................. 10-2019-0033609
Mar. 12, 2020 (KR) .................. 10-2020-0030777

(51) Int. Cl.
*C07D 487/00* (2006.01)
*C07D 519/00* (2006.01)
(Continued)

(52) U.S. Cl.
CPC .......... *C07D 487/00* (2013.01); *C07D 519/00* (2013.01); *H10K 85/626* (2023.02);
(Continued)

(58) Field of Classification Search
CPC .. C07D 487/00; C07D 519/00; H10K 85/654; H10K 85/6574; H10K 85/6576;
(Continued)

(56) References Cited

U.S. PATENT DOCUMENTS

| 2016/0163998 A1 | 6/2016 | Saito et al. |
| 2020/0006668 A1 | 1/2020 | Sun et al. |
| 2020/0013965 A1 | 1/2020 | Yang et al. |

FOREIGN PATENT DOCUMENTS

| KR | 20150121337 A | | 10/2015 |
| KR | 1020180099510 A | * | 9/2018 |
| WO | 2018021841 A1 | | 2/2018 |

* cited by examiner

*Primary Examiner* — Anita Nassiri-Motlagh
(74) *Attorney, Agent, or Firm* — G. Creston Campbell

(57) ABSTRACT

The present disclosure relates to an organic electroluminescent compound, and an organic electroluminescent device comprising the same. It is possible to provide an organic electroluminescent device which can be deposited at a low deposition temperature and/or in which clogging is reduced.

9 Claims, 1 Drawing Sheet

(51) Int. Cl.
*H10K 50/11* (2023.01)
*H10K 85/60* (2023.01)
*H10K 101/30* (2023.01)
*H10K 101/40* (2023.01)

(52) U.S. Cl.
CPC ....... *H10K 85/654* (2023.02); *H10K 85/6572* (2023.02); *H10K 85/6574* (2023.02); *H10K 85/6576* (2023.02); *H10K 50/11* (2023.02); *H10K 2101/30* (2023.02); *H10K 2101/40* (2023.02)

(58) Field of Classification Search
CPC ............. H10K 85/626; H10K 85/6572; H10K 2101/40; H10K 2101/30; H10K 50/11
USPC ..................................................... 252/301.16
See application file for complete search history.

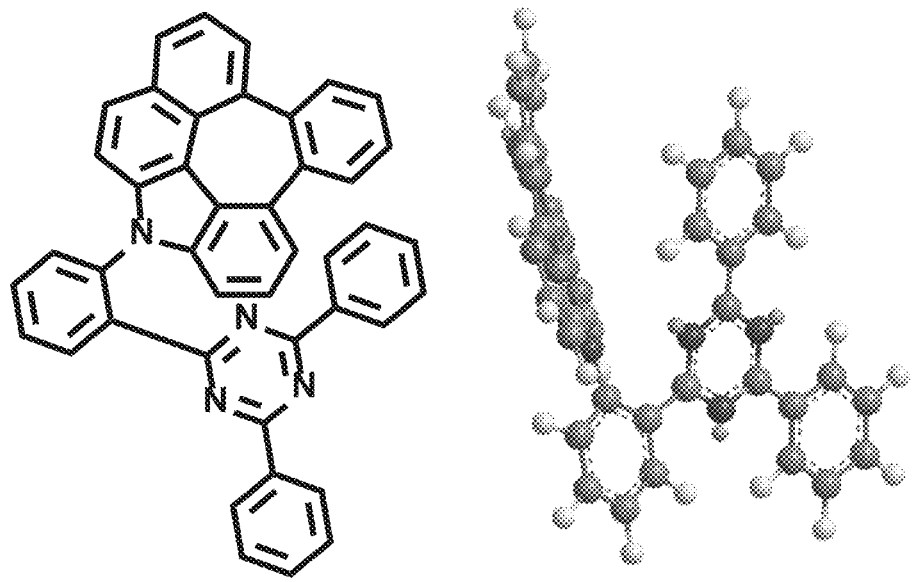
A-1
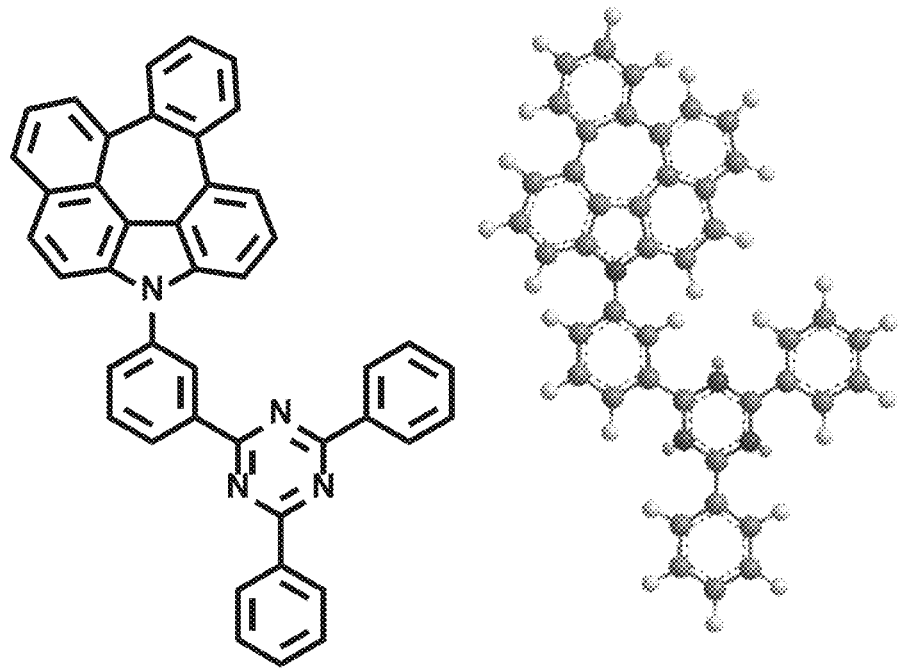
R-1

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

A small molecular green organic electroluminescent device (OLED) was first developed by Tang, et al., of Eastman Kodak in 1987 by using TPD/ALq3 bi-layer consisting of a light-emitting layer and a charge transport layer. Thereafter, the development of OLEDs was rapidly effected and OLEDs have been commercialized. An organic electroluminescent device changes electric energy into light by applying electricity to an organic light-emitting material, and commonly comprises an anode, a cathode, and an organic layer formed between the two electrodes. The organic layer of the OLED may comprise a hole injection layer, a hole transport layer, a hole auxiliary layer, a light-emitting auxiliary layer, an electron blocking layer, a light-emitting layer (containing host and dopant materials), an electron buffer layer, a hole blocking layer, an electron transport layer, an electron injection layer, etc. The materials used in the organic layer can be classified into a hole injection material, a hole transport material, a hole auxiliary material, a light-emitting auxiliary material, an electron blocking material, a light-emitting material, an electron buffer material, a hole blocking material, an electron transport material, an electron injection material, etc., depending on functions.

In the field, an organic electroluminescent material which can improve luminous efficiency, lifespan characteristic, power efficiency, etc., of an organic electroluminescent device is being researched. In addition, by improving the thermal characteristic of an organic electroluminescent material, attempts to prevent material damage in high temperature deposition and improve process flow in device production are conducted.

Korean Patent Application Laying-Open No. 2018-0099510 discloses a compound of a fused structure comprising an azaazulene. However, said reference does not specifically disclose a compound identical to the compound structure of the present disclosure.

DISCLOSURE OF INVENTION

Technical Problem

In order to deposit an organic electroluminescent compound, high temperature is required.

However, compound deterioration often occurs in high temperature. In addition, a compound is put in a source which is a type of a crucible for deposition. Herein, clogging, which is a phenomenon of the entrance of the source being blocked by a deposition material due to uneven heating of the source, occurs.

The objectives of the present disclosure include at least one of the following. First, the present disclosure provides an organic electroluminescent compound of which compound deterioration in deposition is reduced since a deposition in relatively low temperature is possible. Second, the present disclosure provides an organic electroluminescent device which can reduce clogging phenomenon. Third, the present disclosure provides an organic electroluminescent device which is produced by the aforementioned organic electroluminescent compound.

Solution to Problem

The present inventors have found that the above objective can be achieved by an organic electroluminescent compound represented by the following formula 1:

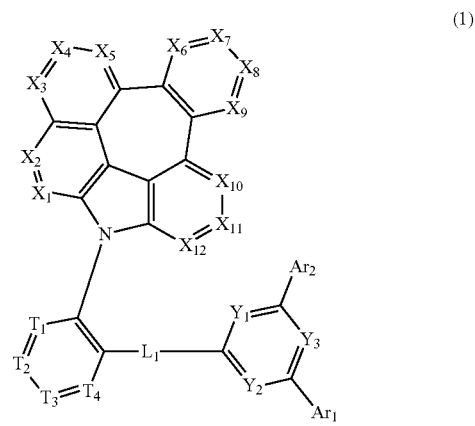

(1)

wherein $X_1$ to $X_{12}$ each independently represent N or $CR_1$;

$T_1$ to $T_4$ each independently represent N or $CR_2$;

$Y_1$ to $Y_a$ each independently represent N or $CR_3$, in which at least one of $Y_1$ to $Y_a$ is N;

$L_1$ represents a single bond, a substituted or unsubstituted (C6-C30)arylene, or a substituted or unsubstituted (3- to 30-membered)heteroarylene; and $Ar_1$, $Ar_2$, and $R_1$ to $R_3$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent to form a ring(s), where if a plurality of $R_1$ to $R_3$ is present, each of $R_1$, each of $R_2$, and each of $R_3$ may be the same or different.

Advantageous Effects of Invention

According to the present disclosure, an organic electroluminescent compound, which may be deposited at a low temperature and/or which may reduce clogging phenomenon, may be obtained. In addition, by using such organic electroluminescent compound, the performance fall of the organic electroluminescent device can be prevented and/or the process of producing the device can be improved.

BRIEF DESCRIPTION OF THE FIGURES

FIG. 1 illustrates a three-dimensional structure of the organic electroluminescent compound of the present disclosure and the conventional organic electroluminescent compound.

MODE FOR THE INVENTION

Hereinafter, the present disclosure will be described in detail. However, the following description is intended to explain the disclosure, and is not meant in any way to restrict the scope of the disclosure.

The term "organic electroluminescent compound" in the present disclosure means a compound that may be used in an organic electroluminescent device. If necessary, the organic electroluminescent compound may be comprised in any layer constituting an organic electroluminescent device.

The term "organic electroluminescent material" in the present disclosure means a material that may be used in an organic electroluminescent device, and may comprise at least one compound. If necessary, the organic electroluminescent material may be comprised in any layer constituting an organic electroluminescent device. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, an electron injection material, etc.

The organic electroluminescent material of the present disclosure may comprise at least one compound represented by formula 1. The compound represented by formula 1 may be comprised in a light-emitting layer, an electron transport layer, and/or an electron buffer layer, etc., but is not limited thereto. When comprised in a light-emitting layer, the compound represented by formula 1 may be comprised as a host material, in which the host material may be a host material of a green or red organic electroluminescent device. Further, when comprised in an electron transport layer, the compound represented by formula 1 may be comprised as an electron transport material. In addition, when comprised in an electron buffer layer, the compound represented by formula 1 may be comprised as an electron buffer material.

Hereinafter, the compound represented by formula 1 will be described in more detail.

Herein, the term "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, isobutyl, tert-butyl, etc. The term "(C2-C30)alkenyl" is meant to be a linear or branched alkenyl having 2 to 30 carbon atoms constituting the chain, in which the number of carbon atoms is preferably 2 to 20, and more preferably 2 to 10. The above alkenyl may include vinyl, 1-propenyl, 2-propenyl, 1-butenyl, 2-butenyl, 3-butenyl, 2-methylbut-2-enyl, etc. The term "(C2-C30)alkynyl" is meant to be a linear or branched alkynyl having 2 to 30 carbon atoms constituting the chain, in which the number of carbon atoms is preferably 2 to 20, and more preferably 2 to 10. The above alkynyl may include ethynyl, 1-propynyl, 2-propynyl, 1-butynyl, 2-butynyl, 3-butynyl, 1-methylpent-2-ynyl, etc. The term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, etc. The term "(3- to 7-membered)heterocycloalkyl" is meant to be a cycloalkyl having 3 to 7, preferably 5 to 7, ring backbone atoms, and including at least one heteroatom selected from the group consisting of B, N, O, S, Si, and P, and preferably the group consisting of O, S, and N. The above heterocycloalkyl may include tetrahydrofuran, pyrrolidine, thiolan, tetrahydropyran, etc. The term "(C6-C30)aryl(ene)" is meant to be a monocyclic or fused ring radical derived from an aromatic hydrocarbon having 6 to 30 ring backbone carbon atoms, in which the number of the ring backbone carbon atoms is preferably 6 to 25, more preferably 6 to 18. The above aryl(ene) may be partially saturated, and may comprise a spiro structure. The above aryl may include phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, azulenyl, etc. More specifically, the above aryl may include phenyl, 1-naphthyl, 2-naphthyl, 1-anthryl, 2-anthryl, 9-anthryl, benzanthryl, 1-phenanthryl, 2-phenanthryl, 3-phenanthryl, 4-phenanthryl, 9-phenanthryl, naphthacenyl, pyrenyl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 1-fluorenyl, 2-fluorenyl, 3-fluorenyl, 4-fluorenyl, 9-fluorenyl, benzofluorenyl, dibenzofluorenyl, 2-biphenylyl, 3-biphenylyl, 4-biphenylyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 3-fluoranthenyl, 4-fluoranthenyl, 8-fluoranthenyl, 9-fluoranthenyl, benzofluoranthenyl, o-tolyl, m-tolyl, p-tolyl, 2,3-xylyl, 3,4-xylyl, 2,5-xylyl, mesityl, o-cumenyl, m-cumenyl, p-cumenyl, p-t-butylphenyl, p-(2-phenylpropyl)phenyl, 4'-methylbiphenylyl, 4"-t-butyl-p-terphenyl-4-yl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, etc.

The term "(3- to 30-membered)heteroaryl(ene)" is meant to be an aryl having 3 to 30 ring backbone atoms, and including at least one, preferably 1 to 4 heteroatoms selected from the group consisting of B, N, O, S, Si, and P. The above heteroaryl(ene) may be a monocyclic ring, or a fused ring condensed with at least one benzene ring; may be partially saturated; may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, and pyridazinyl, and a fused ring-type heteroaryl such as benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, and dihydroacridinyl. More specifically, the above heteroaryl may include 1-pyrrolyl, 2-pyrrolyl, 3-pyrrolyl, pyrazinyl, 2-pyridinyl, 2-pyrimidinyl, 4-pyrimidinyl, 5-pyrimidinyl, 6-pyrimidinyl, 1,2,3-triazin- 4-yl, 1,2,4-triazin-3-yl, 1,3,5-triazin-2-yl, 1-imidazolyl, 2-imidazolyl, 1-pyrazolyl, 1-indolidinyl, 2-indolidinyl, 3-indolidinyl, 5-indolidinyl, 6-indolidinyl, 7-indolidinyl, 8-indolidinyl, 2-imidazopyridinyl, 3-imidazopyridinyl, 5-imidazopyridinyl, 6-imidazopyridinyl, 7-imidazopyridinyl, 8-imidazopyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazolyl-1-yl, azacarbazolyl-2-yl, azacarbazolyl-3-yl, azacarbazolyl-4-yl, azacarbazolyl-5-yl, azacarbazolyl-6-yl, azacarbazolyl-7-yl, azacarbazolyl-8-yl, azacarbazolyl-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, etc. Furthermore, "halogen" includes F, Cl, Br, and I.

In addition, "ortho (o-)," "meta (m-)," and "para (p-)" are prefixes, which represent the relative positions of substituents, respectively. Ortho indicates that two substituents are adjacent to each other, and for example, when two substituents in a benzene derivative occupy positions 1 and 2, it is called an ortho position. Meta indicates that two substituents are at positions 1 and 3, and for example, when two substituents in a benzene derivative occupy positions 1 and 3, it is called a meta position. Para indicates that two substituents are at positions 1 and 4, and for example, when two substituents in a benzene derivative occupy positions 1 and 4, it is called a para position.

Herein, "substituted" in the expression "substituted or unsubstituted" means that a hydrogen atom in a certain functional group is replaced with another atom or another functional group, i.e., a substituent. The substituents of the substituted (C1-C30)alkyl, the substituted (C6-C30)aryl(ene), the substituted (3- to 30-membered)heteroaryl(ene), the substituted (C3-C30)cycloalkyl, the substituted (C1-C30)alkoxy, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, the substituted mono- or di-(C1-C30)alkylamino, the substituted mono- or di-(C6-C30)arylamino, and the substituted (C1-C30)alkyl(C6-C30)arylamino, each independently, may be at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 30-membered) heteroaryl unsubstituted or substituted with a (C6-C30) aryl(s); a (C6-C30)aryl unsubstituted or substituted with a (5- to 30-membered)heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino unsubstituted or substituted with a (C1-C30)alkyl(s); a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30) alkyl(C6-C30)arylboronyl; a (C6-C30)aryl(C1-C30)alkyl; and a (C1-C30)alkyl(C6-C30)aryl. According to one embodiment of the present disclosure, the substituents, each independently, may be at least one selected from the group consisting of deuterium, (C1-C6)alkyl, and/or (C6-C12)aryl. Specifically, the substituents, each independently, may be at least one selected from the group consisting of deuterium, methyl, and/or phenyl, etc.

Formula 1 may be represented by the following formula 2 or formula 3:

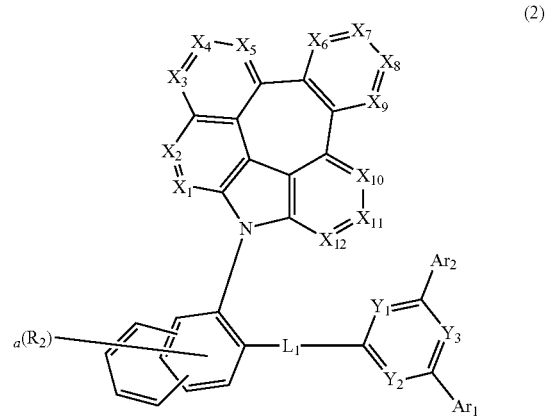

(2)

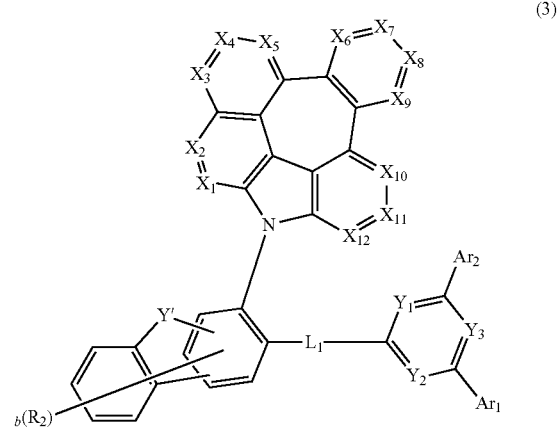

(3)

wherein a and b each independently represent an integer of 1 to 6, in which, if a and b are an integer of 2 or more, each of $R_2$ may be the same or different;

Y' represents $CR_4R_5$, O, or S;

$R_4$ and $R_5$ each independently represent a substituted or unsubstituted (C1-C30)alkyl, or a substituted or unsubstituted (C6-C30)aryl; and $X_1$ to $X_{12}$, $Y_1$ to $Y_3$, $L_1$, $Ar_1$, and $Ar_2$ are as defined in formula 1.

In formula 1, $X_1$ to $X_{12}$ each independently represent N or $CR_1$. According to one embodiment of the present disclosure, $X_1$ to $X_{12}$ each independently represent $CR_1$.

In formula 1, $T_1$ to $T_4$ each independently represent N or $CR_2$.

In formula 1, $Y_1$ to $Y_3$ each independently represent N or $CR_3$, in which at least one of $Y_1$ to $Y_3$ is N.

In formula 1, $L_1$ represents a single bond, a substituted or unsubstituted (C6-C30)arylene, or a substituted or unsubstituted (3- to 30-membered)heteroarylene. According to one embodiment of the present disclosure, $L_1$ represents a single bond, a substituted or unsubstituted (C6-C12)arylene, or a substituted or unsubstituted (5- to 15-membered)heteroarylene. According to another embodiment of the present disclosure, $L_1$ represents a single bond, an unsubstituted (C6-C12)arylene, or an unsubstituted (5- to 15-membered) heteroarylene. The heteroarylene may comprise one or more of nitrogen, oxygen, and sulfur. For example, $L_1$ may represent a single bond, phenylene, pyridylene, etc.

In formula 1, $Ar_1$, $Ar_2$, and $R_1$ to $R_3$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent to form a ring(s), where if a plurality of $R_1$ to $R_3$ is present, each of $R_1$, each of $R_2$, and each of $R_3$ may be the same or different.

According to one embodiment of the present disclosure, $Ar_1$ and $Ar_2$ each independently represent a substituted or unsubstituted (C6-C18)aryl, or a substituted or unsubstituted (5- to 15-membered)heteroaryl. According to another embodiment of the present disclosure, $A_{r1}$ and $Ar_2$ each independently represent a (C6-C18)aryl unsubstituted or substituted with one or more deuterium, or an unsubstituted (5- to 15-membered)heteroaryl. $Ar_1$ and $Ar_2$ may be the same or different from each other. For example, $Ar_1$ and $Ar_2$ may each independently represent phenyl, naphthyl, biphenyl, phenanthrenyl, phenyl substituted with one or more deuterium, dibenzofuranyl, dibenzothiophenyl, etc.

According to one embodiment of the present disclosure, $R_1$ to $R_3$ each independently represent hydrogen, a substituted or unsubstituted (C6-C12)aryl, or a substituted or unsubstituted (5- to 15-membered)heteroaryl; or may be linked to an adjacent substituent to form a ring(s). According to another embodiment of the present disclosure, $R_1$ to $R_3$ each independently represent hydrogen, an unsubstituted (C6-C12)aryl, or an unsubstituted (5- to 15-membered) heteroaryl; or may be linked to an adjacent substituent to form a ring(s). For example, $R_1$ may each independently represent hydrogen, phenyl, etc, or may be linked to an adjacent substituent to form a benzene ring(s). For example, $R_2$ may each independently represent hydrogen, phenyl, pyridyl, etc., or may be linked to an adjacent substituent to form a benzene ring(s), a pyridine ring(s), an indene ring(s) substituted with one or more methyl, an indene ring(s) substituted with one or more phenyl, a benzofuran ring(s), a benzothiophene ring(s), etc. For example, $R_3$ may each independently represent hydrogen.

According to one embodiment of the present disclosure, $X_1$ to $X_{12}$ each independently represent N or $CR_1$; $T_1$ to $T_4$ each independently represent N or $CR_2$; $Y_1$ to $Y_3$ each independently represent N or $CR_3$, in which at least one of $Y_1$ to $Y_3$ is N; $L_1$ represents a single bond, a substituted or unsubstituted (C6-C12)arylene, or a substituted or unsubstituted (5- to 15-membered)heteroarylene; $Ar_1$ and $Ar_2$ each independently represent a substituted or unsubstituted (C6-C18)aryl, or a substituted or unsubstituted (5- to 15-membered)heteroaryl; and $R_1$ to $R_3$ each independently represent hydrogen, a substituted or unsubstituted (C6-C12)aryl, or a substituted or unsubstituted (5- to 15-membered)heteroaryl; or may be linked to an adjacent substituent to form a ring(s).

According to another embodiment of the present disclosure, $X_1$ to $X_{12}$ each independently represent $CR_1$; $T_1$ to $T_4$ each independently represent N or $CR_2$; $Y_1$ to $Y_3$ each independently represent N or $CR_3$, in which at least one of $Y$ to $Y_3$ is N; $L_1$ represents a single bond, an unsubstituted (C6-C12)arylene, or an unsubstituted (5- to 15-membered) heteroarylene; $Ar_1$ and $Ar_2$ each independently represent a (C6-C18)aryl unsubstituted or substituted with one or more deuterium, or an unsubstituted (5- to 15-membered)heteroaryl; and $R_1$ to $R_3$ each independently represent hydrogen, an unsubstituted (C6-C12)aryl, or an unsubstituted (5- to 15-membered)heteroaryl; or may be linked to an adjacent substituent to form a ring(s).

In the formulas of the present disclosure, if adjacent substituents are linked to each other to form a ring(s), the ring may be a substituted or unsubstituted, mono- or polycyclic, (3- to 30-membered) alicyclic or aromatic ring, or the combination thereof. In addition, the formed ring may contain at least one heteroatom selected from B, N, O, S, Si, and P, preferably at least one heteroatom selected from N, O, and S. According to one embodiment of the present disclosure, the number of the ring backbone atoms is 5 to 20. According to another embodiment of the present disclosure, the number of the ring backbone atoms is 5 to 15. For example, the fused ring may be a substituted or unsubstituted dibenzothiophene ring, a substituted or unsubstituted dibenzofuran ring, a substituted or unsubstituted naphthalene ring, a substituted or unsubstituted phenanthrene ring, a substituted or unsubstituted fluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, or a substituted or unsubstituted carbazole ring.

In the formulas of the present disclosure, heteroaryl(ene) may, each independently, contain at least one heteroatom selected from B, N, O, S, Si, and P. In addition, the heteroatom may be bonded to at least one selected from the group consisting of hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.
The compound represented by formula 1 includes the following compounds, but is not limited thereto.
A-1
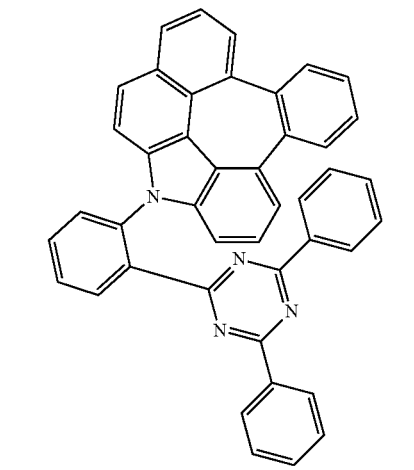
A-2
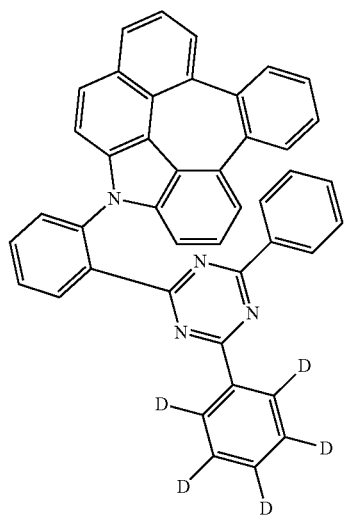
A-3
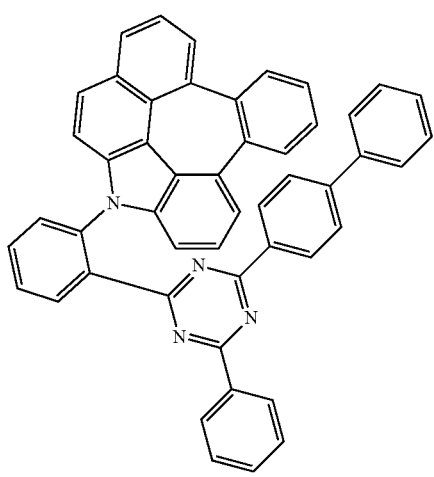
A-4
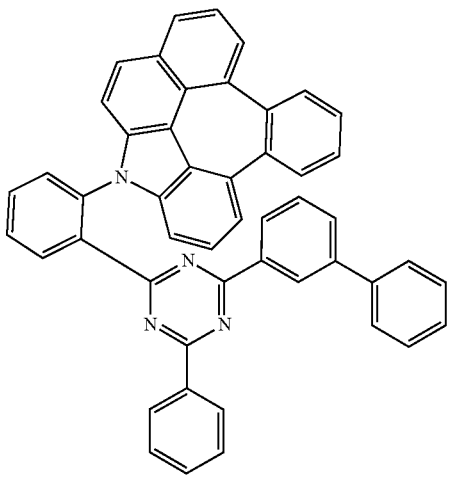
A-5
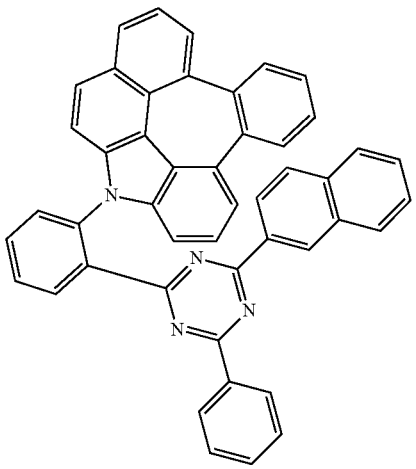
A-6
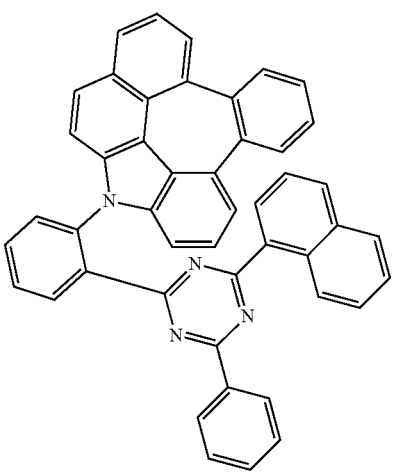

A-7
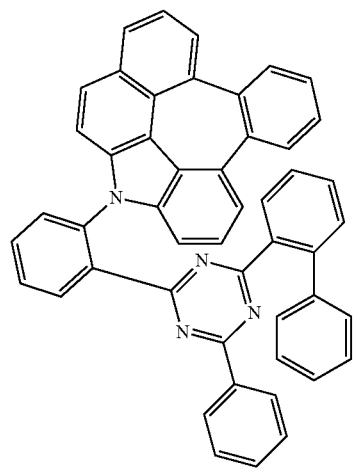
A-8
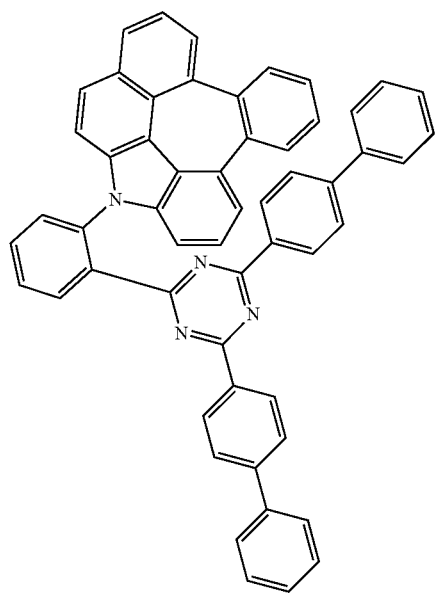
A-9
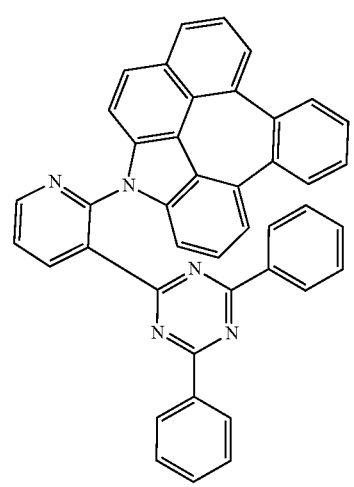
A-10
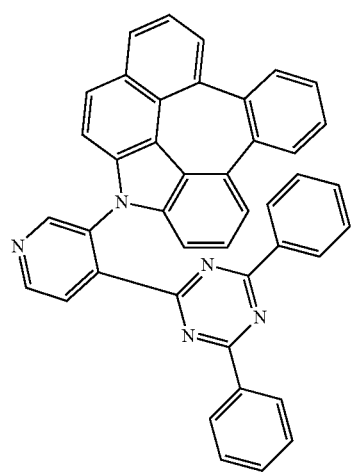
A-11
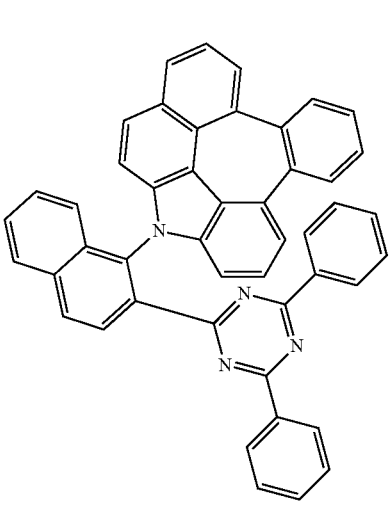
A-12
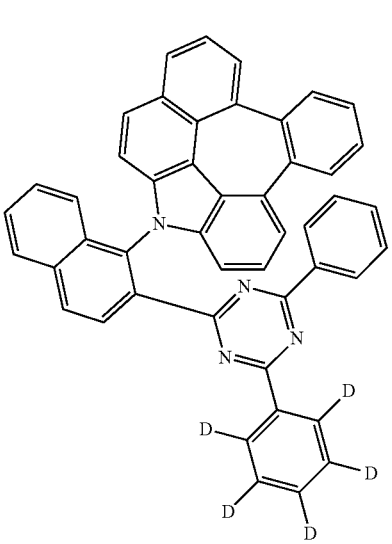

A-13
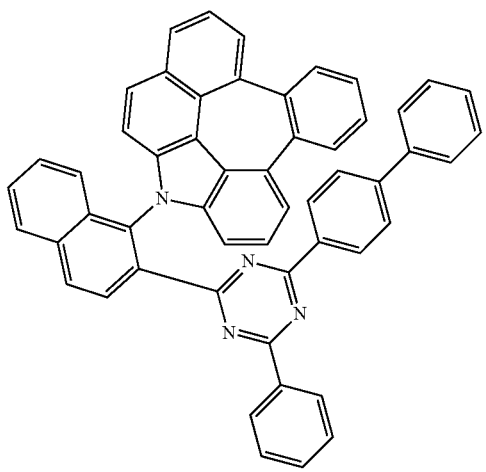
A-14
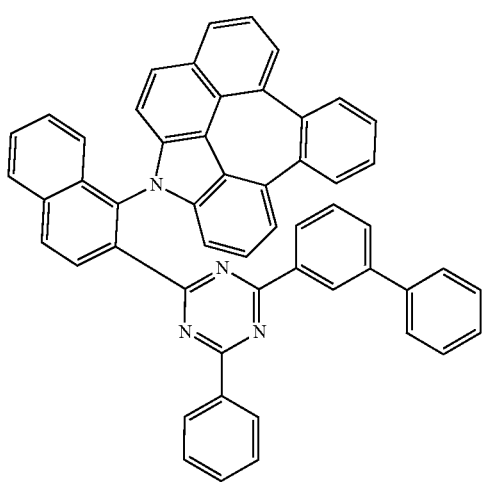
A-15
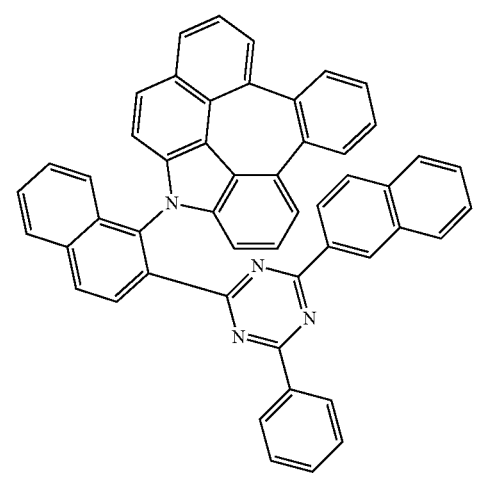
A-16
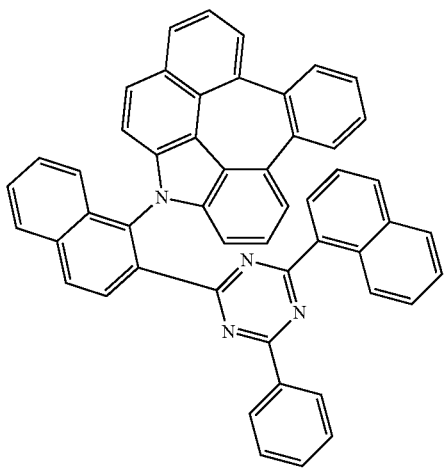
A-17
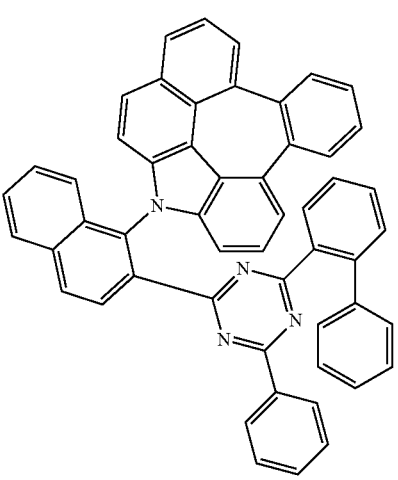
A-18
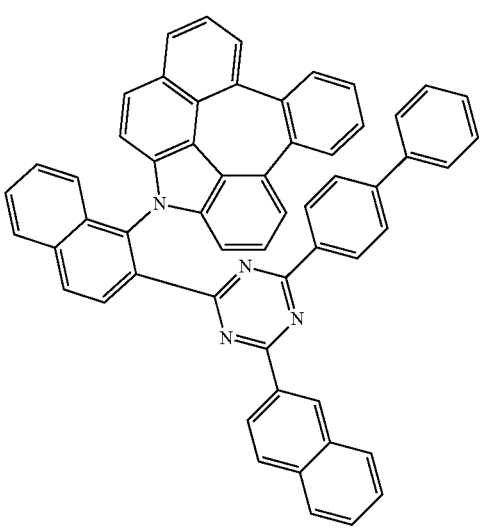

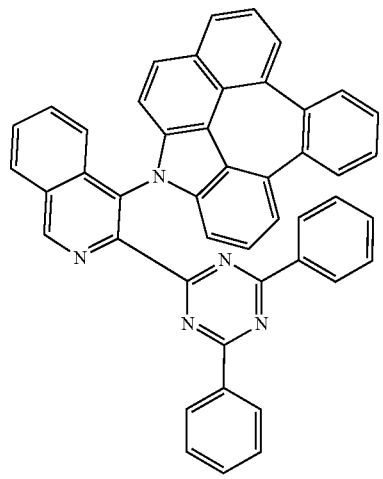
A-19
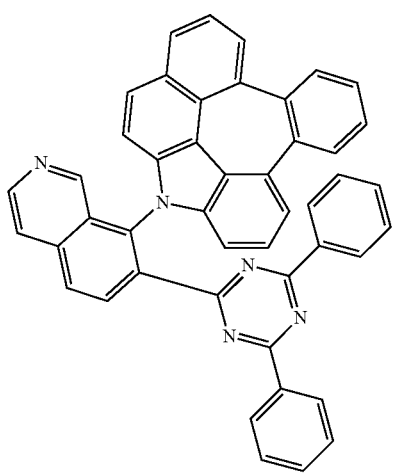
A-20
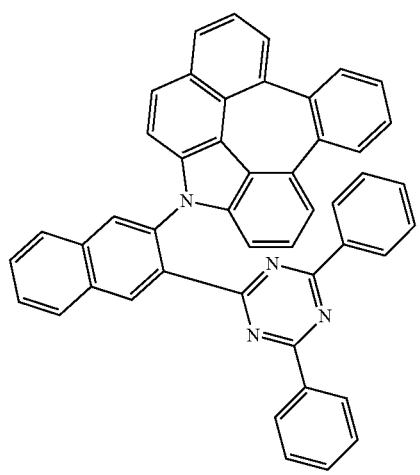
A-21
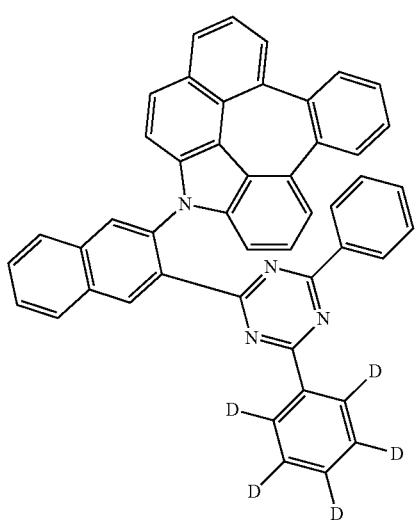
A-22
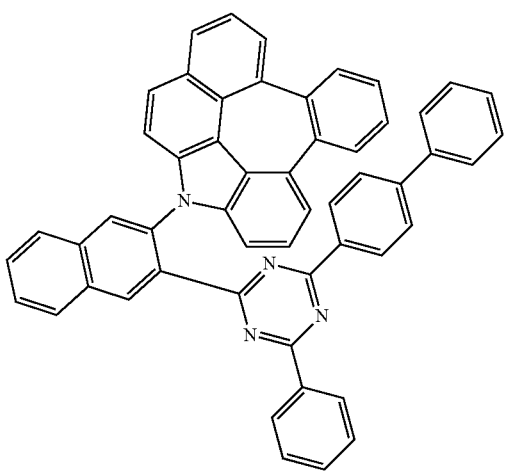
A-23
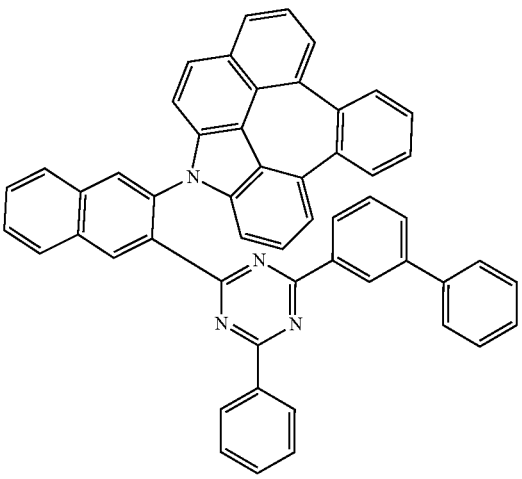
A-24

A-25
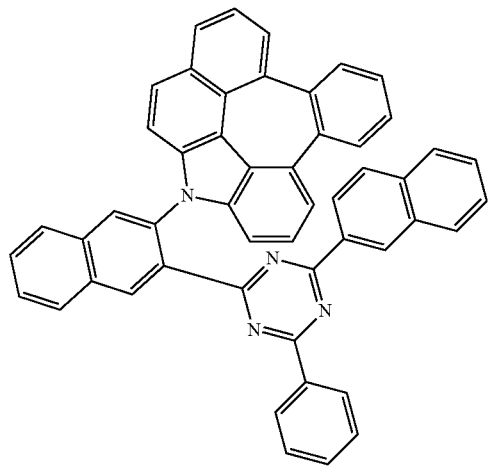
A-26
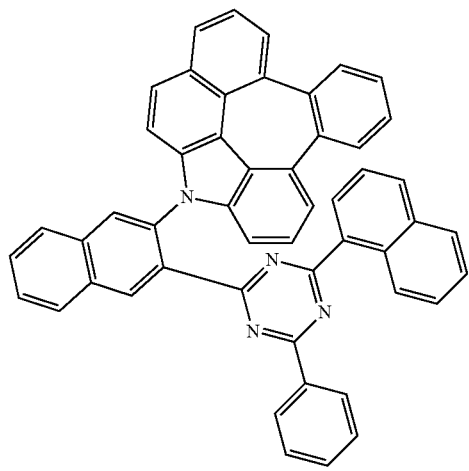
A-27
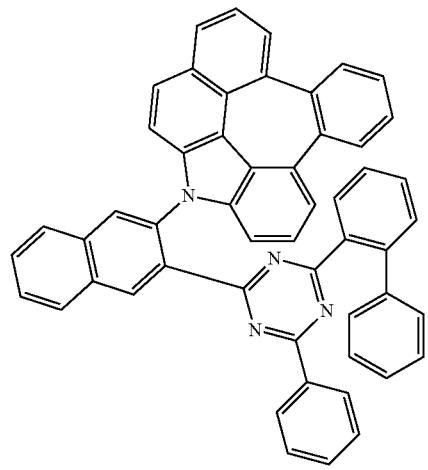
A-28
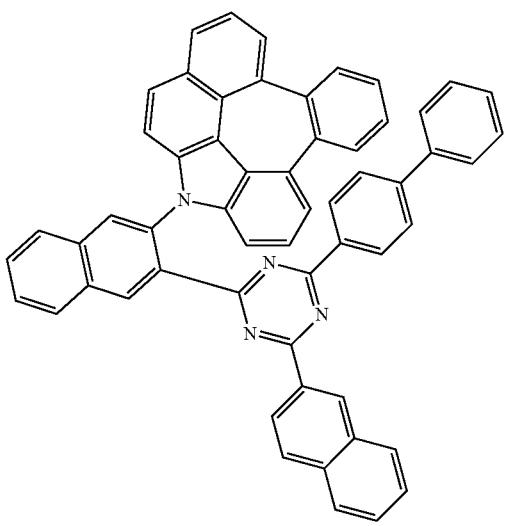
A-29
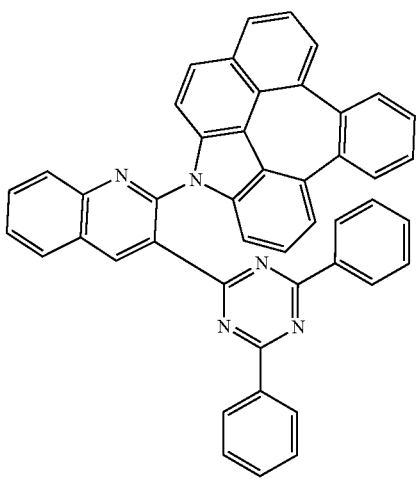
A-30
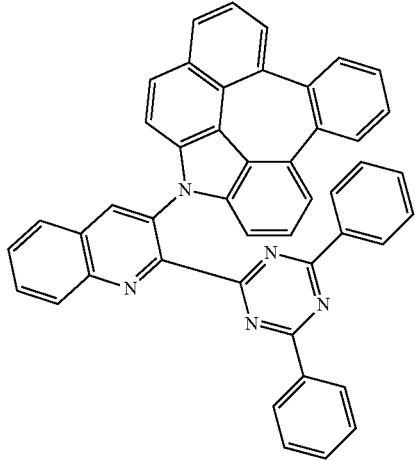

A-31
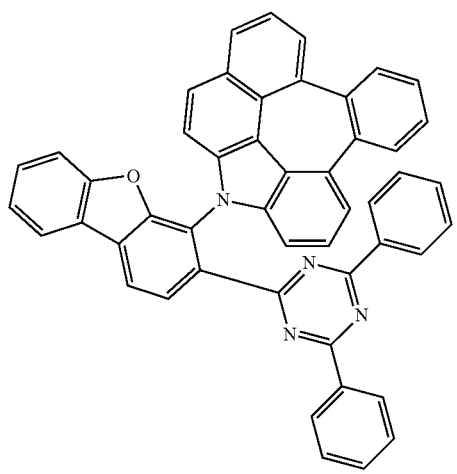
A-32
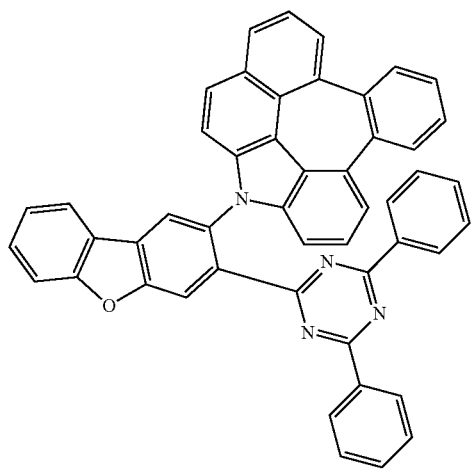
A-33
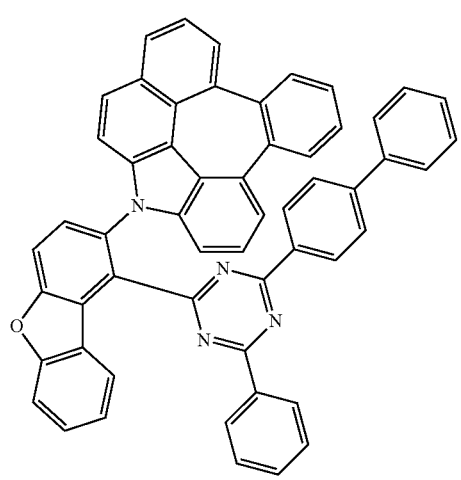
A-34
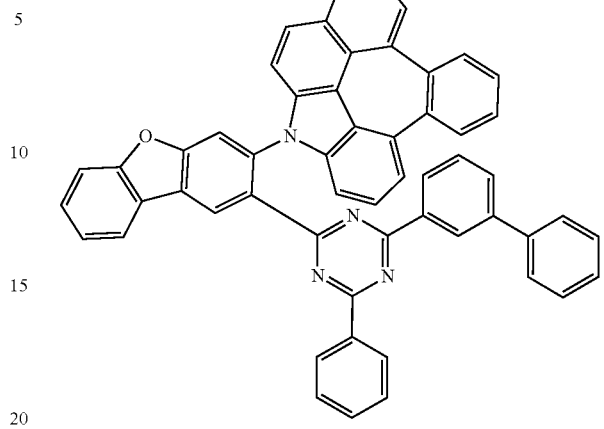
A-35
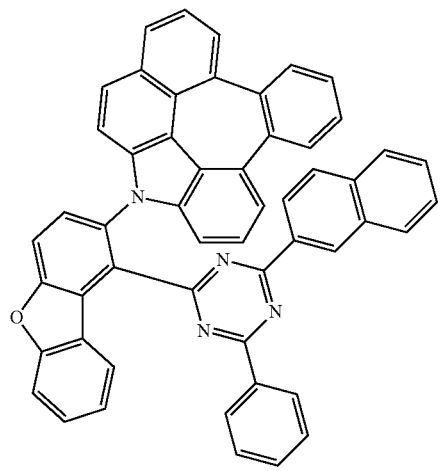
A-36
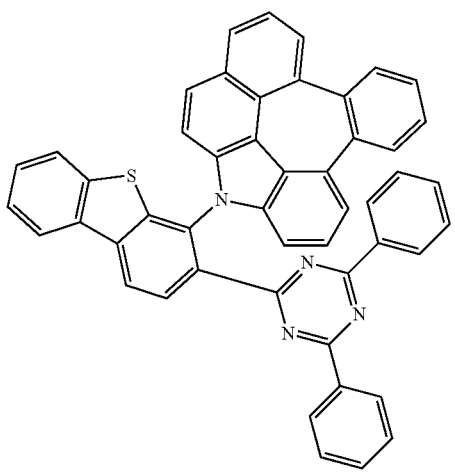

A-37
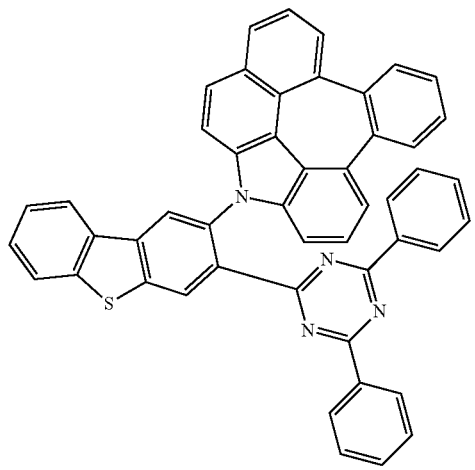
A-38
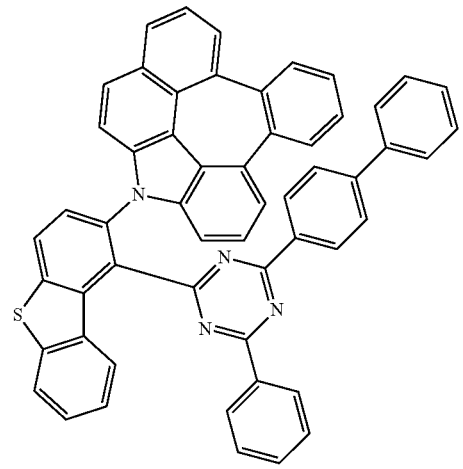
A-39
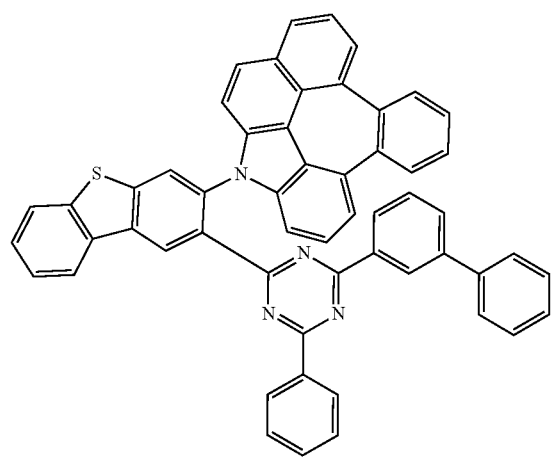
A-40
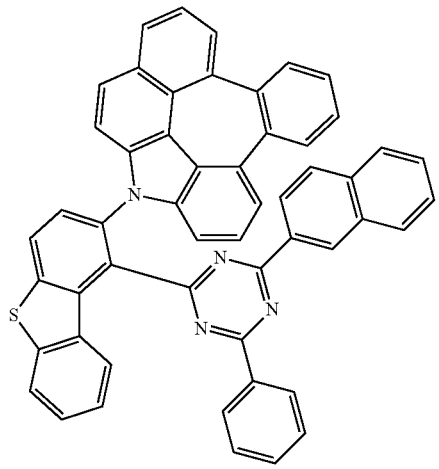
A-41
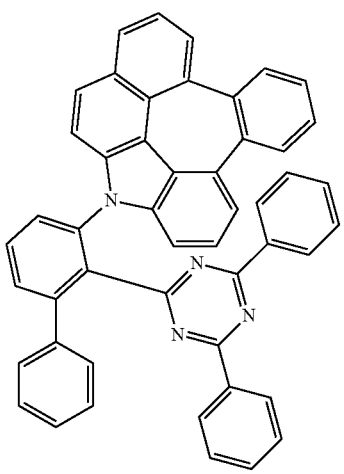
A-42
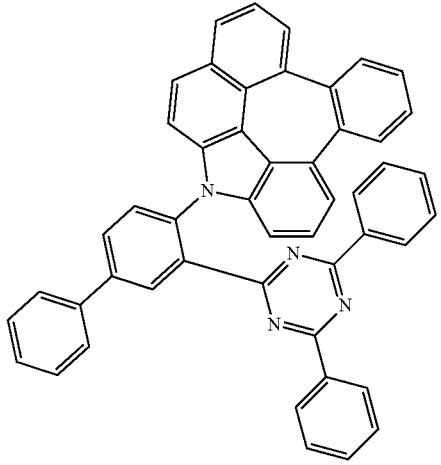

A-43
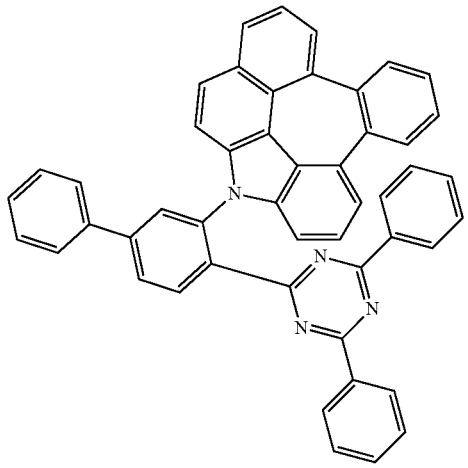
A-46
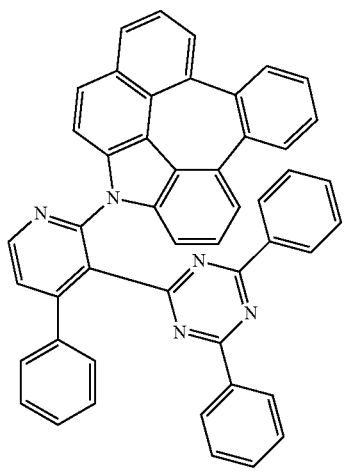
A-44
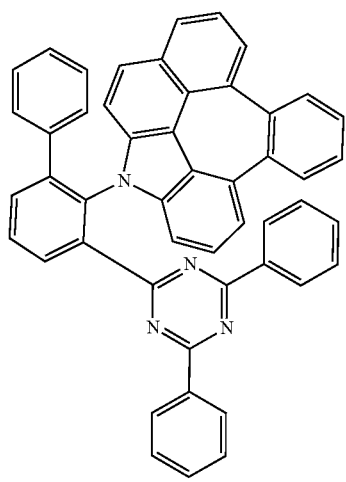
A-47
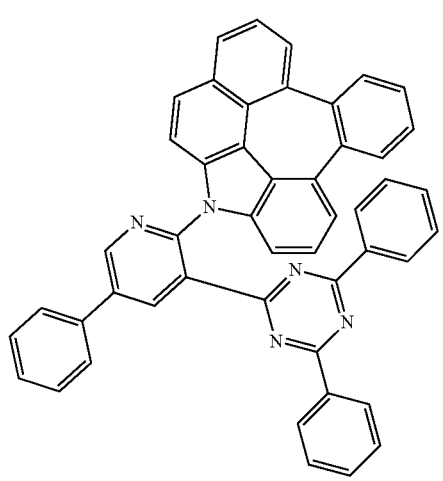
A-45
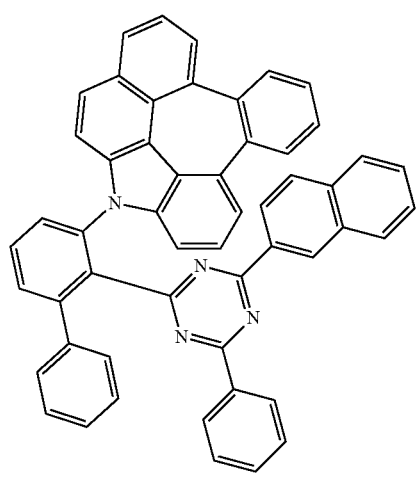
A-48
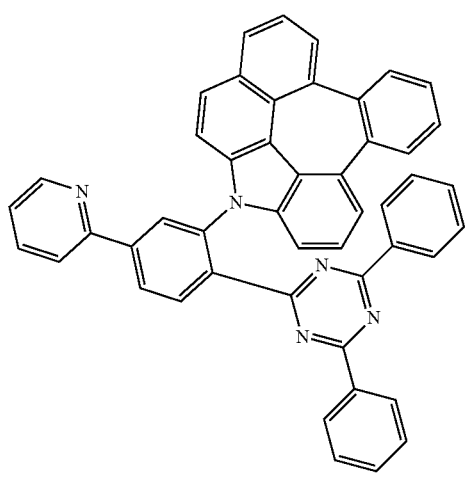

-continued
A-49
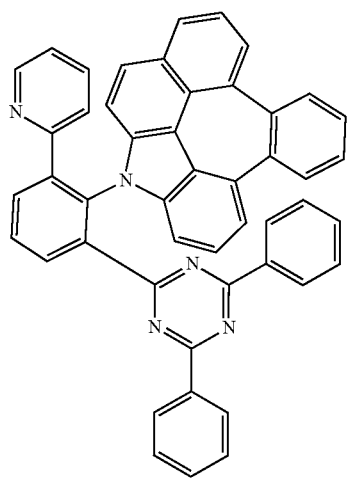
A-50
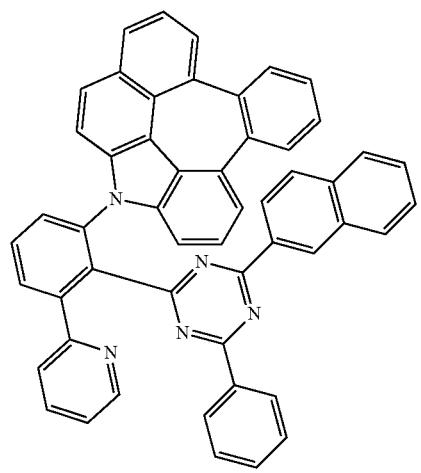
A-51
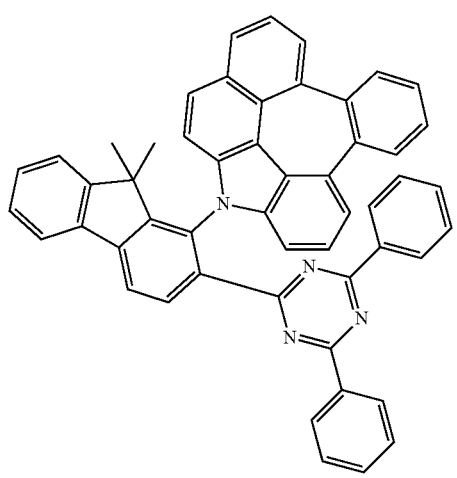
-continued
A-52
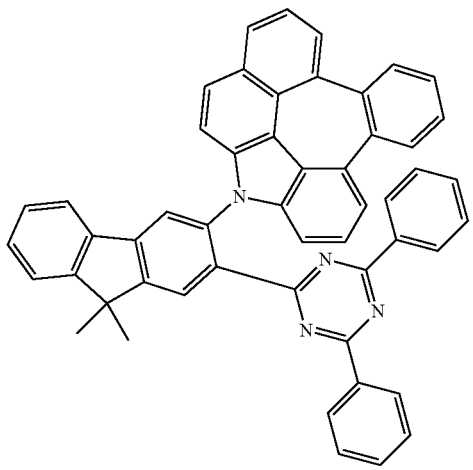
A-53
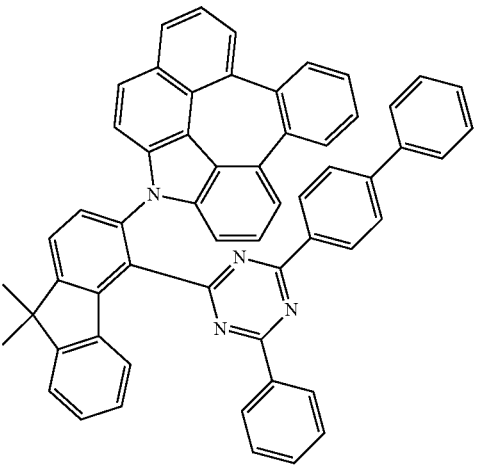
A-54
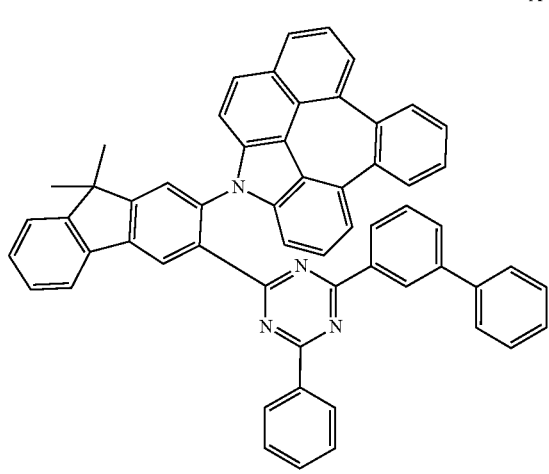

A-55
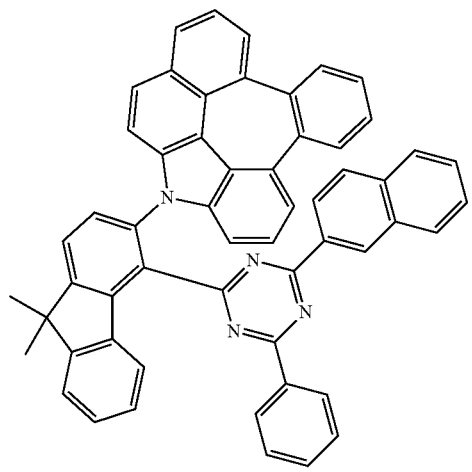
A-58
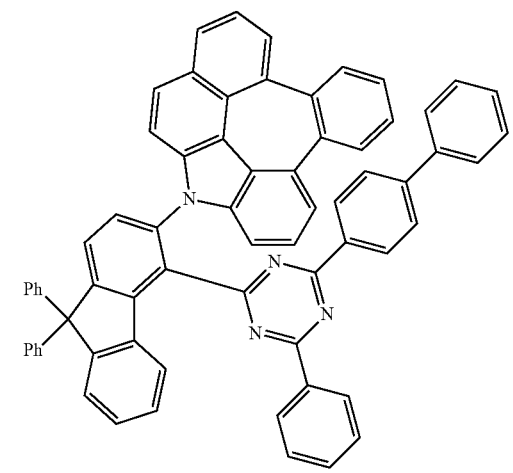
A-56
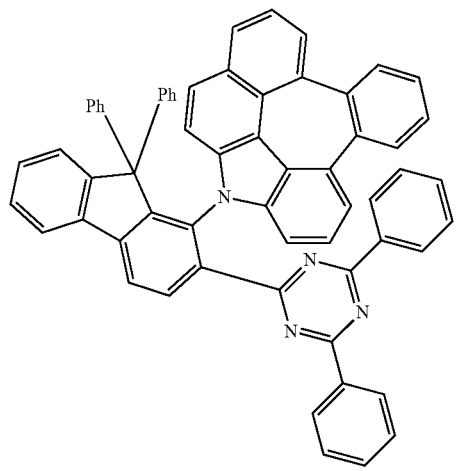
A-59
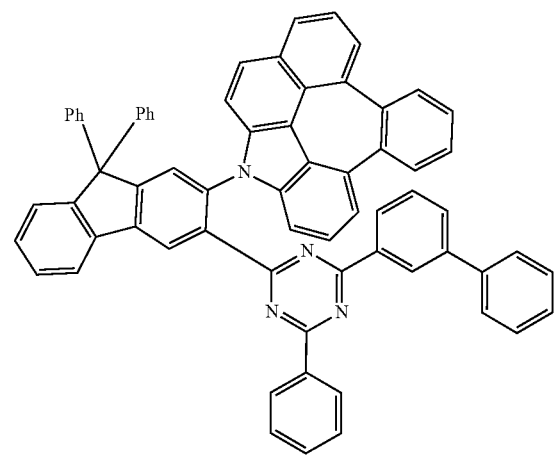
A-57
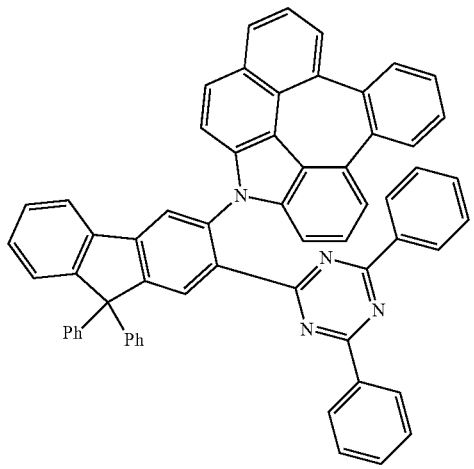
A-60
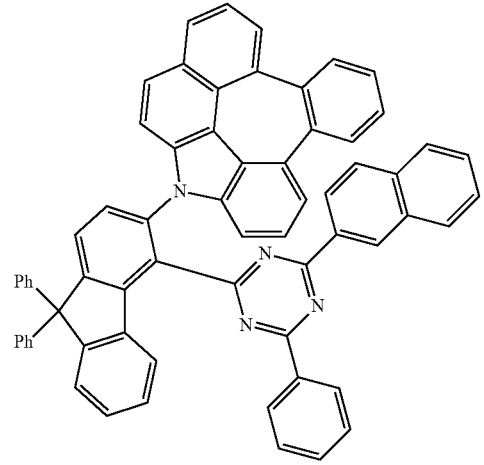

A-61
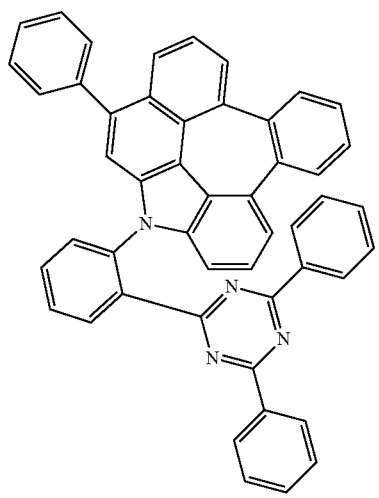
A-62
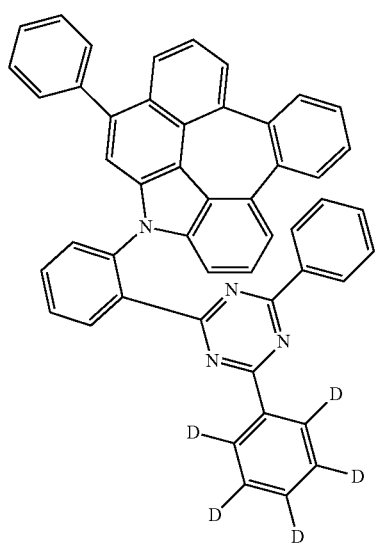
A-63
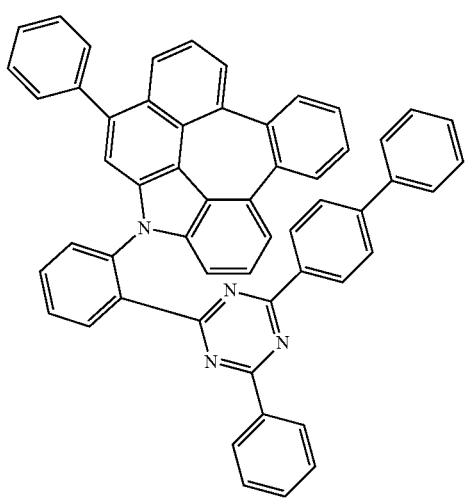
A-64
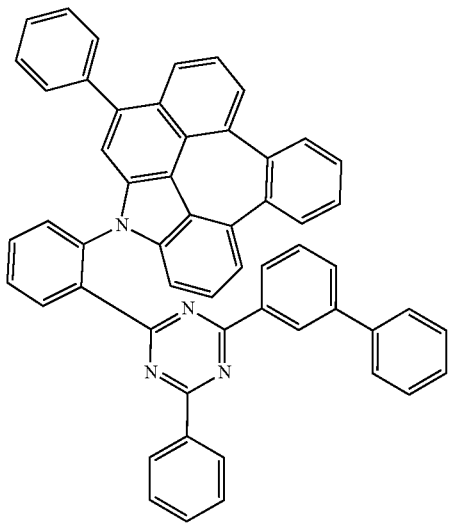
A-65
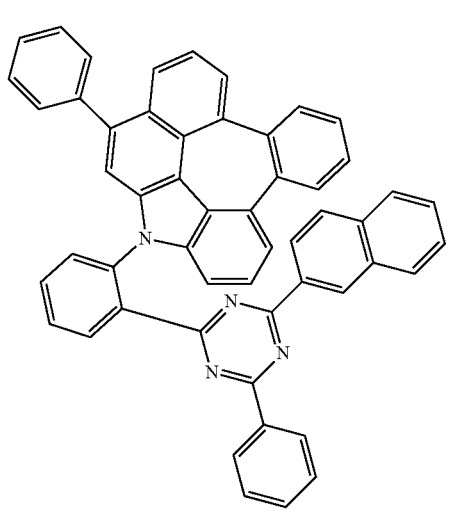
A-66
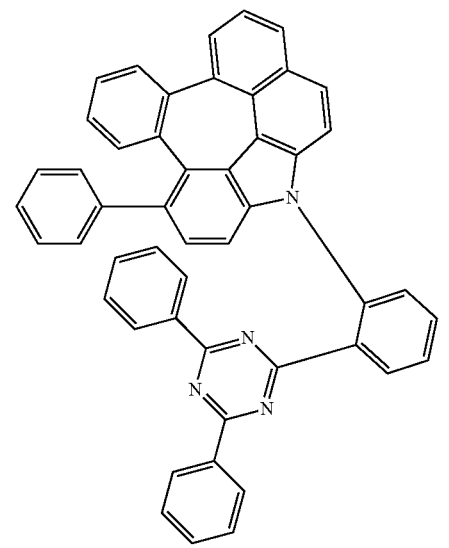

A-67
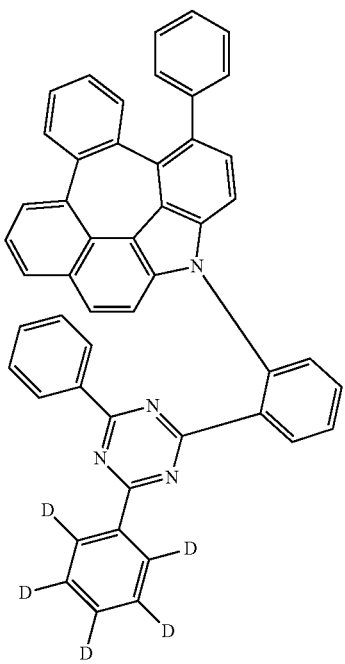
A-68
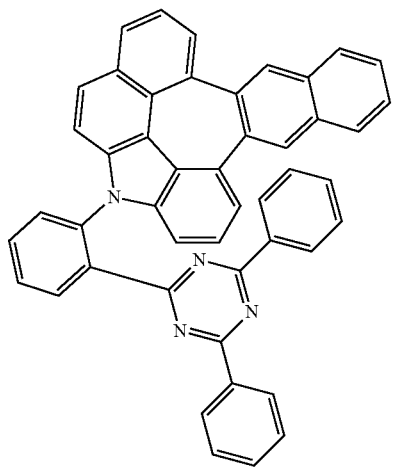
A-69
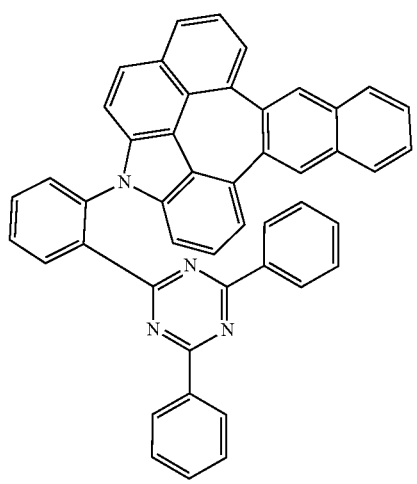
A-70
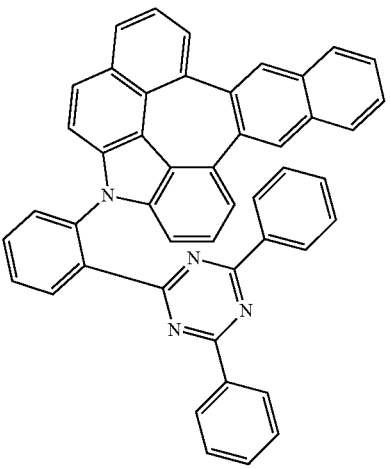
A-71
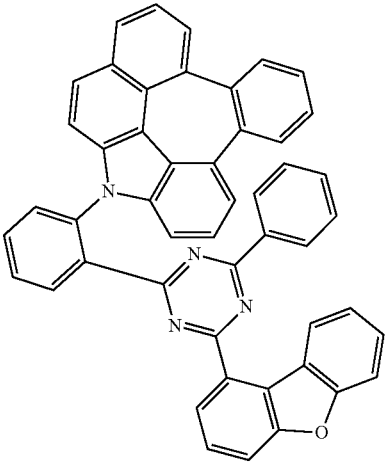
A-72
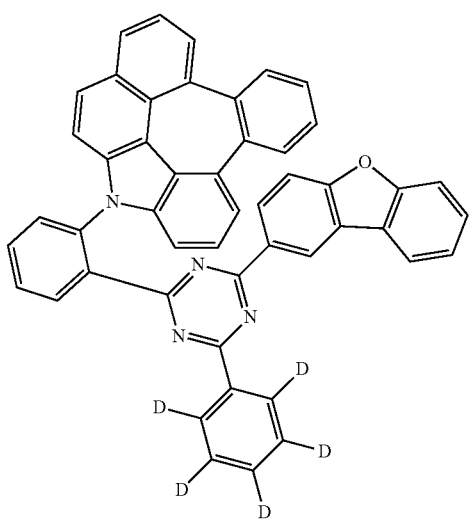

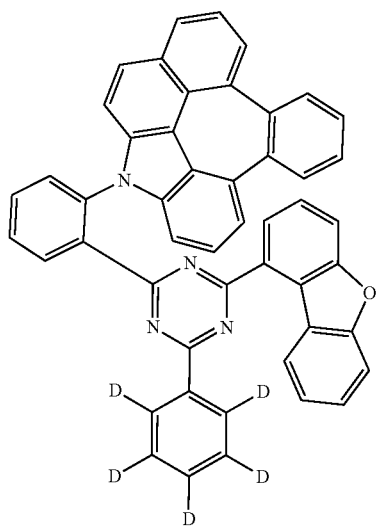
A-73
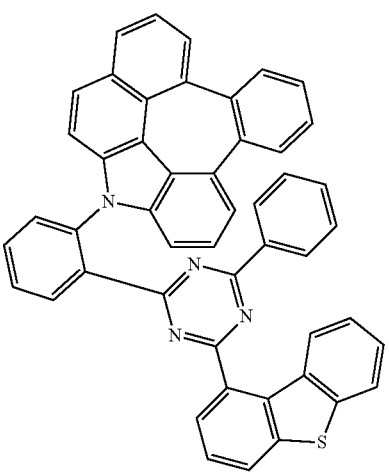
A-76
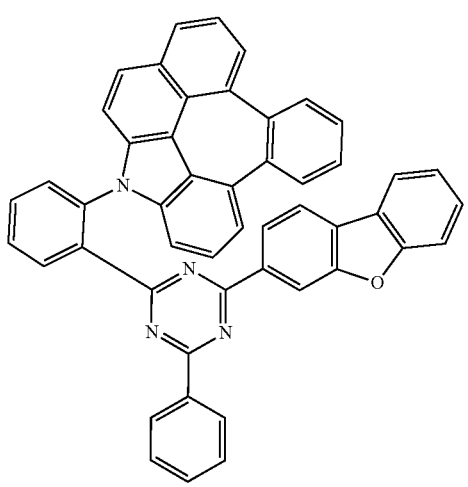
A-74
A-77
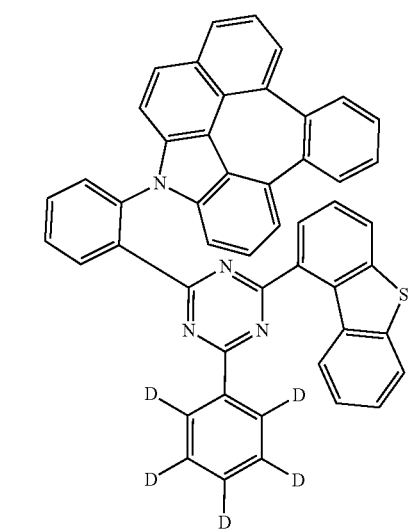
A-75
A-78

A-79
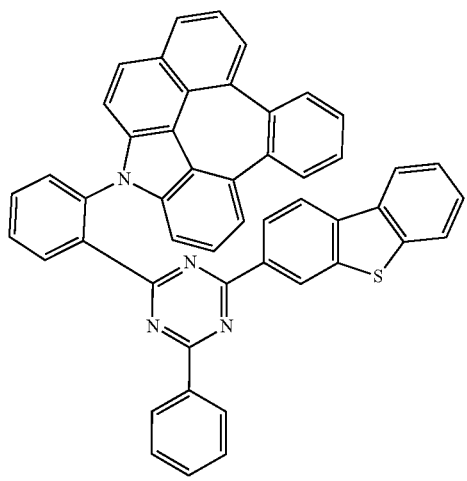
A-80
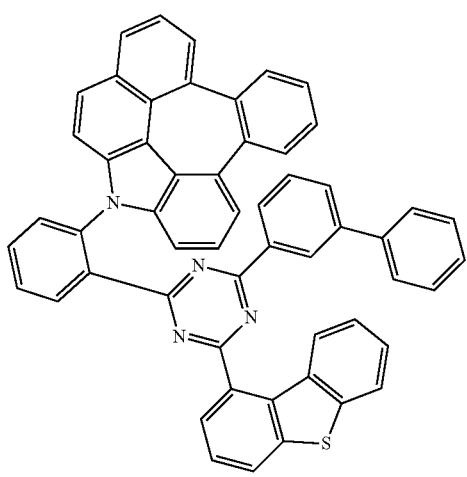
A-81
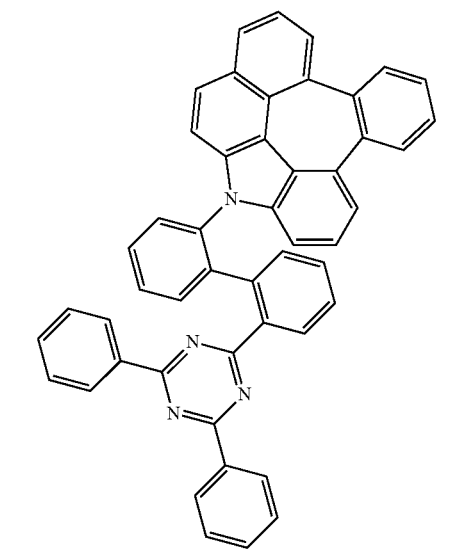
A-82
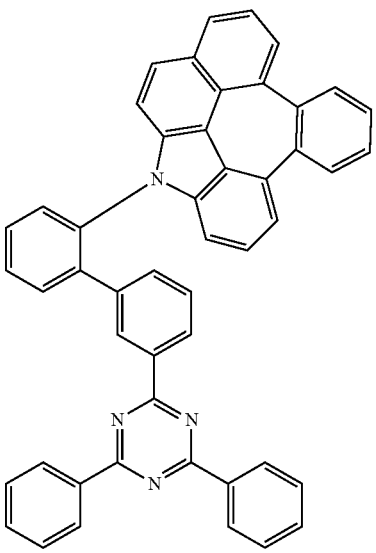
A-83
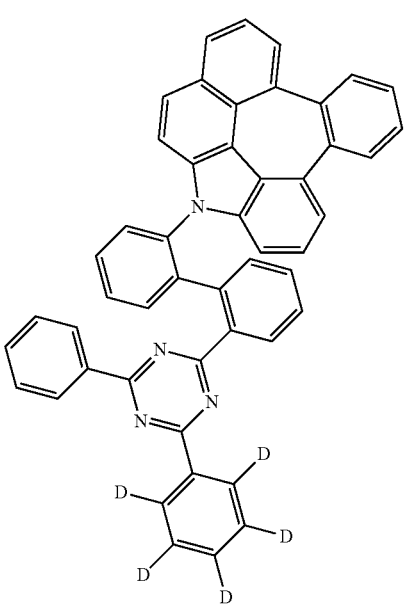

A-84
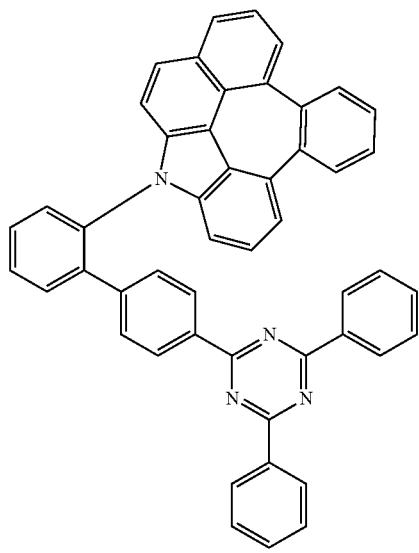
A-86
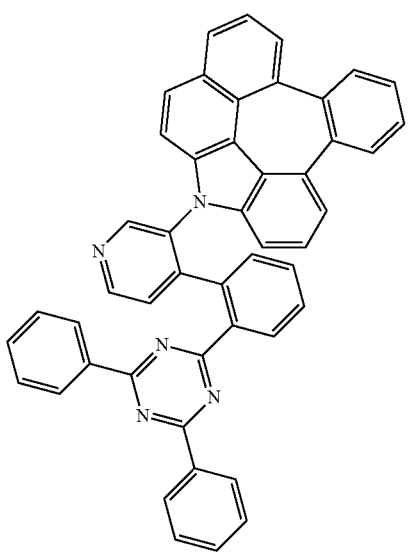
A-85
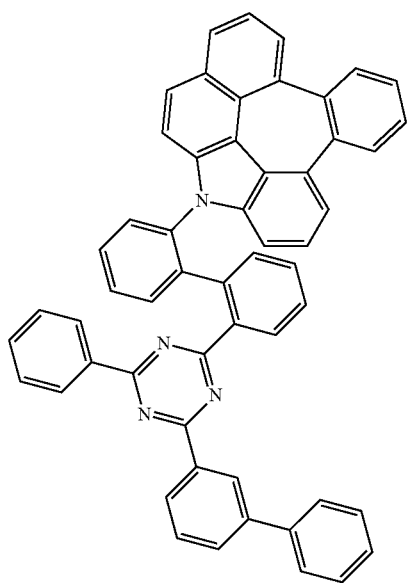
A-87
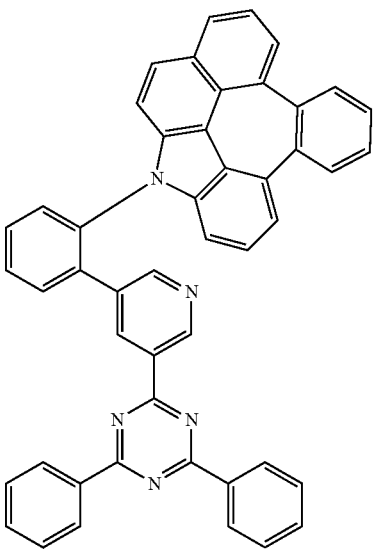

A-88
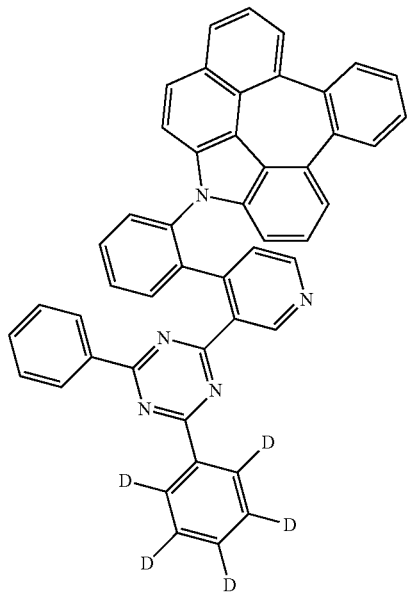
A-89
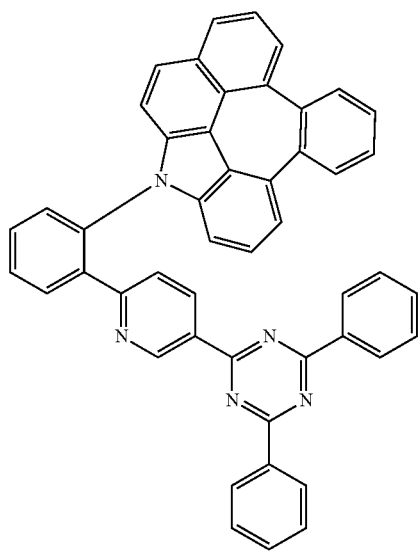
A-90
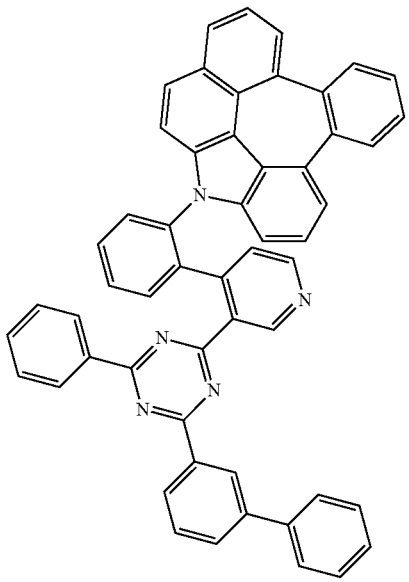
A-91
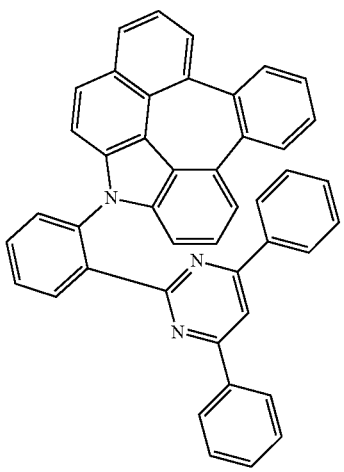
A-92
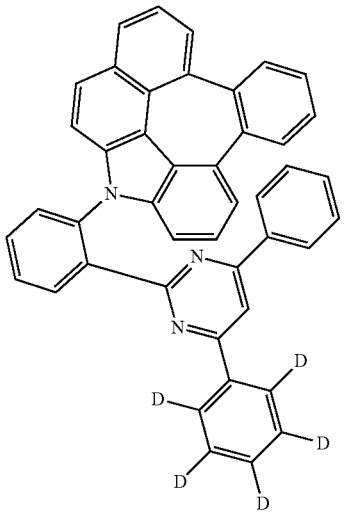

A-93
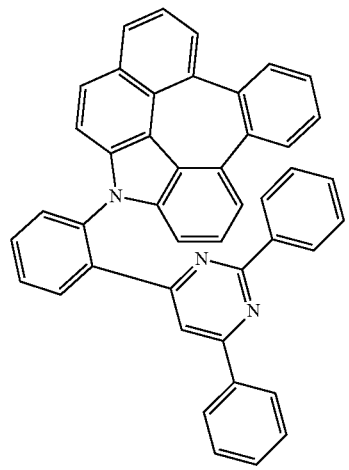
A-94
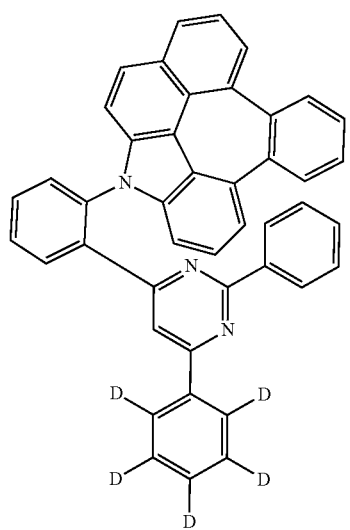
A-95
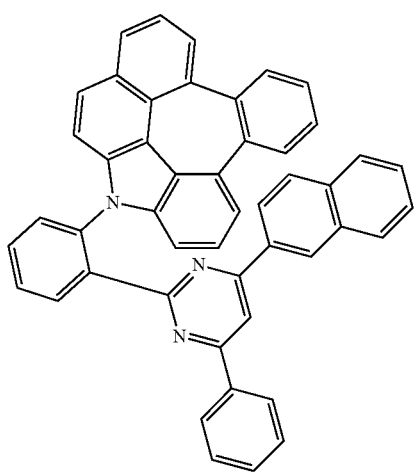
A-96
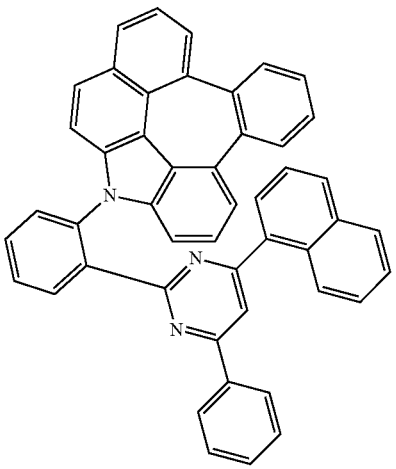
A-97
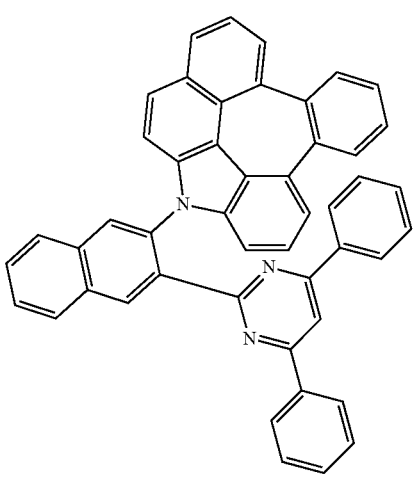
A-98
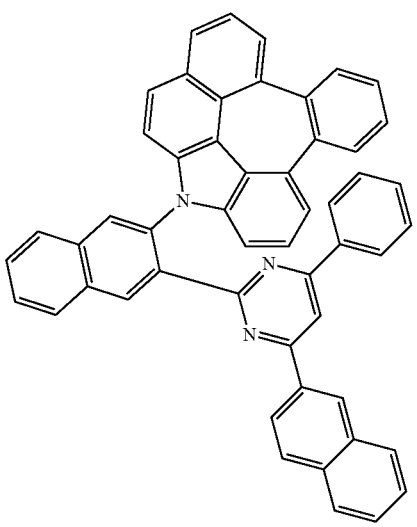

A-99
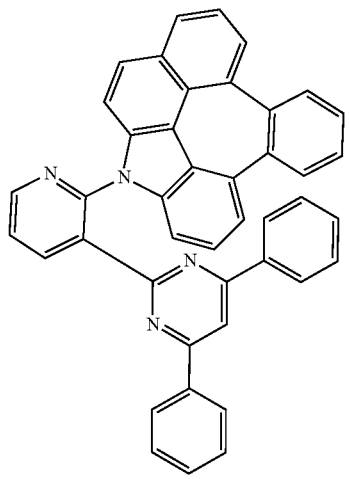
A-100
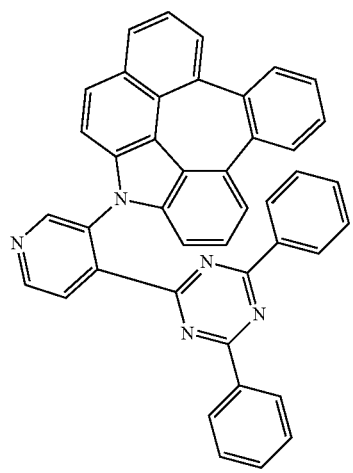
A-101
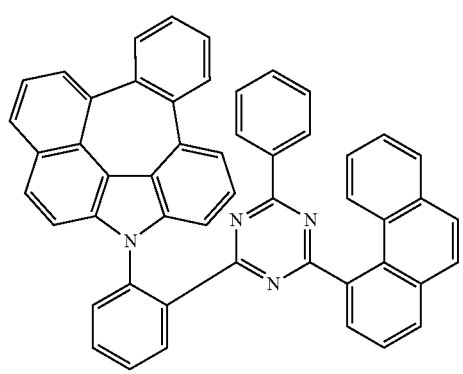
A-102
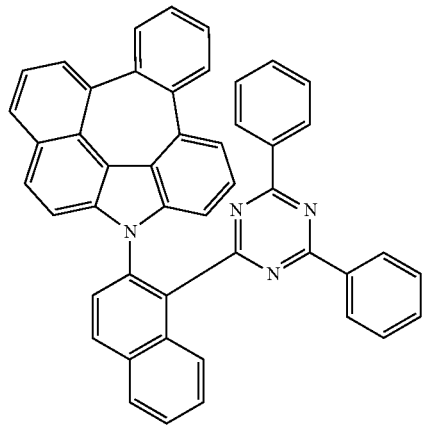
A-103
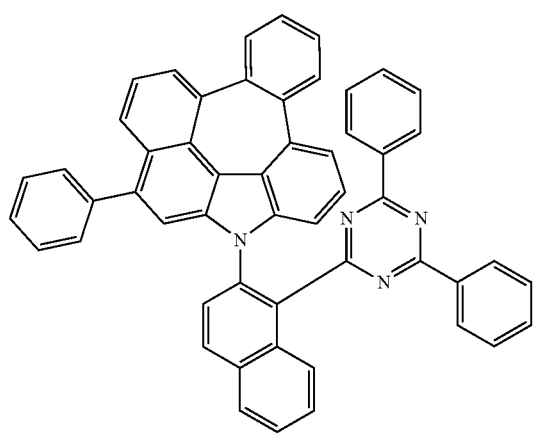
A-104
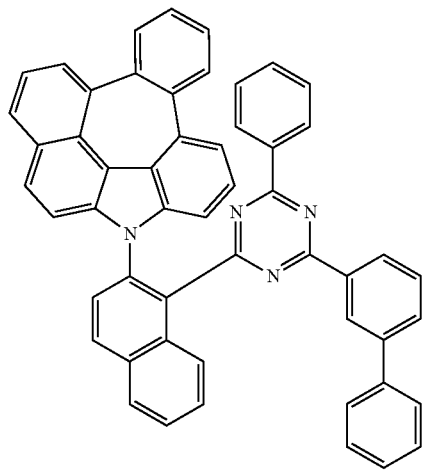

A-105

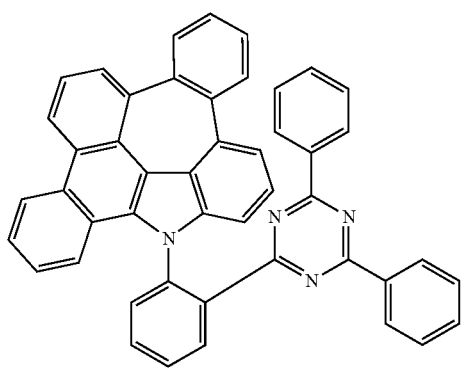

The compound represented by formula 1 according to the present disclosure may be produced by a synthetic method known to one skilled in the art. For example, the organic electroluminescent compound of the present disclosure may be synthesized as shown in the following reaction scheme, but is not limited thereto.

[Reaction Scheme 1]

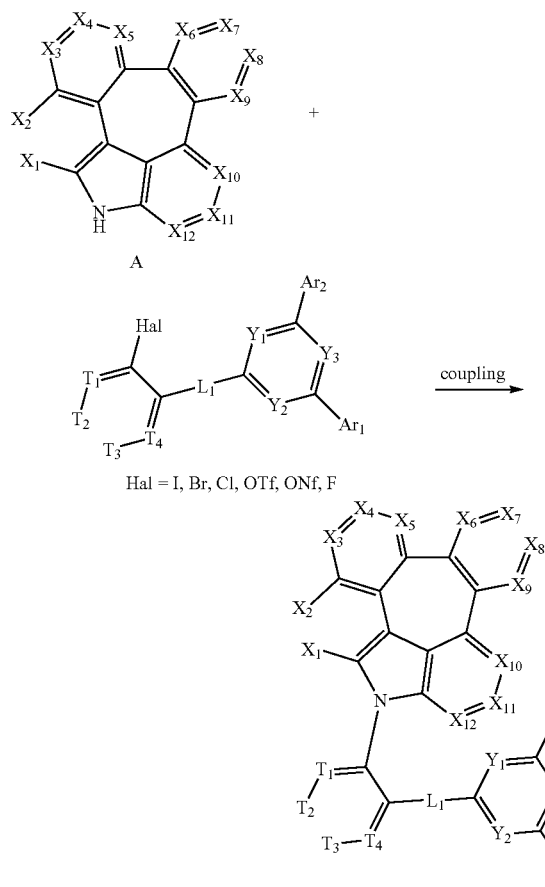

In reaction scheme 1, $X_1$ to $X_{12}$, $T_1$ to $T_4$, $Y_1$ to $Y_3$, $L_1$, $Ar_1$, and $Ar_2$ are as defined in formula 1.

Compound A may be produced by referring to the method disclosed in Korean Patent Application Laying-Open No. 2018-0099510. Although illustrative synthesis examples of the compound represented by formula 1 were described above, one skilled in the art will be able to readily understand that all of them are based on a Buchwald-Hartwig cross-coupling reaction, an N-arylation reaction, a Suzuki cross-coupling reaction, an Intramolecular acid-induced cyclization reaction, a Pd(II)-catalyzed oxidative cyclization reaction, an $SN_1$ substitution reaction, an $SN_2$ substitution reaction, and a Phosphine-mediated reductive cyclization reaction, and the above reactions proceed even when substituents, which are defined in formula 1 above but are not specified in the specific synthesis examples, are bonded.

The present disclosure provides an organic electroluminescent material comprising the compound represented by formula 1, and an organic electroluminescent device comprising the organic electroluminescent material.

The organic electroluminescent material may consist of the compound according to the present disclosure alone, or may further comprise conventional materials included in organic electroluminescent materials.

The organic electroluminescent compound represented by formula 1 of the present disclosure may be comprised in at least one of a light-emitting layer, a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer, preferably in a light-emitting layer. When used in a light-emitting layer, the organic electroluminescent compound represented by formula 1 of the present disclosure may be comprised as a host material. Preferably, the light-emitting layer may further comprise at least one dopant. If necessary, the organic electroluminescent compound of the present disclosure may be used as a co-host material. That is, the light-emitting layer may further include an organic electroluminescent compound other than the organic electroluminescent compound represented by formula 1 of the present disclosure (first host material) as a second host material. In this case, the weight ratio between the first host material and the second host material is in the range of 1:99 to 99:1. When two or more materials are included in one layer, mixed deposition may be performed to form a layer, or a co-deposition may be performed separately to form a layer.

The second host material may be selected from any of the known host materials. Preferably, the second host material may be selected from the group consisting of the compounds represented by the following formulas 11 to 16:

 (11)

 (12)

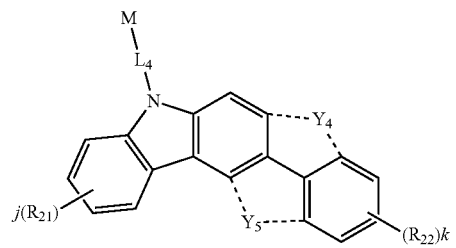 (13)

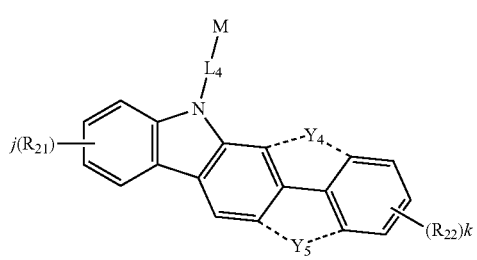

(14)

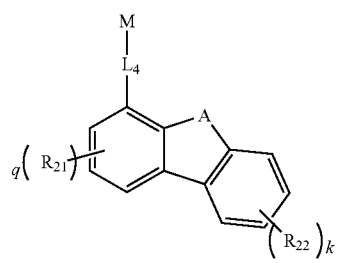

(15)

wherein Cz represents the following structure:

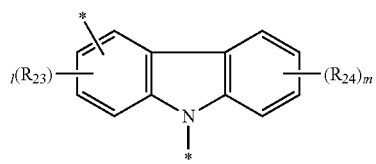

A represents —O— or —S—;

$R_{21}$ to $R_{24}$ each independently represent hydrogen, deuterium, a halogen, a substituted or unsubstituted (C1-C30)alkyl, a substituted or unsubstituted (C6-C30)aryl, a substituted or unsubstituted (5- to 30-membered)heteroaryl, or —$SiR_{25}R_{26}R_{27}$, where $R_{25}$ to $R_{27}$ each independently represent a substituted or unsubstituted (C1-C30)alkyl, or a substituted or unsubstituted (C6-C30)aryl; $L_4$ represents a single bond, a substituted or unsubstituted (C6-C30)arylene, or a substituted or unsubstituted (5- to 30-membered)heteroarylene; M represents a substituted or unsubstituted (C6-C30)aryl, or a substituted or unsubstituted (5- to 30-membered)heteroaryl; $Y_4$ and $Y_5$ each independently represent —O—, —S—, —N($R_{31}$)—, or —C($R_{32}$)($R_{33}$)—, and $Y_4$ and $Y_5$ are not present simultaneously; $R_{31}$ to $R_{33}$ each independently represent a substituted or unsubstituted (C1-C30)alkyl, a substituted or unsubstituted (C6-C30)aryl, or a substituted or unsubstituted (5- to 30-membered)heteroaryl, in which $R_{32}$ and $R_{33}$ may be the same or different; and h and i each independently represent an integer of 1 to 3; j, k, l, and m each independently represent an integer of 1 to 4; q represents an integer of 1 to 3; and where h, i, j, k, l, m, or q is an integer of 2 or more, each of (Cz-$L_4$), each of (Cz), each of $R_{21}$, each of $R_{22}$, each of $R_{23}$, or each of $R_{24}$ may be the same or different.

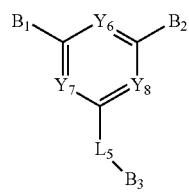

(16)

wherein $Y_6$ to $Y_8$ each independently represent $CR_{34}$ or N;

$R_{34}$ represents hydrogen, a substituted or unsubstituted (C1-C30)alkyl, a substituted or unsubstituted (C6-C30)aryl, or a substituted or unsubstituted (5- to 30-membered)heteroaryl;

$B_1$ and $B_2$ each independently represent hydrogen, a substituted or unsubstituted (C6-C30)aryl, or a substituted or unsubstituted (5- to 30-membered)heteroaryl;

$B_3$ represents a substituted or unsubstituted (C6-C30)aryl, or a substituted or unsubstituted (5- to 30-membered)heteroaryl; and $L_5$ represents a single bond, a substituted or unsubstituted (C6-C30)arylene, or a substituted or unsubstituted (5- to 30-membered)heteroarylene.

Specifically, the examples of the second host material include the following, but are not limited thereto.

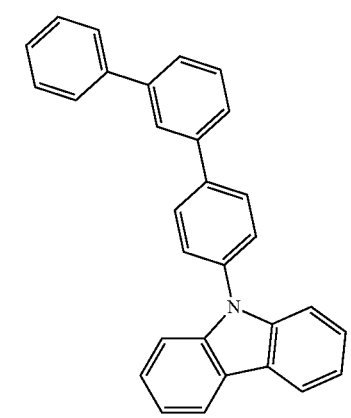

B-1

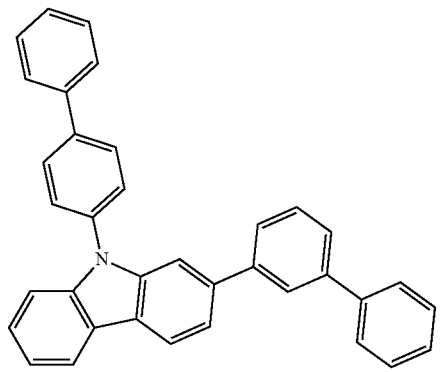

B-2

B-3
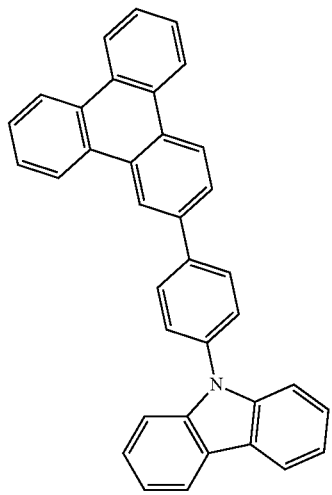
B-4
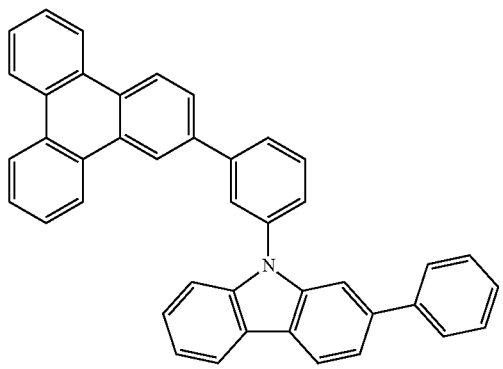
B-5
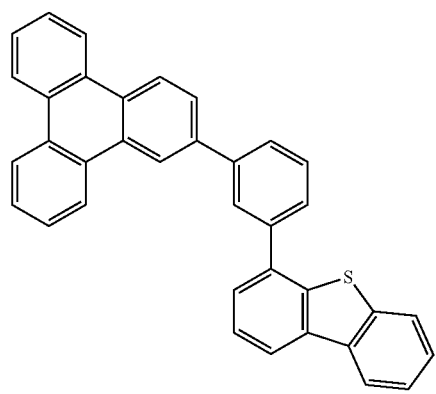
B-6
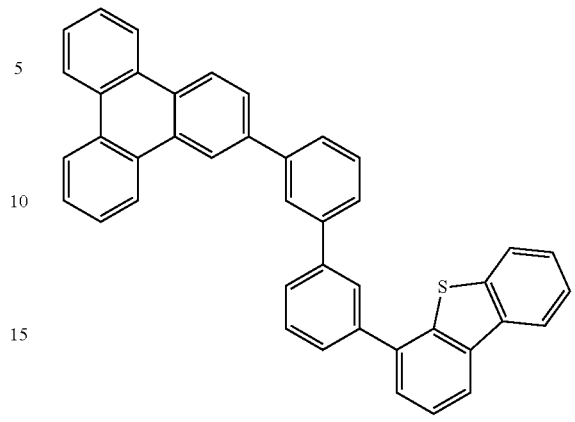
B-7
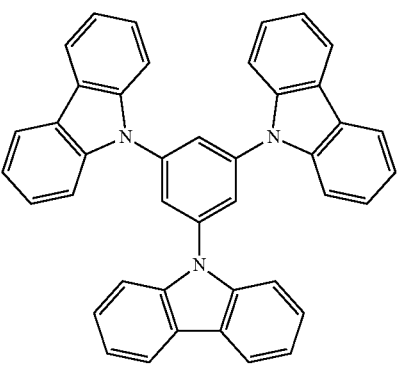
B-8
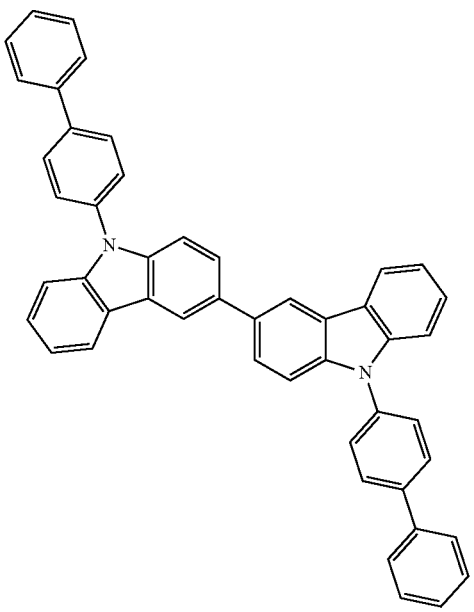

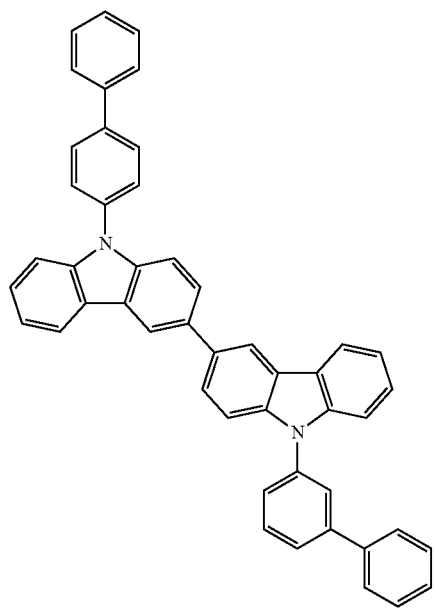
B-9
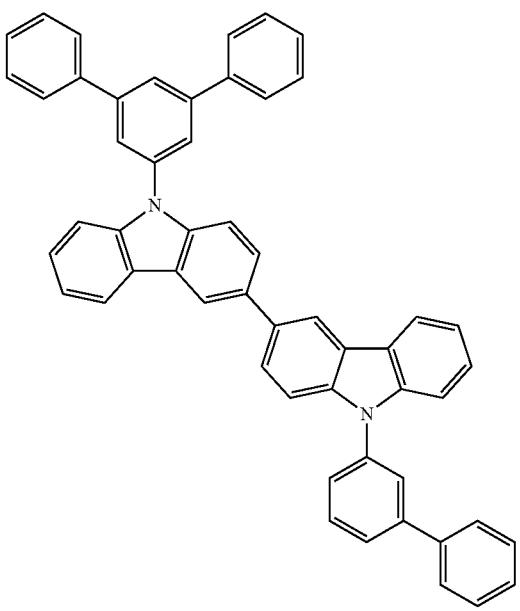
B-11
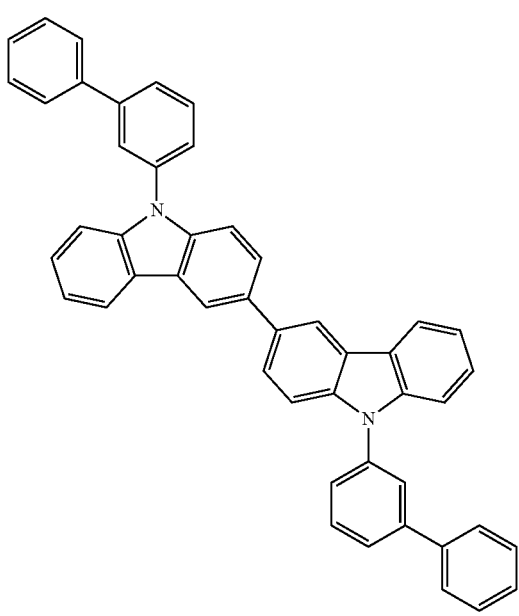
B-10
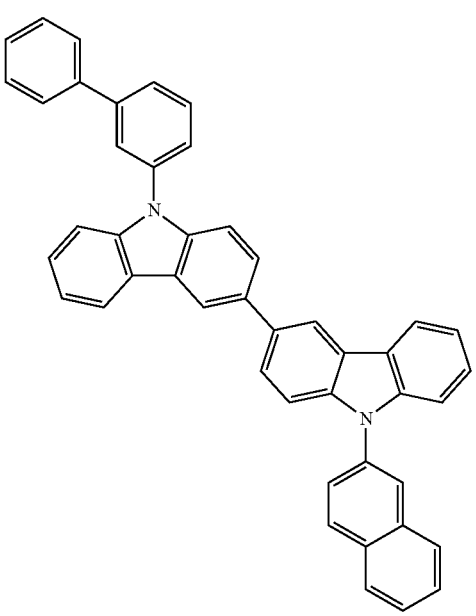
B-12

-continued
B-13
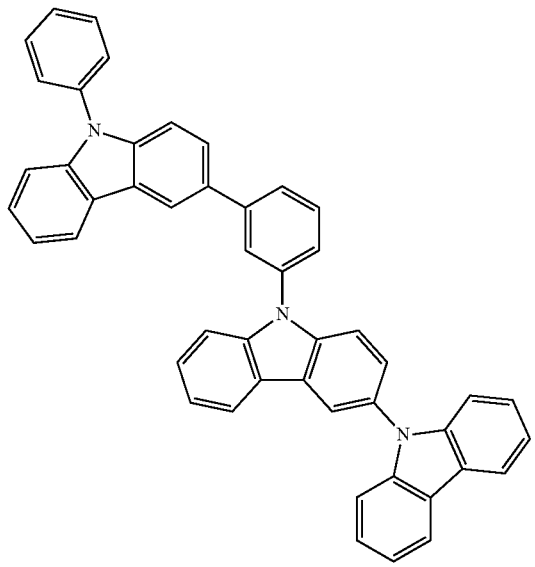
B-14
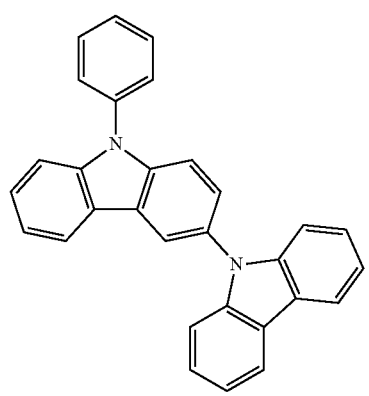
B-15
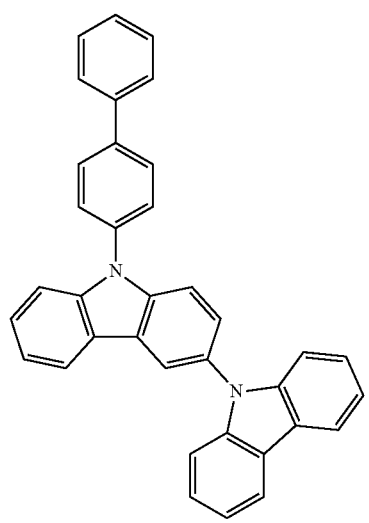
-continued
B-16
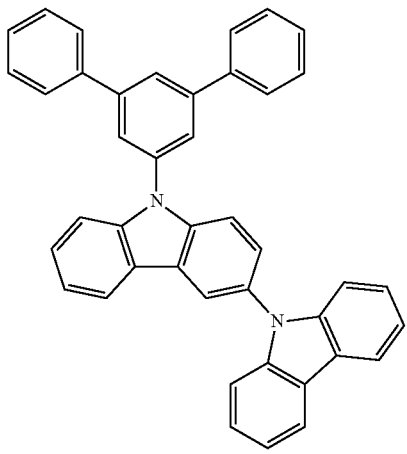
B-17
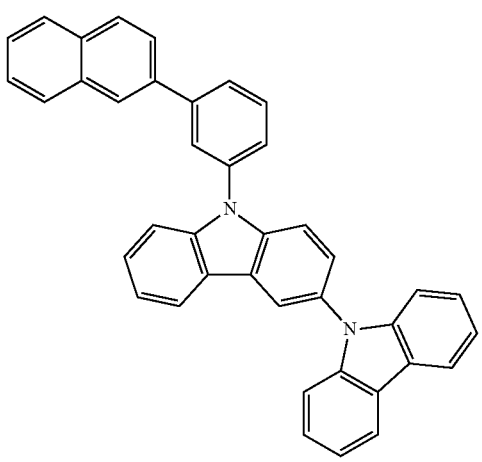
B-18
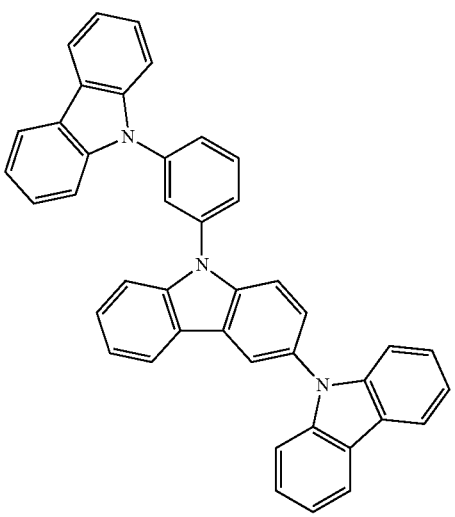

-continued
B-19
B-22
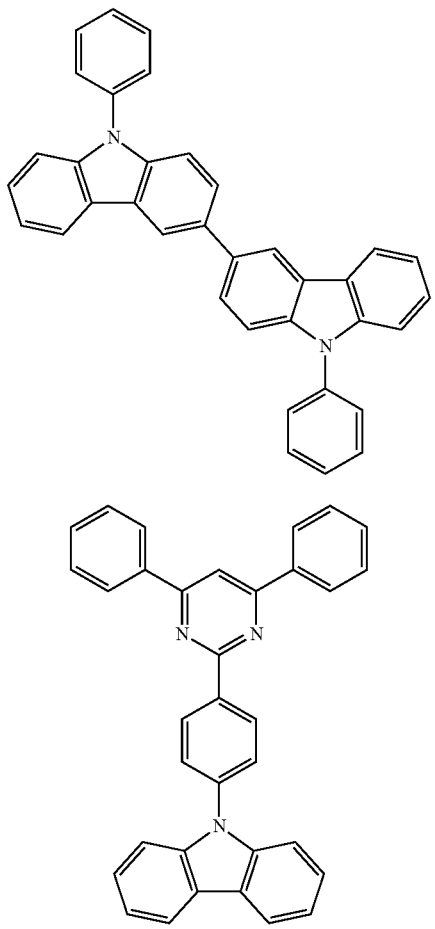
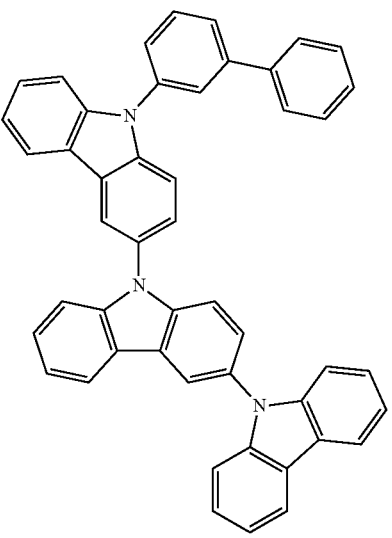
B-20
B-21
B-23
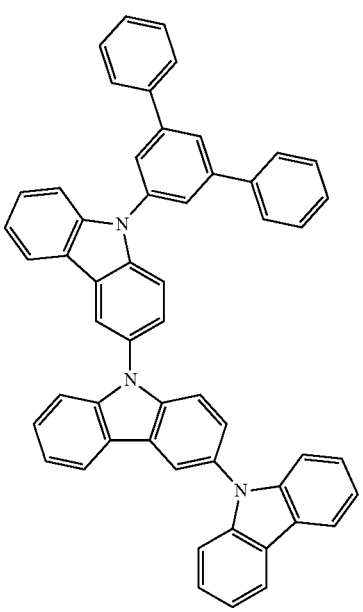

-continued
B-24
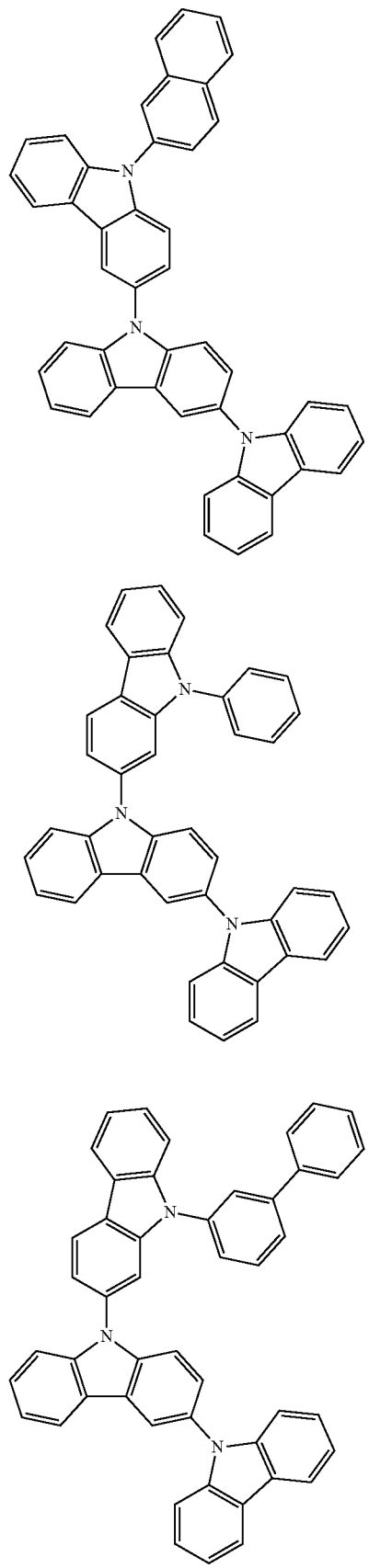
B-25
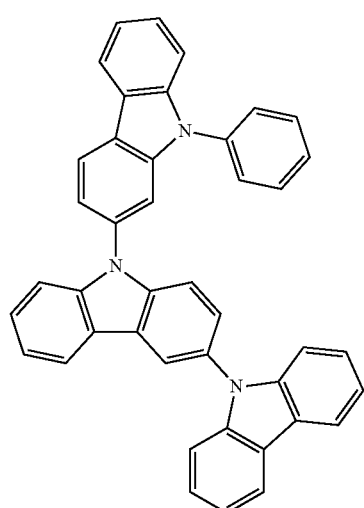
B-26
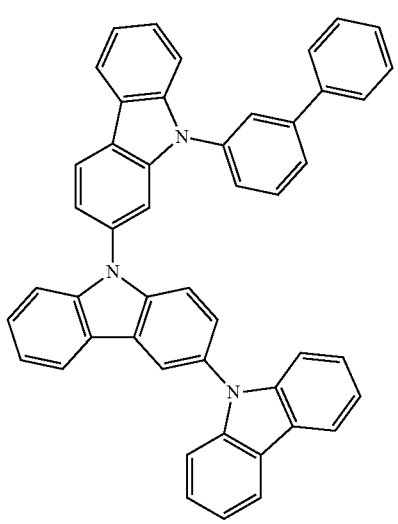
-continued
B-27
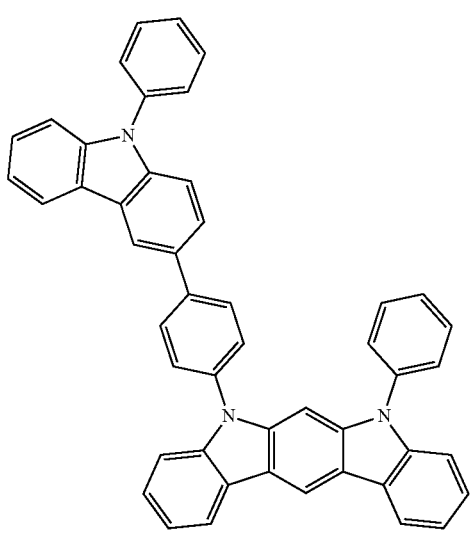
B-28
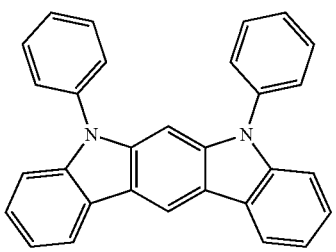
B-29
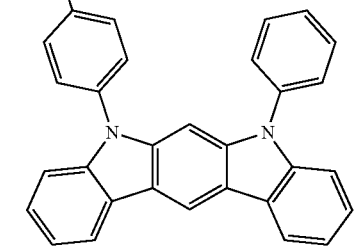
B-30
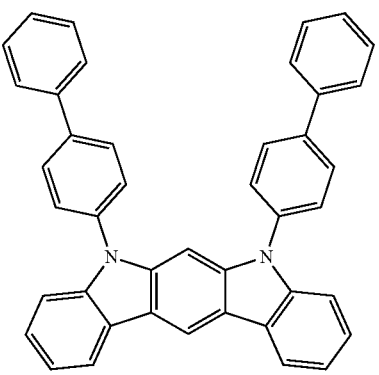

B-31
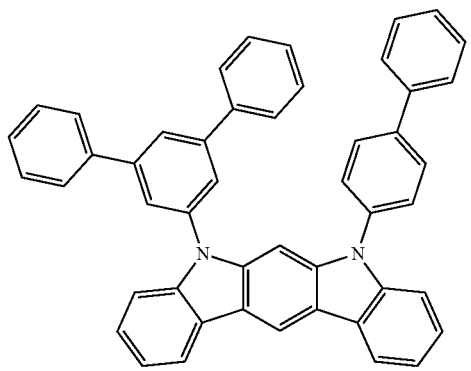
B-32
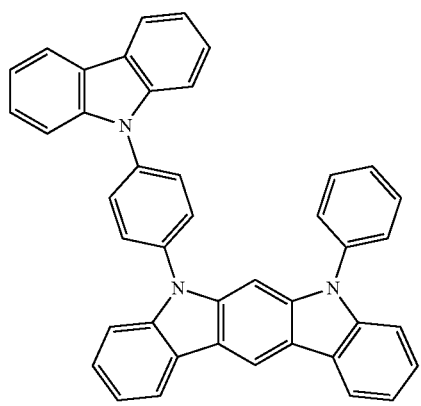
B-33
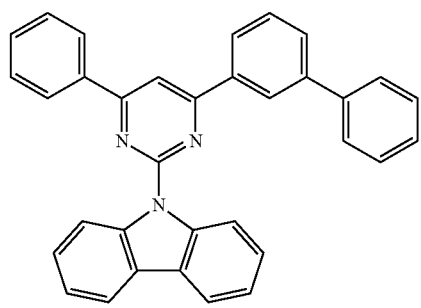
B-34
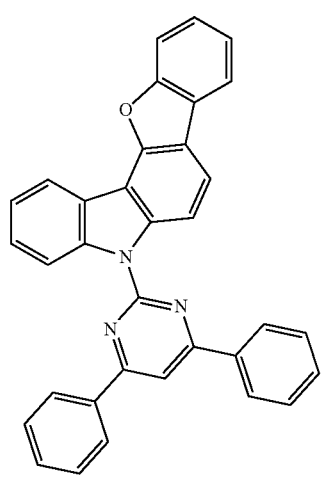
B-35
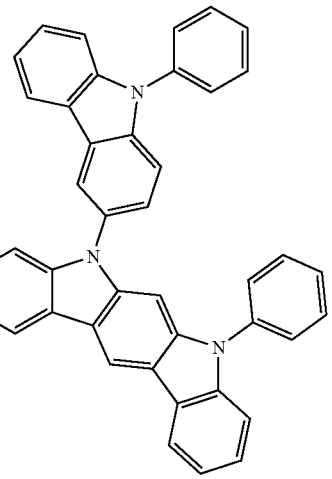
B-36
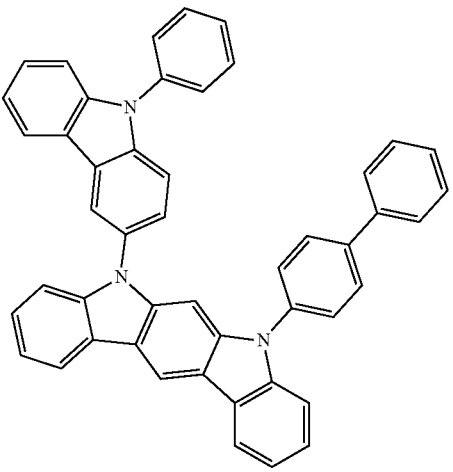
B-37
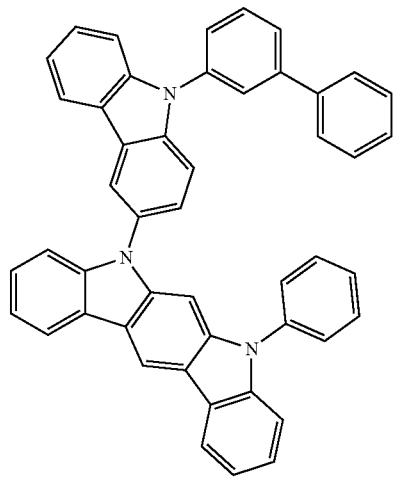

B-38
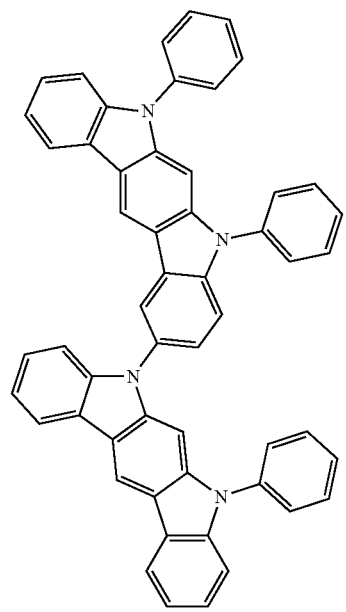
B-39
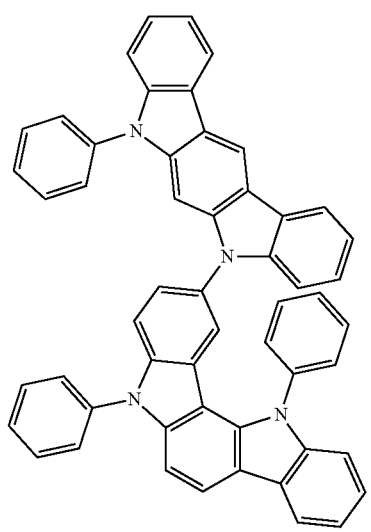
B-40
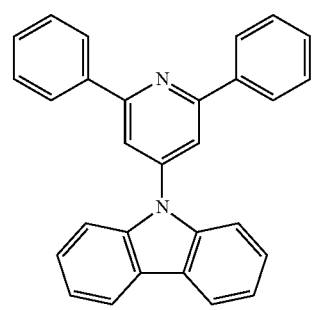
B-41
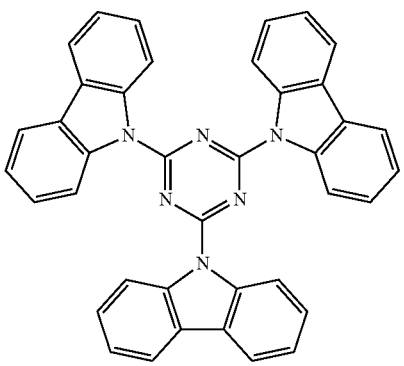
B-42
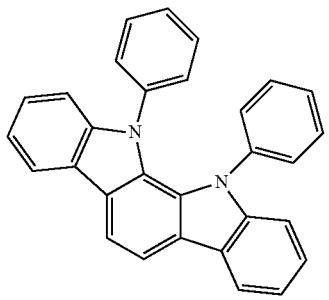
B-43
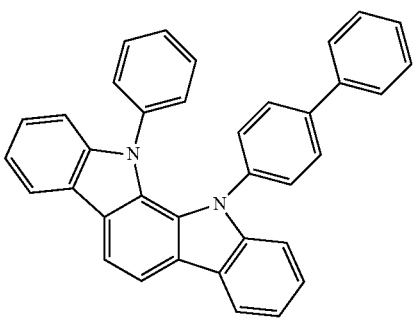
B-44
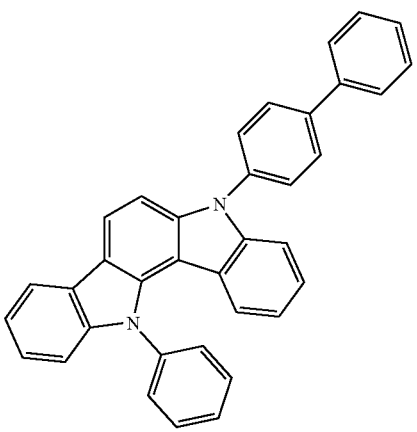

B-45
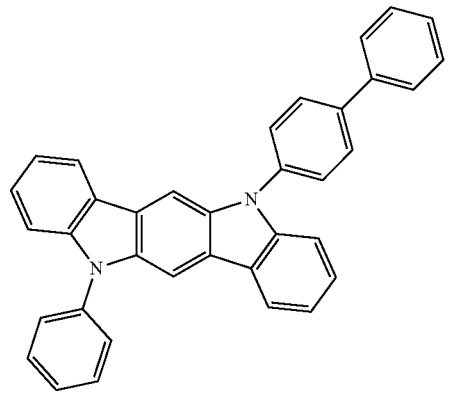
B-46
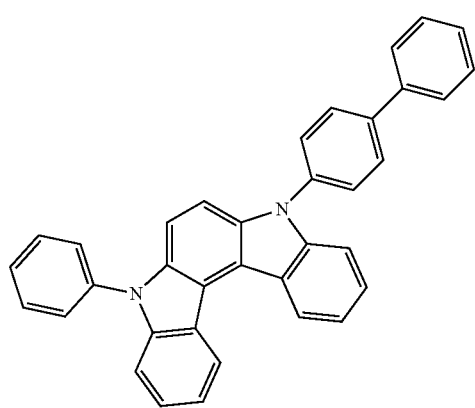
B-47
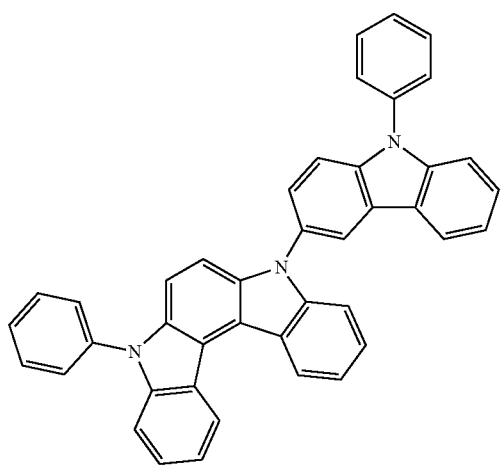
B-48
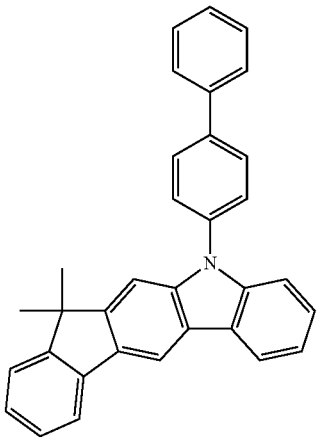
B-49
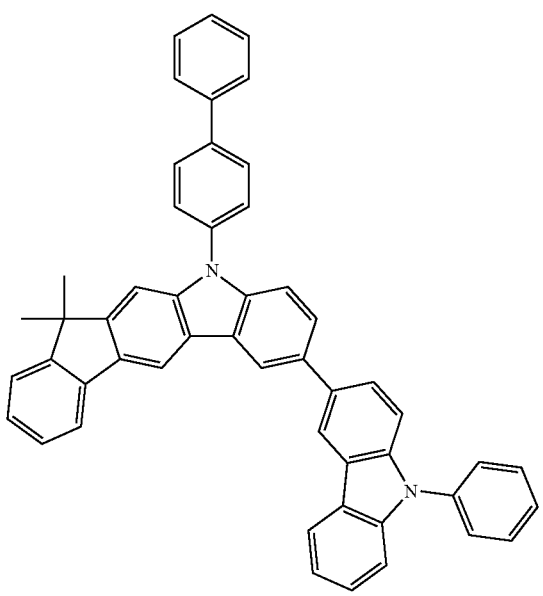
B-50
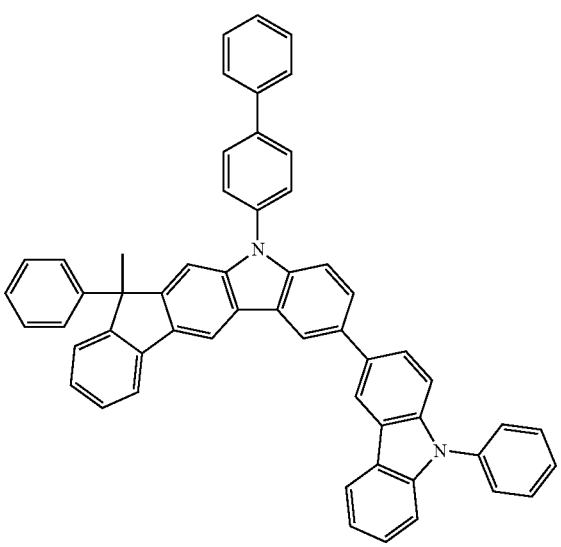

B-51
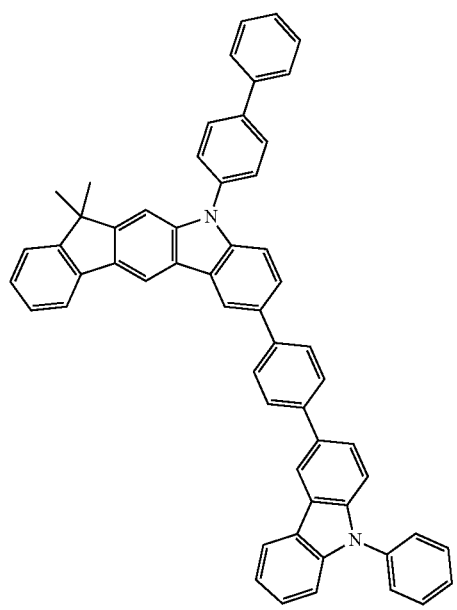
B-52
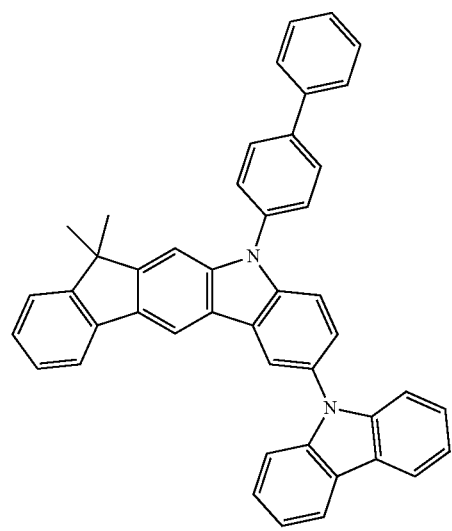
B-53
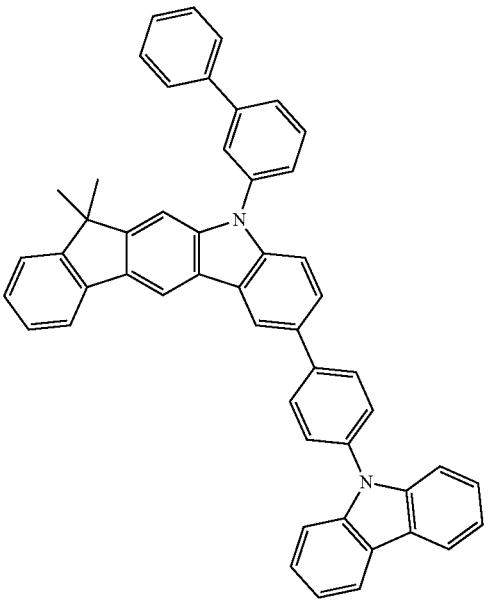
B-54
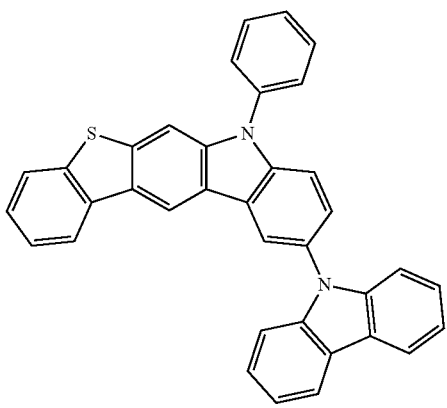
B-55
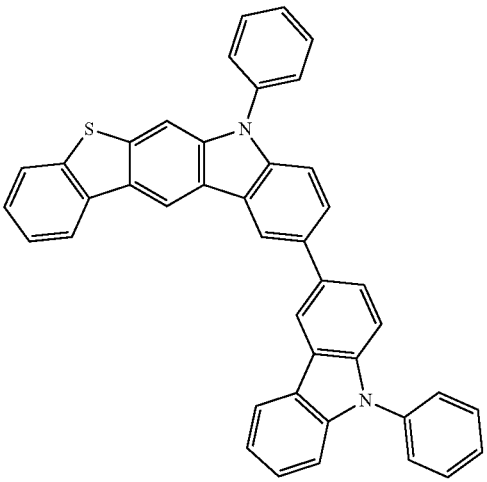

B-56
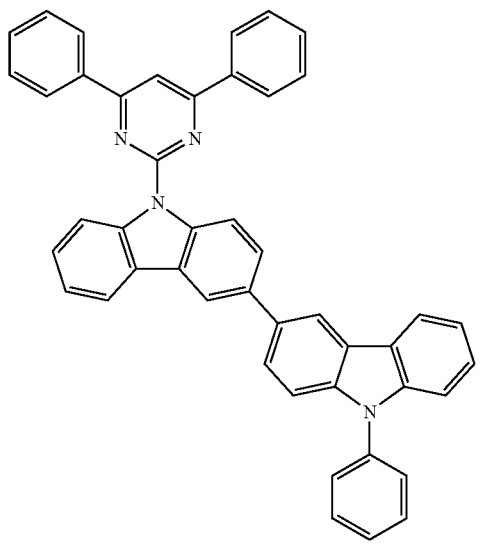
B-57
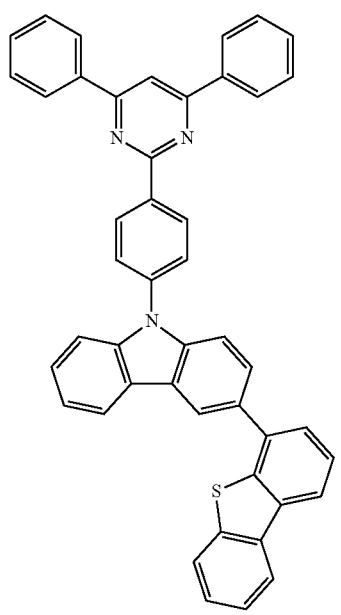
B-58
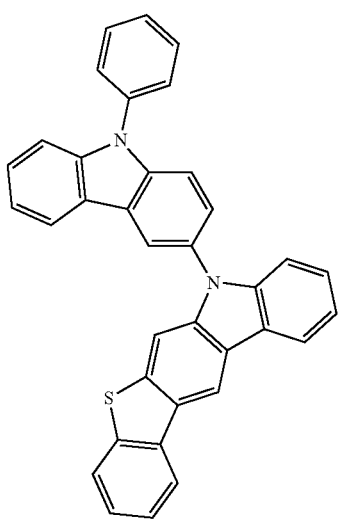
B-59
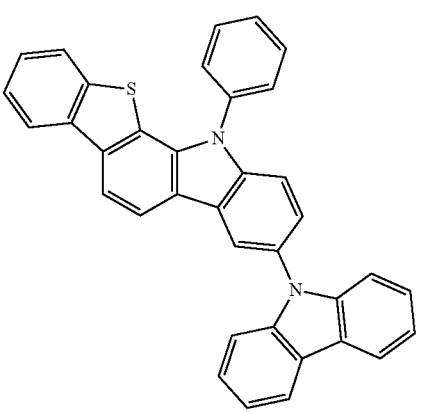
B-60
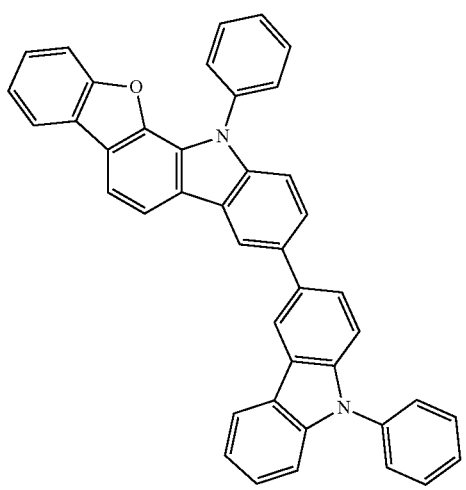
B-61
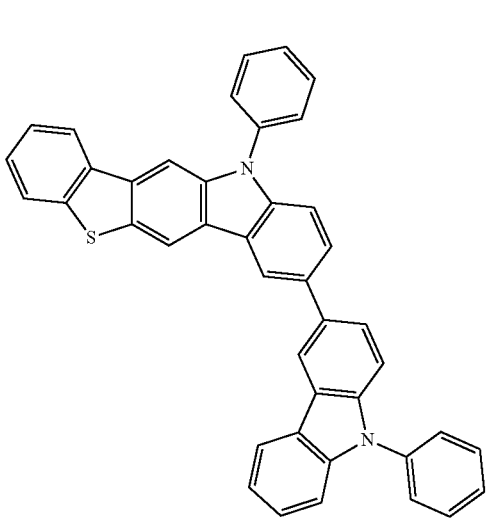

B-62
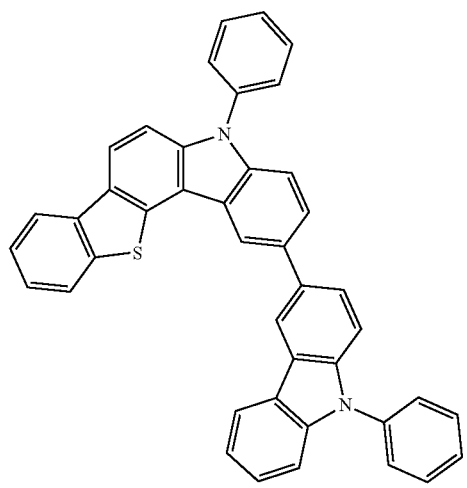
B-64
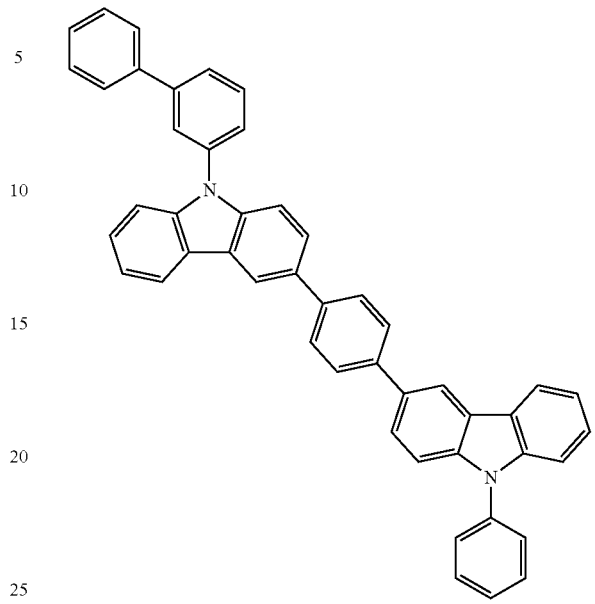
B-63
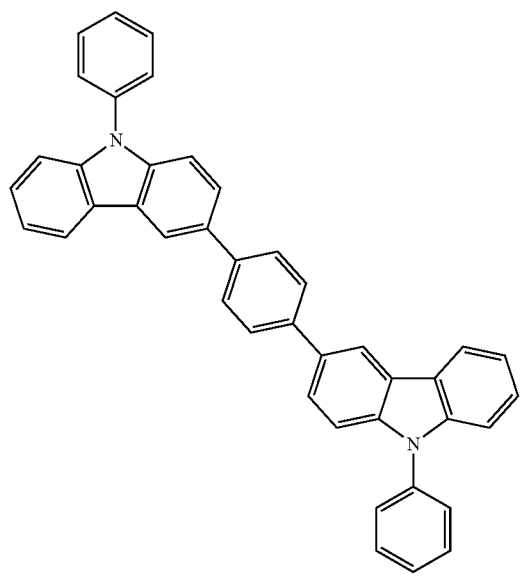
B-65
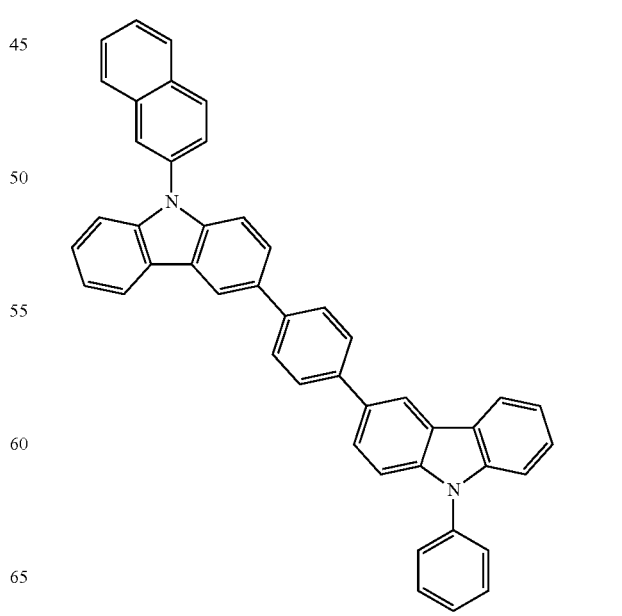

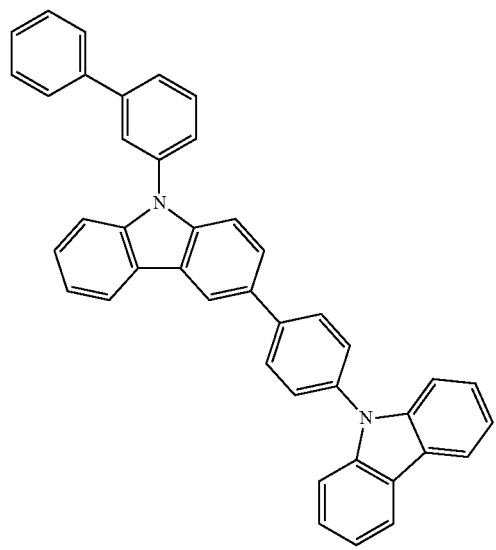
B-66
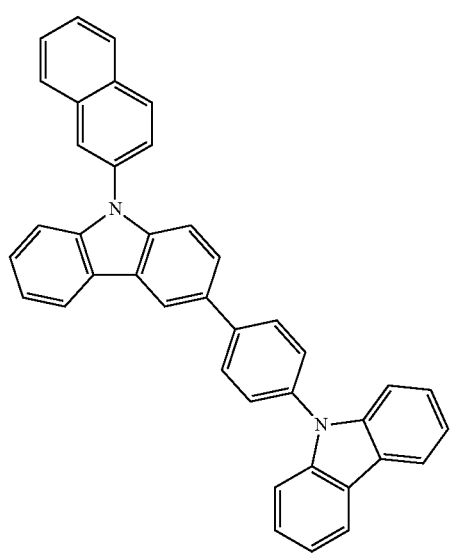
B-67
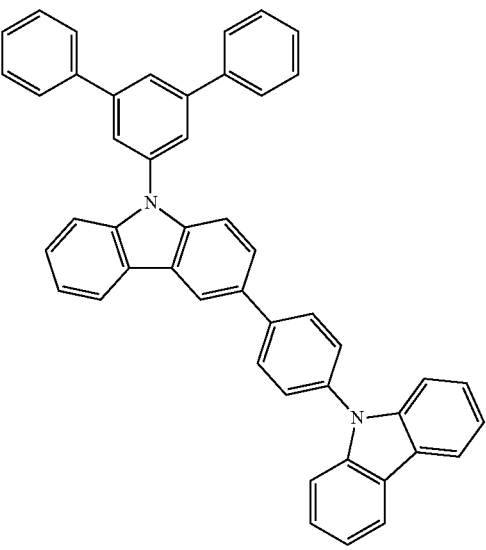
B-68
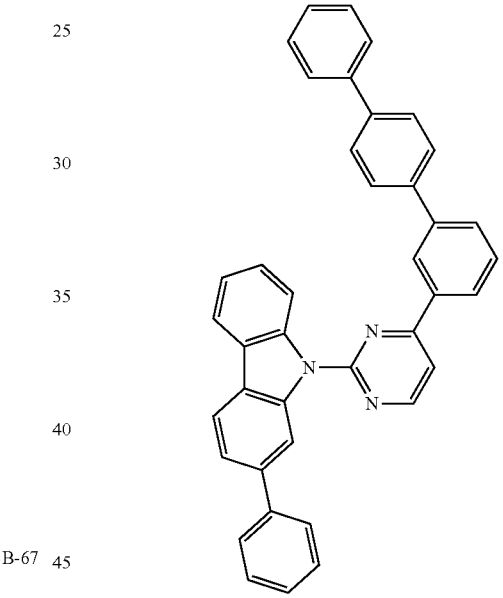
B-69
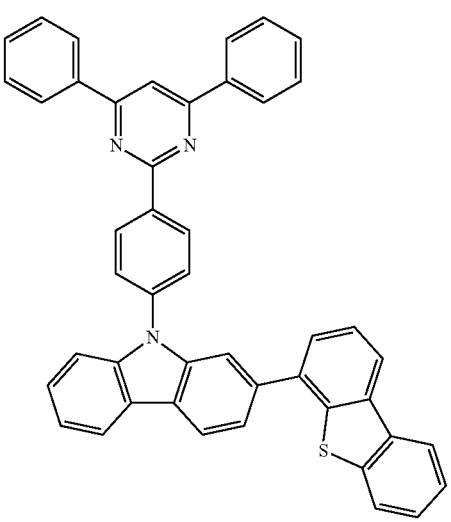
B-70

-continued
B-71
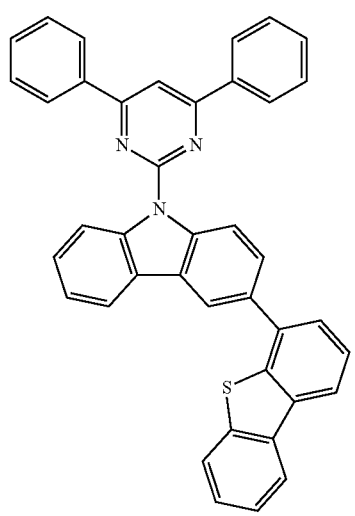
B-72
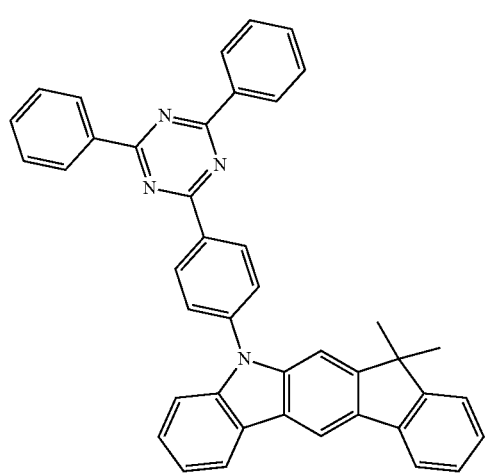
B-73
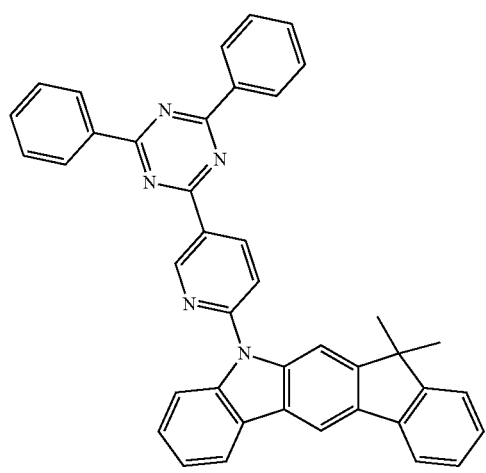
-continued
B-74
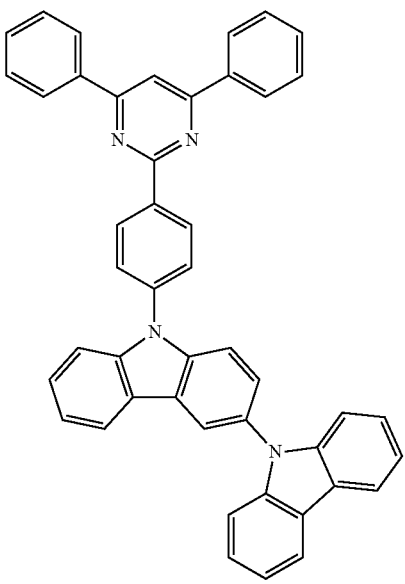
B-75
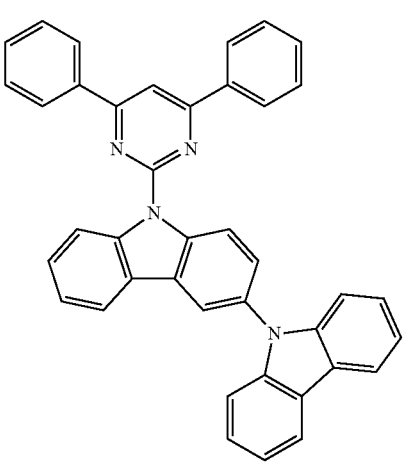
B-76
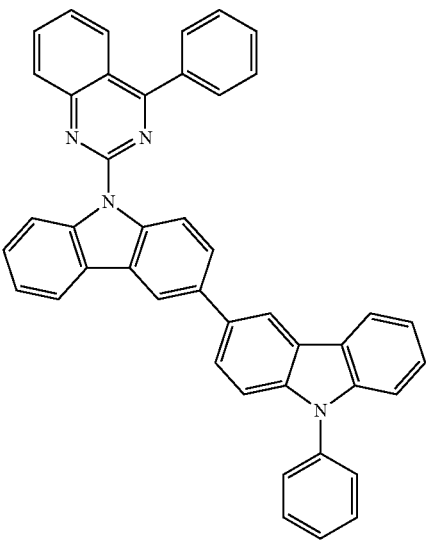

B-77
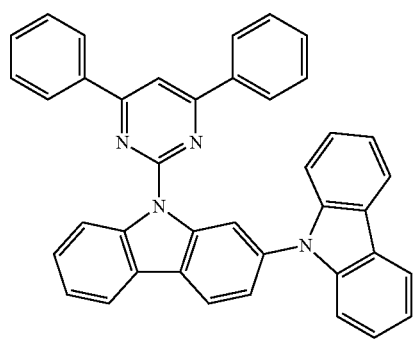
B-78
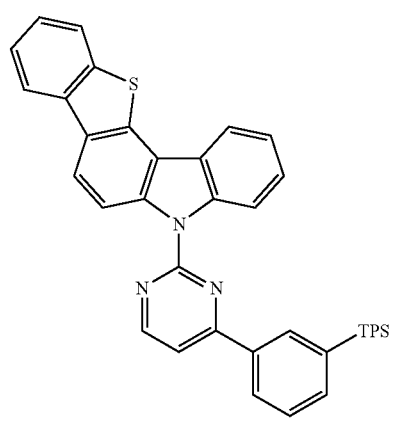
B-79
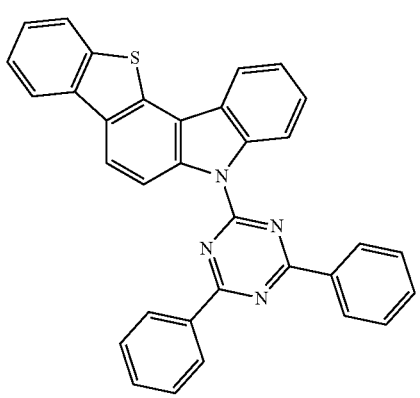
B-80
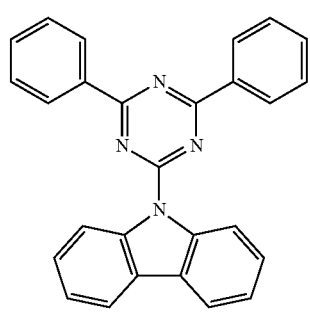
B-81
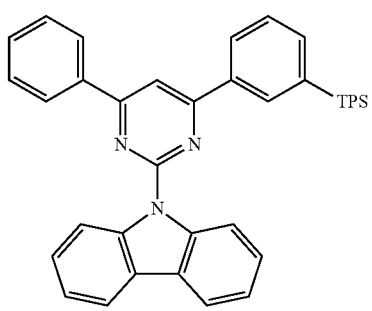
B-82
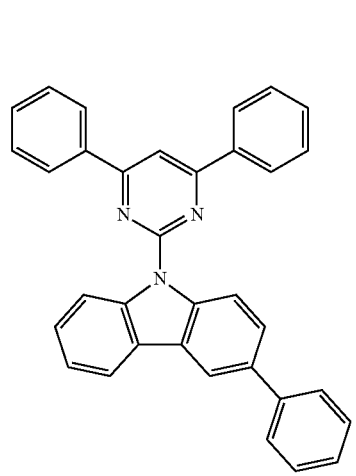
B-83
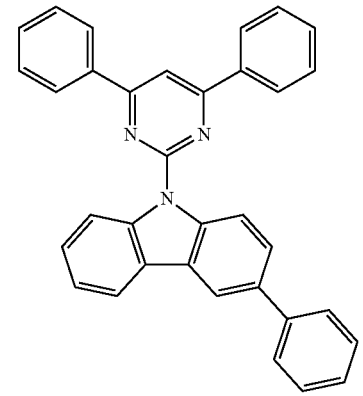
B-84
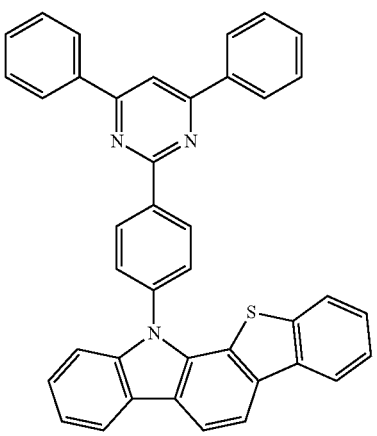

-continued
B-85
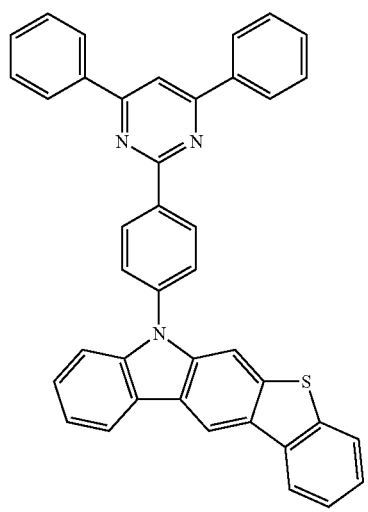
B-86
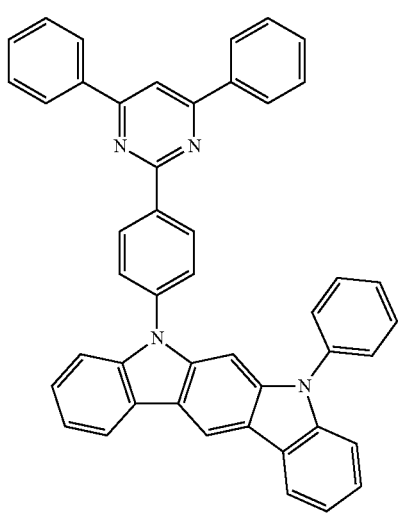
B-87
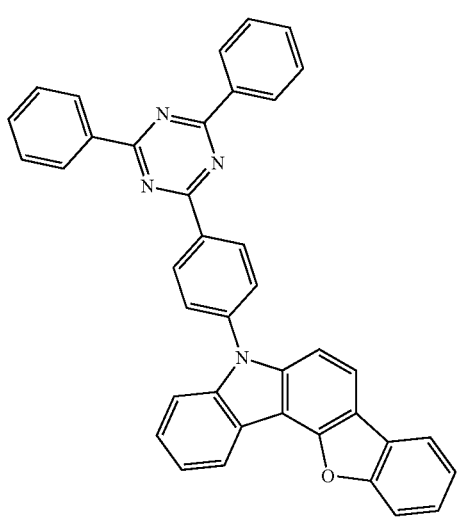
-continued
B-88
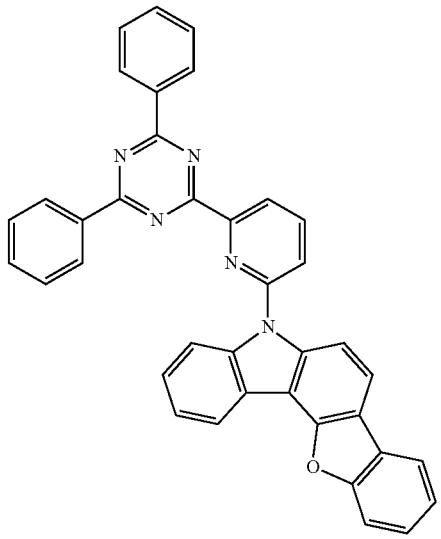
B-89
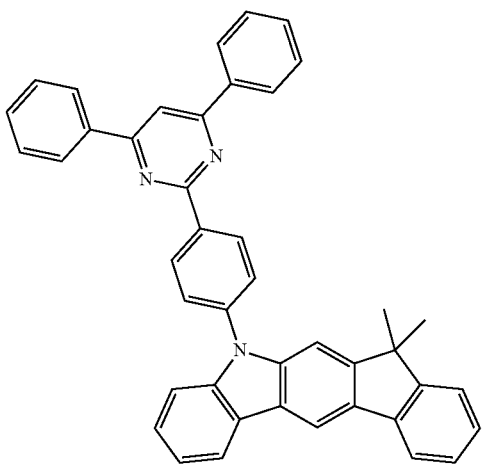
B-90
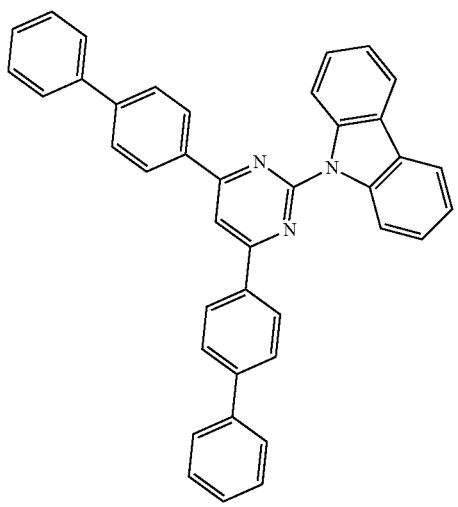

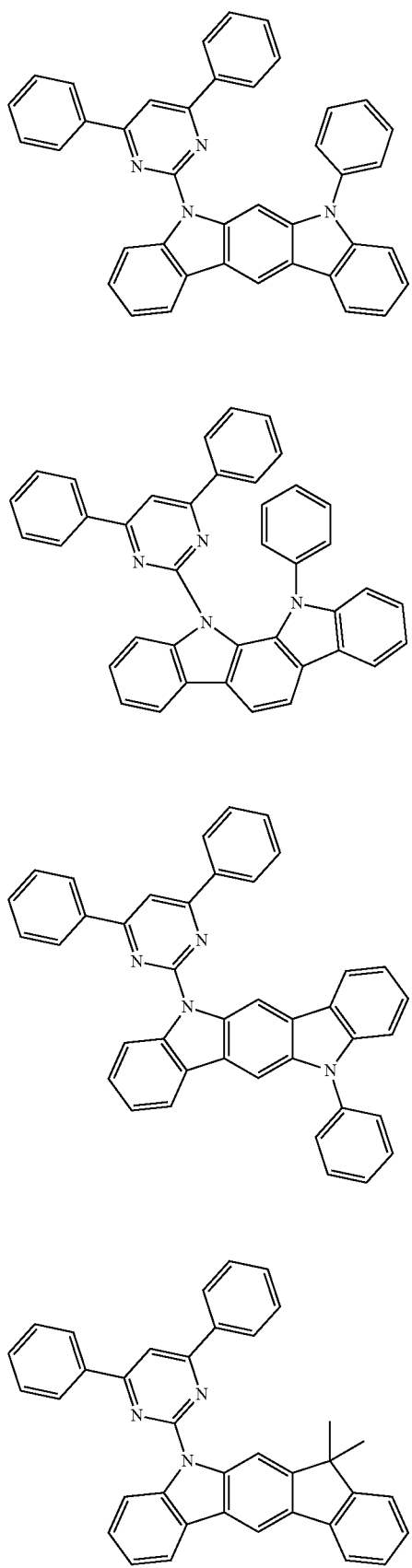
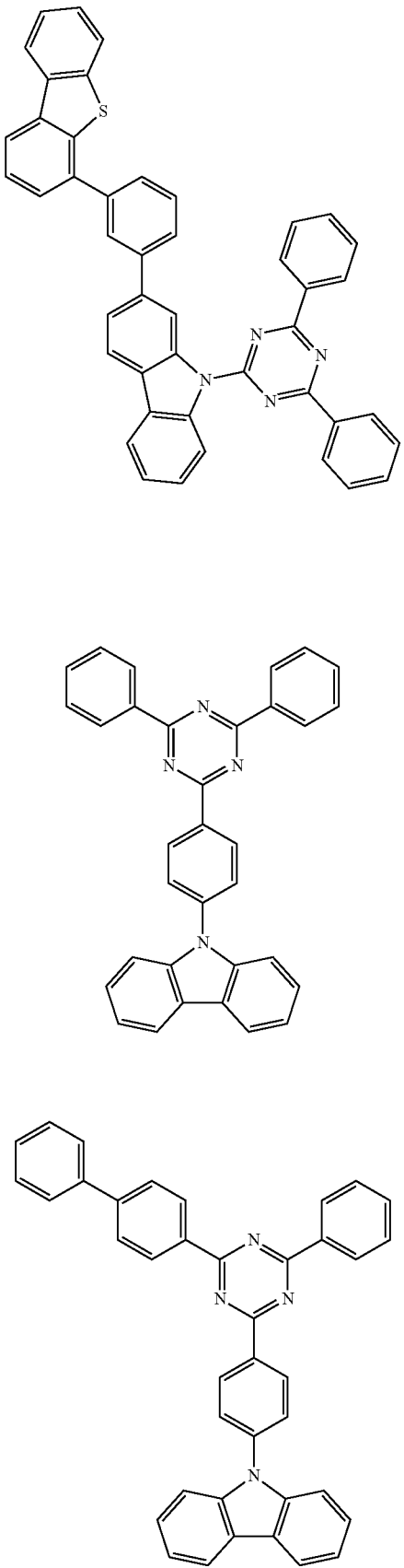

B-98
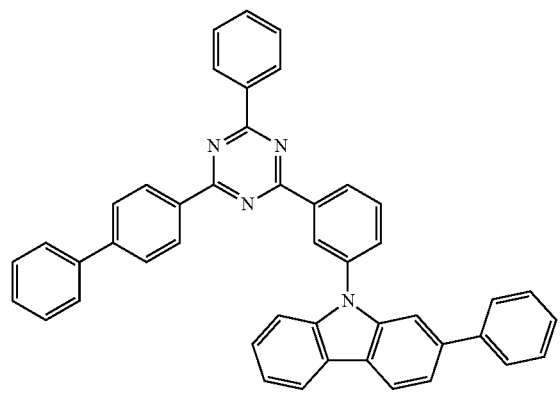
B-99
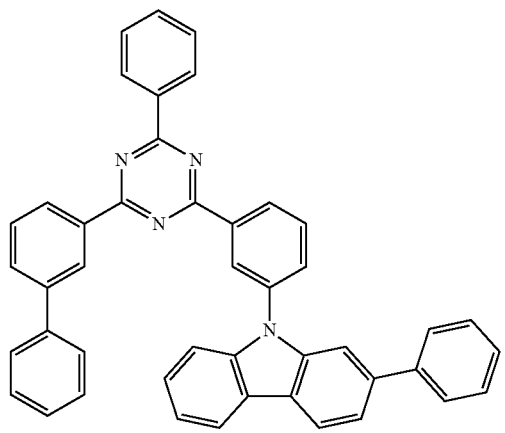
B-100
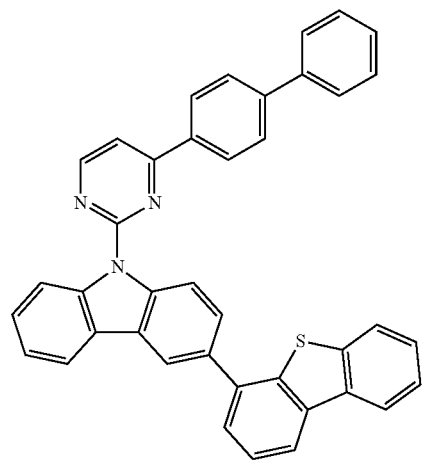
B-101
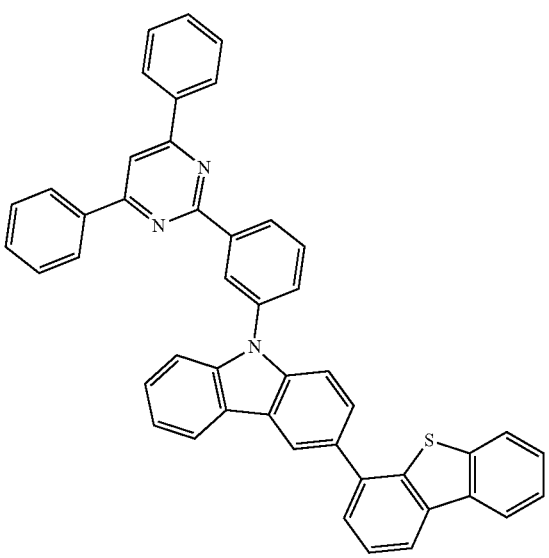
B-102
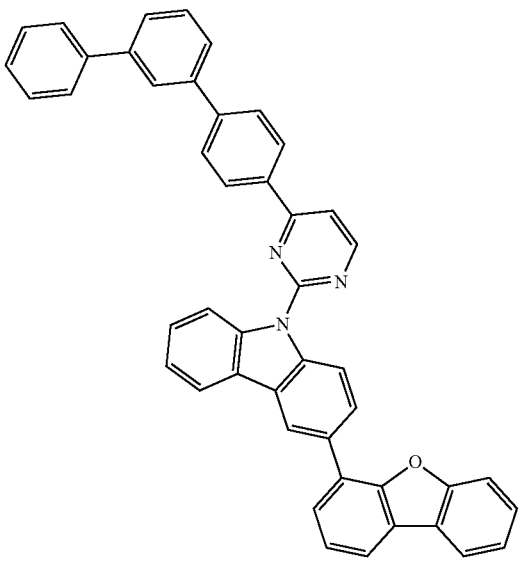

-continued
B-103
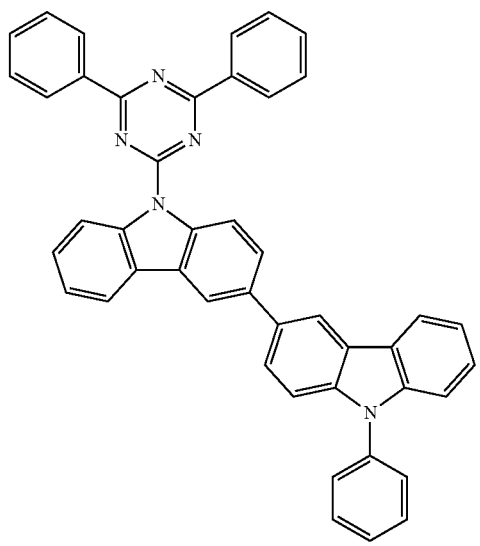
B-104
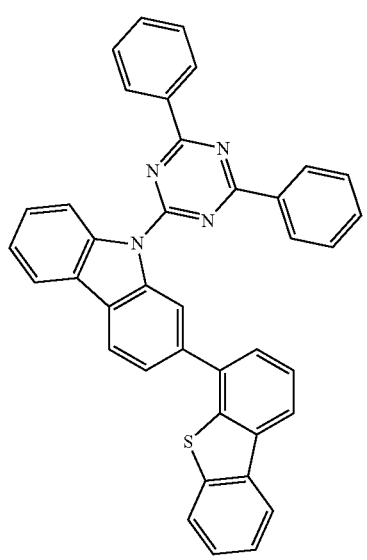
B-105
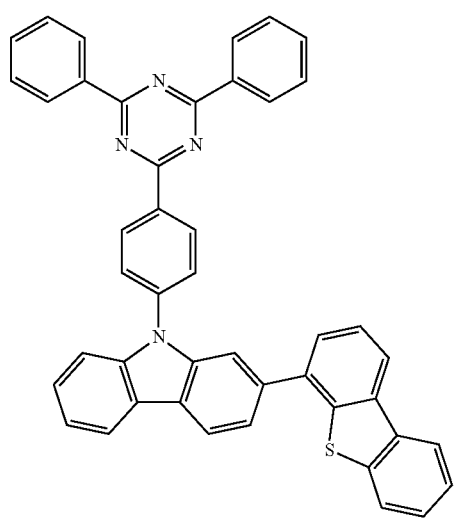
-continued
B-106
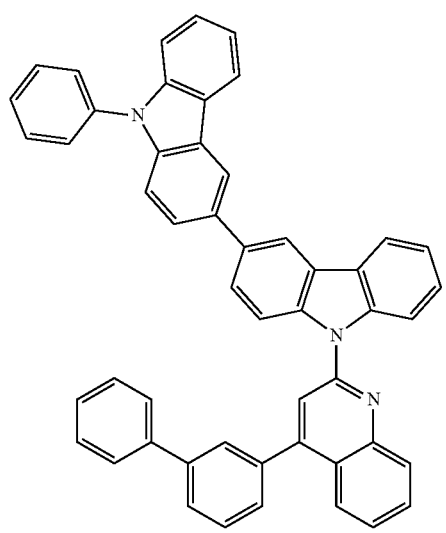
B-107
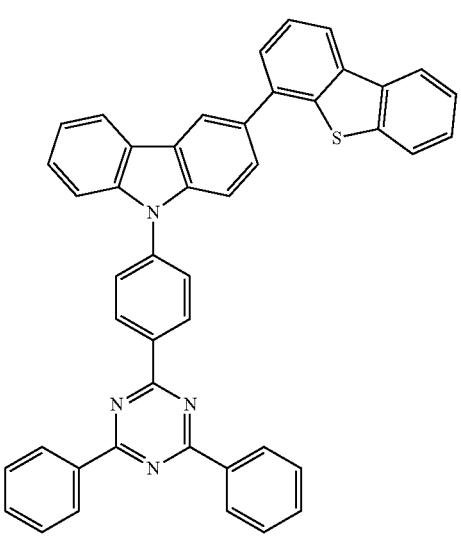
B-108
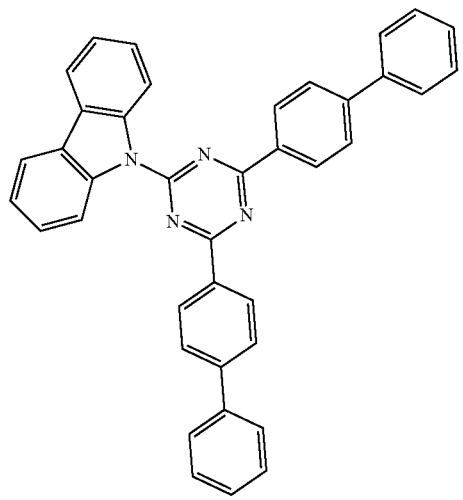

B-109
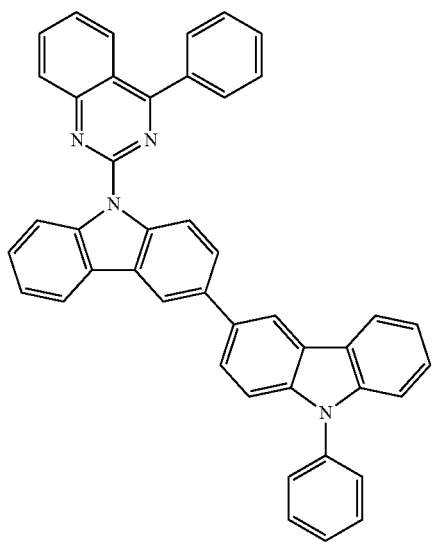
B-112
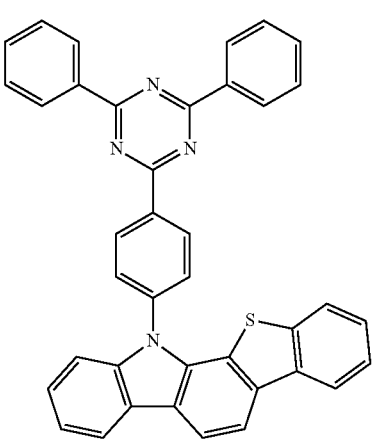
B-110
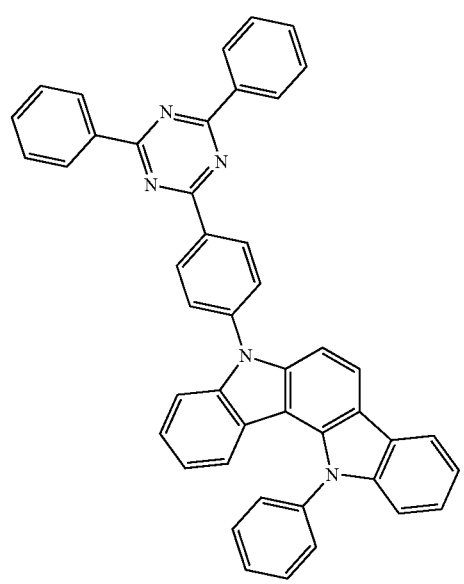
B-113
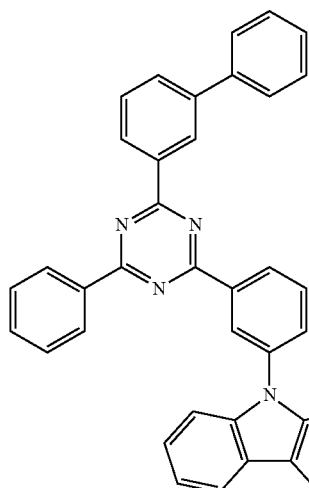
B-111
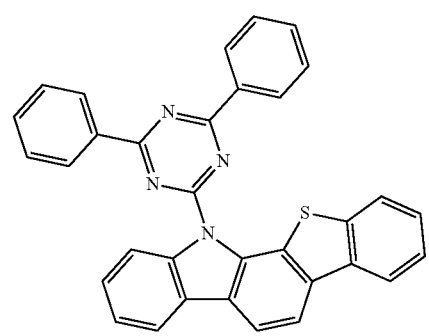
B-114
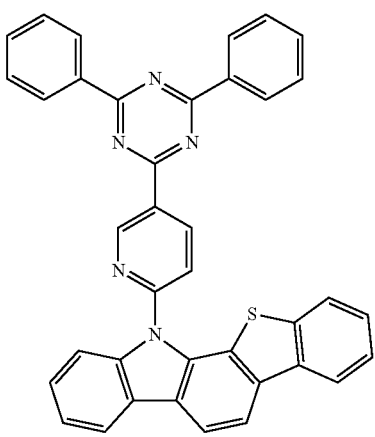

B-115
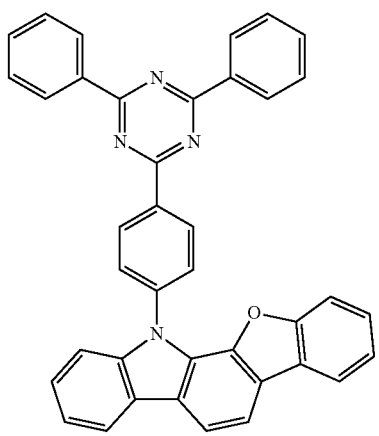
B-116
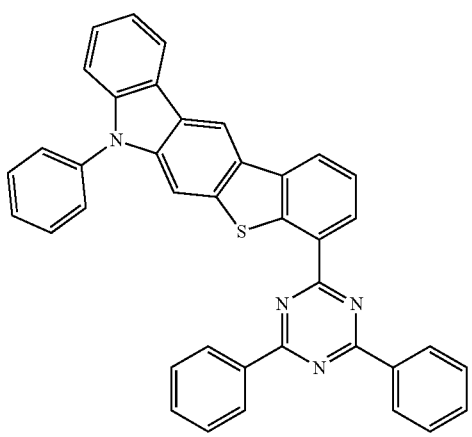
B-117
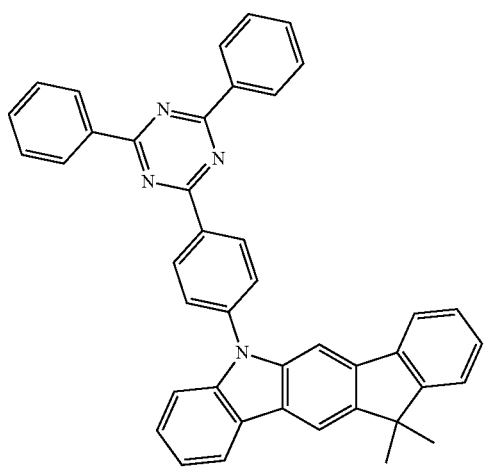
B-118
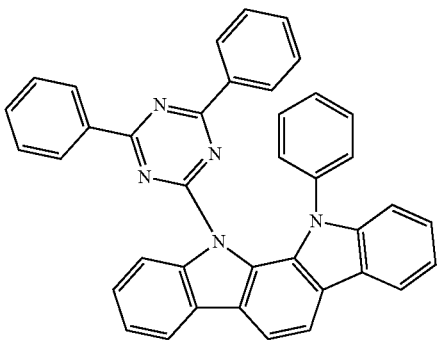
B-119
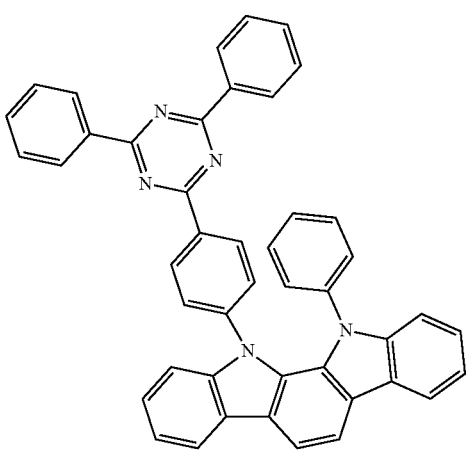
B-120
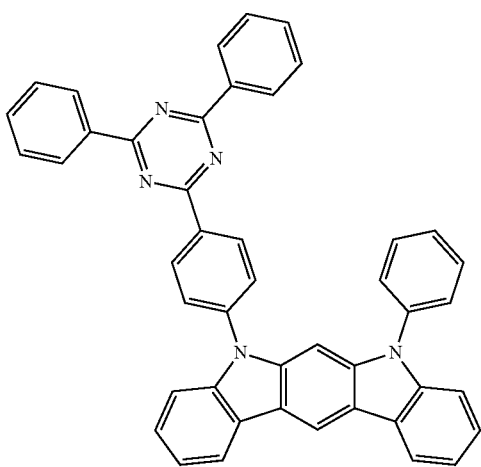

B-121
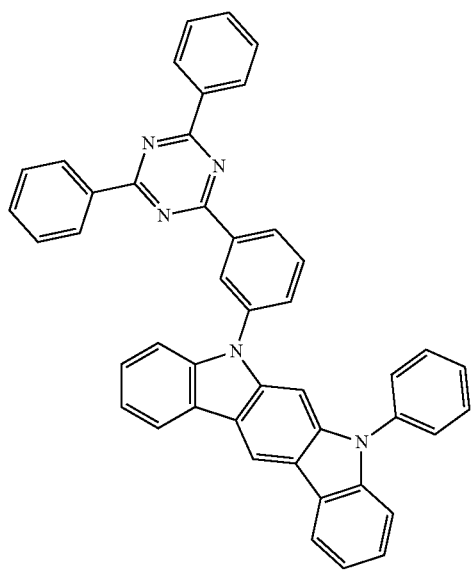
B-122
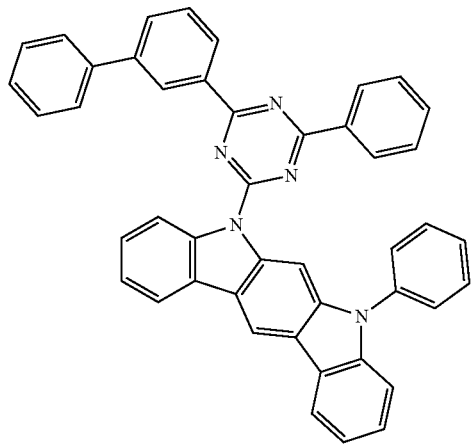
B-123
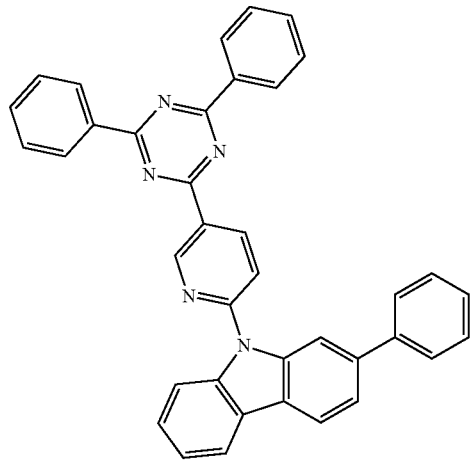
B-124
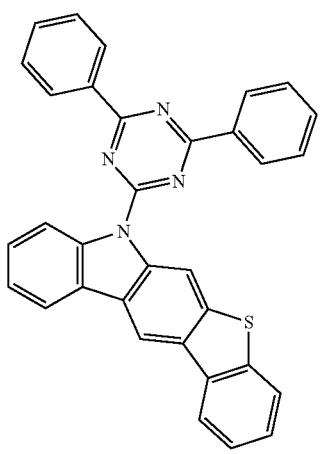
B-125
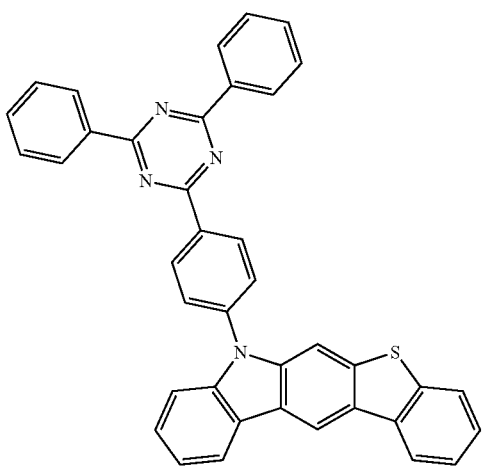
B-126
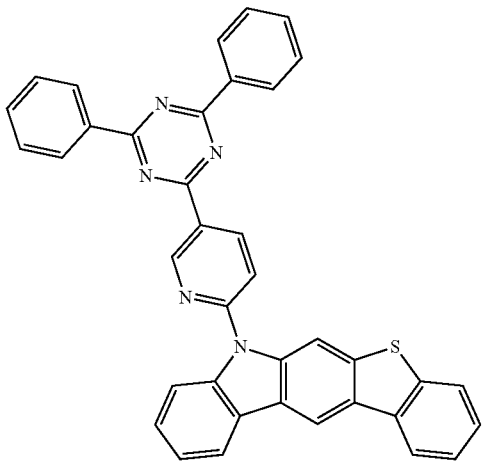

B-127
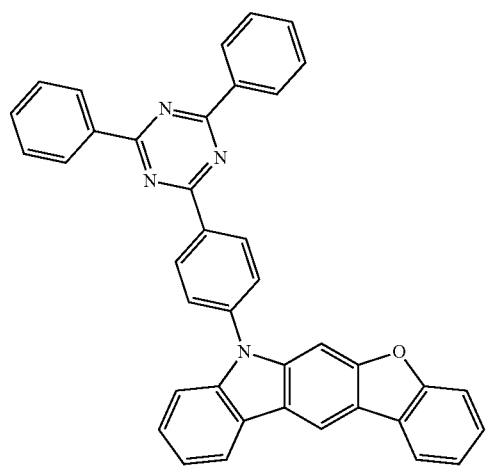
B-128
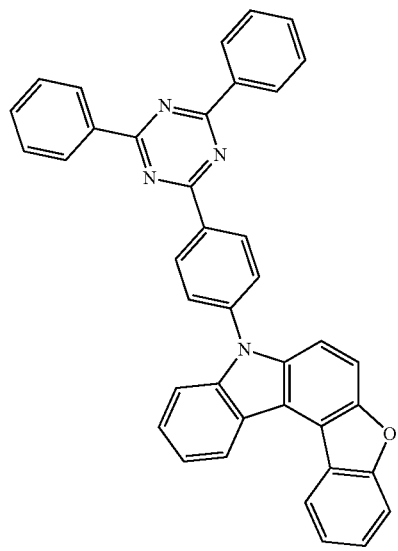
B-129
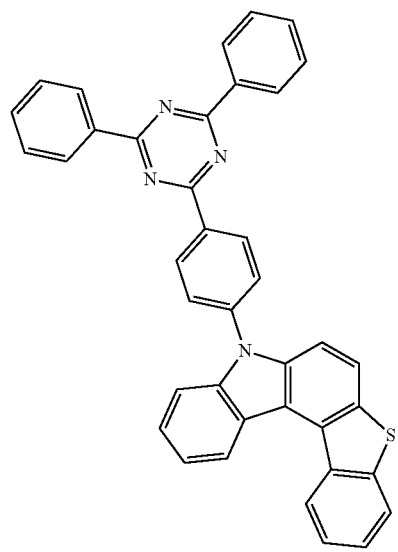
B-130
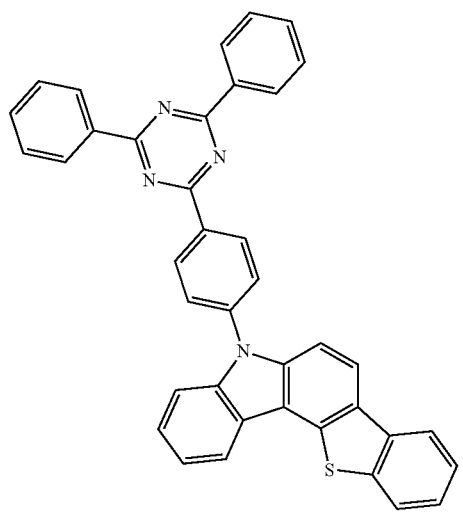
B-131
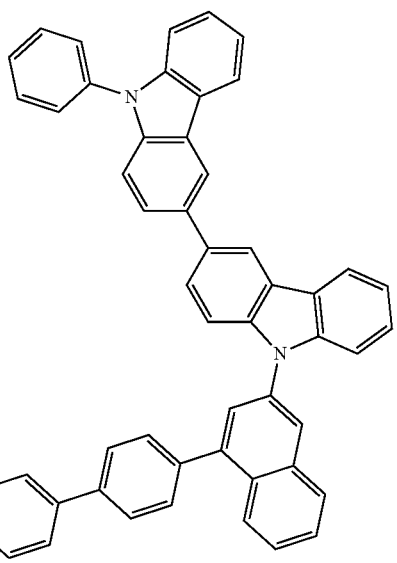
B-132
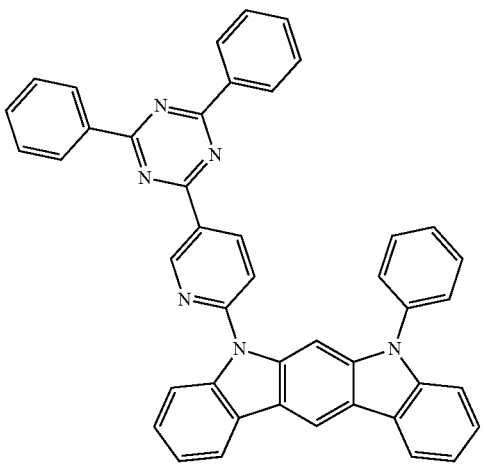

B-133
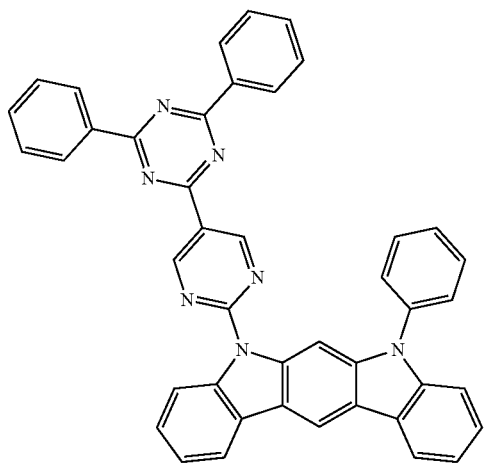
B-134
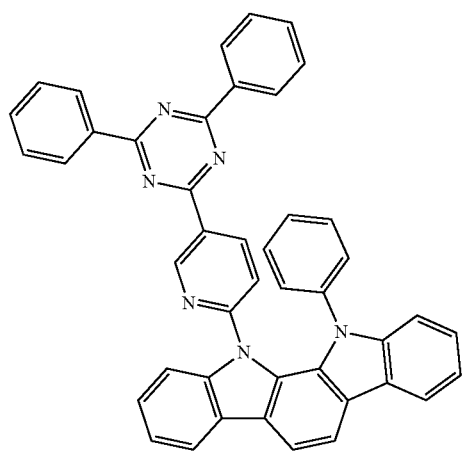
B-135
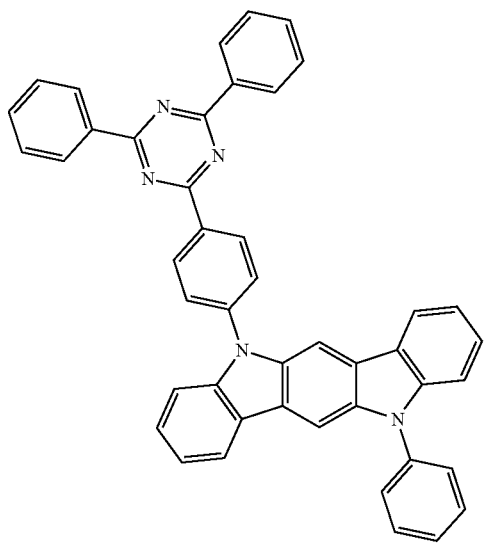
B-136
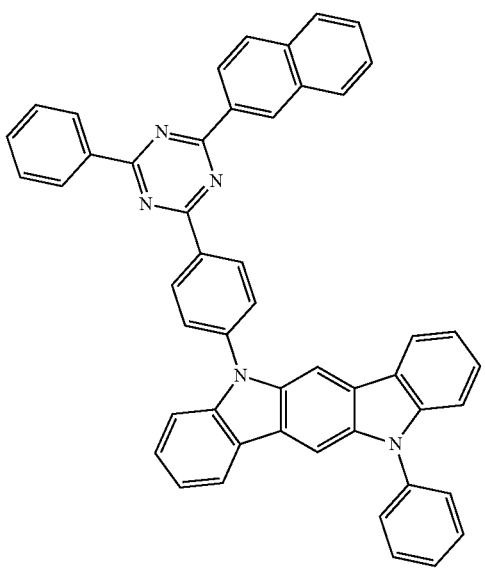
B-137
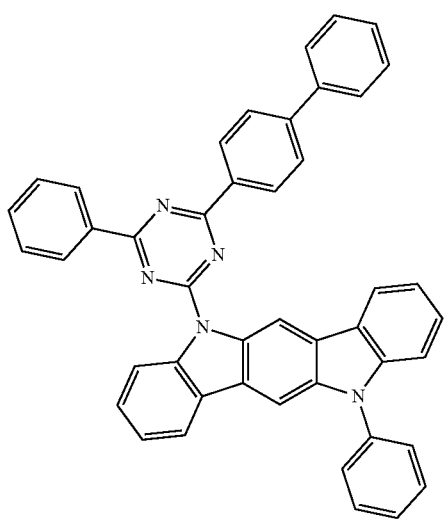
B-138
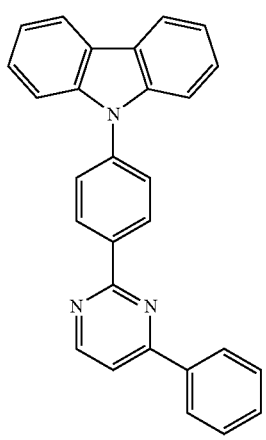

B-139
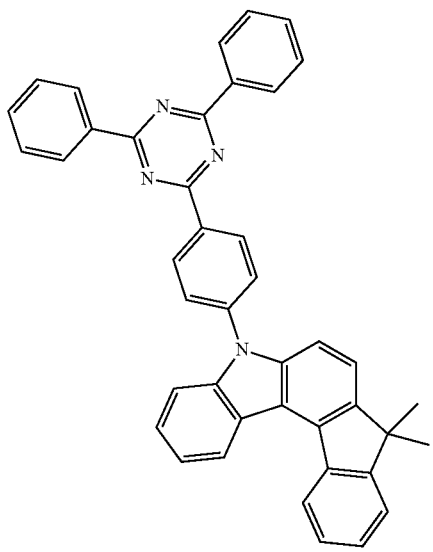
B-140
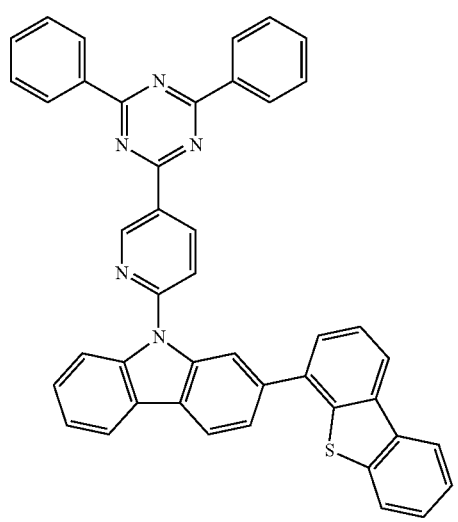
B-141
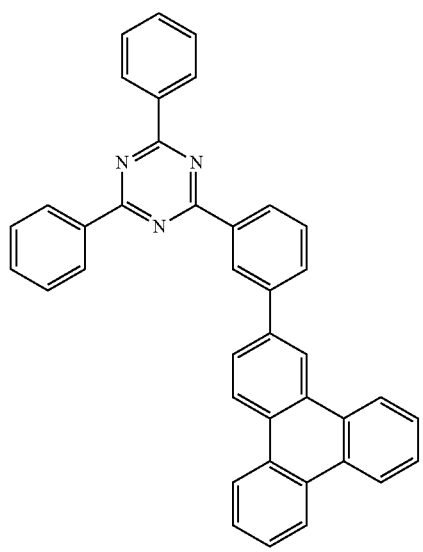
B-142
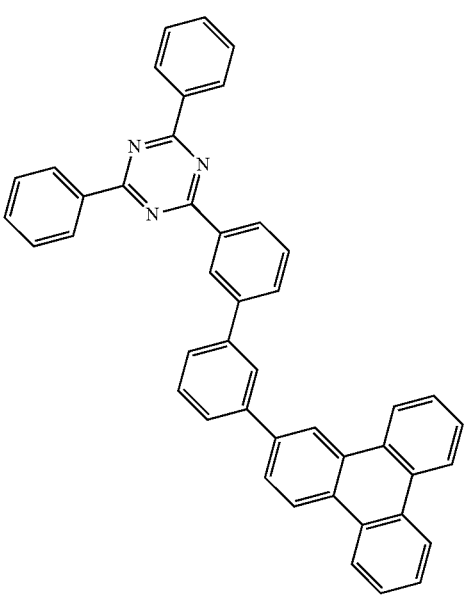
B-143
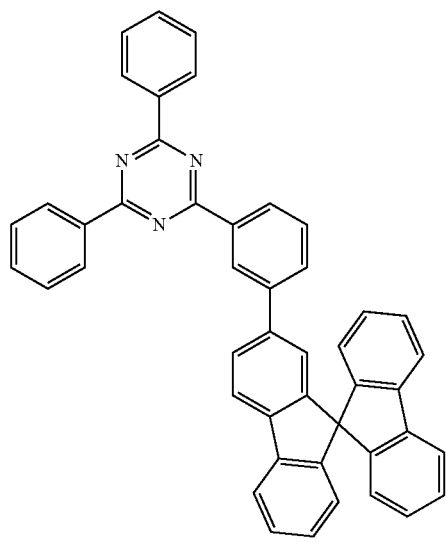
B-144
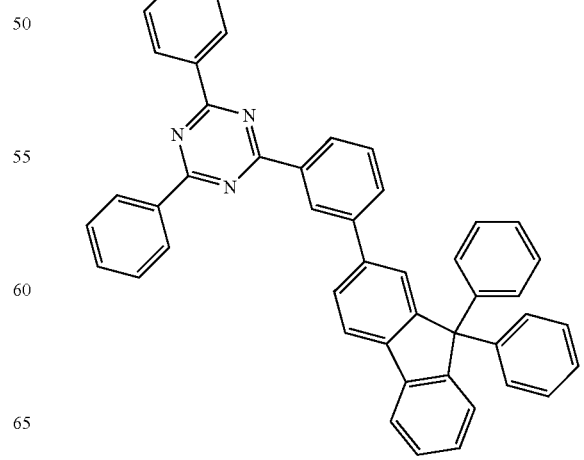

B-145
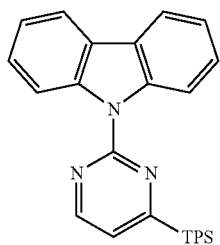
B-146
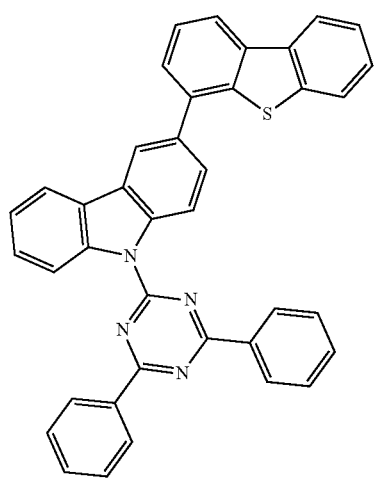
B-147
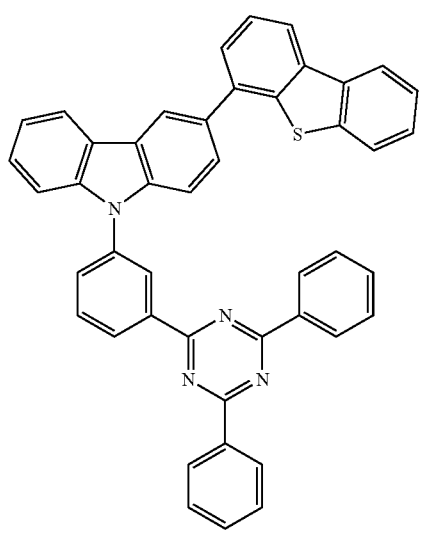
B-148
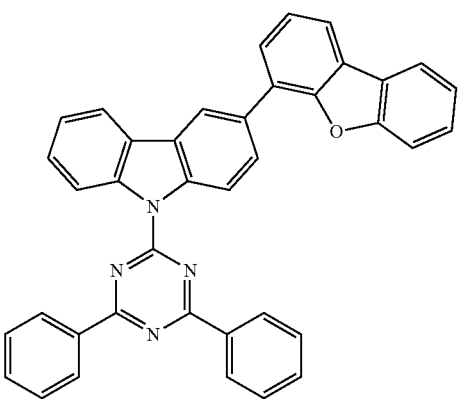
B-149
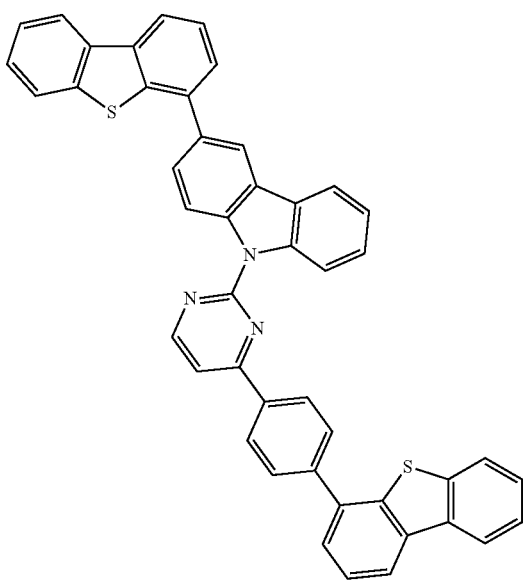
B-150
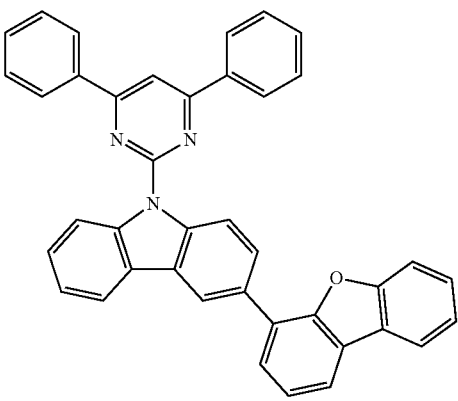

B-151
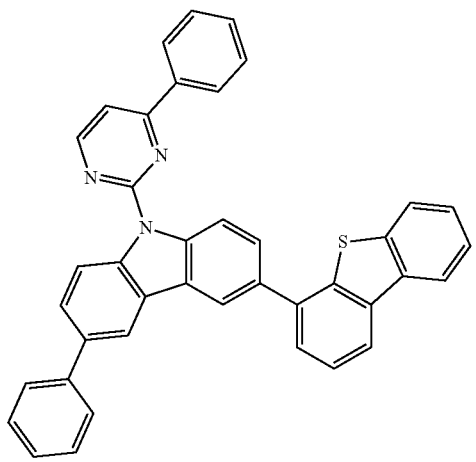
B-152
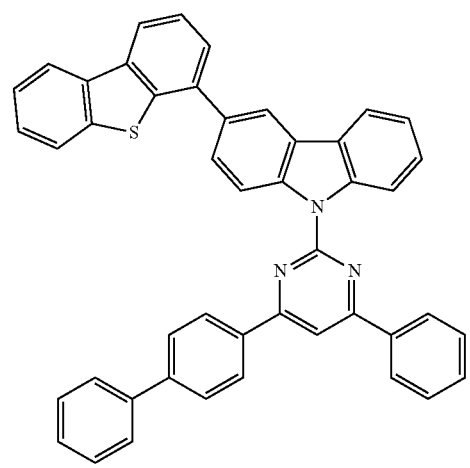
B-153
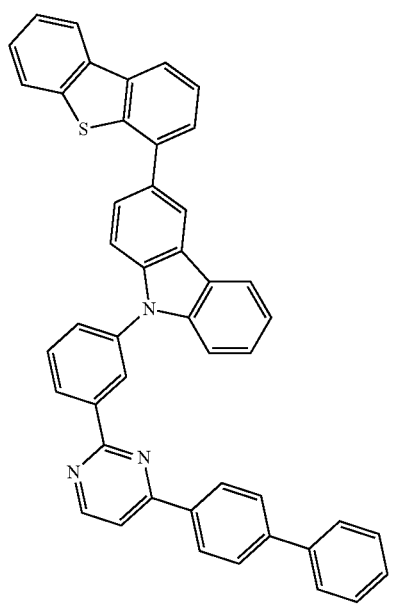
B-154
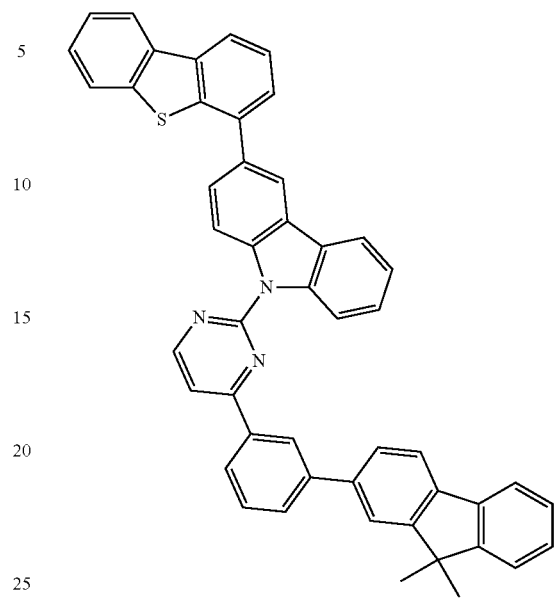
B-155
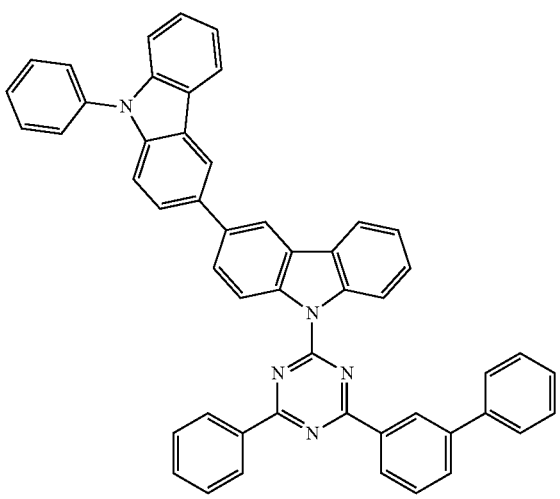

B-156
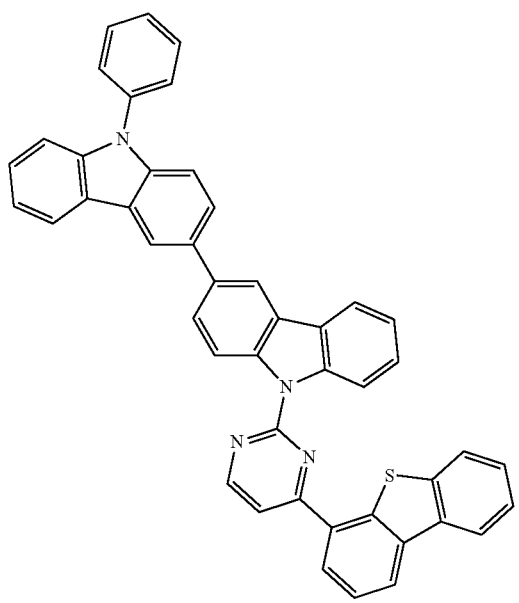
B-158
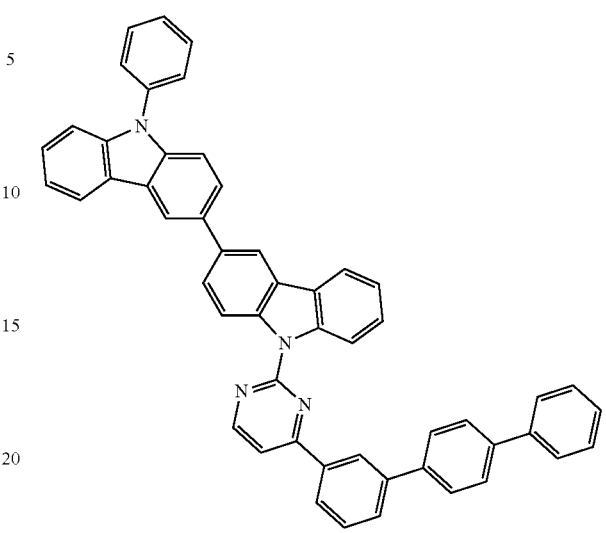
B-157
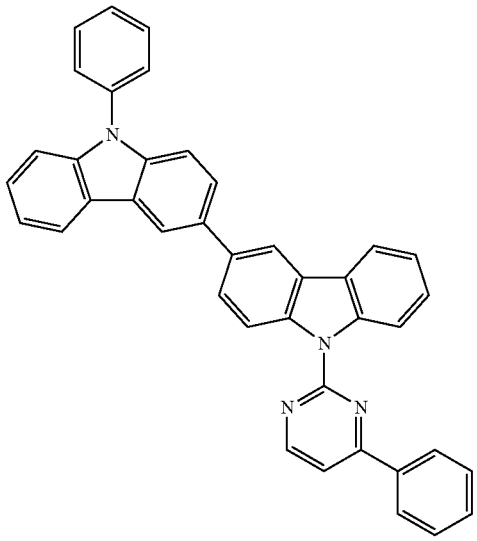
B-159
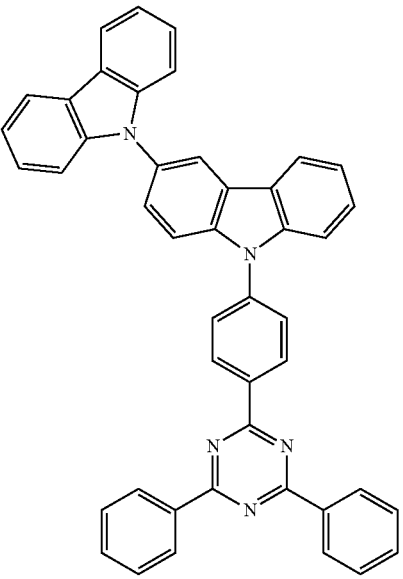

B-160
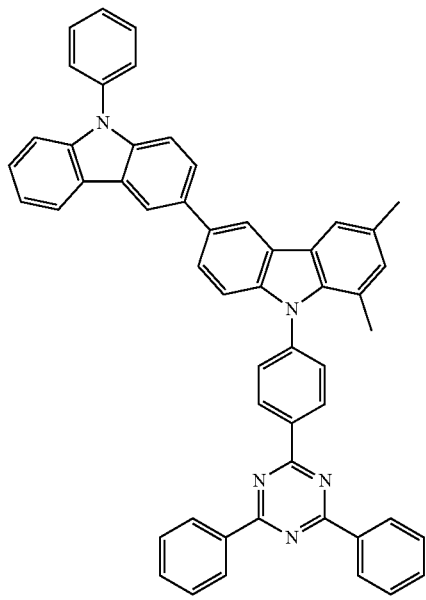
B-161
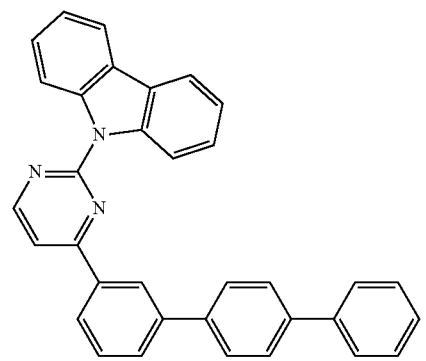
B-162
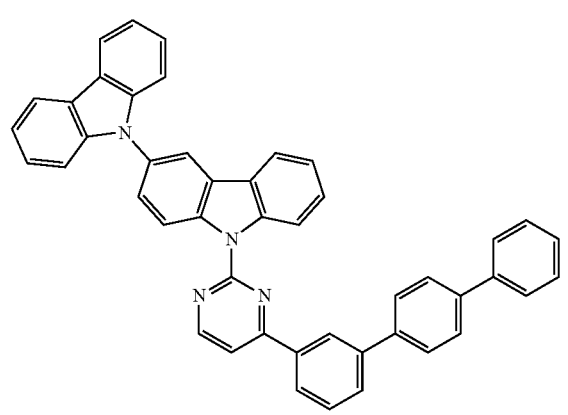
B-163
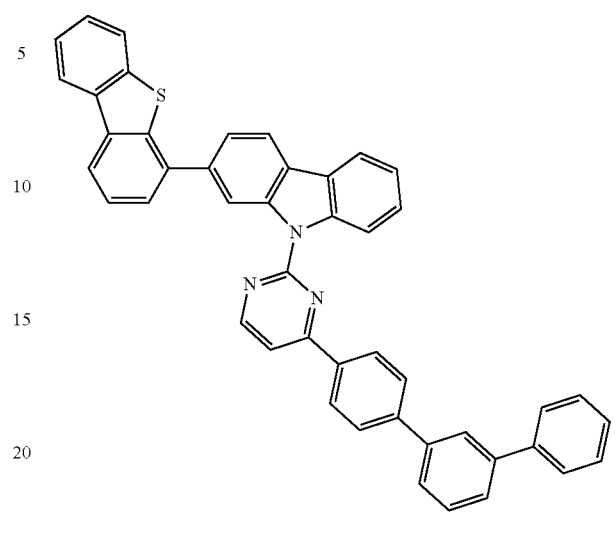
B-164
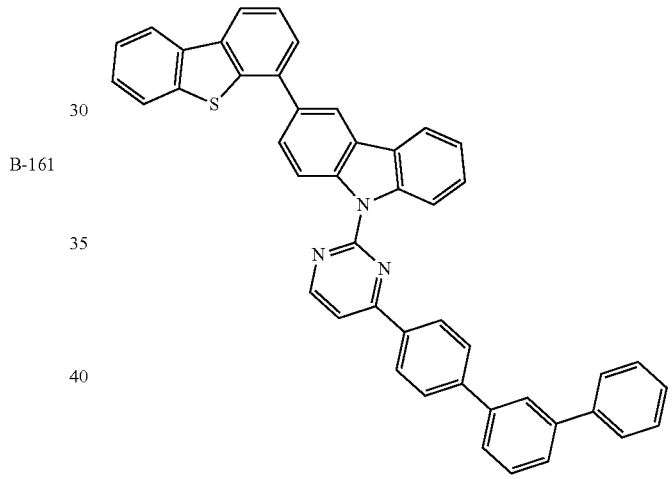
B-165
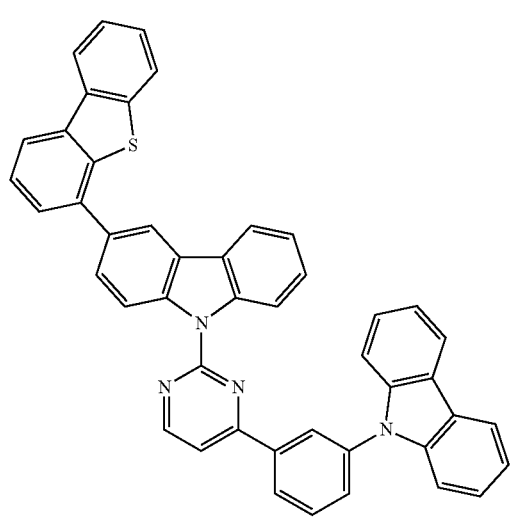

B-166
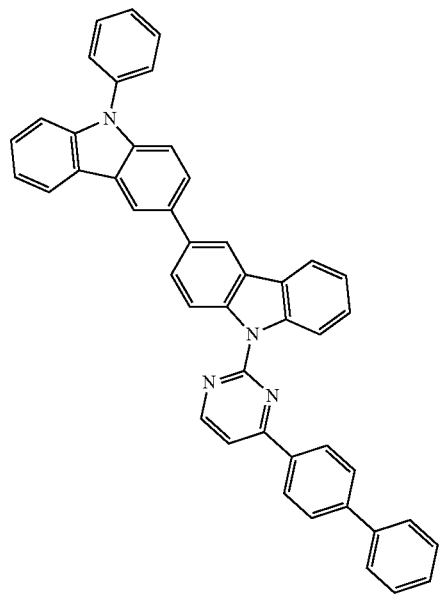
B-167
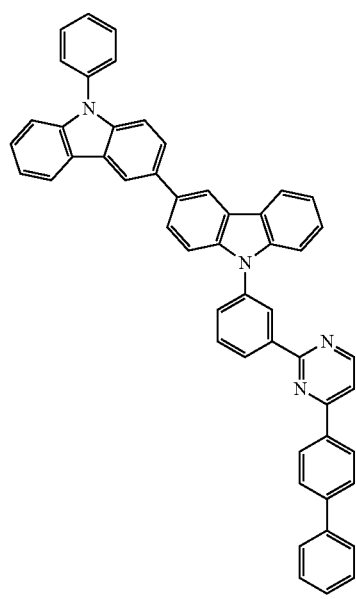
B-168
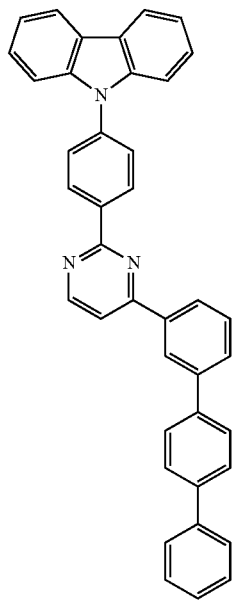
B-169
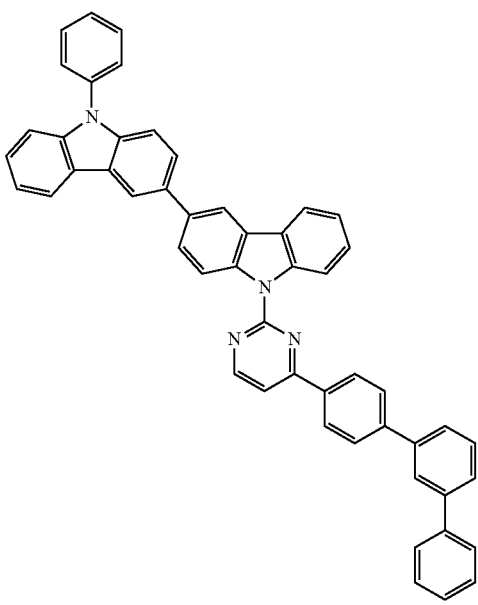

B-170
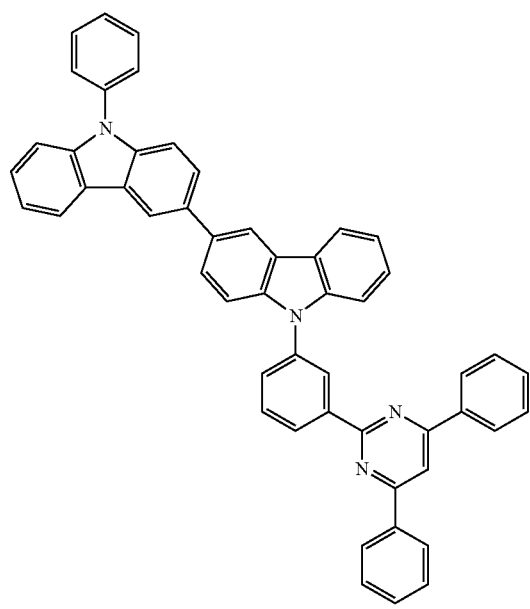
B-172
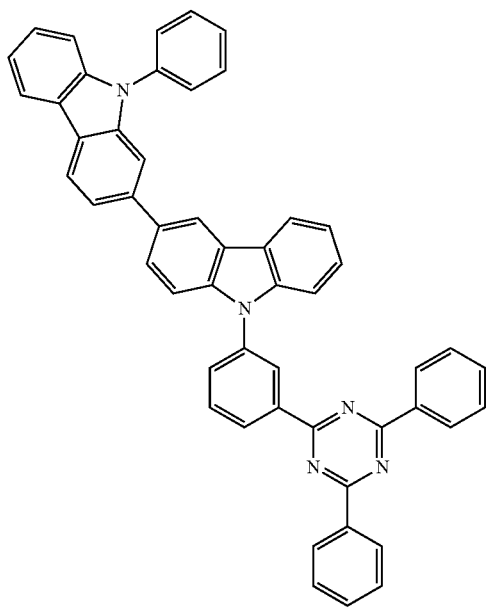
B-171
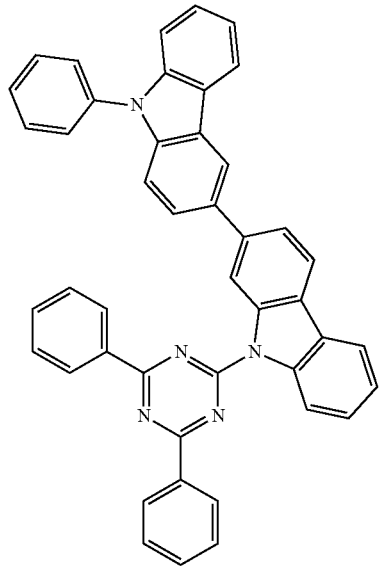
B-173
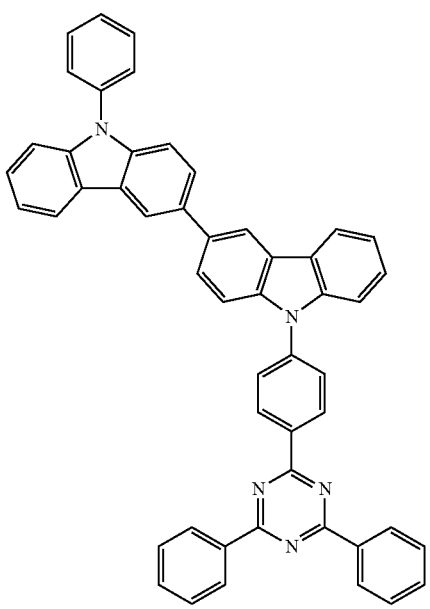

B-174
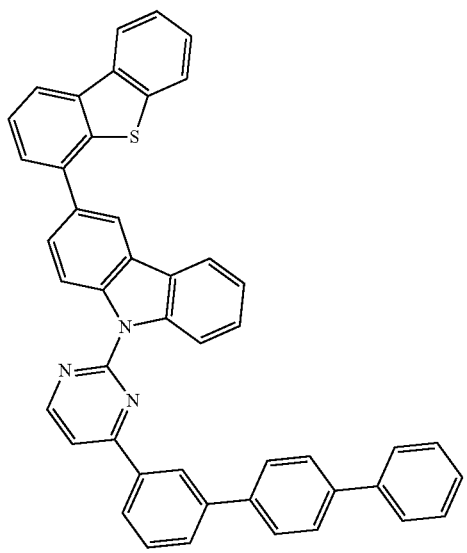
B-175
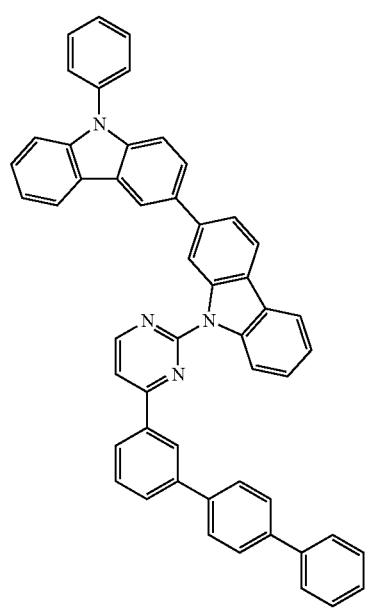
B-176
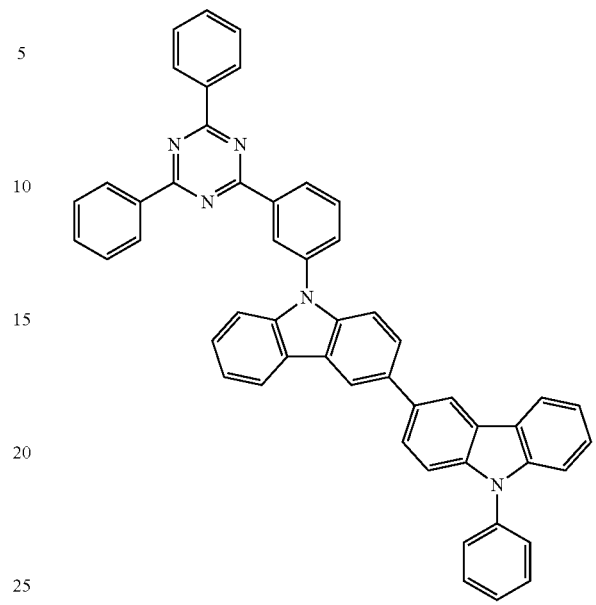
B-177
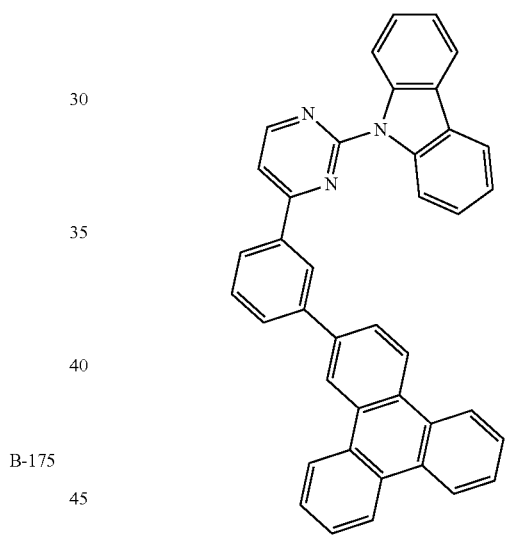
B-178
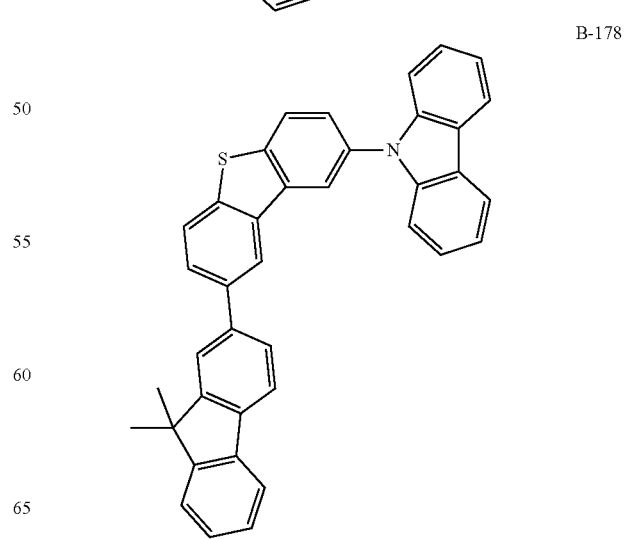

B-179
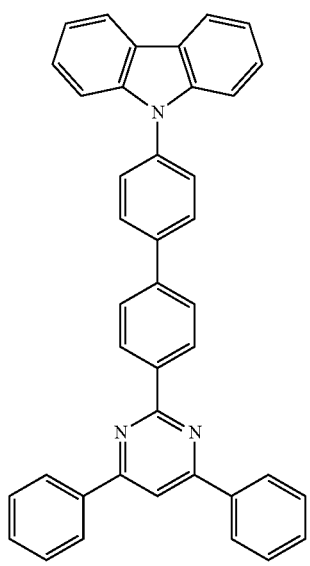
B-181
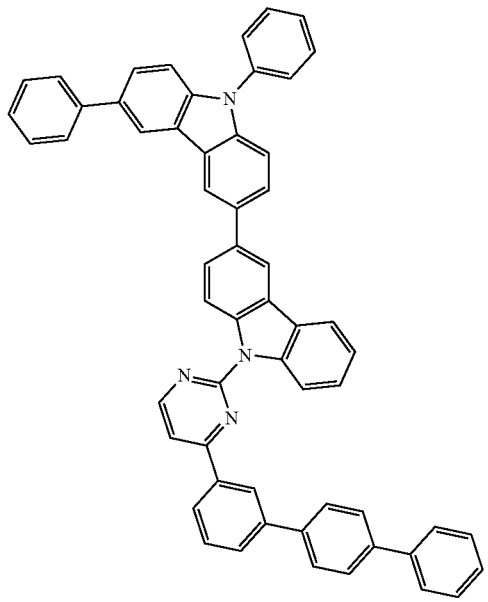
B-180
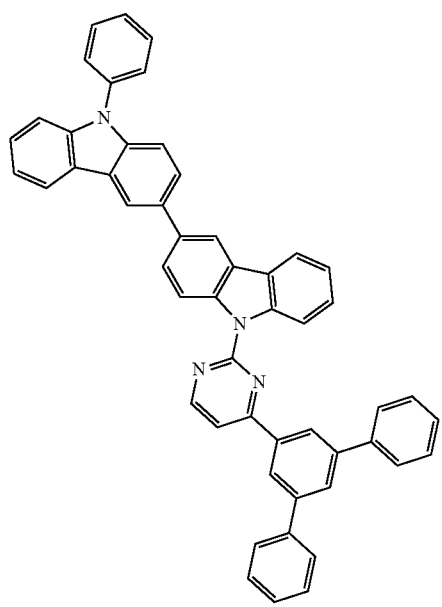
B-182
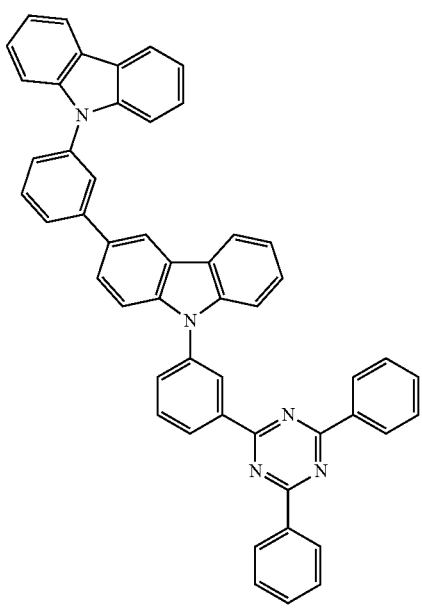

B-183
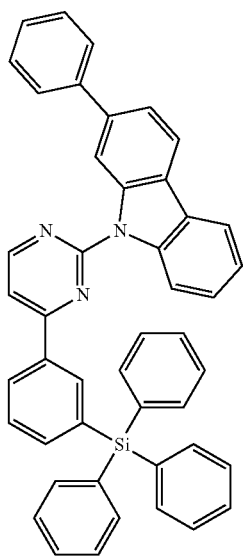
B-185
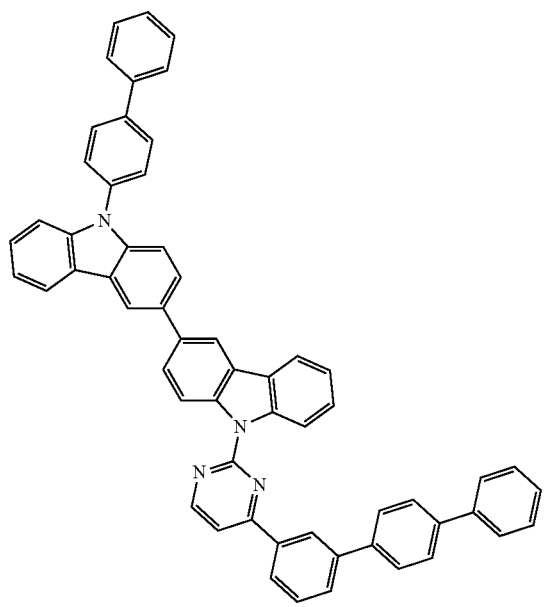
B-186
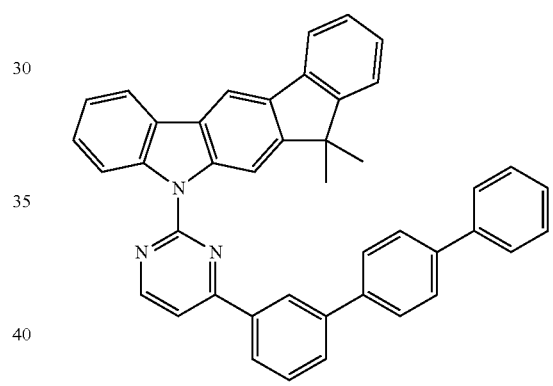
B-184
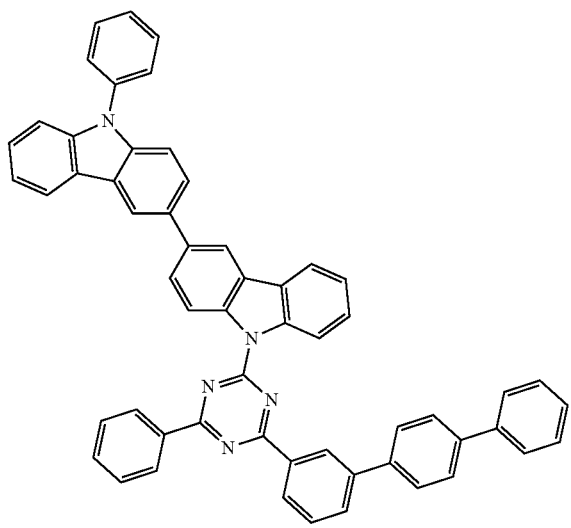
B-187
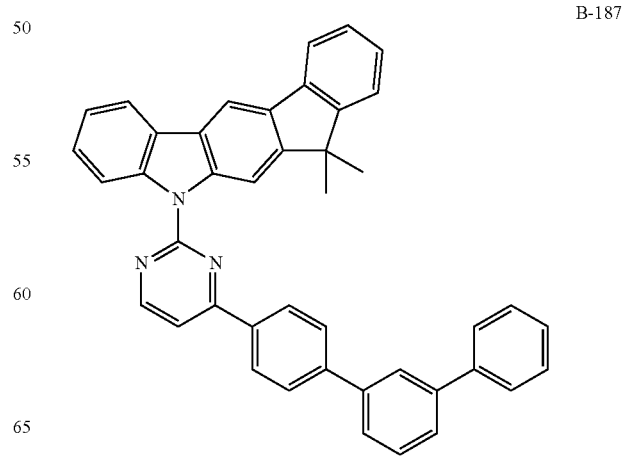

B-188
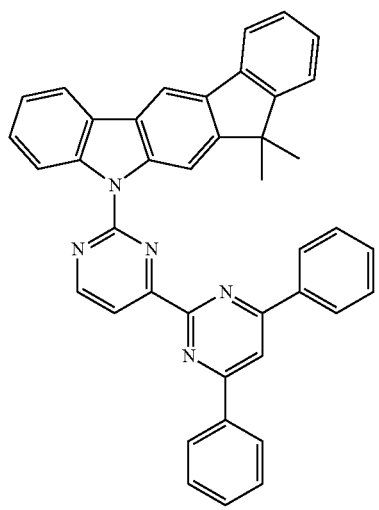
B-191
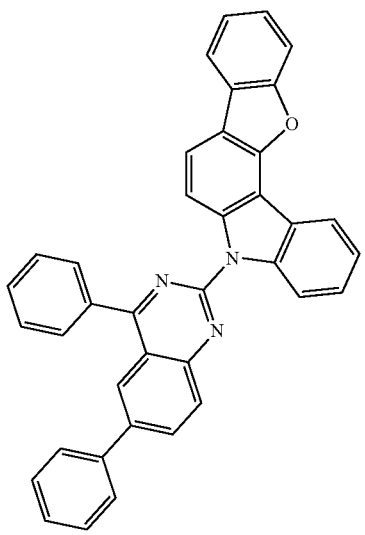
B-189
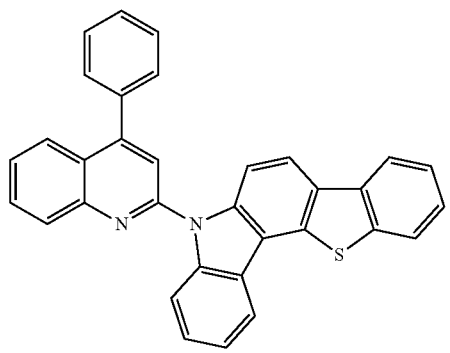
B-192
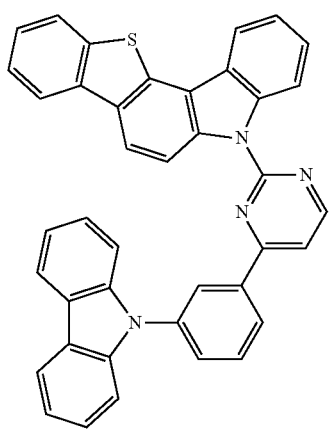
B-190
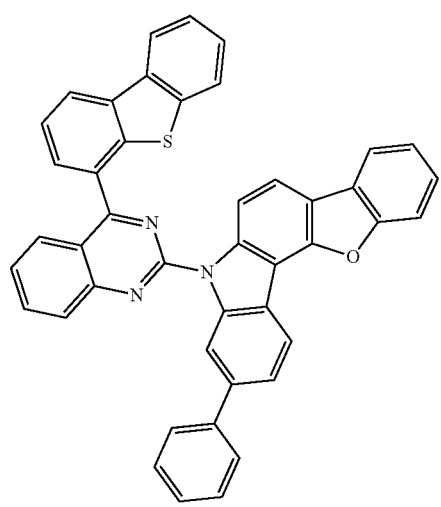
B-193
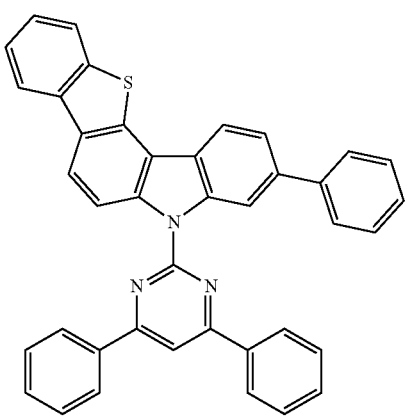

B-194
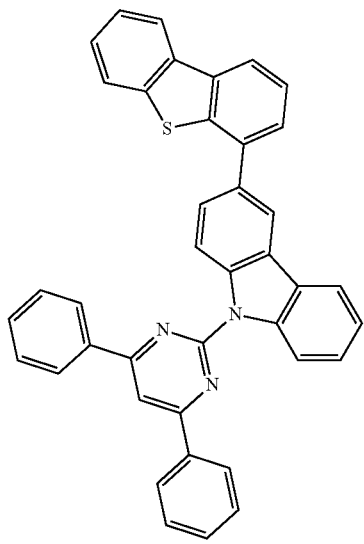

B-195
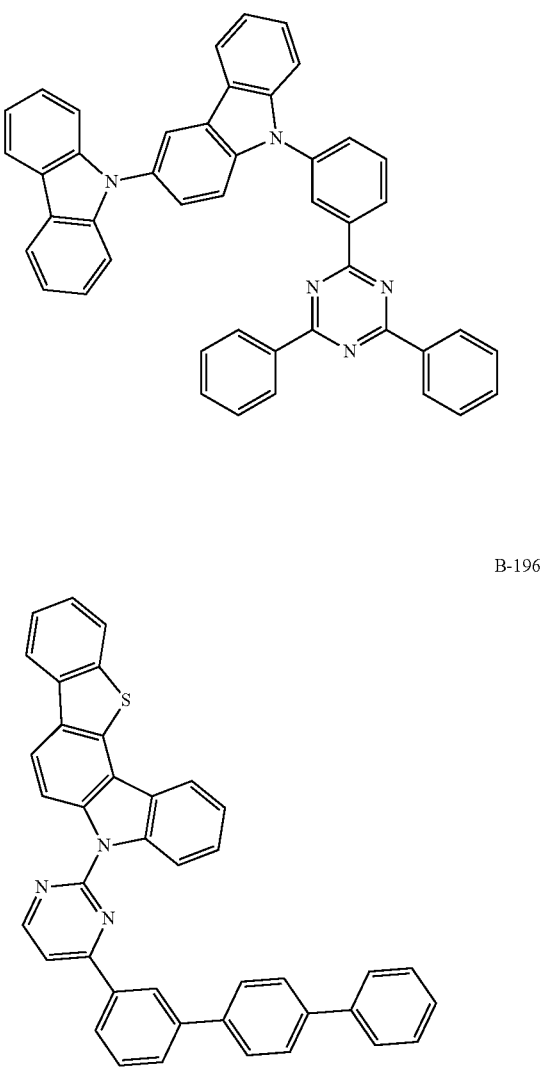

B-196

B-197
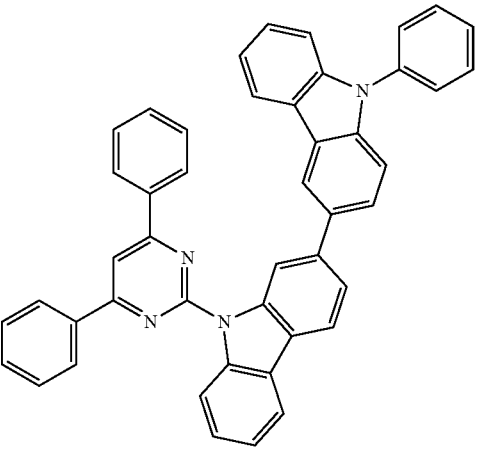

wherein TPS represents a triphenylsilyl group.

The dopant comprised in the organic electroluminescent device of the present disclosure is at least one phosphorescent or fluorescent dopant, preferably at least one phosphorescent dopant. The phosphorescent dopant material applied to the organic electroluminescent device of the present disclosure is not particularly limited, but may be preferably selected from the metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant comprised in the organic electroluminescent device of the present disclosure may be exemplified as a compound represented by the following formula 101, but is not limited thereto.

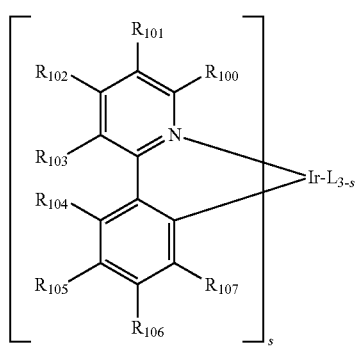
(101)

In formula 101, L is selected from the following structures 1 to 3:

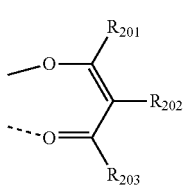
[Structure 1]

-continued

[Structure 2]

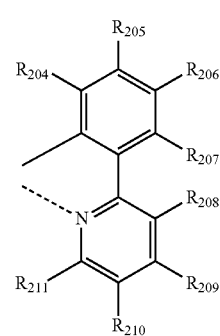

[Structure 3]

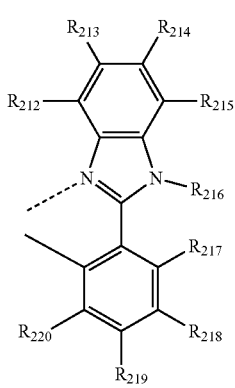

$R_{100}$ to $R_{10}$ each independently represent hydrogen, deuterium, a halogen, a (C1-C30)alkyl unsubstituted or substituted with a halogen(s), a substituted or unsubstituted (C3-C30)cycloalkyl, a substituted or unsubstituted (C6-C30)aryl, a cyano, a substituted or unsubstituted (3- to 30-membered) heteroaryl, or a substituted or unsubstituted (C1-C30) alkoxy; or may be linked to an adjacent $R_{100}$ to $R_{103}$ to form a substituted or unsubstituted fused ring with a pyridine, e.g., a substituted or unsubstituted quinoline, a substituted or unsubstituted isoquinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline or a substituted or unsubstituted indenoquinoline; $R_{104}$ to $R_{107}$ each independently represent hydrogen, deuterium, a halogen, a (C1-C30)alkyl unsubstituted or substituted with a halogen(s), a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30)alkoxy; or may be linked to adjacent $R_{104}$ to $R_{107}$ to form a substituted or unsubstituted fused ring with a benzene, e.g., a substituted or unsubstituted naphthyl, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted benzothienopyridine;

$R_{201}$ to $R_{220}$ each independently represent hydrogen, deuterium, a halogen, a (C1-C30)alkyl unsubstituted or substituted with a halogen(s), a substituted or unsubstituted (C3-C30)cycloalkyl, or a substituted or unsubstituted (C6-C30) aryl; or may be linked to adjacent $R_{201}$ to $R_{220}$ to form a substituted or unsubstituted fused ring; and s represents an integer of 1 to 3.

The specific examples of the dopant compound are as follows, but are not limited thereto.

D-1

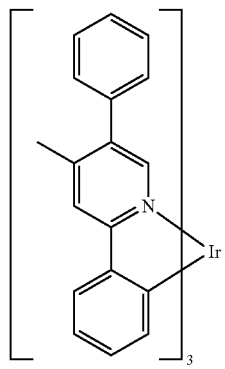

D-2

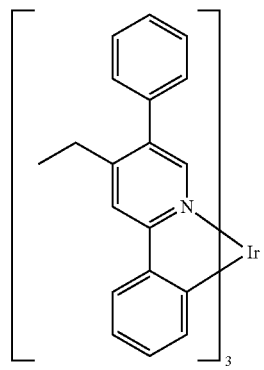

D-3

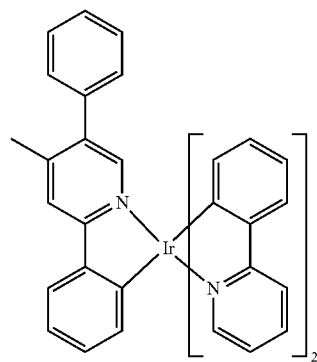

D-4

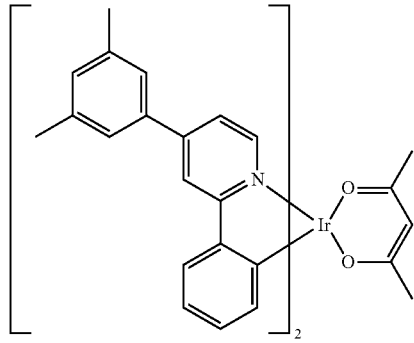

D-5
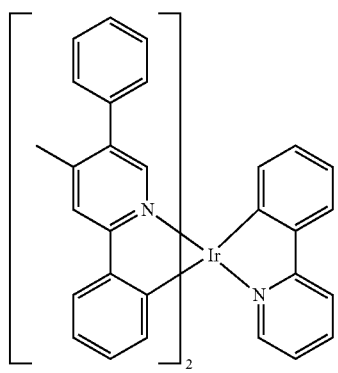
D-6
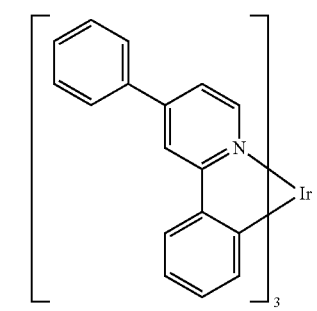
D-7
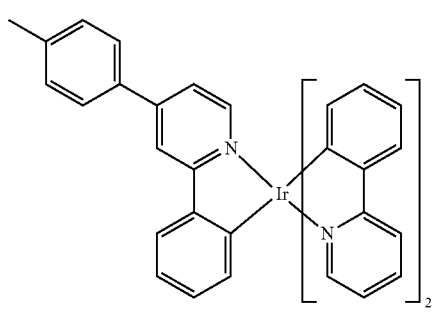
D-8
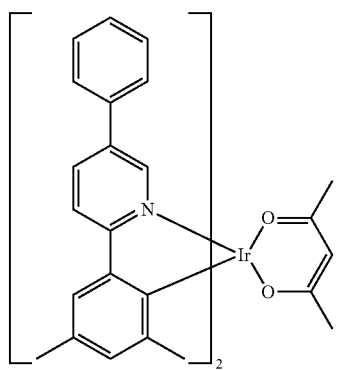
D-9
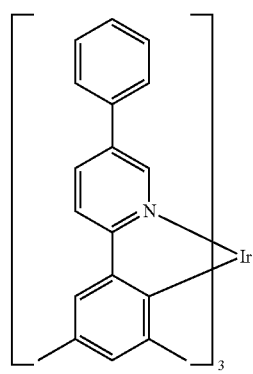
D-10
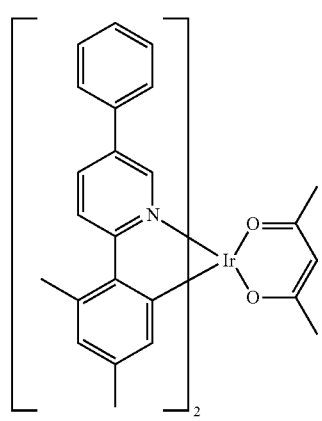
D-11
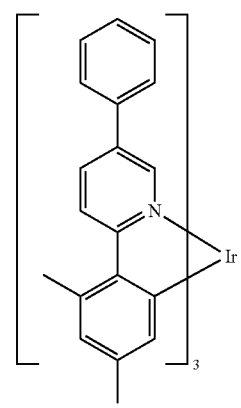
D-12
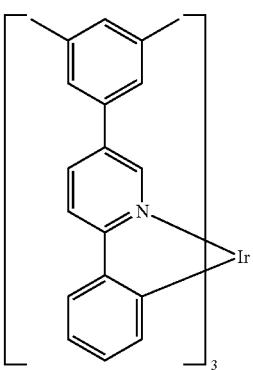

D-13 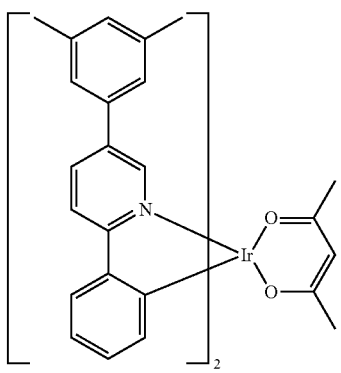
D-14 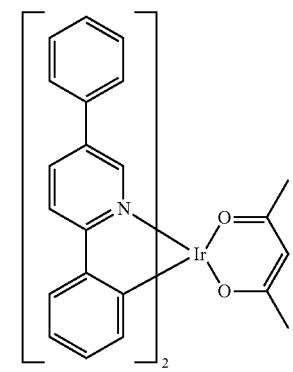
D-15 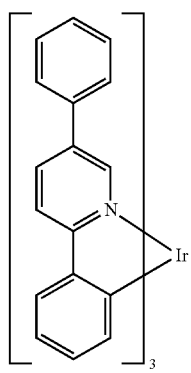
D-16 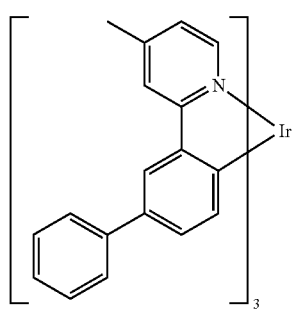
D-17 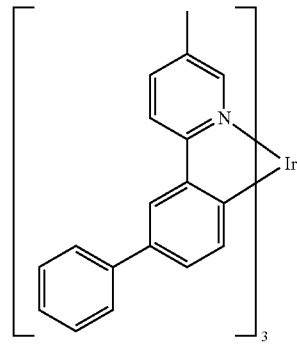
D-18 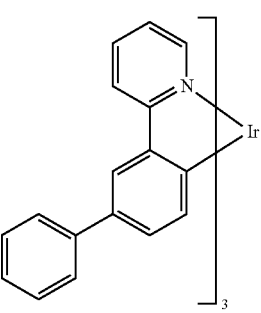
D-19 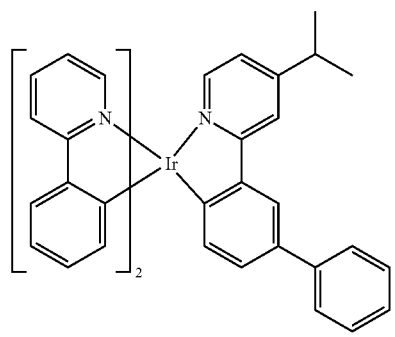
D-20 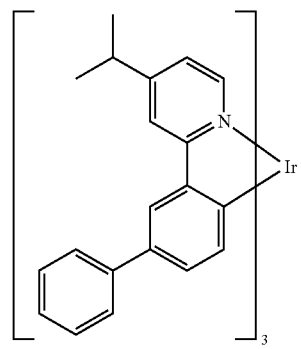

D-21
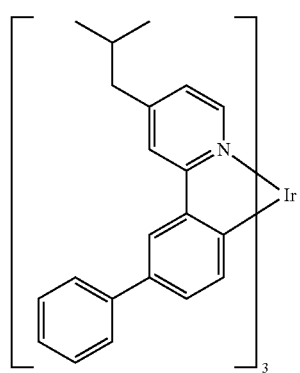
D-22
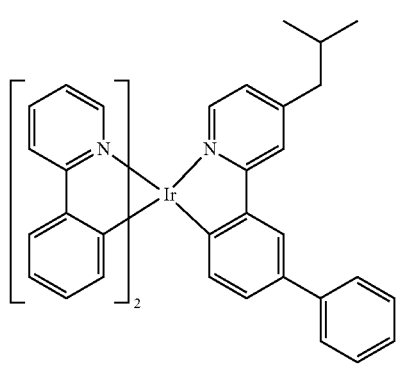
D-23
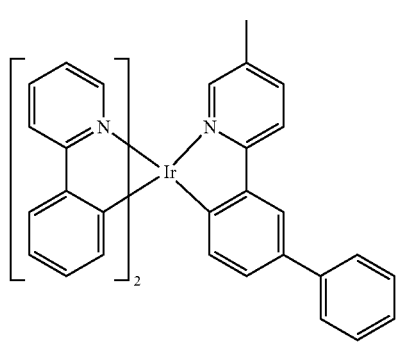
D-24
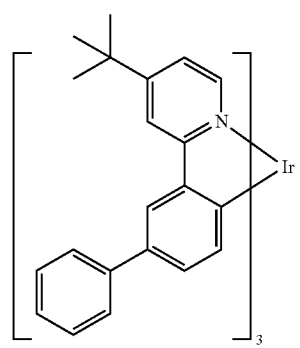
D-25
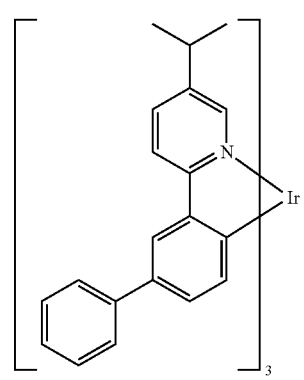
D-26
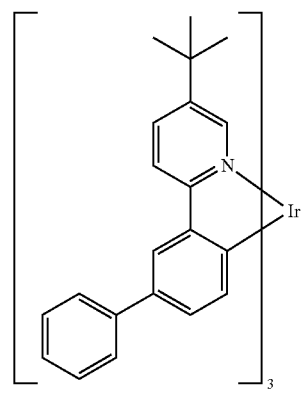
D-27
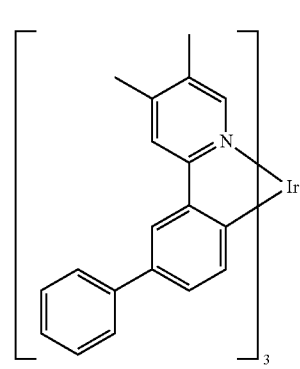
D-28
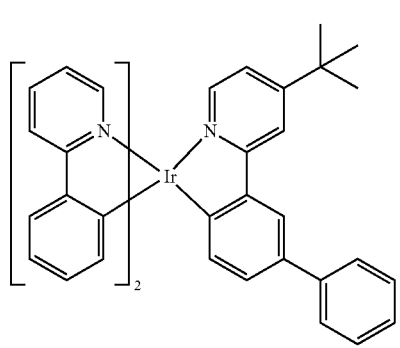

-continued
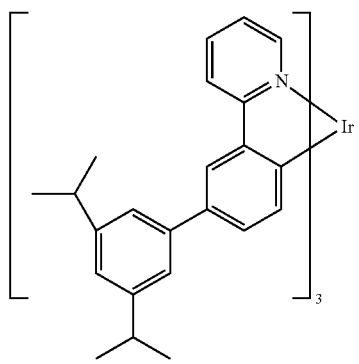 D-29
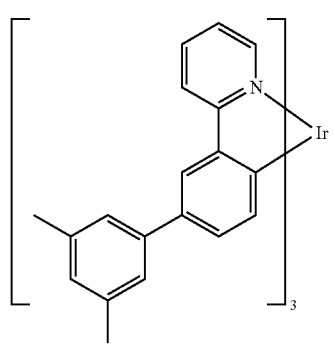 D-30
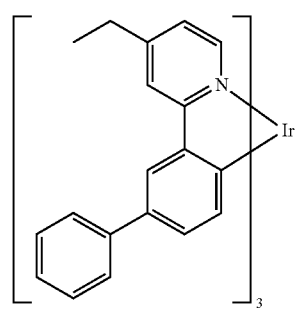 D-31
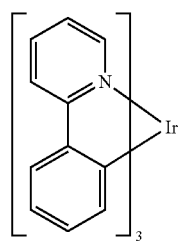 D-32
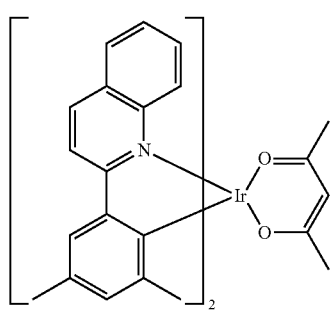 D-33
-continued
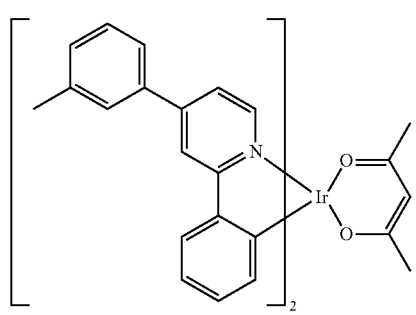 D-34
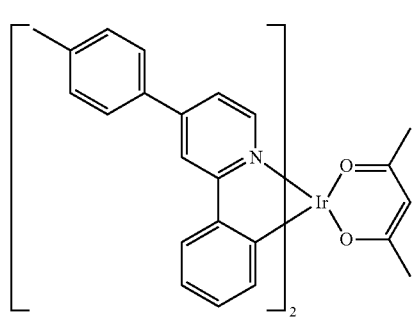 D-35
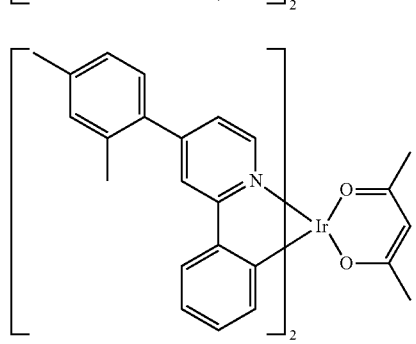 D-36
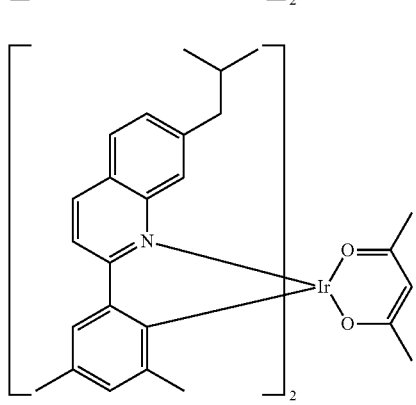 D-37
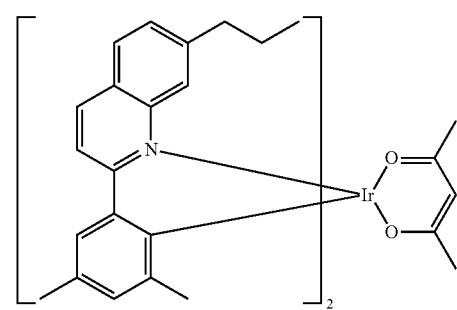 D-38

D-39
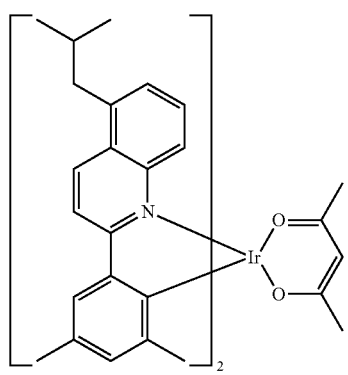
D-40
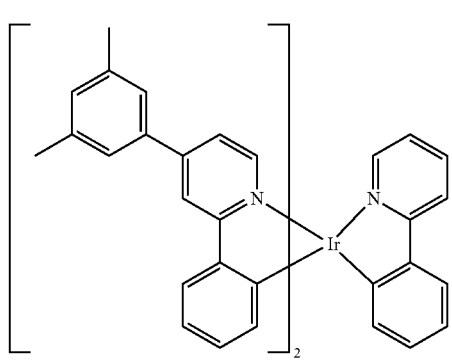
D-41
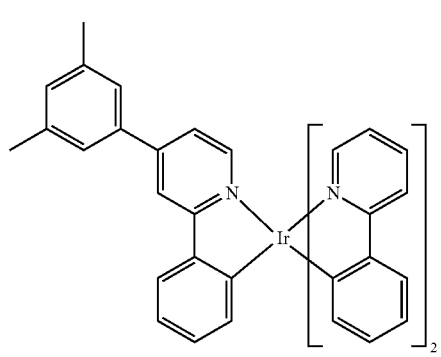
D-42
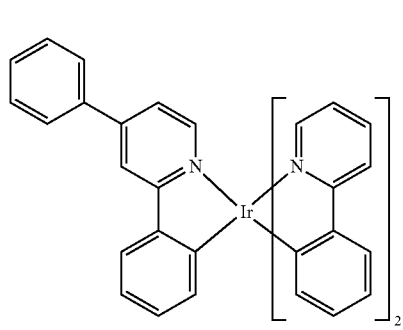
D-43
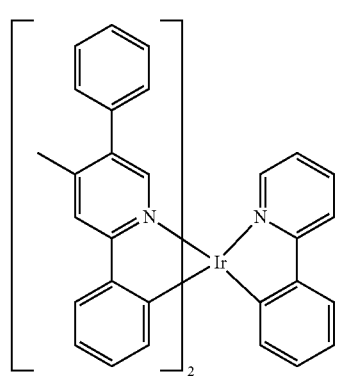
D-44
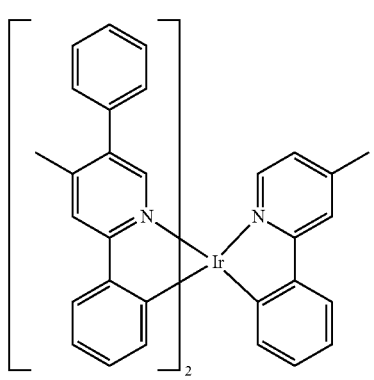
D-45
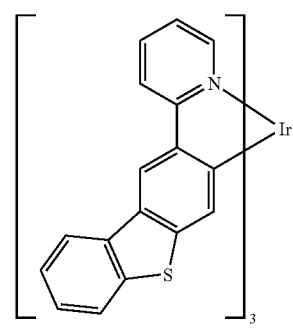
D-46
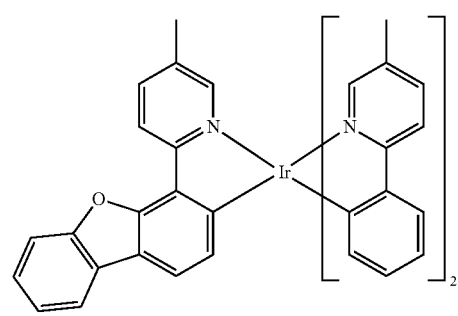

D-47
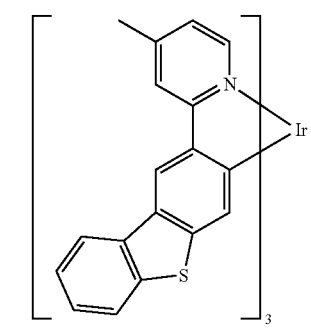
D-48
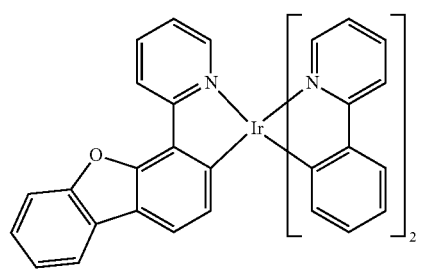
D-49
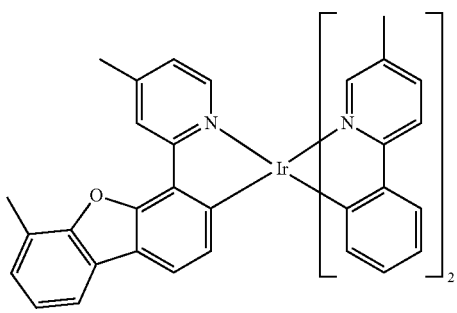
D-50
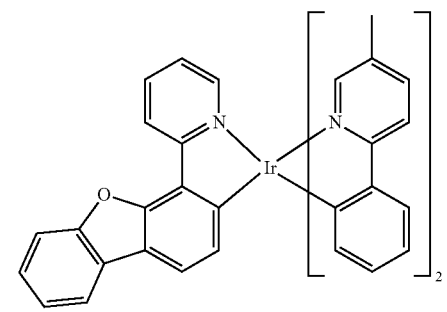
D-51
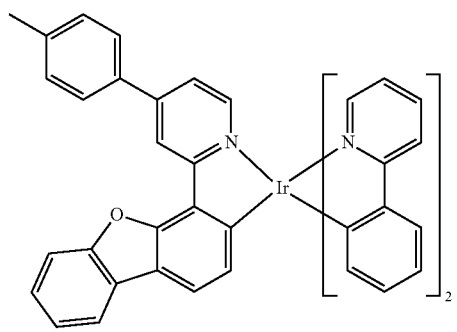
D-52
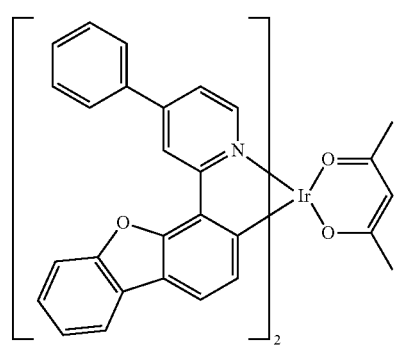
D-53
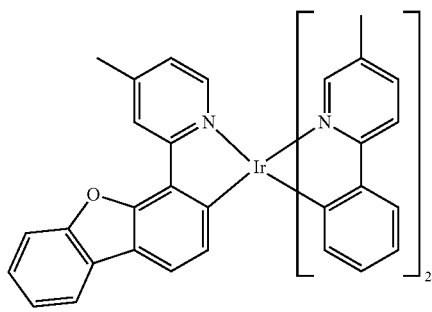
D-54
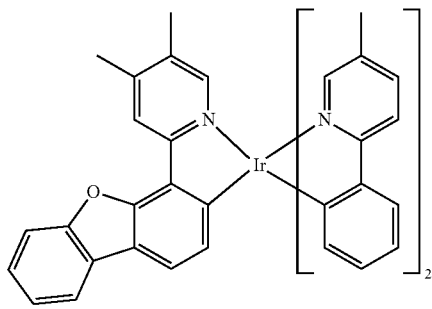
D-55
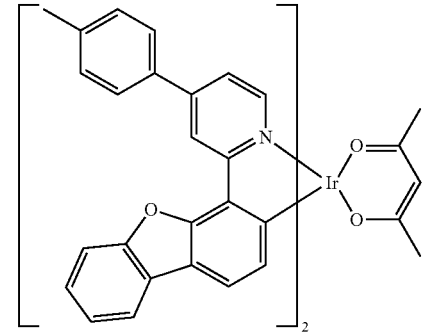
D-56
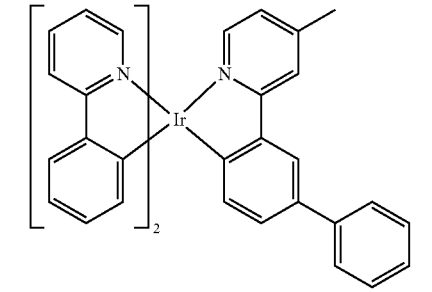

D-57
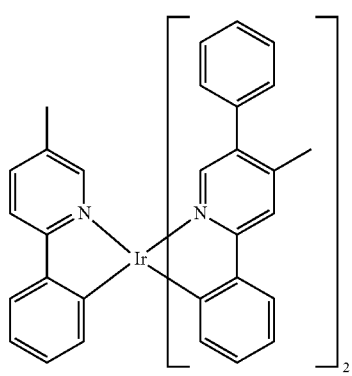
D-58
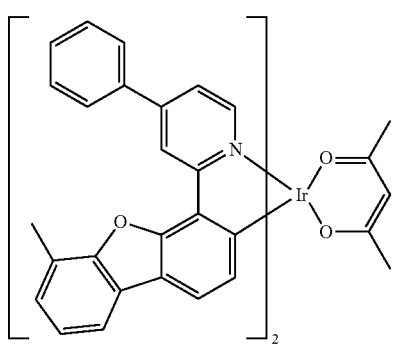
D-59
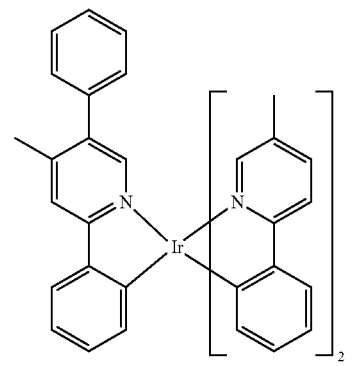
D-60
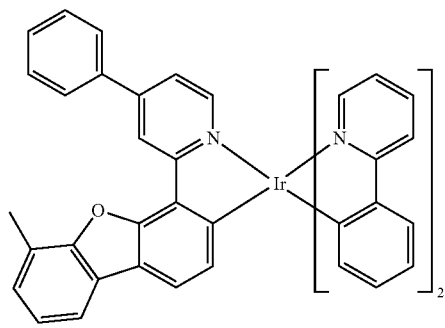
D-61
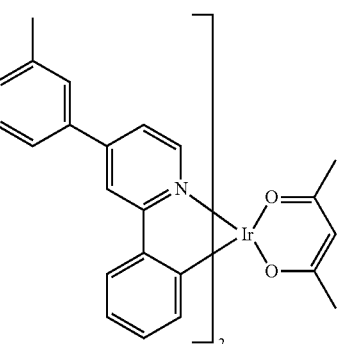
D-62
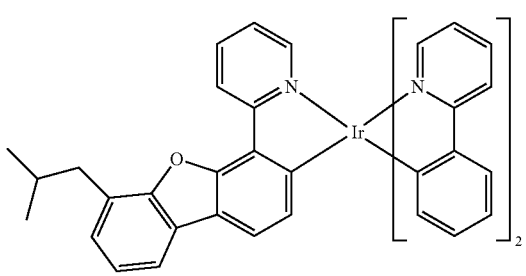
D-63
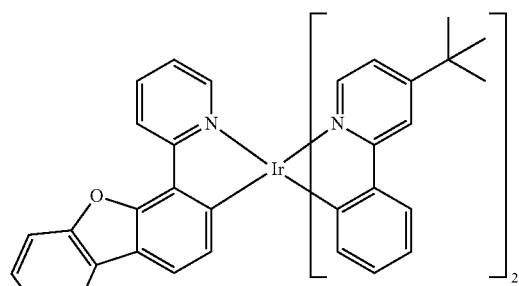
D-64

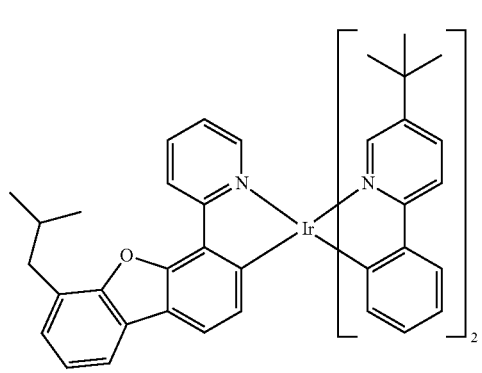
D-65
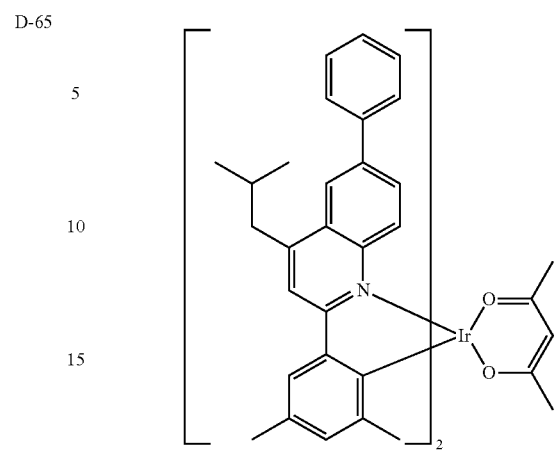
D-69
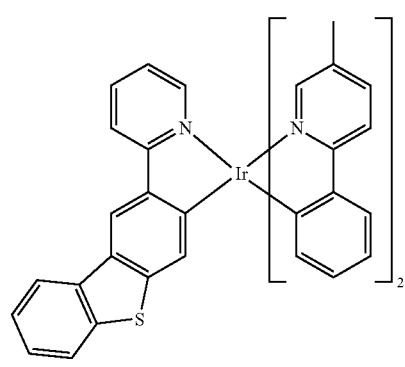
D-66
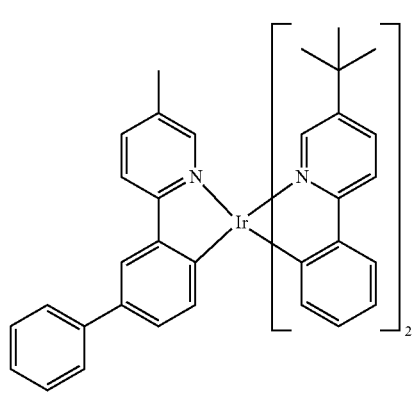
D-70
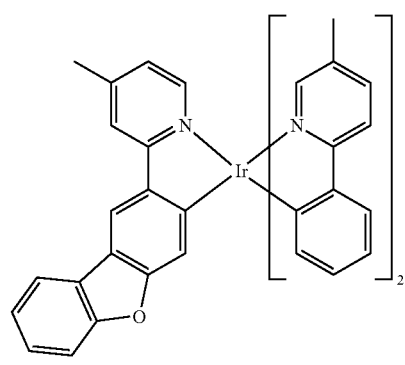
D-67
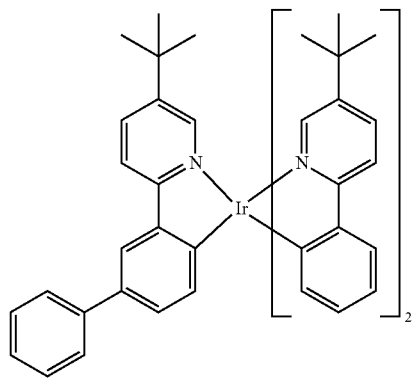
D-71
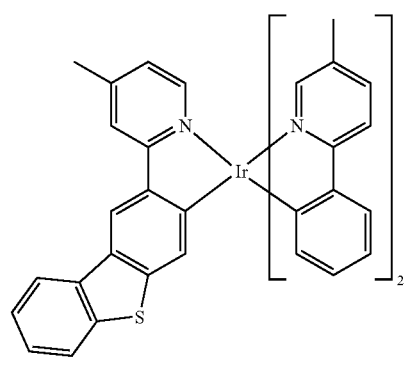
D-68
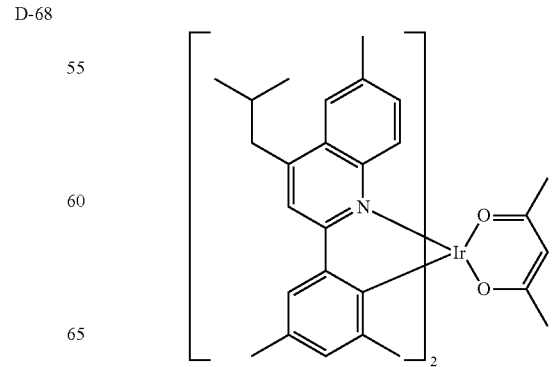
D-72

-continued
D-73
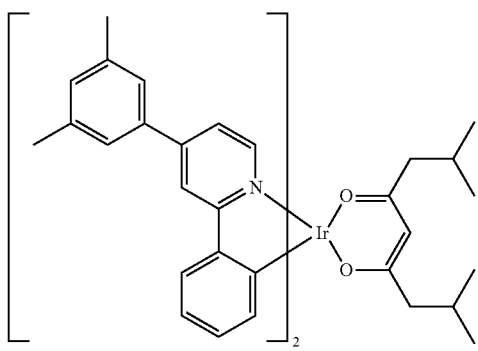
D-74
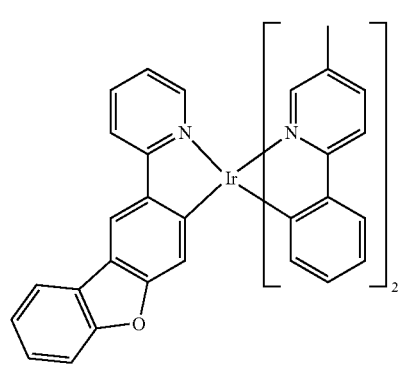
D-75
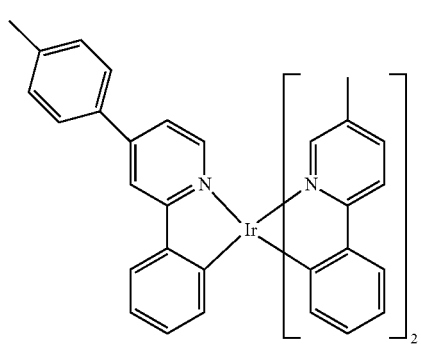
D-76
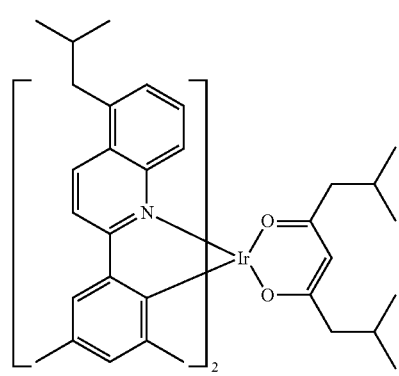
-continued
D-77
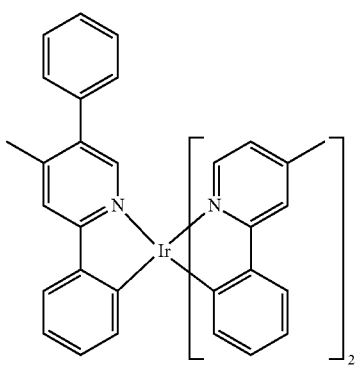
D-78
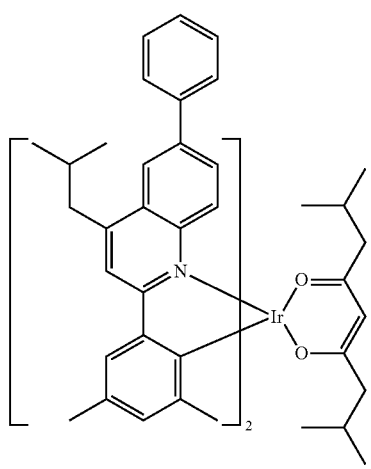
D-79
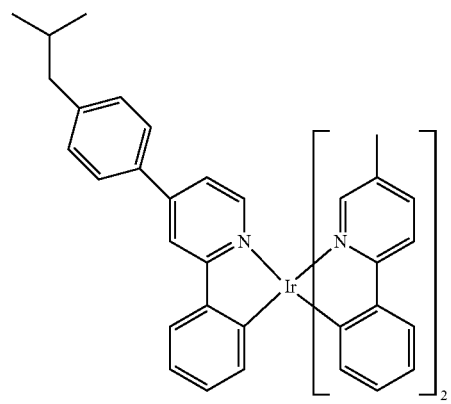
D-80
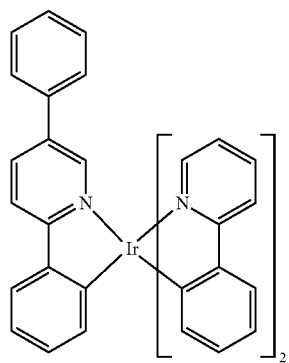

-continued
D-81
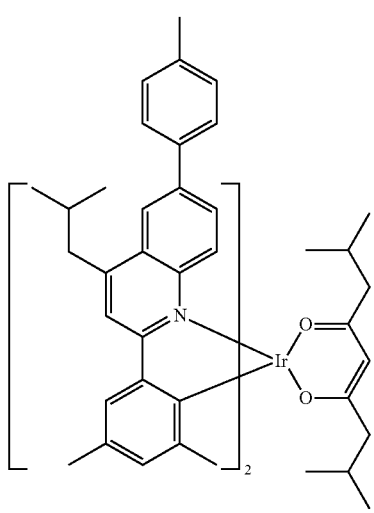
D-82
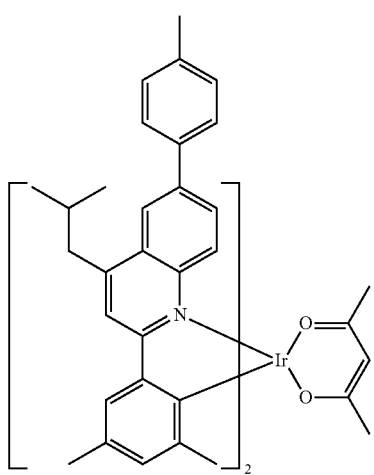
D-83
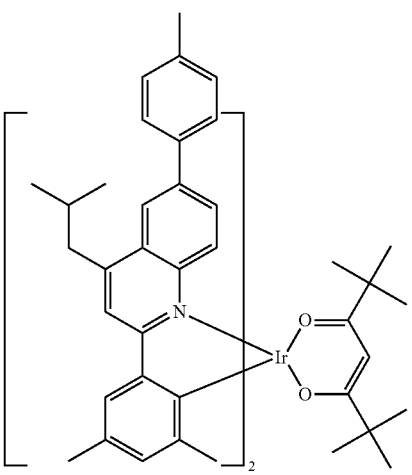
-continued
D-84
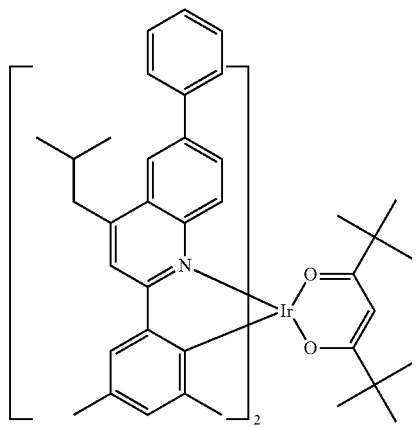
D-85
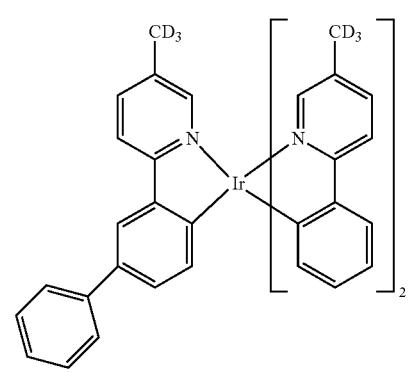
D-86
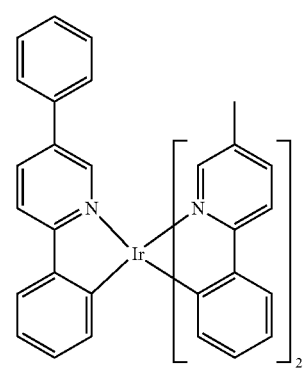
D-87
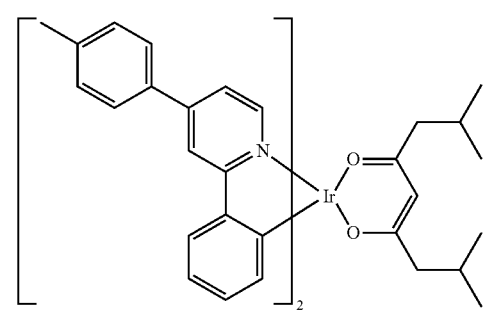

D-88
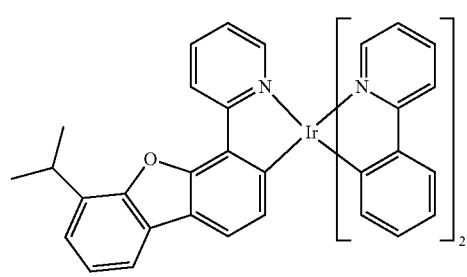
D-89
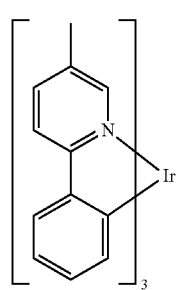
D-90
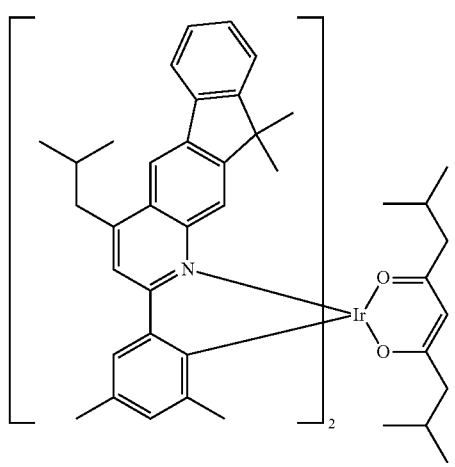
D-91
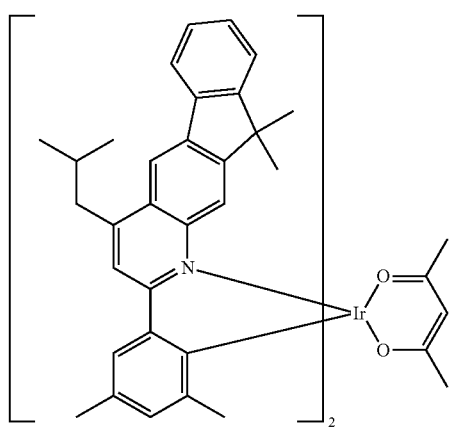
D-92
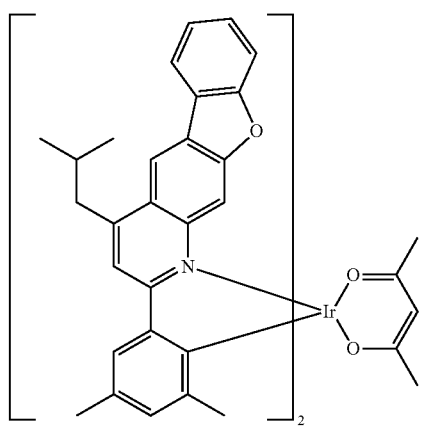
D-93
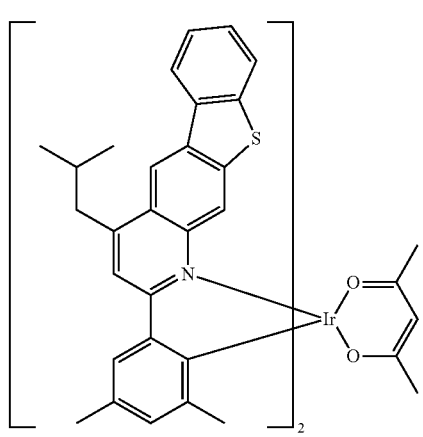
D-94
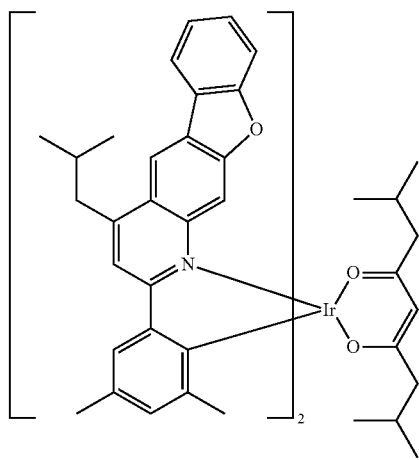

D-95
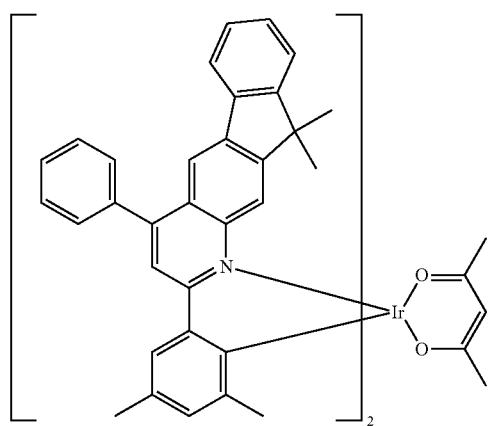
D-96
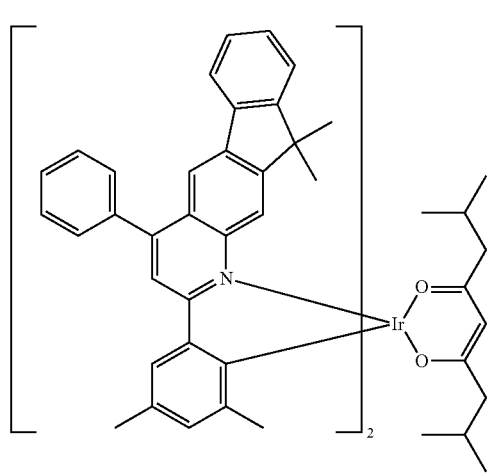
D-97
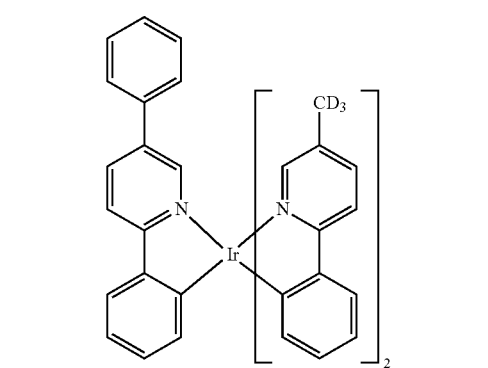
D-98
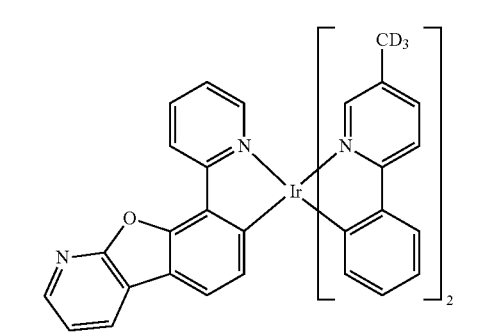
D-99
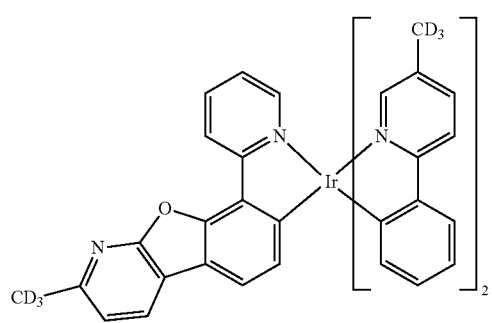
D-100
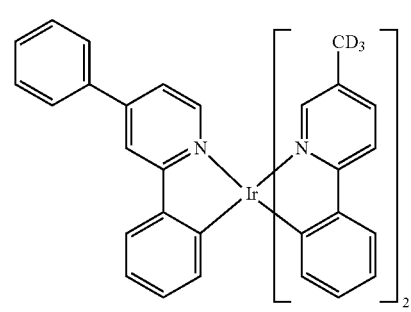
D-101
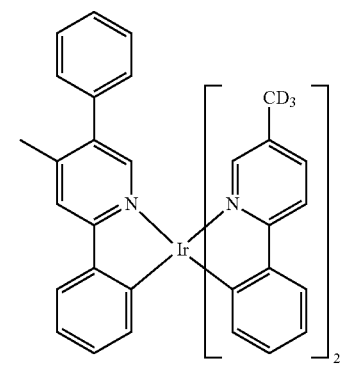
D-102
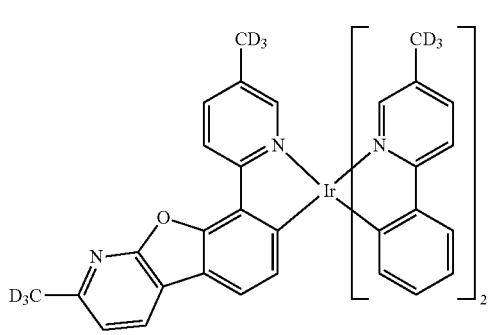

D-103 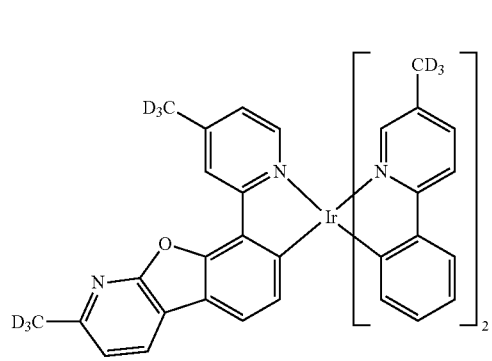
D-107 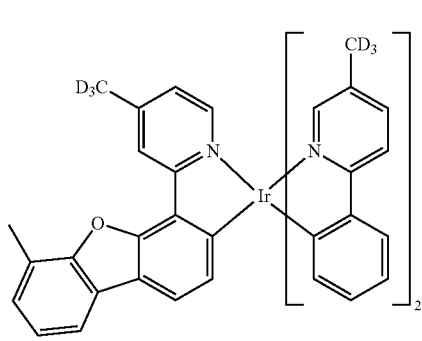
D-104 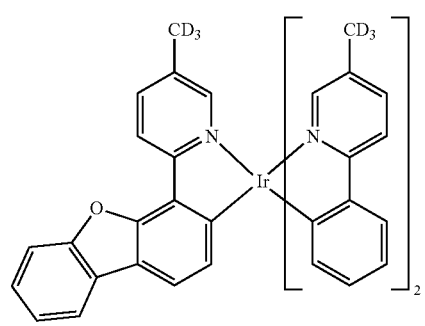
D-108 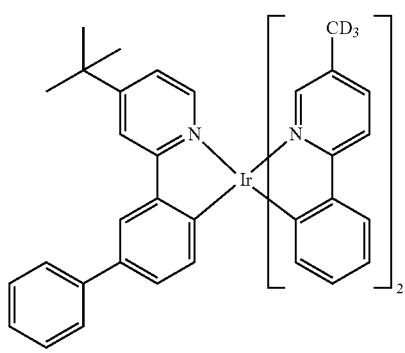
D-105 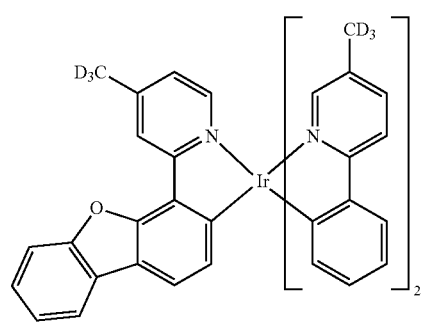
D-109 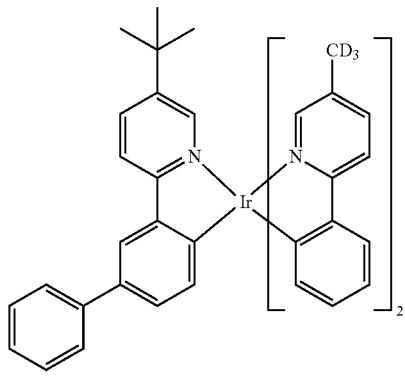
D-106 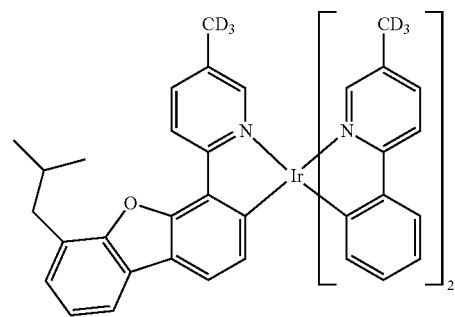
D-110 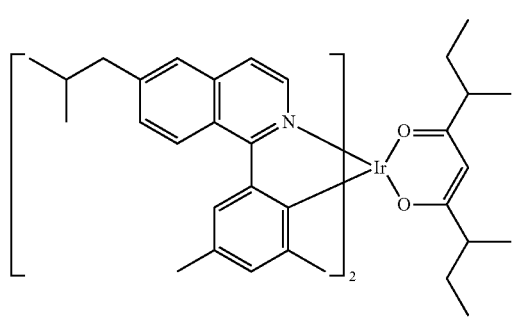

D-111
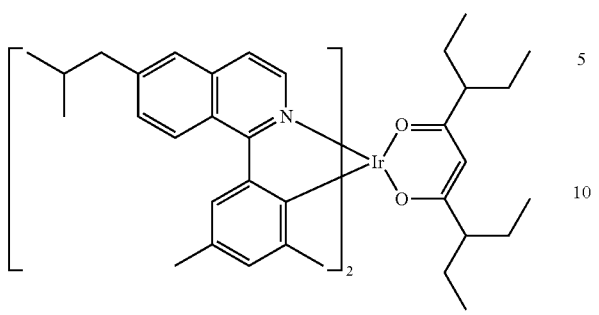
D-112
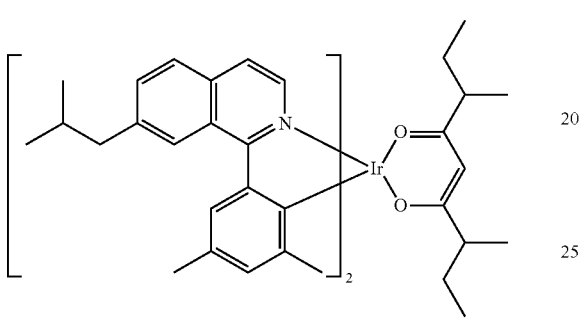
D-113
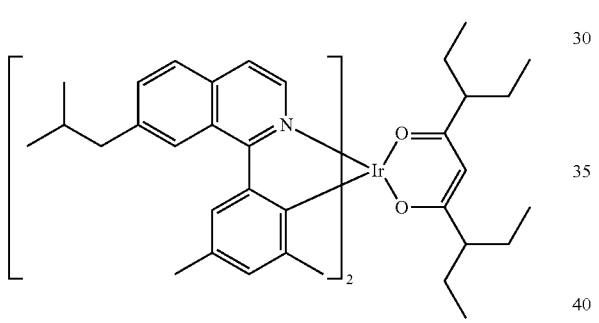
D-114
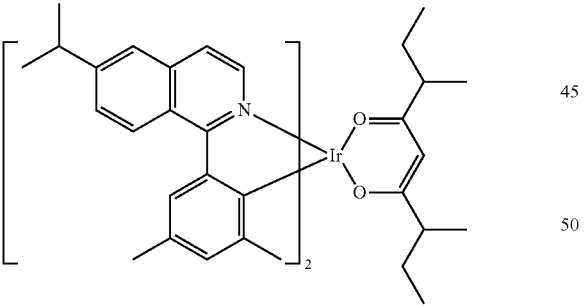
D-115
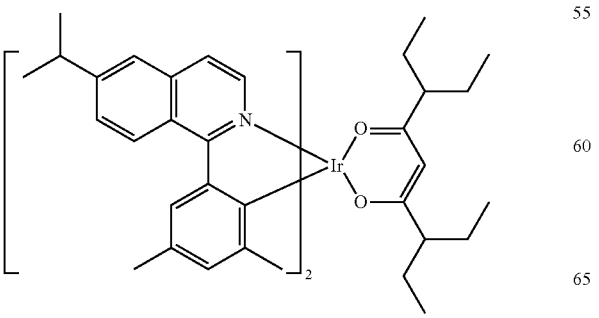
D-116
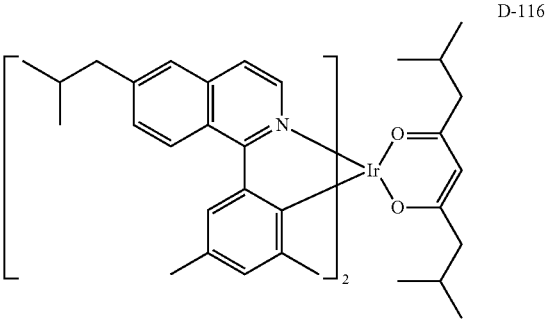
D-117
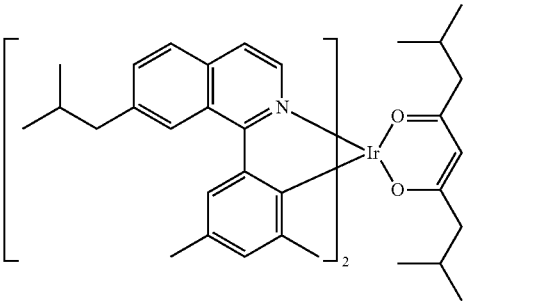
D-118
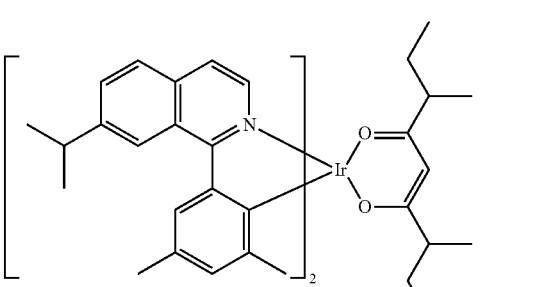
D-119
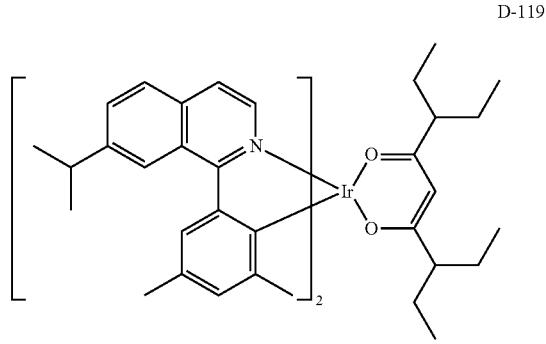
D-120
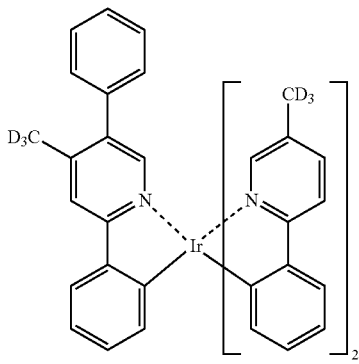

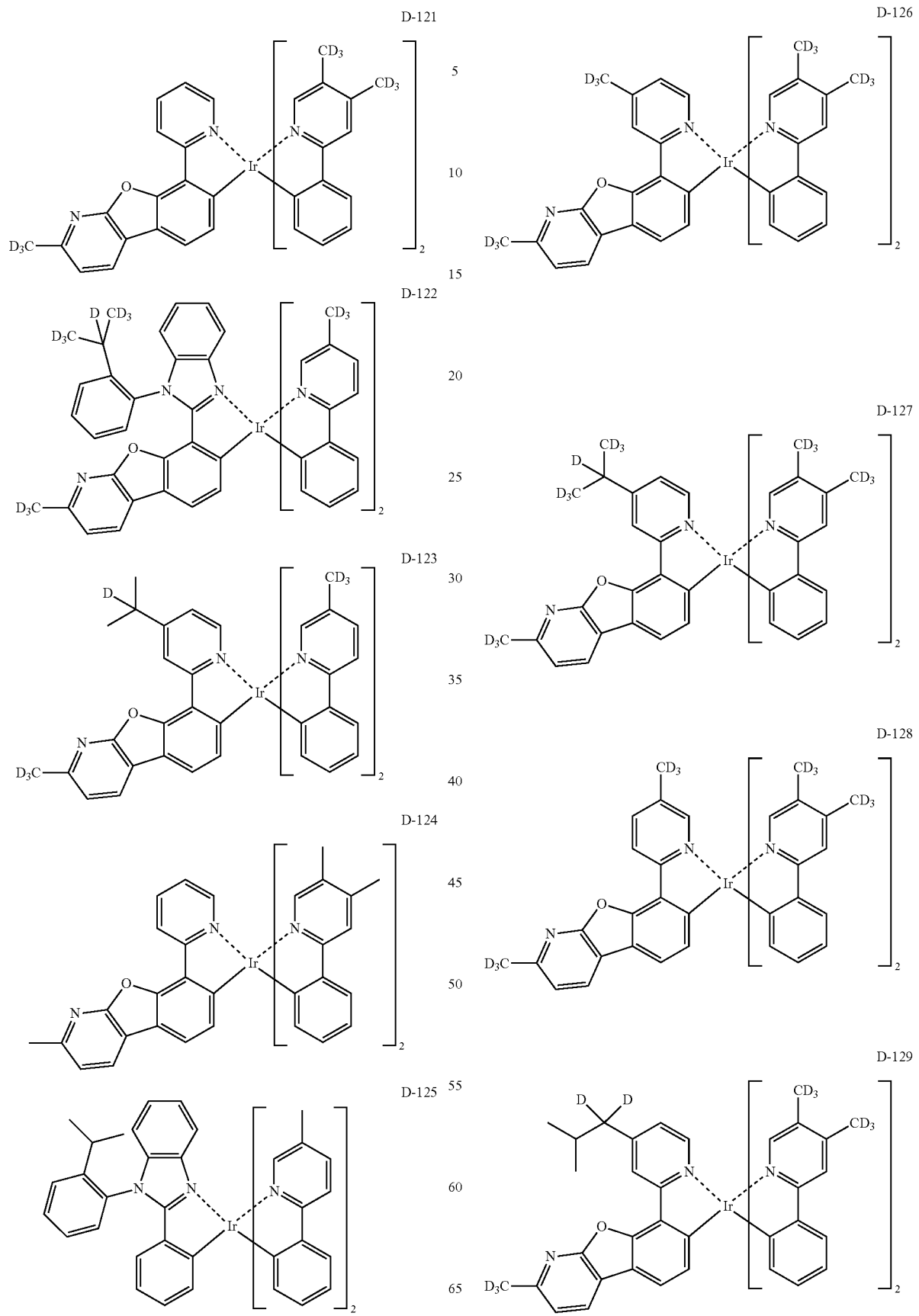

-continued

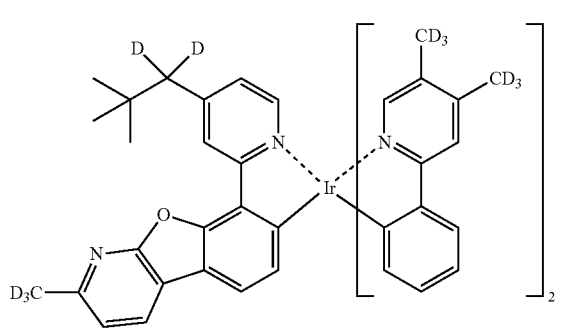
D-130

The organic electroluminescent device according to the present disclosure comprises a first electrode; a second electrode; and at least one organic layer between the first and second electrodes.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer. Each of the layers may further consist of multi-layers.

The first electrode and the second electrode may each be formed with a transmissive conductive material, a transflective conductive material, or a reflective conductive material. The organic electroluminescent device may be a top emission type, a bottom emission type, or both-sides emission type according to the kinds of the material forming the first electrode and the second electrode. In addition, the hole injection layer may be further doped with a p-dopant, and the electron injection layer may be further doped with an n-dopant.

According to one embodiment of the present disclosure, the organic electroluminescent device according to the present disclosure may further comprise an azine-based compound as at least one selected from an electron transport material, an electron injection material, an electron buffer material, and a hole blocking material, in addition to the organic electroluminescent compound of the present disclosure.

The organic layer may further comprise at least one compound selected from the group consisting of arylamine-based compounds and styrylarylamine-based compounds.

In addition, in the organic electroluminescent device of the present disclosure, the organic layer may further comprise at least one metal selected from the group consisting of metals of Group 1, metals of Group 2, transition metals of the 4$^{th}$ period, transition metals of the 5$^{th}$ period, lanthanides and organic metals of d-transition elements of the Periodic Table, or at least one complex compound comprising said metal.

The organic electroluminescent device of the present disclosure may emit white light by further including at least one light-emitting layer containing a blue, red, or green light-emitting compound, which is known in the art, besides the compound of the present disclosure. In addition, it may further include a yellow or orange light-emitting layer, if necessary.

In the organic electroluminescent device of the present disclosure, at least one layer selected from a chalcogenide layer, a metal halide layer and a metal oxide layer (hereinafter, "a surface layer") may be preferably placed on an inner surface(s) of one or both electrodes. Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. The surface layer may provide operation stability for the organic electroluminescent device. Preferably, the chalcogenide includes $SiO_X$ ($1 \leq X \leq 2$), $AlO_X$ ($1 \leq X \leq 1.5$), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

A hole injection layer, a hole transport layer, or an electron blocking layer, or a combination thereof may be used between the anode and the light-emitting layer. The hole injection layer may be multilayers in order to lower the hole injection barrier (or hole injection voltage) from the anode to the hole transport layer or the electron blocking layer, wherein each of the multilayers may use two compounds simultaneously. The hole transport layer or the electron blocking layer may also be multilayers.

An electron buffer layer, a hole blocking layer, an electron transport layer, or an electron injection layer, or a combination thereof can be used between the light-emitting layer and the cathode. The electron buffer layer may be multilayers in order to control the injection of the electron and improve the interfacial properties between the light-emitting layer and the electron injection layer, wherein each of the multilayers may use two compounds simultaneously. The hole blocking layer or the electron transport layer may also be multilayers, wherein each of the multilayers may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. In addition, the hole auxiliary layer may be placed between the hole transport layer (or hole injection layer) and the light-emitting layer, and may be effective to promote or block the hole transport rate (or the hole injection rate), thereby enabling the charge balance to be controlled. Further, the electron blocking layer may be placed between the hole transport layer (or hole injection layer) and the light-emitting layer, and may block overflowing electrons from the light-emitting layer and confine the excitons in the light-emitting layer to prevent light leakage. When an organic electroluminescent device includes two or more hole transport layers, the hole transport layer, which is further included, may be used as a hole auxiliary layer or an electron blocking layer. The hole auxiliary layer and the electron blocking layer may have an effect of improving the efficiency and/or the lifespan of the organic electroluminescent device.

In the organic electroluminescent device of the present disclosure, a mixed region of an electron transport compound and a reductive dopant, or a mixed region of a hole transport compound and an oxidative dopant is preferably placed on at least one surface of a pair of electrodes. In this case, the electron transport compound is reduced to an anion, and thus it becomes easier to inject and transport electrons from the mixed region to an electroluminescent medium. Further, the hole transport compound is oxidized to a cation, and thus it becomes easier to inject and transport holes from the mixed region to the electroluminescent medium. Preferably, the oxidative dopant includes various Lewis acids and acceptor compounds; and the reductive dopant includes alkali metals, alkali metal compounds, alkaline earth metals, rare-earth metals, and mixtures thereof. A reductive dopant layer may be employed as a charge-generating layer to produce an organic electroluminescent device having two or more light-emitting layers, which emits white light.

An organic electroluminescent material according to one embodiment of the present disclosure may be used as light-emitting materials for a white organic light-emitting device. The white organic light-emitting device has been suggested to have various structures such as a parallel arrangement (side-by-side) method, a stacking method, or color conversion material (CCM) method, etc., according to the arrangement of R (red), G (green), B (blue), or YG (yellowish green) light-emitting units. In addition, the organic electroluminescent material according to one embodiment of the present disclosure may also be applied to the organic electroluminescent device comprising a quantum dot (QD).

In order to form each layer of the organic electroluminescent device of the present disclosure, dry film-forming methods such as vacuum evaporation, sputtering, plasma, ion plating, etc., or wet film-forming methods such as ink jet printing, spin coating, dip coating, flow coating, etc., can be used. The first and second host compounds of the present disclosure may be co-evaporated or mixture-evaporated to form a film.

When using a wet film-forming method, a thin film can be formed by dissolving or diffusing the materials forming each layer into any suitable solvent such as ethanol, chloroform, tetrahydrofuran, dioxane, etc. The solvent is not particularly limited as long as the material constituting each layer is soluble or dispersible in the solvents, which do not cause any problems in forming a film.

It is possible to produce a display system, e.g., a display system for smartphones, tablets, notebooks, PCs, TVs, or cars, or a lighting system, e.g., an outdoor or indoor lighting system, by using the organic electroluminescent device of the present disclosure.

Hereinafter, the preparation method of the compound of the present disclosure, and the properties thereof will be explained in detail with reference to the representative compounds of the present disclosure. However, the present disclosure is not limited to the following examples.

Example 1: Preparation of Compound A-1

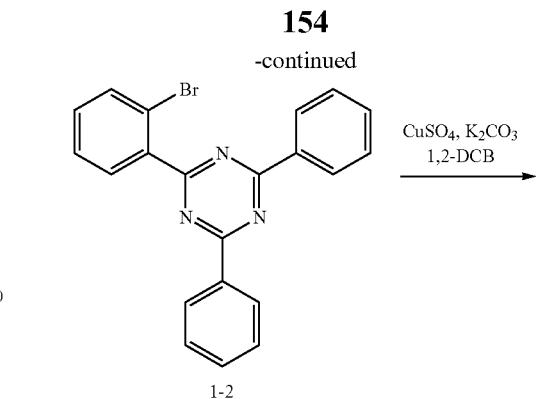

Compound 1-1 (20.0 g, 69 mmol), compound 1-2 (29.3 g, 76 mmol), copper sulfate (4.4 g, 27.6 mmol), potassium carbonate (19.0 g, 137 mmol), and o-dichlorobenzene (343 mL) were introduced into a flask, and the mixture was refluxed for 18 hours. The reaction solution was cooled to room temperature and added dropwise to methanol (4 L) to obtain a solid product. The obtained solid compound was purified by column chromatography to obtain 14.4 g of yellow solid compound A-1 (yield: 35%). (M.P.=210° C., deposition temperature (DT)=300° C.)

Example 2: Preparation of Compound A-2

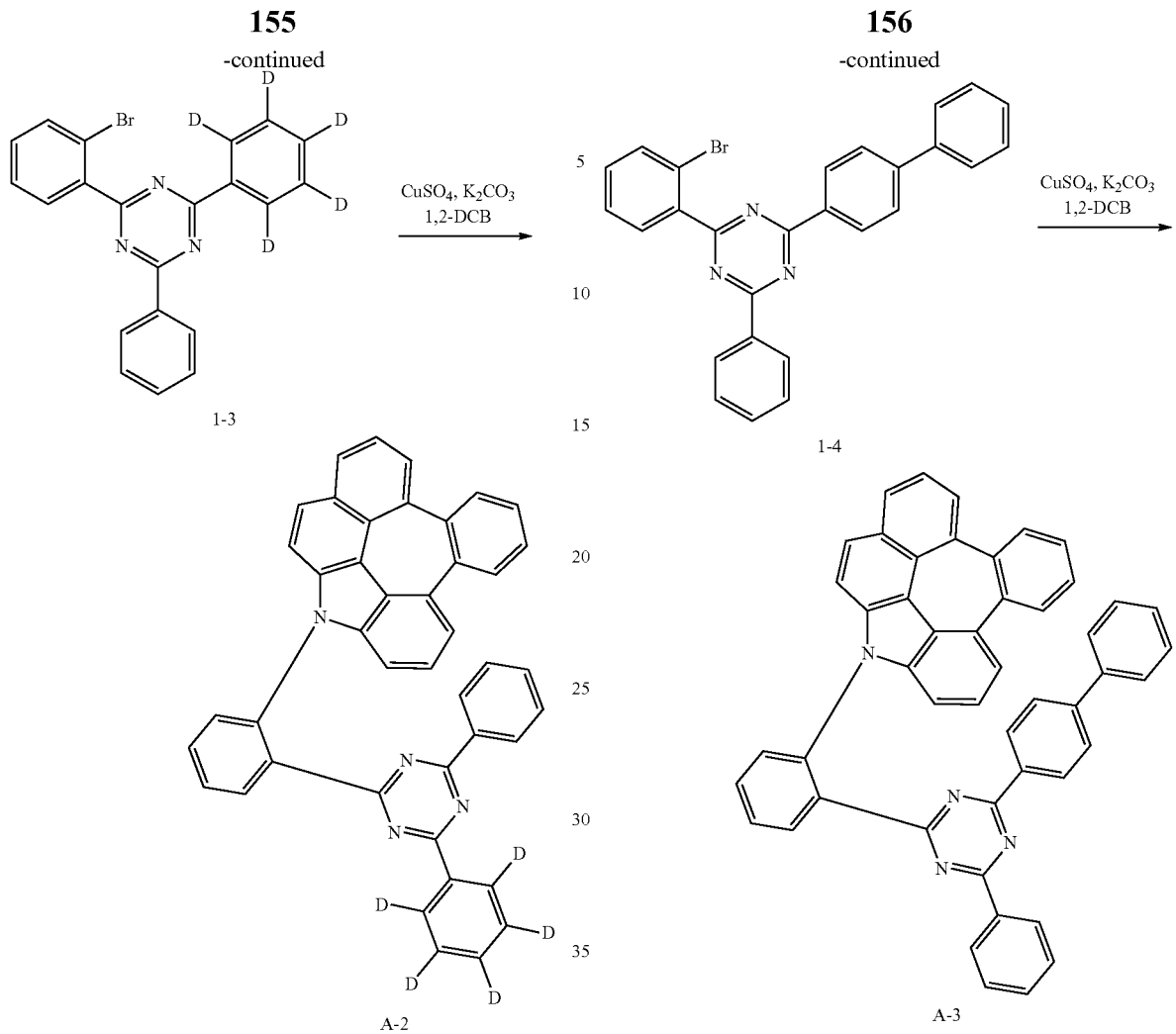

Compound 1-1 (16.4 g, 56 mmol), compound 1-3 (22.1 g, 56 mmol), copper sulfate (3.6 g, 22.4 mmol), potassium carbonate (15.6 g, 112 mmol), and o-dichlorobenzene (282 mL) were introduced into a flask, and the mixture was refluxed for 18 hours. The reaction solution was cooled to room temperature and added dropwise to methanol (4 L) to obtain a solid product. The obtained solid compound was purified by column chromatography to obtain 6.1 g of yellow solid compound A-2 (yield: 18%). (M.P.=214° C., deposition temperature (DT)=300° C.)

Compound 1-1 (7.5 g, 25.8 mmol), compound 1-4 (12.0 g, 25.8 mmol), copper sulfate (2.0 g, 12.8 mmol), potassium carbonate (7.1 g, 51.4 mmol), and o-dichlorobenzene (258 mL) were introduced into a flask, and the mixture was refluxed for 18 hours. The reaction solution was cooled to room temperature and added dropwise to methanol (4 L) to obtain a solid product. The obtained solid compound was purified by column chromatography to obtain 8 g of yellow solid compound A-3 (yield: 44%). (M.P.=230° C., deposition temperature (DT)=343° C.)

Example 3: Preparation of Compound A-3

Example 4: Preparation of Compound A-4

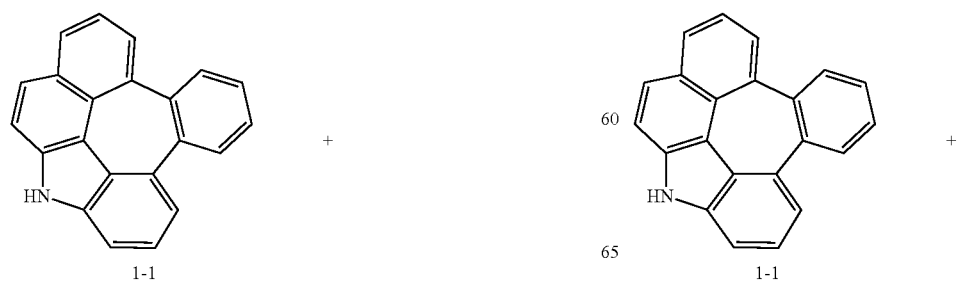

-continued

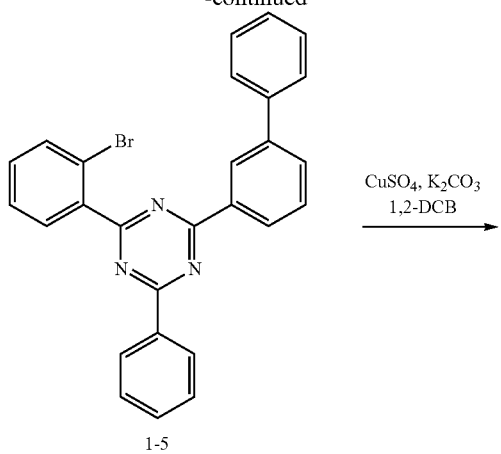

Example 5: Preparation of Compound A-5

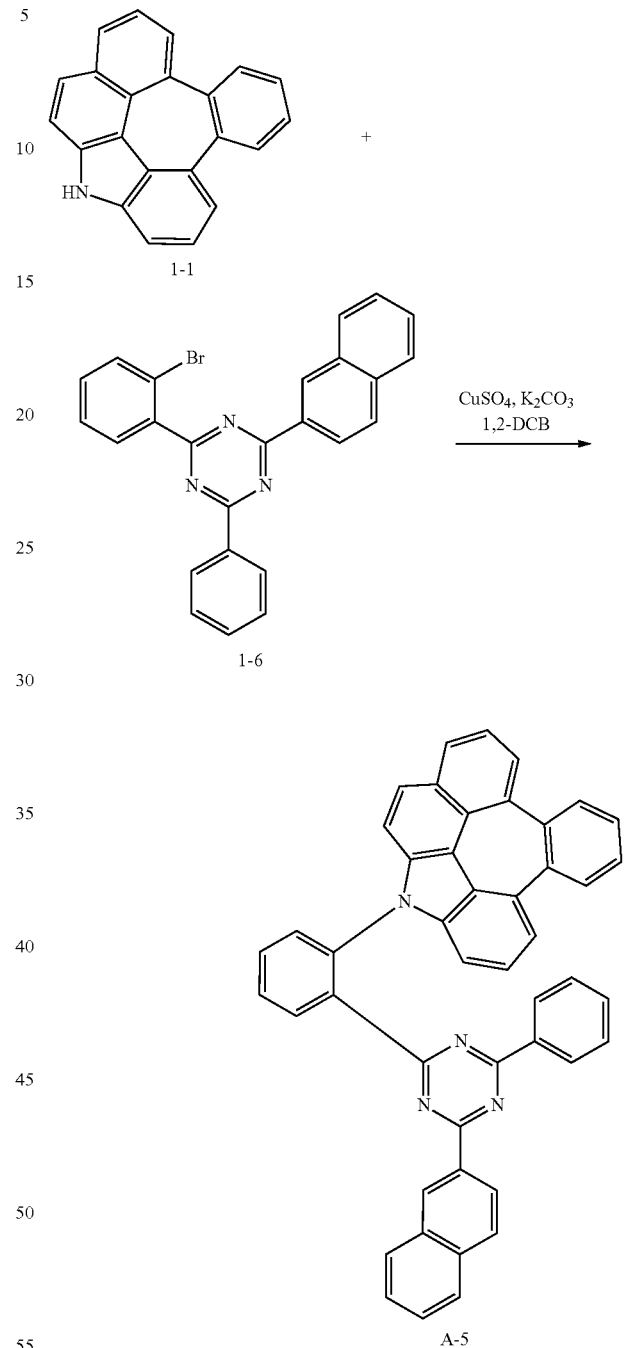

Compound 1-1 (6.0 g, 20.5 mmol), compound 1-5 (9.5 g, 20.5 mmol), copper sulfate (1.6 g, 10.2 mmol), potassium carbonate (5.6 g, 40.9 mmol), and o-dichlorobenzene (105 mL) were introduced into a flask, and the mixture was refluxed for 18 hours. The reaction solution was cooled to room temperature and added dropwise to methanol (4 L) to obtain a solid product. The obtained solid compound was purified by column chromatography to obtain 1.8 g of yellow solid compound A-4 (yield: 12%). (M.P.=137° C., deposition temperature (DT)=330° C.)

Compound 1-1 (12.9 g, 44.3 mmol), compound 1-6 (14.6 g, 33.2 mmol), copper sulfate (3.5 g, 22.1 mmol), potassium carbonate (12.2 g, 88.6 mmol), and o-dichlorobenzene (342 mL) were introduced into a flask, and the mixture was refluxed for 18 hours. The reaction solution was cooled to room temperature and added dropwise to methanol (4 L) to obtain a solid product. The obtained solid compound was purified by column chromatography to obtain 9.5 g of yellow solid compound A-5 (yield: 33%). (M.P.=223° C., deposition temperature (DT)=330° C.)

Example 6: Preparation of Compound A-7

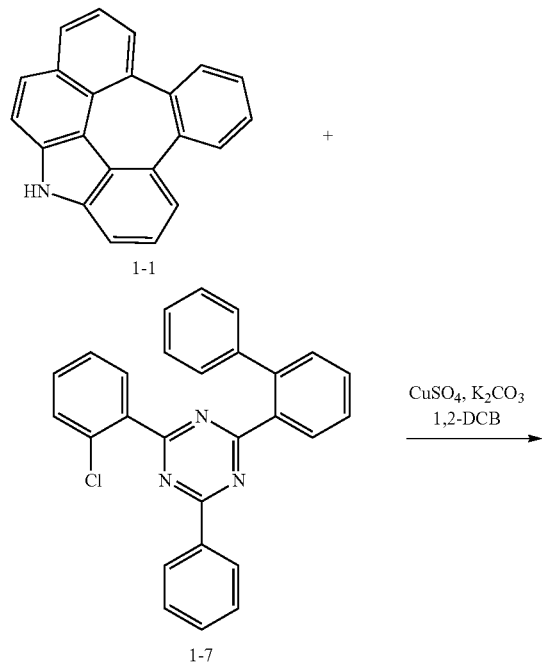

Example 7: Preparation of Compound A-9

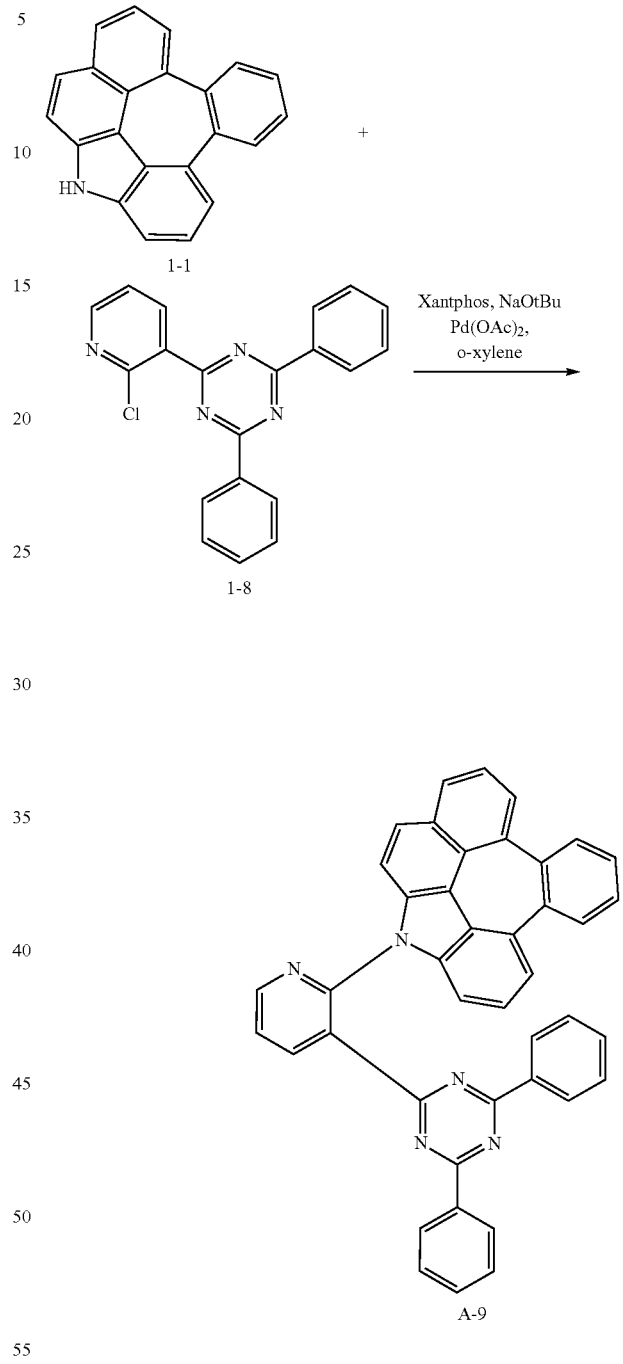

Compound 1-1 (8.3 g, 28.6 mmol), compound 1-7 (12.0 g, 28.6 mmol), copper sulfate (2.3 g, 14.3 mmol), potassium carbonate (7.7 g, 57.2 mmol), and o-dichlorobenzene (150 mL) were introduced into a flask, and the mixture was refluxed for 18 hours. The reaction solution was cooled to room temperature and added dropwise to methanol (4 L) to obtain a solid product. The obtained solid compound was purified by column chromatography to obtain 4.4 g of yellow solid compound A-7 (yield: 22%). (M.P.=242° C., deposition temperature (DT)=320° C.)

Compound 1-1 (2.8 g, 9.6 mmol), compound 1-8 (5.0 g, 14.5 mmol), 4,5-bis(diphenylphosphino)-9,9-dimethylxanthene (xantphos) ligand (0.8 g, 1.4 mmol), sodium tert-butoxide (2.8 g, 29.0 mmol), palladium acetate (Pd(OAc)$_2$) (0.15 g, 0.6 mmol), and o-xylene (48) mL were introduced into a flask, and the mixture was refluxed for 18 hours. The reaction solution was cooled to room temperature, extracted with water and ethyl acetate, and dried in vacuum to obtain a solid product. The obtained solid compound was purified by column chromatography to obtain 1.5 g of yellow solid compound A-9 (yield: 26%). (M.P.=240° C., deposition temperature (DT)=306° C.)

Example 8: Preparation of Compound A-21

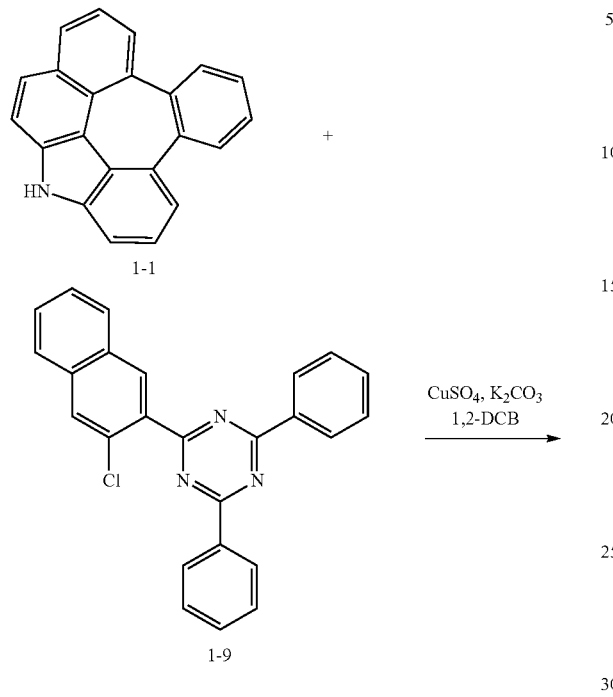

Example 9: Preparation of Compound A-61

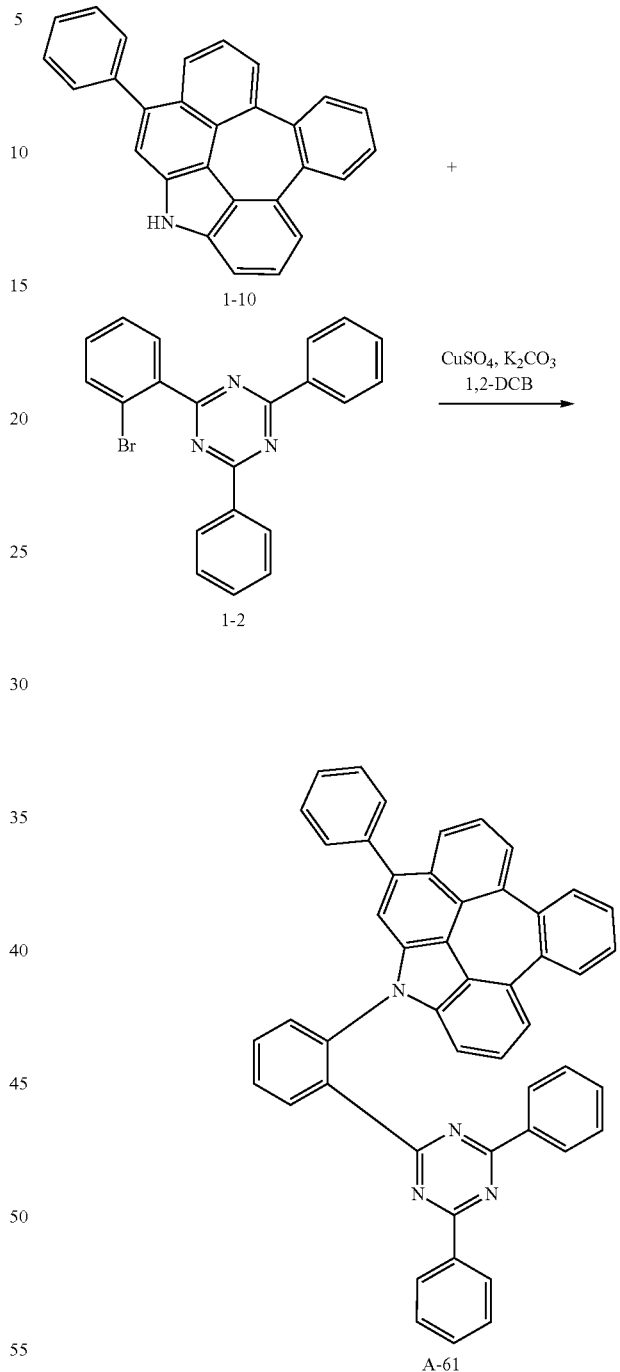

Compound 1-1 (9.0 g, 30.9 mmol), compound 1-9 (12.2 g, 30.9 mmol), copper sulfate (2.5 g, 15.4 mmol), potassium carbonate (8.5 g, 61.8 mmol), and o-dichlorobenzene (150 mL) were introduced into a flask, and the mixture was refluxed for 18 hours. The reaction solution was cooled to room temperature and added dropwise to methanol (4 L) to obtain a solid product. The obtained solid compound was purified by column chromatography to obtain 13.1 g of yellow solid compound A-21 (yield: 65%). (M.P.=258° C., deposition temperature (DT)=331° C.)

Compound 1-10 (5.0 g, 13.6 mmol), compound 1-2 (5.8 g, 15.0 mmol), copper sulfate (0.87 g, 5.4 mmol), potassium carbonate (3.76 g, 27.2 mmol), and o-dichlorobenzene (70 mL) were introduced into a flask, and the mixture was refluxed for 18 hours. The reaction solution was cooled to room temperature and added dropwise to methanol (4 L) to obtain a solid product. The obtained solid compound was purified by column chromatography to obtain 3.0 g of yellow solid compound A-61 (yield: 33%). (M.P.=266° C., deposition temperature (DT)=319° C.)

Example 10: Preparation of Compound A-71

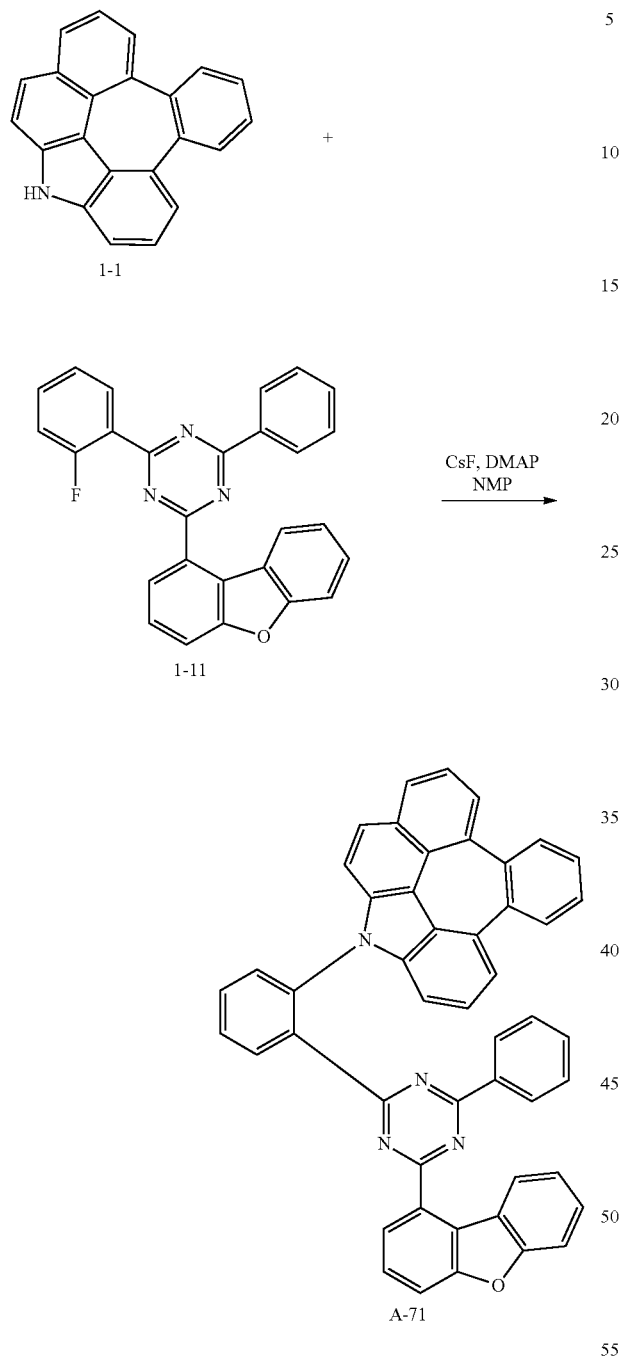

Example 11: Preparation of Compound A-82

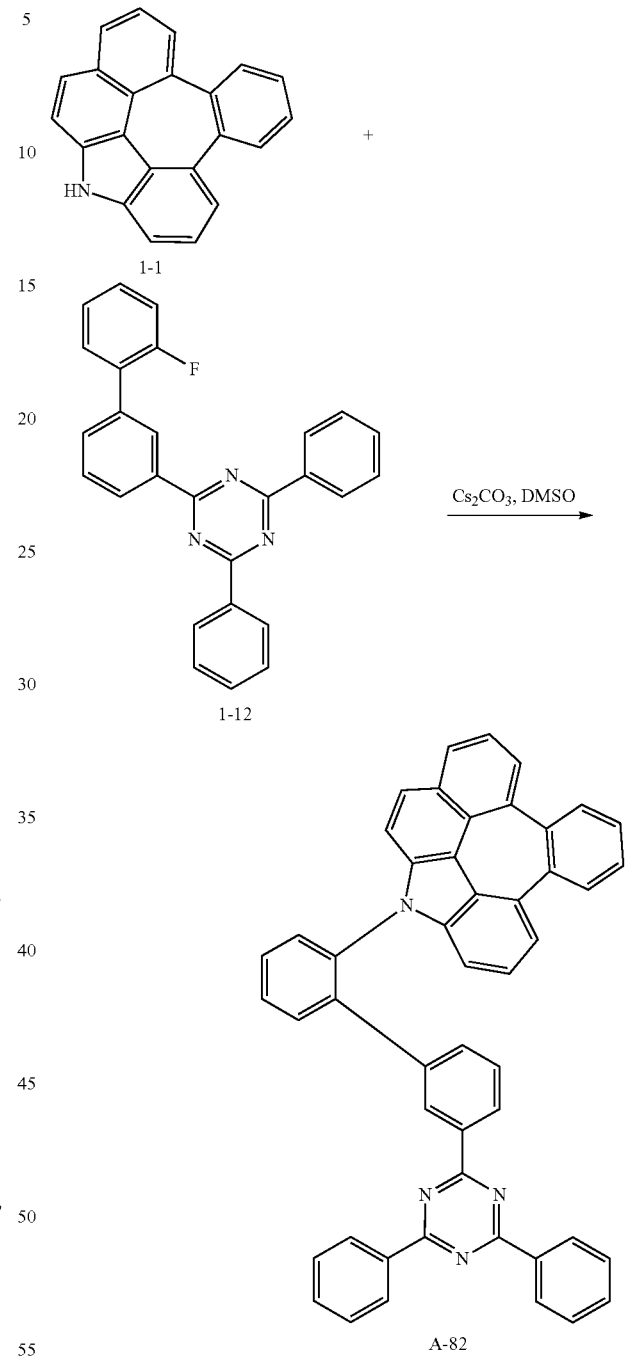

Compound 1-1 (7.2 g, 24.7 mmol), compound 1-11 (10.3 g, 24.7 mmol), cesium fluoride (18.8 g, 123.4 mmol), 4-dimethylaminopyridine (DMAP) (0.15 g, 1.23 mmol), and 1-methyl-2-pyrrolidinone (NMP) (125 mL) were introduced into a flask, and the mixture was refluxed for 18 hours. The reaction solution was cooled to room temperature and added dropwise to methanol (4 L) to obtain a solid product. The obtained solid compound was purified by column chromatography to obtain 7.7 g of yellow solid compound A-71 (yield: 45%). (M.P.=153° C., deposition temperature (DT)= 317° C.)

Compound 1-1 (5.2 g, 17.7 mmol), compound 1-12 (6.0 g, 14.9 mmol), cesium carbonate (12.1 g, 37.2 mmol), and dimethyl sulfoxide (DMSO) (100 mL) were introduced into a flask, and the mixture was refluxed for 18 hours. The reaction solution was cooled to room temperature and added dropwise to methanol (4 L) to obtain a solid product. The obtained solid compound was purified by column chromatography to obtain 1.8 g of yellow solid compound A-82 (yield: 18%). (M.P.=271° C., deposition temperature (DT)= 318° C.)

Example 12: Preparation of Compound A-84

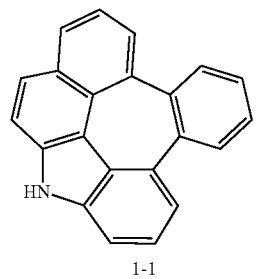
1-1

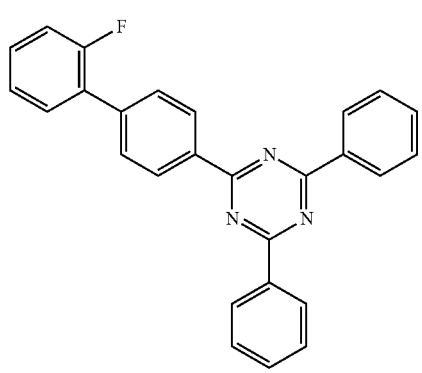
1-13

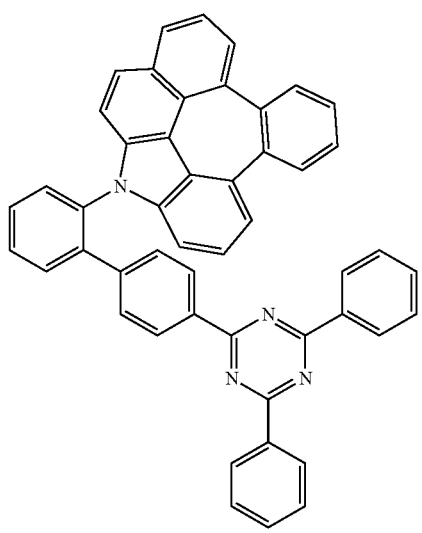
A-84

Compound 1-1 (5.2 g, 17.7 mmol), compound 1-13 (6.0 g, 14.9 mmol), cesium carbonate (14.5 g, 44.6 mmol), and dimethyl sulfoxide (100 mL) were introduced into a flask, and the mixture was refluxed for 18 hours. The reaction solution was cooled to room temperature and added dropwise to methanol (4 L) to obtain a solid product. The obtained solid compound was purified by column chromatography to obtain 1.4 g of yellow solid compound A-84 (yield: 14%). (M.P.=177° C., deposition temperature (DT)= 354° C.)

Example 13: Preparation of Compound A-101

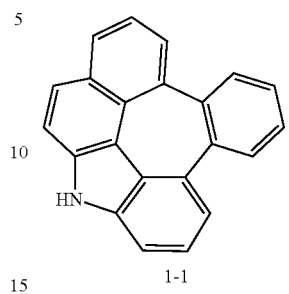
1-1

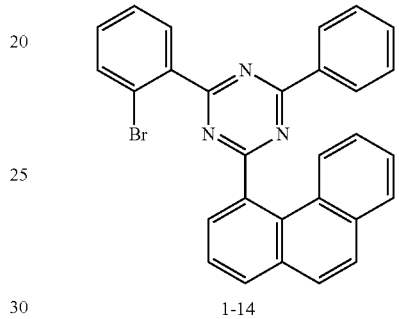
1-14

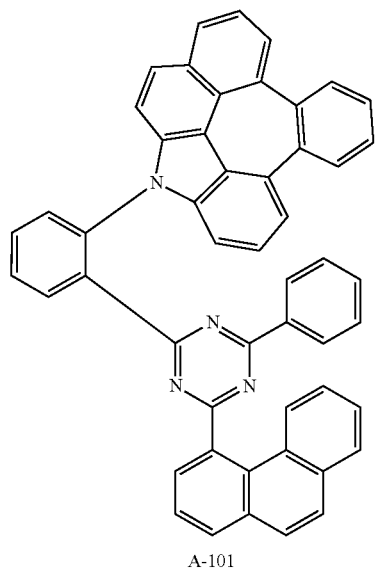
A-101

Compound 1-1 (4.5 g, 15.4 mmol), compound 1-14 (6.6 g, 15.4 mmol), cesium fluoride (11.7 g, 77.2 mmol), 4-dimethylaminopyridine (0.1 g, 0.77 mmol), and 1-methyl-2-pyrrolidinone (80 mL) were introduced into a flask, and the mixture was refluxed for 18 hours. The reaction solution was cooled to room temperature and added dropwise to methanol (4 L) to obtain a solid product. The obtained solid compound was purified by column chromatography to obtain 6.4 g of yellow solid compound A-101 (yield: 59%). (M.P.=156° C., deposition temperature (DT)=332° C.)

Example 14: Preparation of Compound A-102

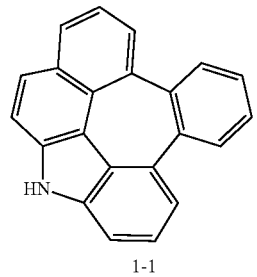

1-1

+

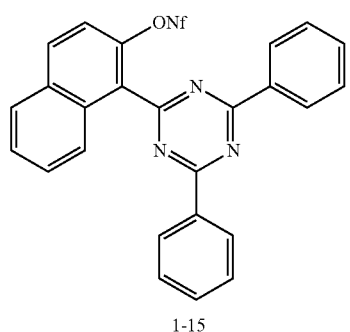

1-15

→ CuSO₄, K₃PO₄
1,2-DCB

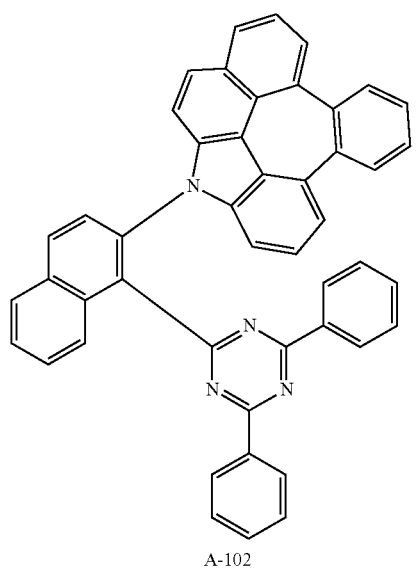

A-102

Compound 1-1 (6.8 g, 23.3 mmol), compound 1-15 (12.8 g, 19.4 mmol), copper sulfate (1.5 g, 9.7 mmol), tripotassium phosphate (8.2 g, 38.8 mmol), and o-dichlorobenzene (100 mL) were introduced into a flask, and the mixture was refluxed for 18 hours. The reaction solution was cooled to room temperature and added dropwise to methanol (4 L) to obtain a solid product. The obtained solid compound was purified by column chromatography to obtain 3.0 g of yellow solid compound A-102 (yield: 24%). (M.P.=159° C., deposition temperature (DT)=324° C.)

Example 15: Preparation of Compound A-103

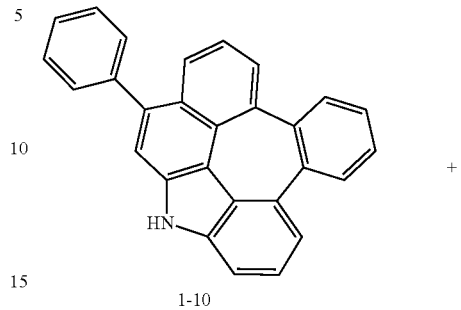

1-10

+

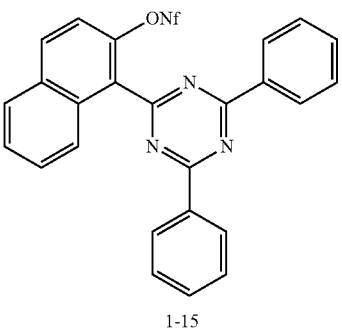

1-15

→ CuSO₄, K₃PO₄
1,2-DCB

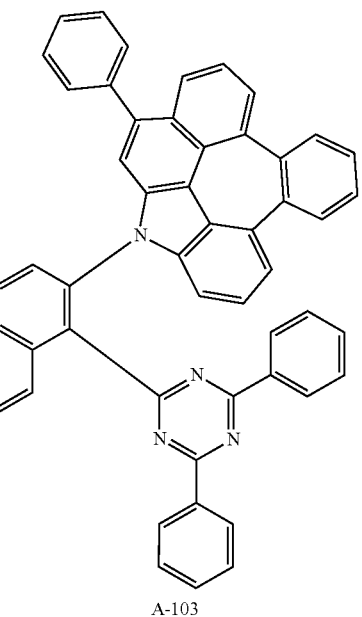

A-103

Compound 1-10 (13.4 g, 36.5 mmol), compound 1-15 (20.0 g, 30.4 mmol), copper sulfate (2.4 g, 15.2 mmol), tripotassium phosphate (12.9 g, 60.8 mmol), and o-dichlorobenzene (160 mL) were introduced into a flask, and the mixture was refluxed for 18 hours. The reaction solution was cooled to room temperature and added dropwise to methanol (4 L) to obtain a solid product. The obtained solid compound was purified by column chromatography to obtain 3 g of yellow solid compound A-103 (yield: 14%). (M.P.=325° C., deposition temperature (DT)=349° C.)

Example 16: Preparation of Compound A-104

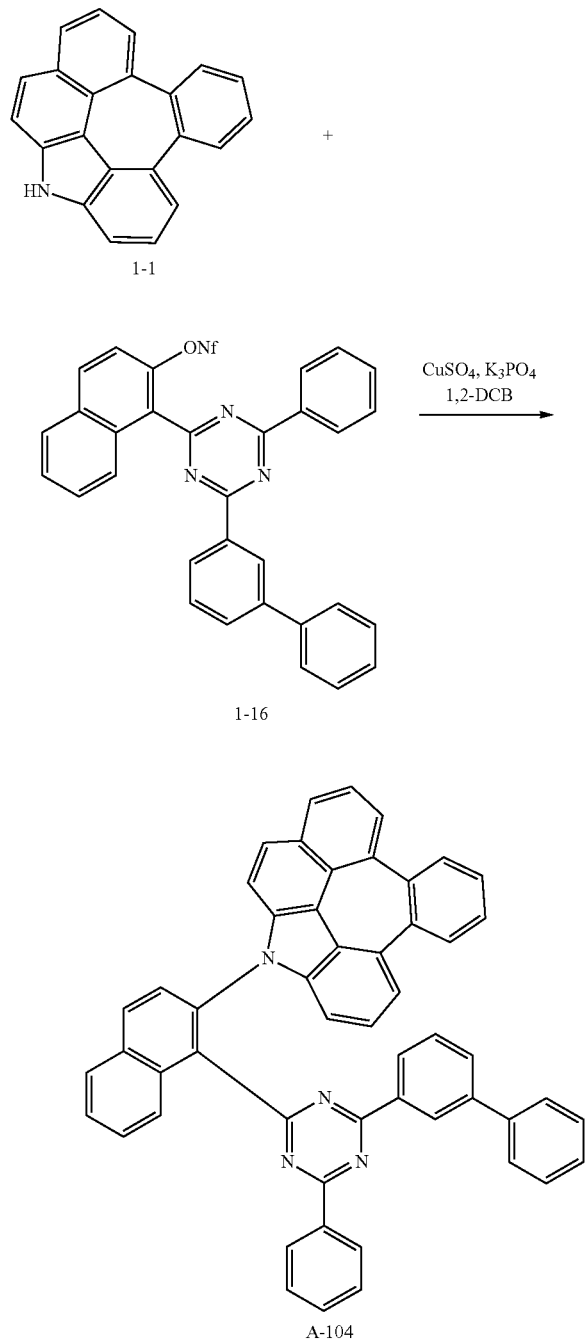

Compound 1-1 (12.0 g, 40.9 mmol), compound 1-16 (25.0 g, 34.1 mmol), copper sulfate (2.7 g, 17.1 mmol), tripotassium phosphate (14.5 g, 68.2 mmo), and o-dichlorobenzene (230 mL) were introduced into a flask, and the mixture was refluxed for 18 hours. The reaction solution was cooled to room temperature and added dropwise to methanol (5 L) to obtain a solid product. The obtained solid compound was purified by column chromatography to obtain 7.5 g of yellow solid compound A-104 (yield: 28%). (M.P.=238° C., deposition temperature (DT)=350° C.)

Example 17: Preparation of Compound A-105

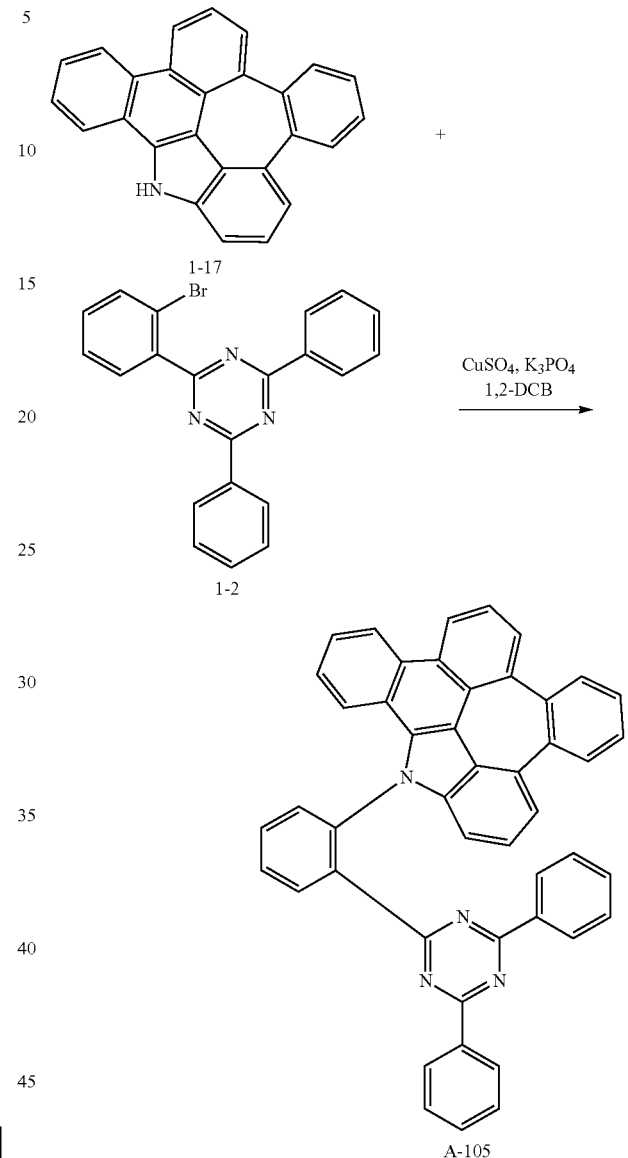

Compound 1-17 (17.0 g, 49.8 mmol), compound 1-2 (19.3 g, 49.8 mmol), copper sulfate (4.0 g, 24.9 mmol), potassium carbonate (13.8 g, 99.6 mmol), and o-dichlorobenzene (250 mL) were introduced into a flask, and the mixture was refluxed for 18 hours. The reaction solution was cooled to room temperature and added dropwise to methanol (5 L) to obtain a solid product. The obtained solid compound was purified by column chromatography to obtain 8.4 g of yellow solid compound A-105 (yield: 26%). (M.P.=267° C., deposition temperature (DT)=302° C.)

Comparative Example: Producing an OLED Deposited with a Comparative Compound as a Host An OLED comprising a comparative compound was produced as follows: A transparent electrode indium tin oxide (ITO) thin film (10 Ω/sq) on a glass substrate for an OLED (GEOMATEC CO., LTD., Japan) was subjected to an ultrasonic washing with acetone, ethanol, and distilled water, sequentially, and then was stored in isopropyl alcohol. The ITO substrate was mounted on a substrate holder of a vacuum vapor deposition apparatus. Compound HI-1 was introduced into a cell of the vacuum vapor deposition apparatus, and the pressure in the chamber of the apparatus was then controlled to $10^{-8}$ torr. Thereafter, an electric current was applied to the cell to evaporate the above-introduced material, thereby forming a first hole injection layer having a thickness of 80 nm on the ITO substrate. Next, compound HI-2 was introduced into another cell of the vacuum vapor deposition apparatus and was evaporated by applying an electric current to the cell, thereby forming a second hole injection layer having a thickness of 5 nm on the first hole injection layer. Compound HT-1 was then introduced into another cell of the vacuum vapor deposition apparatus and was evaporated by applying an electric current to the cell, thereby forming a first hole transport layer having a thickness of 10 nm on the second hole injection layer. Compound HT-2 was then introduced into another cell of the vacuum vapor deposition apparatus and was evaporated by applying an electric current to the cell, thereby forming a second hole transport layer having a thickness of 60 nm on the first hole transport layer. After forming the hole injection layers and the hole transport layers, a light-emitting layer was formed thereon as follows: The compound shown in Table 1 was introduced into one cell of the vacuum vapor depositing apparatus as a host, and compound D-39 was introduced into another cell as a dopant. The two materials were evaporated at different rates, and respectively deposited in a doping amount of 3 wt % based on the total amount of the host and dopant to form a light-emitting layer having a thickness of 40 nm on the second hole transport layer. Next, compound ET-1 and compound EI-1 were evaporated at a rate of 1:1 in two other cells to deposit an electron transport layer having a thickness of 35 nm on the light-emitting layer. After depositing compound EI-1 as an electron injection layer having a thickness of 2 nm on the electron transport layer, an Al cathode having a thickness of 80 nm was deposited on the electron injection layer by another vacuum vapor deposition apparatus. Thus, an OLED was produced.

The melting point (M.P.) and deposition temperature (DT) of the host compound used in the preparation process above are 285° C. and 350° C., respectively.

Device Examples 1 to 5: Producing an OLED Deposited with a Compound According to the Present Disclosure as a Host An OLED was produced in the same manner as in the Comparative Example, except that the compound shown in Table 1 was used as a host of the light-emitting layer.

The driving voltage, luminous efficiency, and CIE color coordinates at a luminance of 1,000 nit of the OLEDs produced in the Comparative Example and Device Examples 1 to 5, and the deposition temperature (DT) of the compounds used are provided in Table 1 below.

TABLE 1

|  | Host | Driving Voltage (V) | Luminous Efficiency (cd/A) | Color Coordinate (x) | Color Coordinate (y) | Deposition Temperature (DT) |
| --- | --- | --- | --- | --- | --- | --- |
| Comparative Example | R-1 | 2.8 | 30.2 | 0.658 | 0.341 | 350° C. |
| Device Example 1 | A-2 | 3.1 | 32.2 | 0.660 | 0.340 | 300° C. |
| Device Example 2 | A-1 | 3.1 | 32.2 | 0.659 | 0.340 | 300° C. |
| Device Example 3 | A-4 | 3.2 | 31.8 | 0.659 | 0.340 | 330° C. |
| Device Example 4 | A-5 | 3.0 | 32.5 | 0.660 | 0.339 | 330° C. |
| Device Example 5 | A-7 | 3.2 | 32.1 | 0.659 | 0.340 | 320° C. |

The OLED produced by using the organic electroluminescent compound according to the present disclosure as a host had lower deposition temperature and higher luminous efficiency compared to the OLED produced by using the comparative compound as a host.

Without intending to be limited by theory, in a compound wherein a fused structure comprising azaazulene and a nitrogen-containing 6-membered heterocyclic structure are bonded via a linker, when the linker is a phenylene or a fused phenylene, and the fused structure comprising azaazulene and the nitrogen-containing 6-membered heterocyclic structure are bonded to each other in ortho position, the planes of the two structures are twisted, and thus the HOMO and LUMO values increase. Accordingly, compared to the meta and para positions, it is understood that electrons and holes can be more efficiently transported to the dopant.

In addition, without intending to be limited by theory, within a molecule of an organic electroluminescent compound, in accordance with two planes being twisted, crystallinity may be lowered due to a decrease of the interaction between molecules. Thus, the melting point of the compound is lowered, thereby enabling the decrease of clogging in deposition.

Further, due to the decrease of the deposition temperature of the host compound, the deposition of the material at low temperature is possible. Thus, the decomposition of the compound in deposition can be reduced. That is, in the preparation process of the organic electroluminescent device, thermal stability can increase. FIG. 1 illustrates a three-dimensional structure of the organic electroluminescent compound of the present disclosure and the conventional organic electroluminescent compound.

TABLE 2
Organic Electroluminescent Material Used in
the Device Examples and the Comparative Example
Hole Injection Layer/
Hole Transport Layer
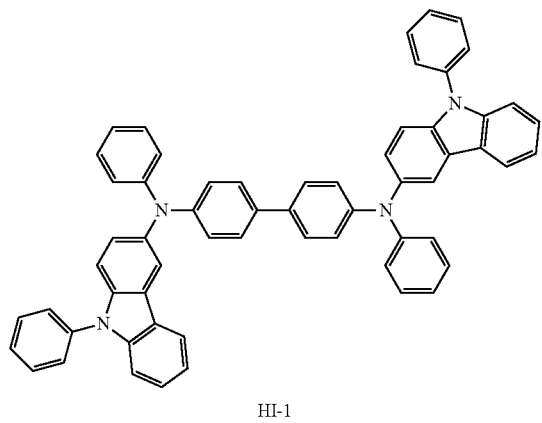 [SMILES: c1ccc(N(c2ccc(-c3ccc(N(c4ccccc4)c4ccc5c(c4)c4ccccc4n5-c4ccccc4)cc3)cc2)c2ccc3c(c2)c2ccccc2n3-c2ccccc2)cc1 ; [I-]]
HI-1
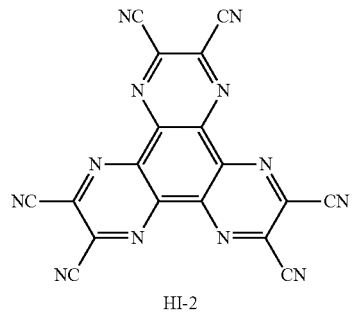
HI-2
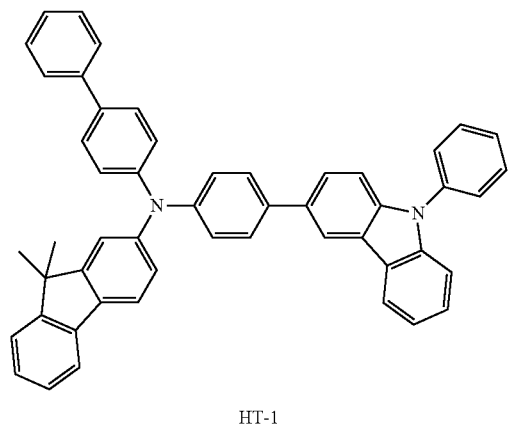
HT-1
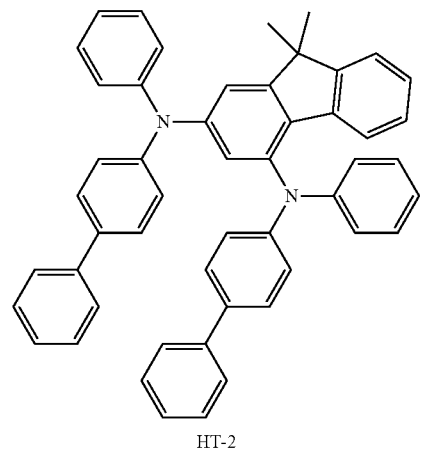
HT-2
Light-Emitting Layer
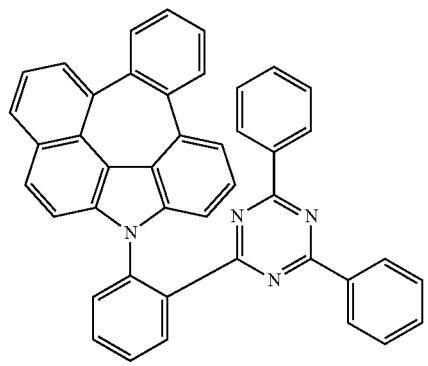
A-1
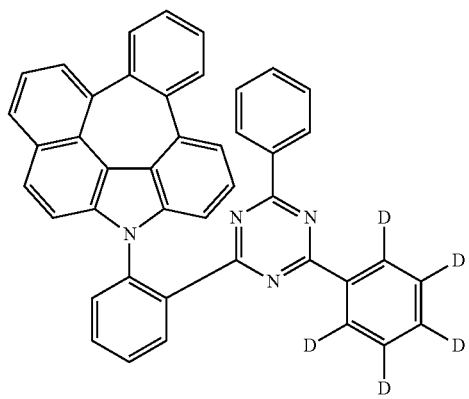
A-2

TABLE 2-continued
Organic Electroluminescent Material Used in
the Device Examples and the Comparative Example
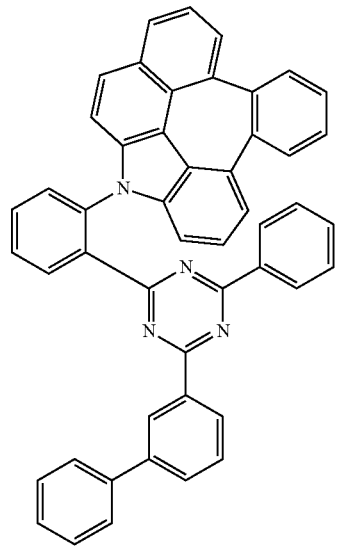
A-4
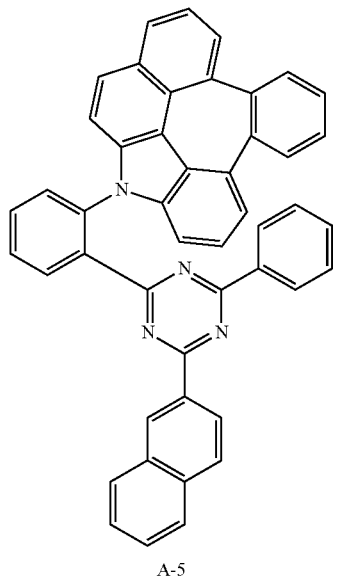
A-5
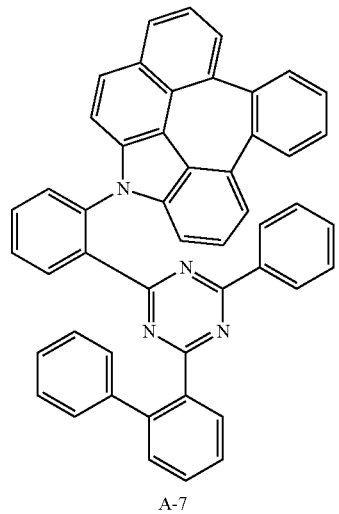
A-7
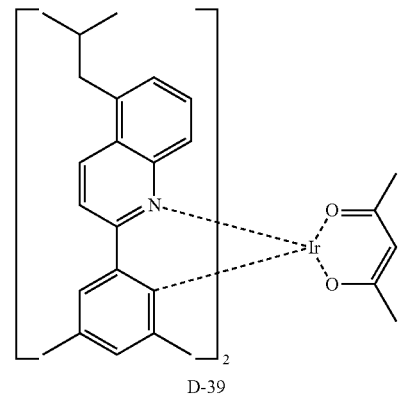
D-39

TABLE 2-continued
Organic Electroluminescent Material Used in
the Device Examples and the Comparative Example
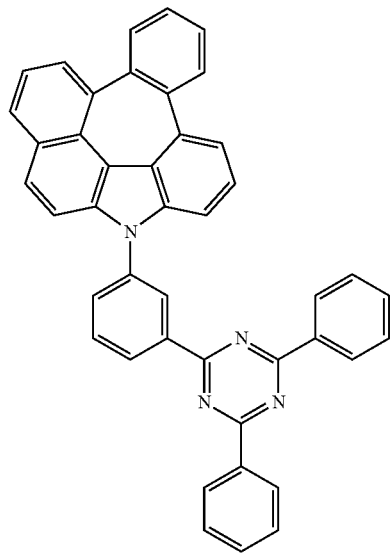
R-1
| Electron Transport Layer/ Electron injection Layer | | |
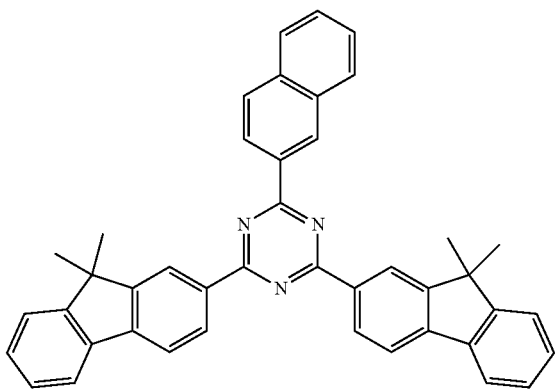
ET-1
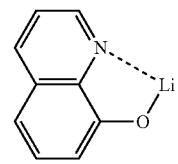
EI-1

The invention claimed is:
1. An organic electroluminescent compound represented by the following formula 1:

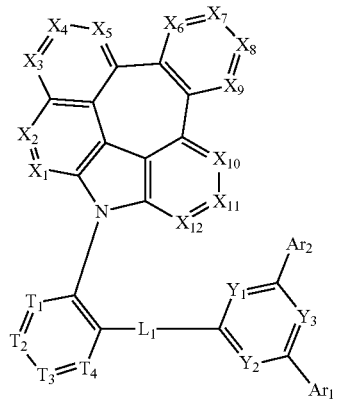

(1)

wherein
$X_1$ to $X_{12}$ each independently represent N or $CR_1$;
$T_1$ to $T_4$ each independently represent N or $CR_2$;
$Y_1$ to $Y_3$ each independently represent N or $CR_3$, in which at least one of $Y_1$ to $Y_3$ is N;
$L_1$ represents a single bond, a substituted or unsubstituted (C6-C30)arylene, or a substituted or unsubstituted (3- to 30-membered)heteroarylene; and
$Ar_1$, $Ar_2$, and $R_1$ to $R_3$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent to form a ring(s), where if a plurality of $R_1$ to $R_3$ is present, each of $R_1$, each of $R_2$, and each of $R_3$ may be the same or different.

2. The organic electroluminescent compound according to claim 1, wherein substituents of the substituted (C1-C30) alkyl, the substituted (C6-C30)aryl(ene), the substituted (3- to 30-membered)heteroaryl(ene), the substituted (C3-C30) cycloalkyl, the substituted (C1-C30)alkoxy, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, the substituted mono- or di-(C1-C30)alkylamino, the substituted mono- or di-(C6-C30)arylamino, and the substituted (C1-C30)alkyl (C6-C30)arylamino in $L_1$, $Ar_1$, $Ar_2$, and $R_1$ to $R_3$ each independently are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 30-membered) heteroaryl unsubstituted or substituted with a (C6-C30) aryl(s); a (C6-C30)aryl unsubstituted or substituted with a (5- to 30-membered)heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino unsubstituted or substituted with a (C1-C30)alkyl(s); a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30) alkyl(C6-C30)arylboronyl; a (C6-C30)aryl(C1-C30)alkyl; and a (C1-C30)alkyl(C6-C30)aryl.

3. The organic electroluminescent compound according to claim 1, wherein formula 1 is represented by the following formula 2 or formula 3:

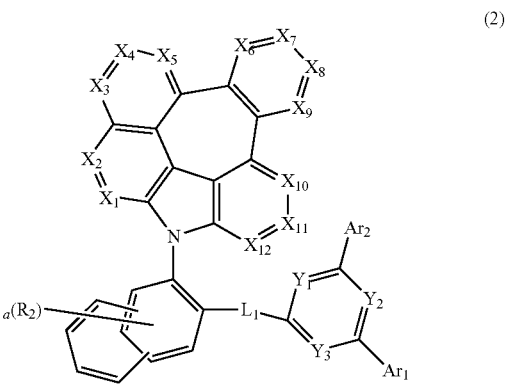

(2)

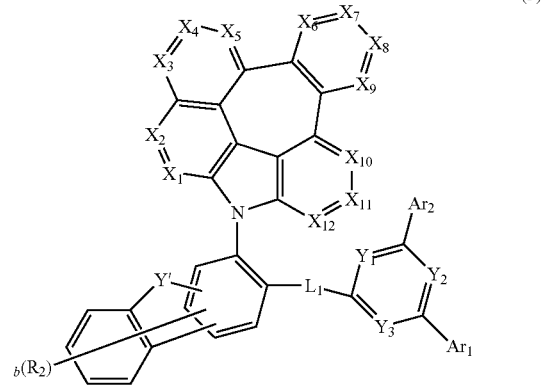

(3)

wherein
a and b each independently represent an integer of 1 to 6, in which, if a and b are an integer of 2 or more, each of $R_2$ may be the same or different;
Y' represents $CR_4R_5$, O, or S;
$R_4$ and $R_5$ each independently represent a substituted or unsubstituted (C1-C30)alkyl, or a substituted or unsubstituted (C6-C30)aryl; and
$X_1$ to $X_{12}$, $Y_1$ to $Y_3$, $L_1$, $Ar_1$, and $Ar_2$ are as defined in claim 1.

4. The organic electroluminescent compound according to claim 1, wherein
$X_1$ to $X_{12}$ each independently represent N or $CR_1$;
$T_1$ to $T_4$ each independently represent N or $CR_2$;
$Y_1$ to $Y_3$ each independently represent N or $CR_3$, in which at least one of $Y_1$ to $Y_3$ is N;
$L_1$ represents a single bond, a substituted or unsubstituted (C6-C12)arylene, or a substituted or unsubstituted (5- to 15-membered)heteroarylene;

Ar₁ and Ar₂ each independently represent a substituted or unsubstituted (C6-C18)aryl, or a substituted or unsubstituted (5- to 15-membered)heteroaryl; and R₁ to R₃ each independently represent hydrogen, a substituted or unsubstituted (C6-C12)aryl, or a substituted or unsubstituted (5- to 15-membered)heteroaryl; or may be linked to an adjacent substituent to form a ring(s).

5. The organic electroluminescent compound according to claim 1, wherein

X₁ to X₁₂ each independently represent CR₁;

T₁ to T₄ each independently represent N or CR₂;

Y₁ to Y₃ each independently represent N or CR₃, in which at least one of Y₁ to Y₃ is N;

L₁ represents a single bond, an unsubstituted (C6-C12) arylene, or an unsubstituted (5- to 15-membered)heteroarylene;

Ar₁ and Ar₂ each independently represent a (C6-C18)aryl unsubstituted or substituted with one or more deuterium, or an unsubstituted (5- to 15-membered)heteroaryl; and R₁ to R₃ each independently represent hydrogen, an unsubstituted (C6-C12)aryl, or an unsubstituted (5- to 15-membered)heteroaryl; or may be linked to an adjacent substituent to form a ring(s).

6. The organic electroluminescent compound according to claim 1, wherein the compound represented by formula 1 is selected from the following:

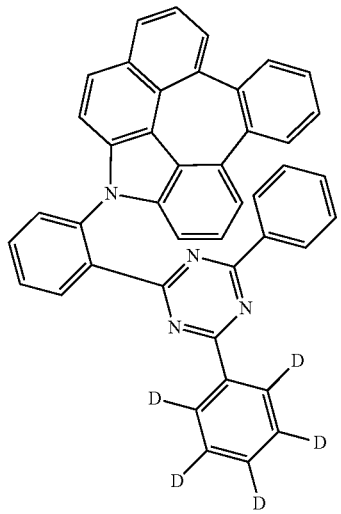

A-2

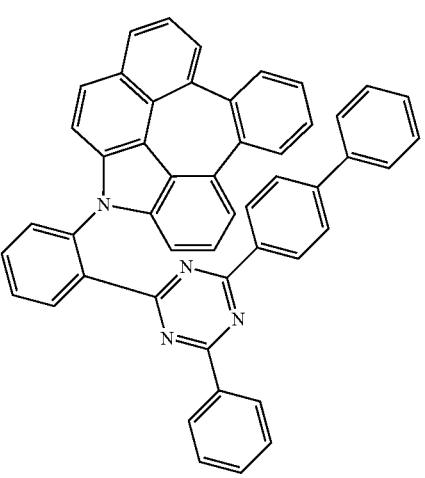

A-3

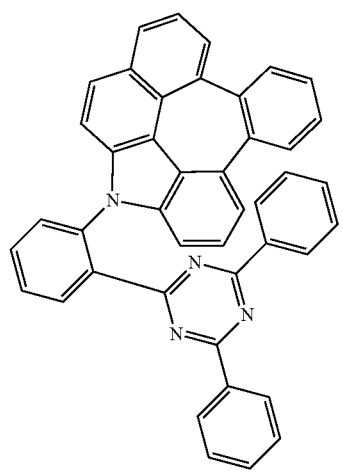

A-1

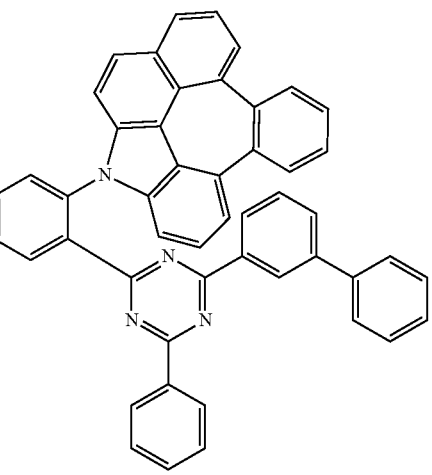

A-4

A-5
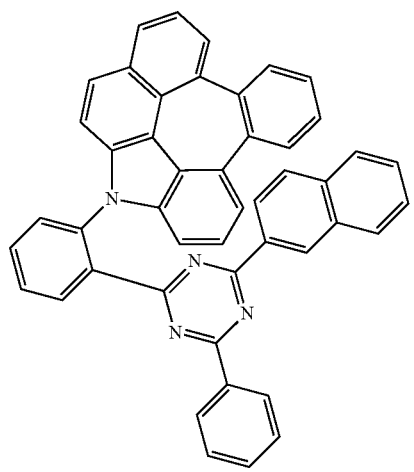
A-6
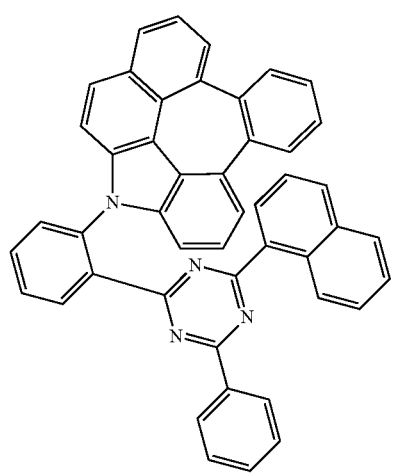
A-7
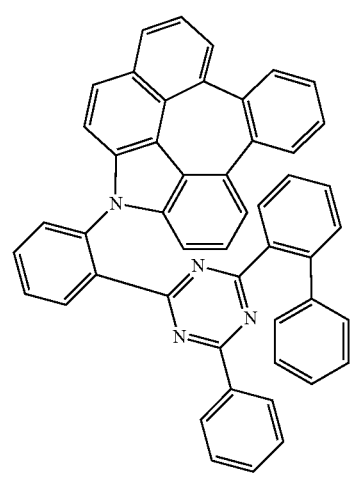
A-8
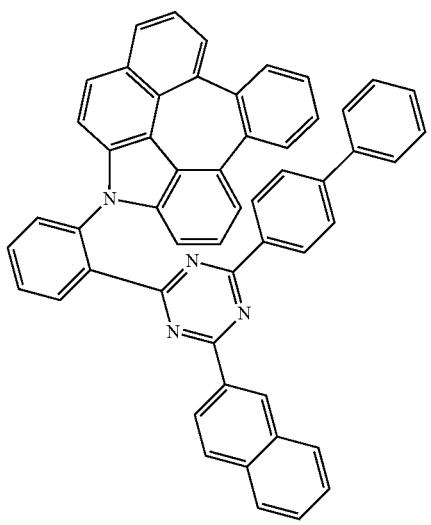
A-9
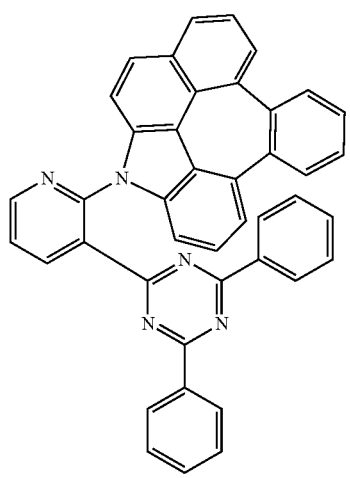
A-10
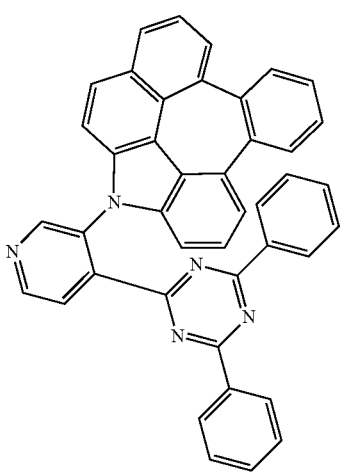

A-11
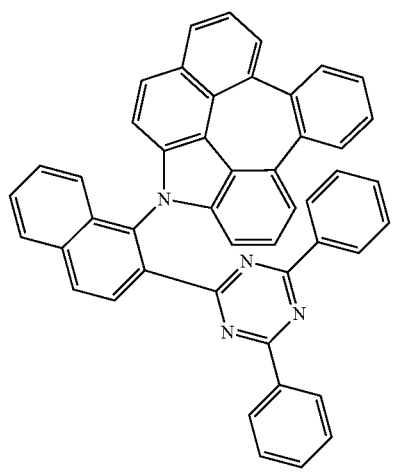
A-14
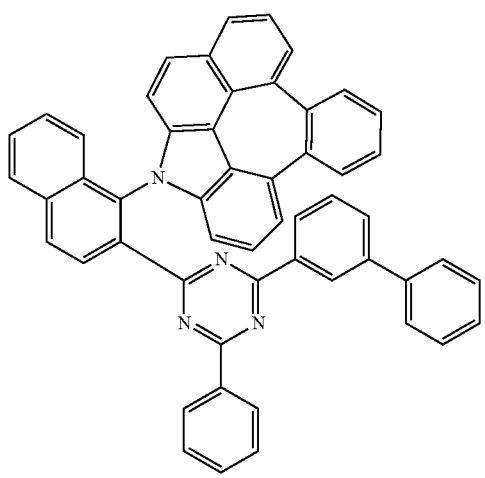
A-12
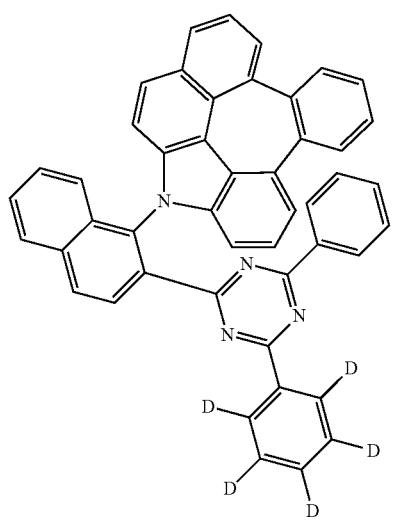
A-15
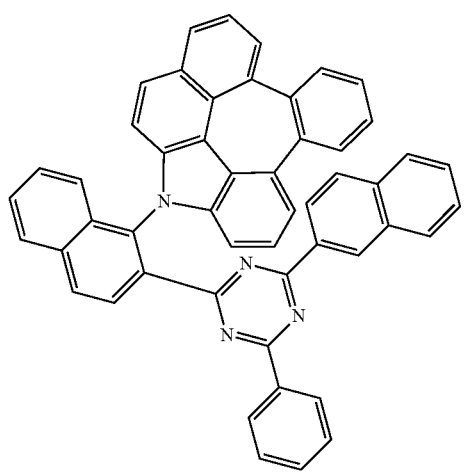
A-13
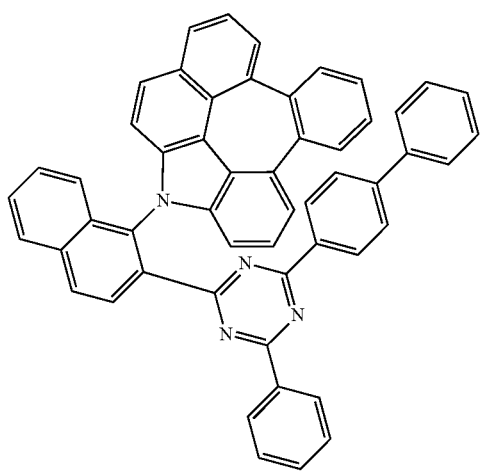
A-16
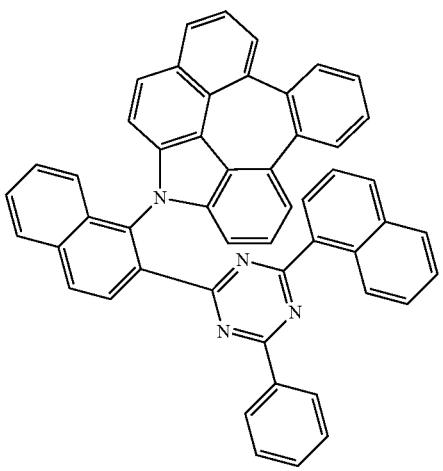

A-17
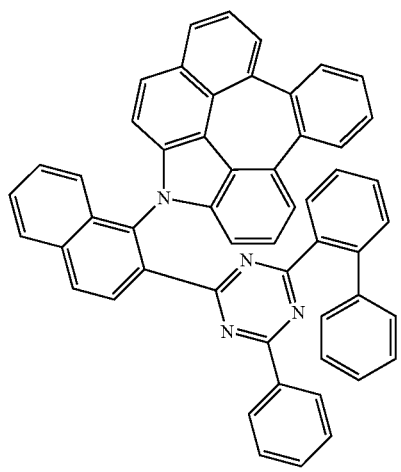
A-20
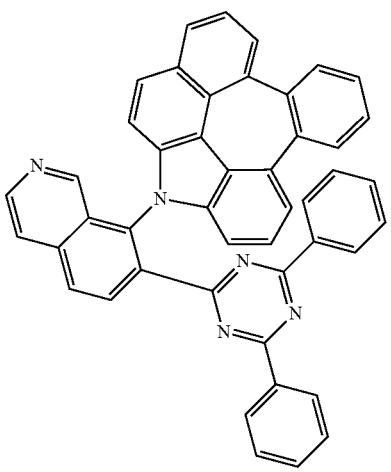
A-18
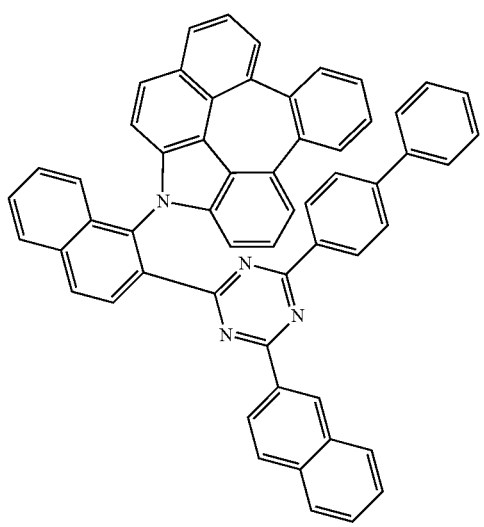
A-21
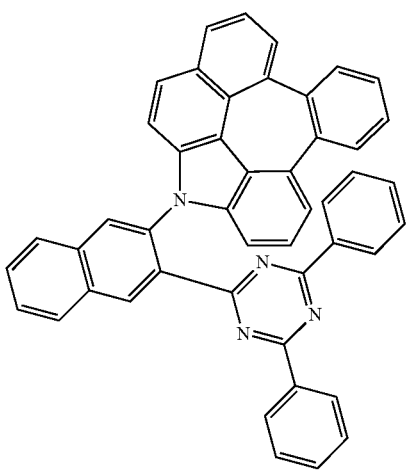
A-19
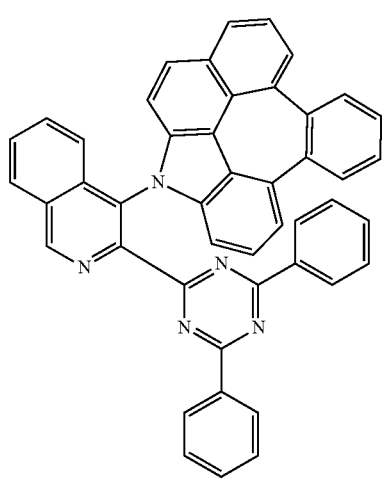
A-22
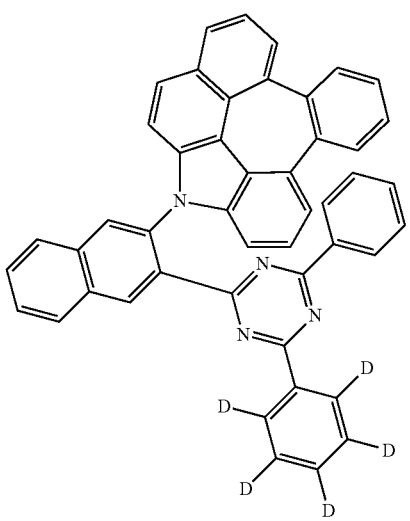

A-23
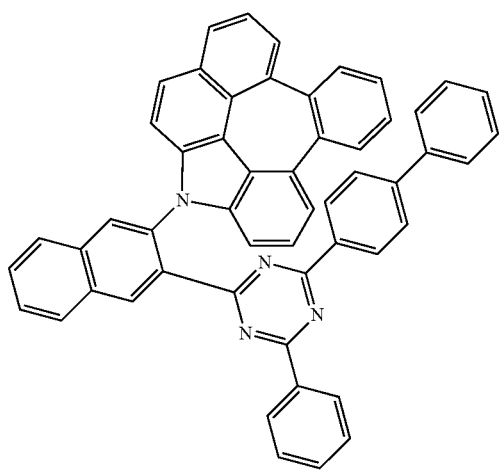
A-24
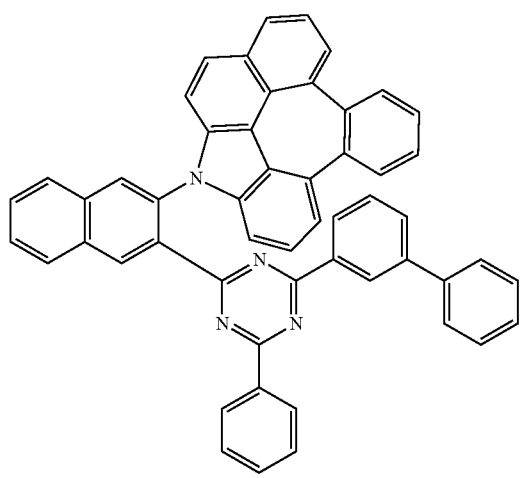
A-25
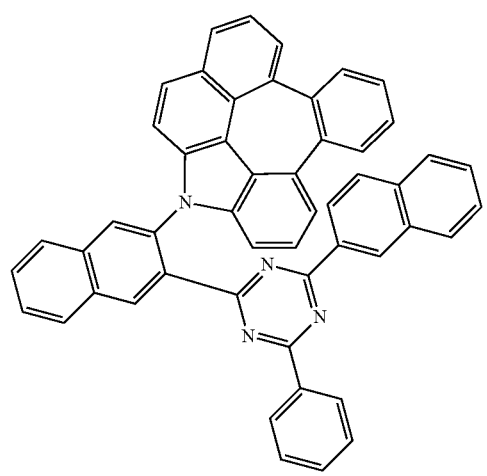
A-26
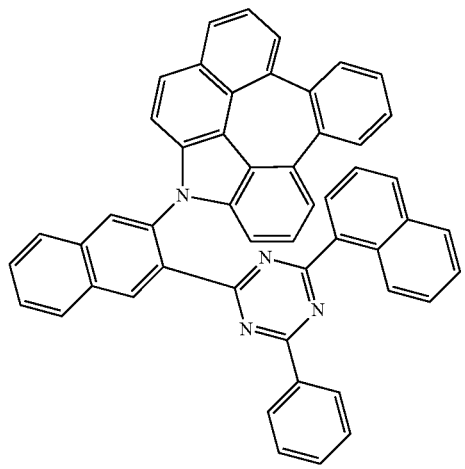
A-27
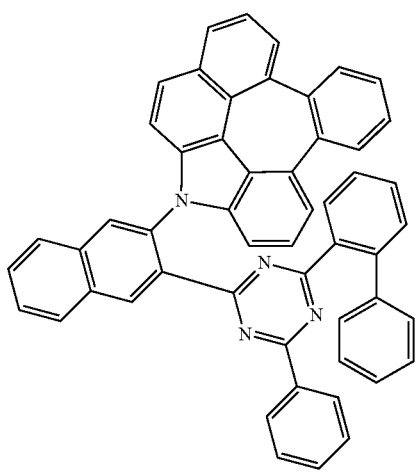
A-28
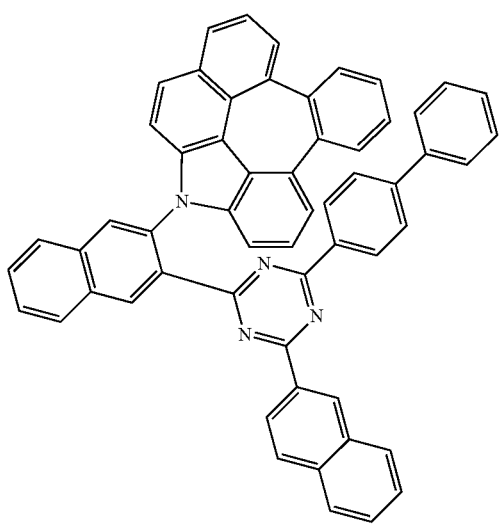

A-29
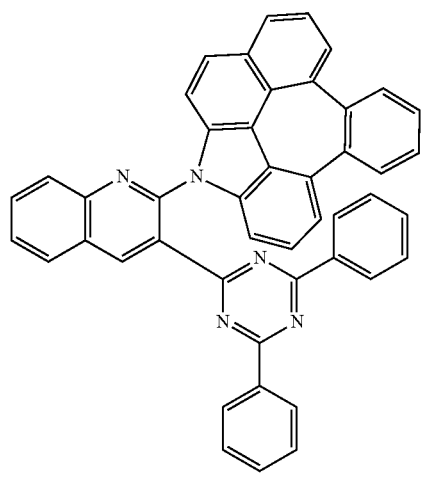
A-32
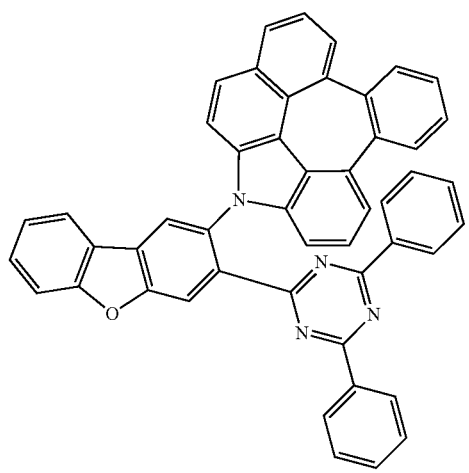
A-30
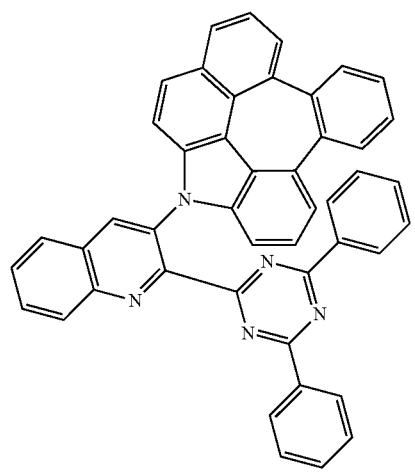
A-33
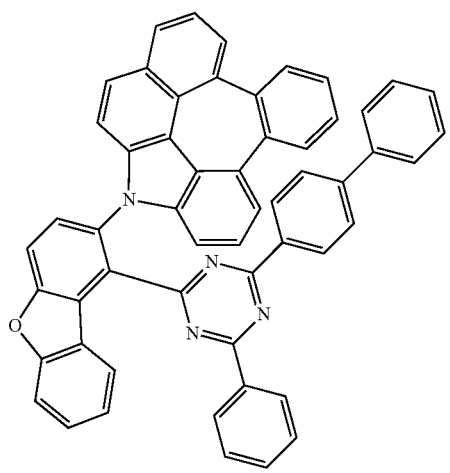
A-31
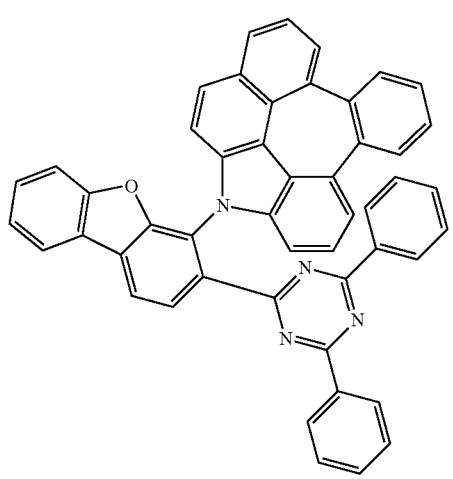
A-34
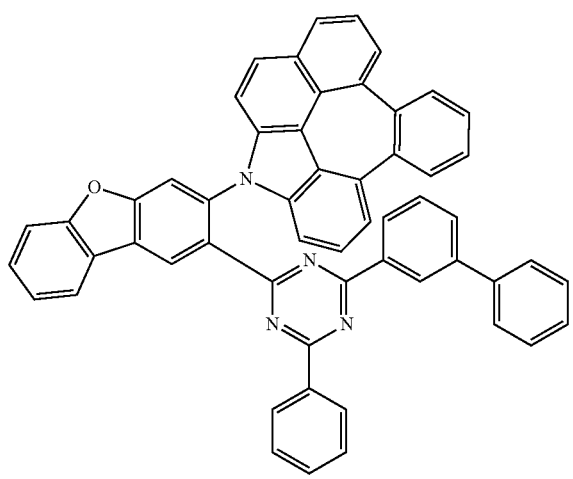

-continued
A-35
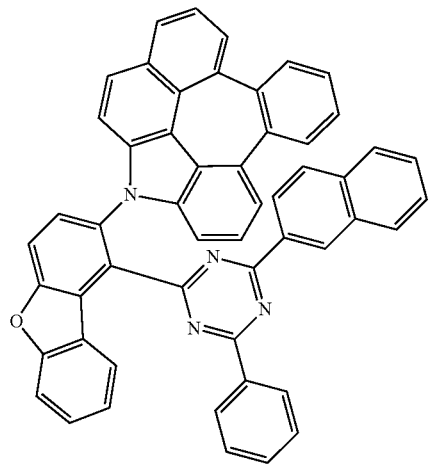
A-38
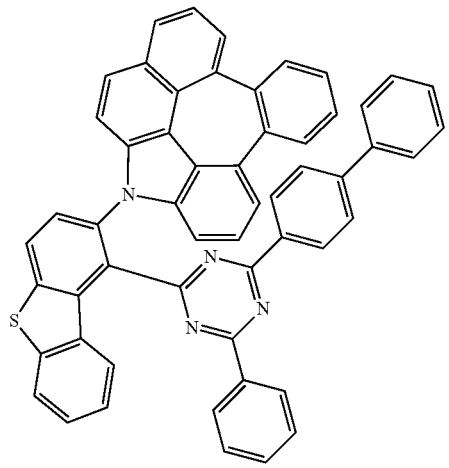
A-36
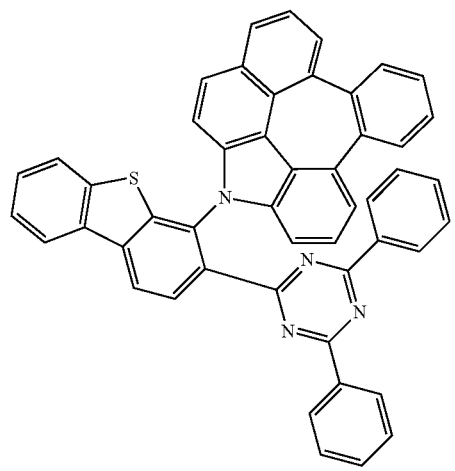
A-39
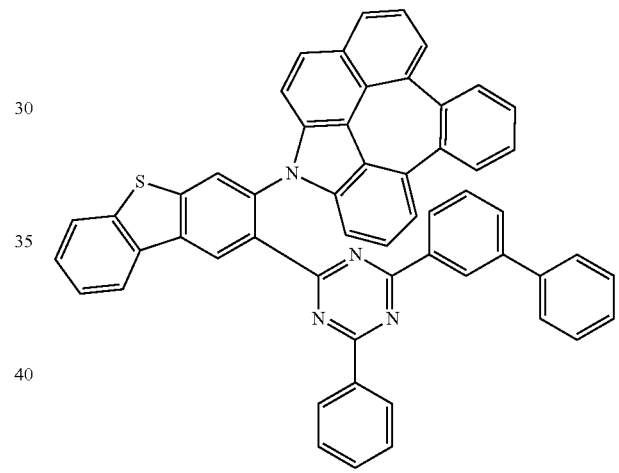
A-37
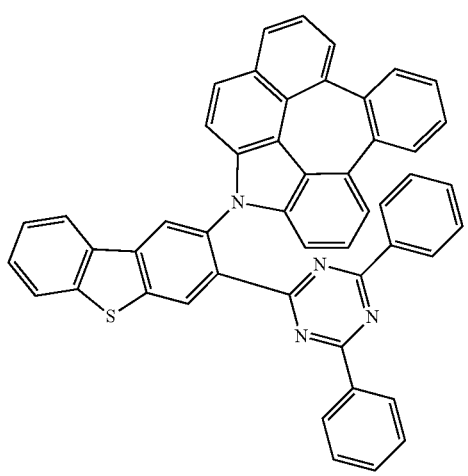
A-40
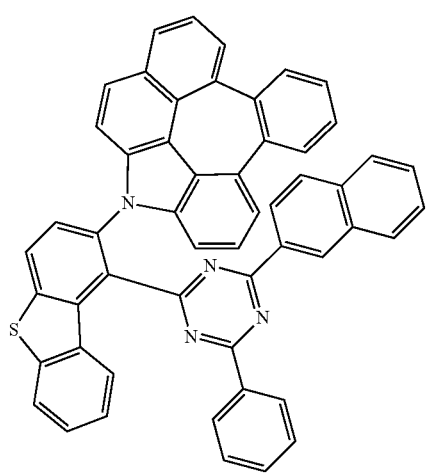

A-41
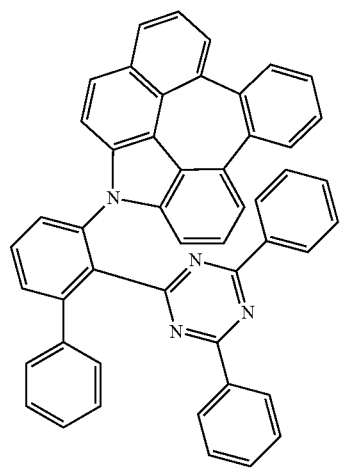
A-44
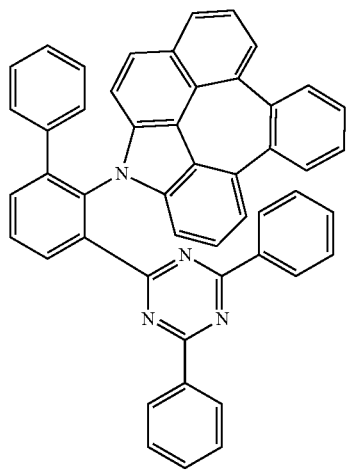
A-42
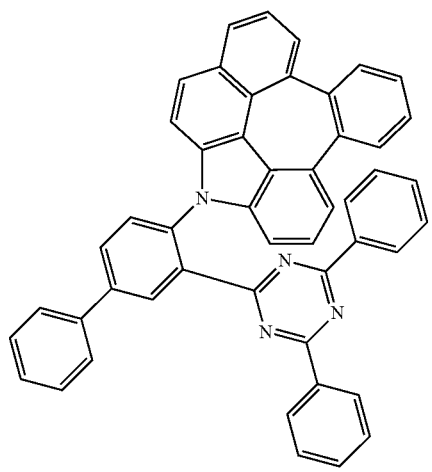
A-45
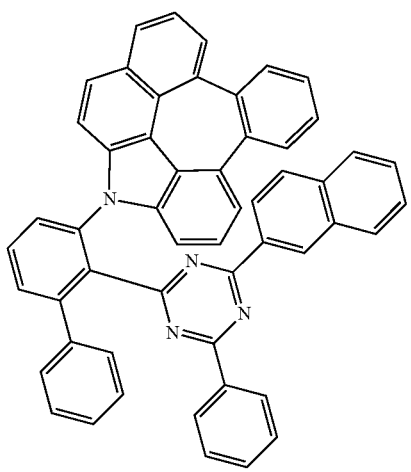
A-43
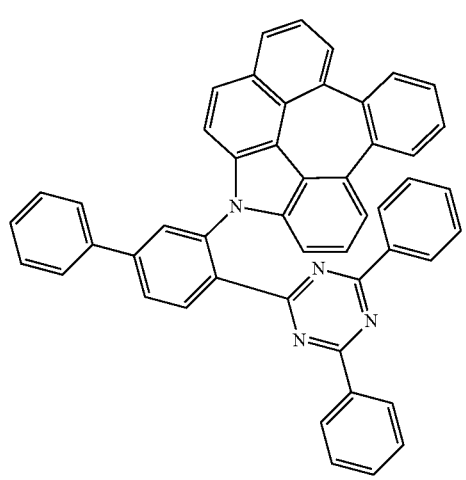
A-46
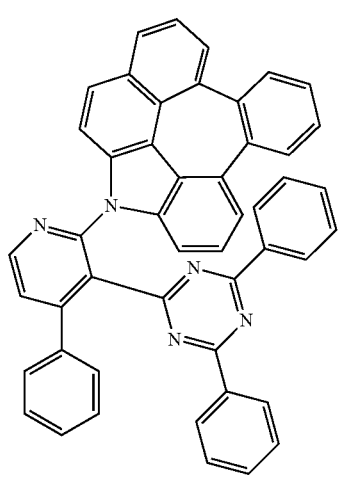

A-47
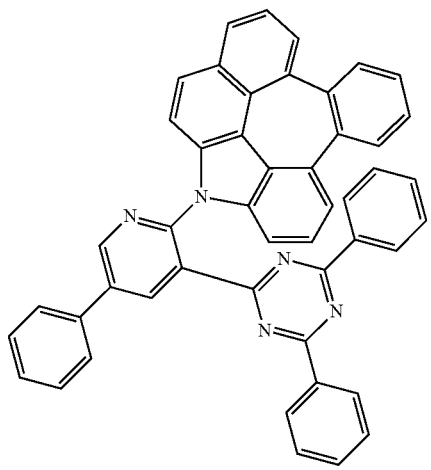
A-48
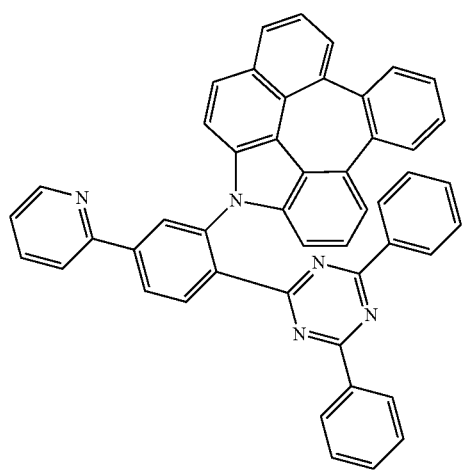
A-49
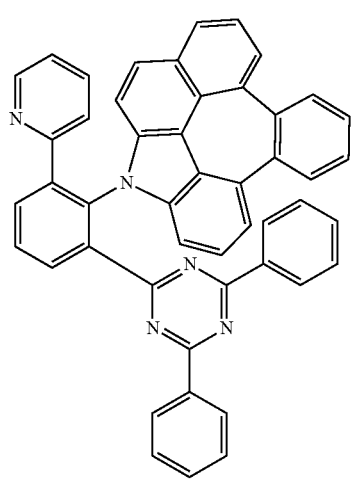
A-50
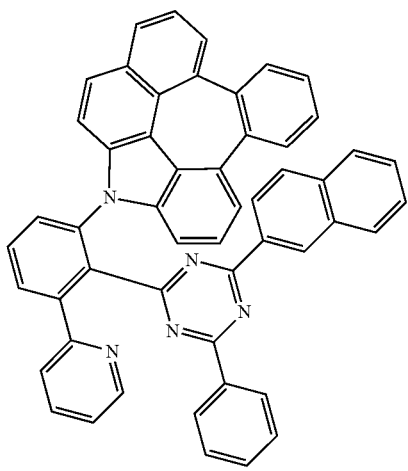
A-51
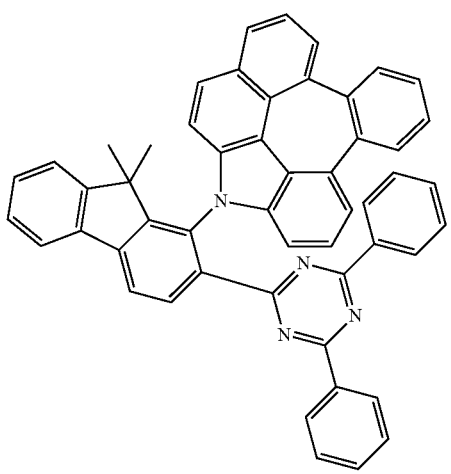
A-52

A-53
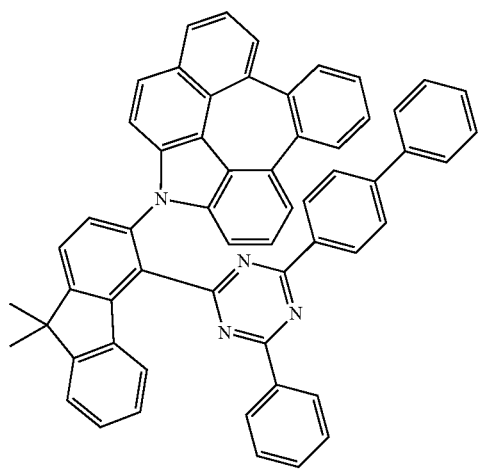
A-54
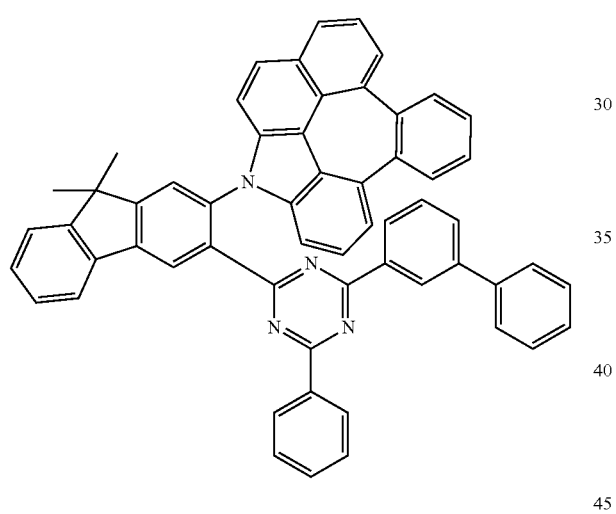
A-55
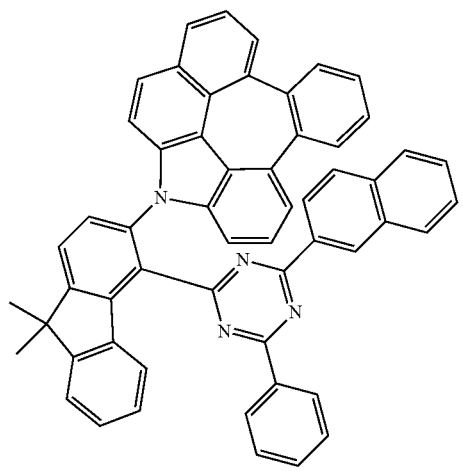
A-56
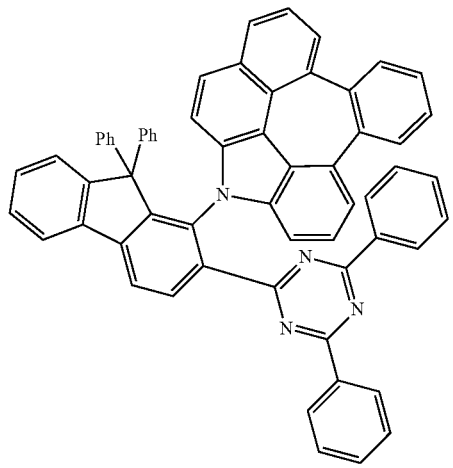
A-57
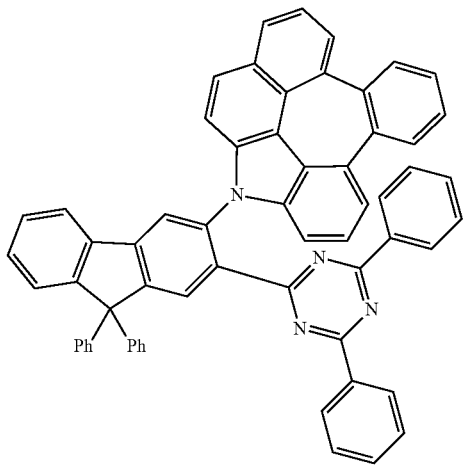
A-58
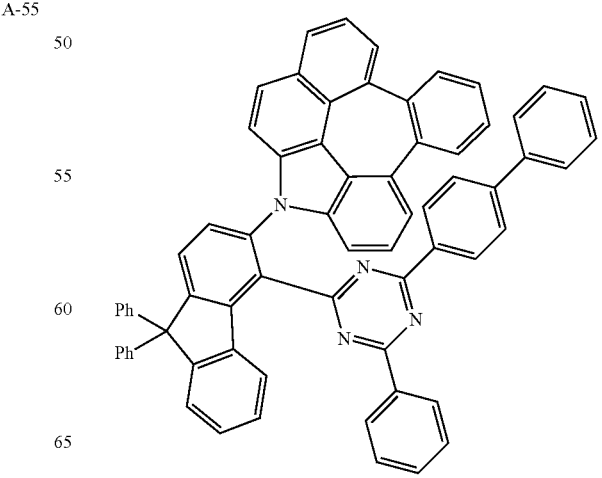

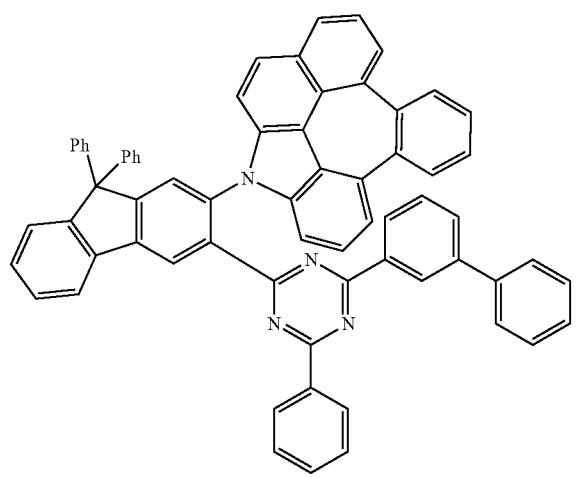
A-59
A-60
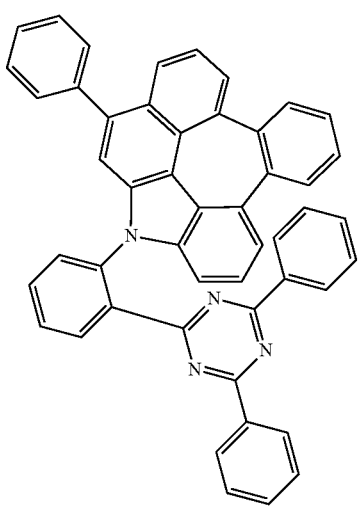
A-61
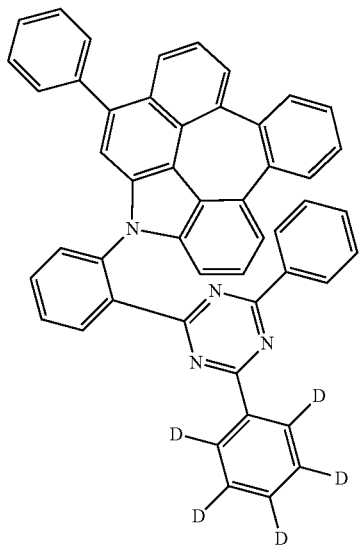
A-62
A-63
A-64

A-65
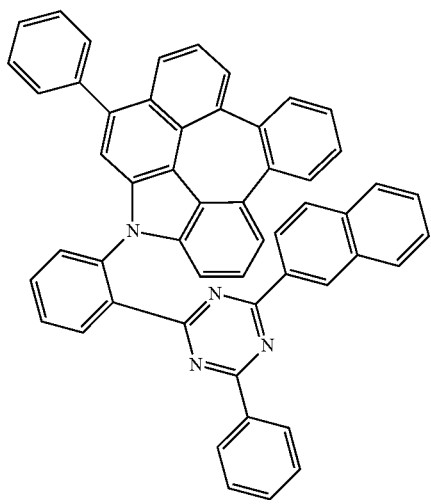
A-66
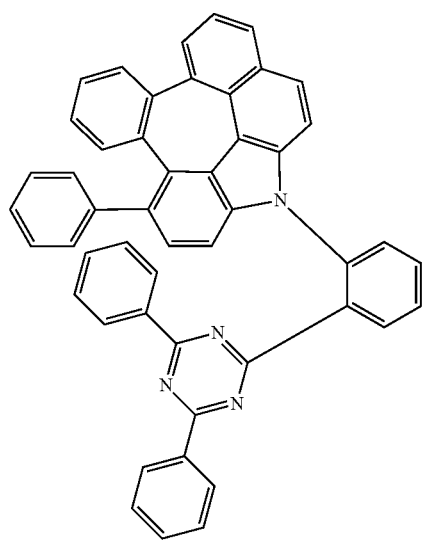
A-67
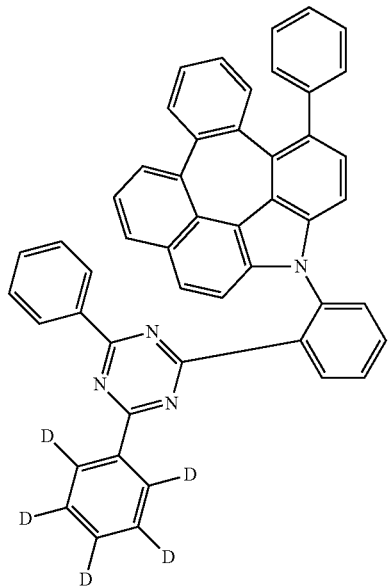
A-68
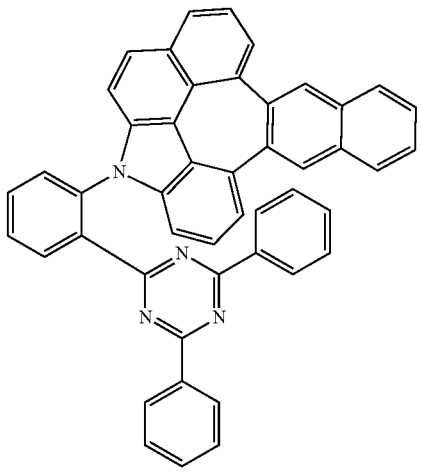
A-69
A-70
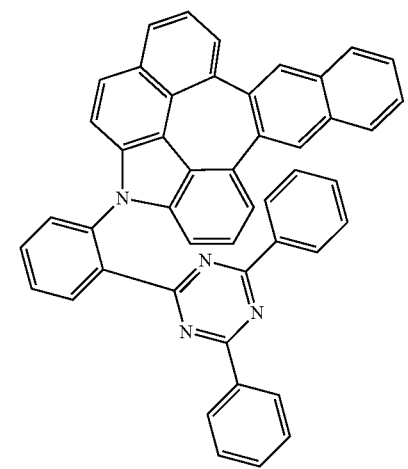

A-71 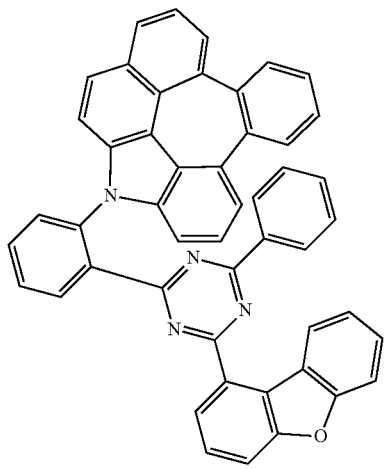
A-72 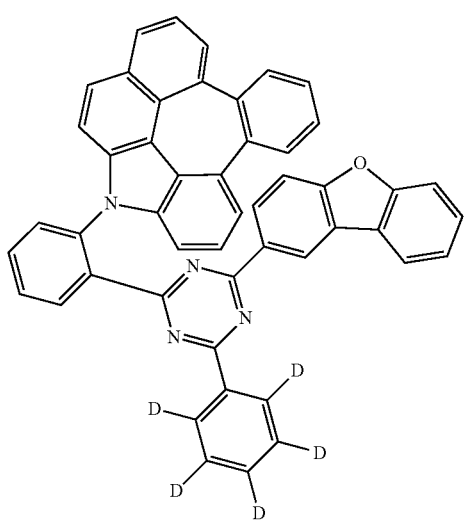
A-73 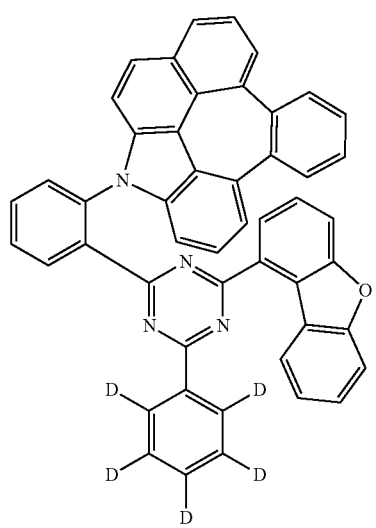
A-74 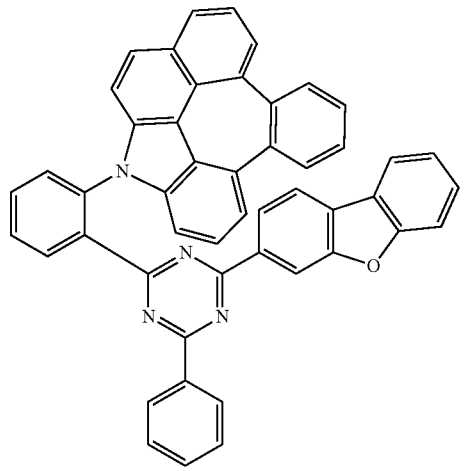
A-75 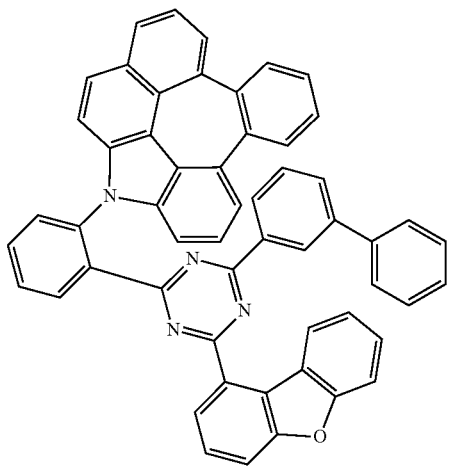
A-76 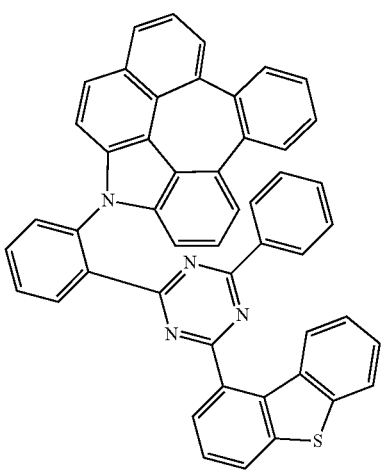

A-77
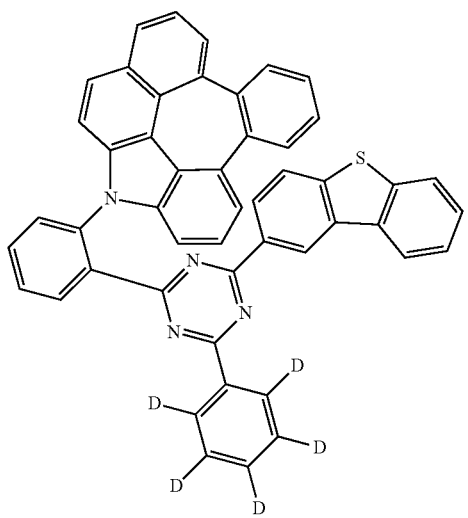
A-78
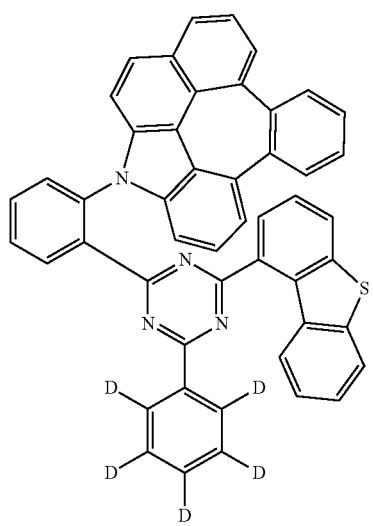
A-79
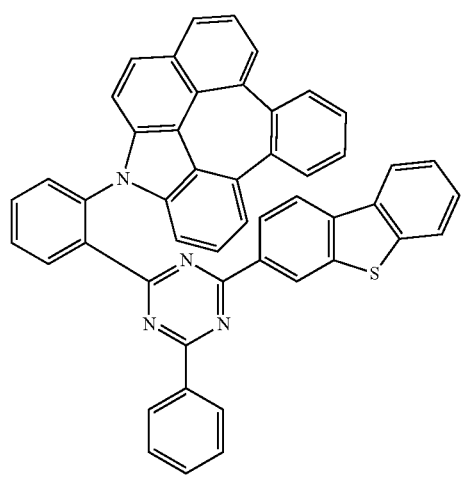
A-80
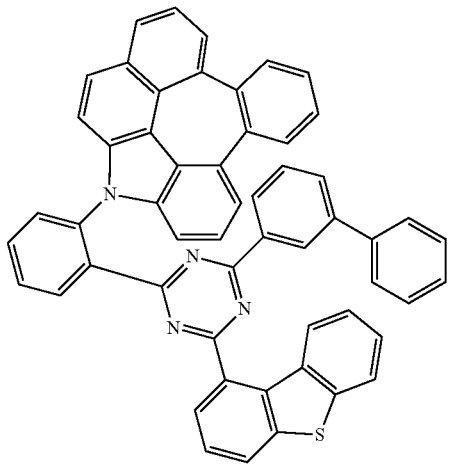
A-81
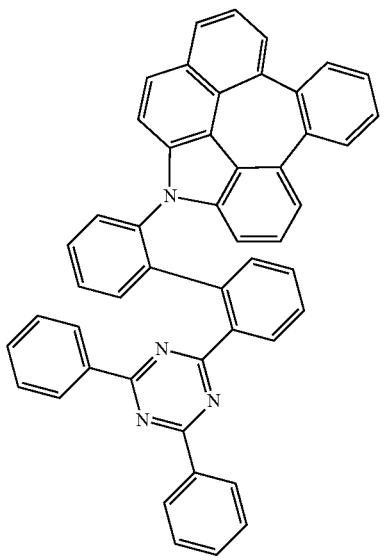
A-82
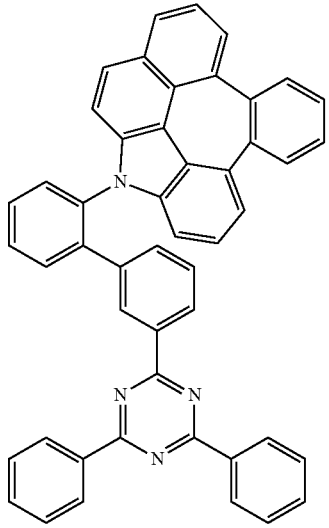

A-83
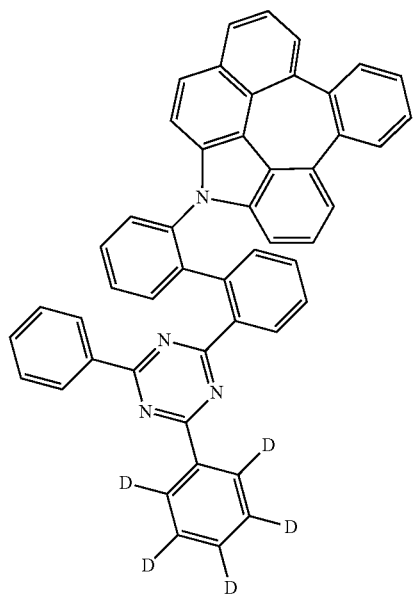
A-84
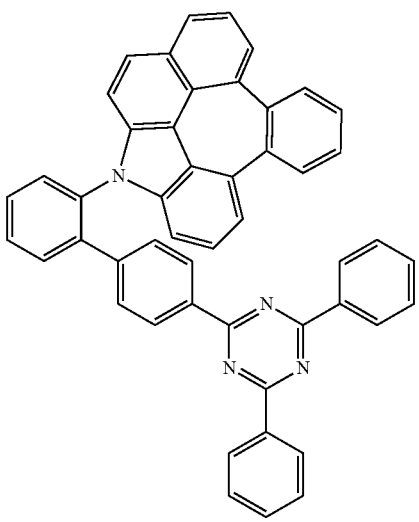
A-85
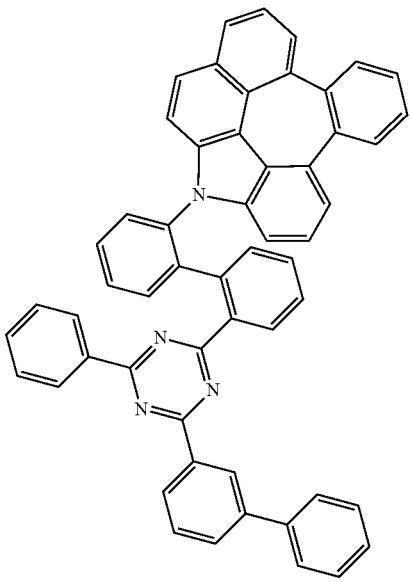
A-86
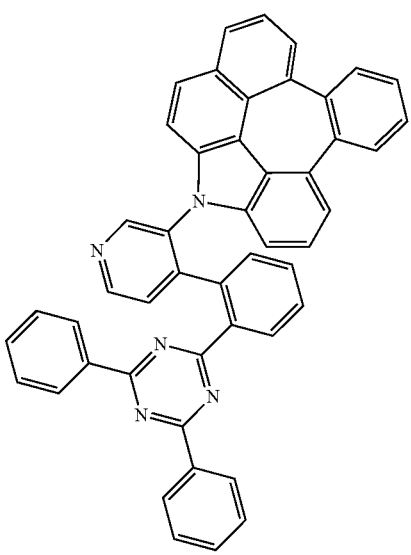
A-87

A-88
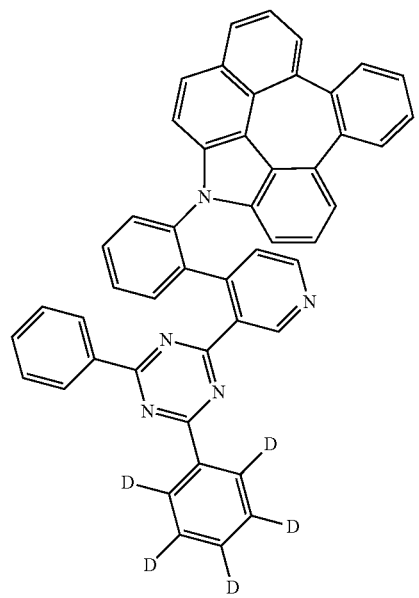
A-90
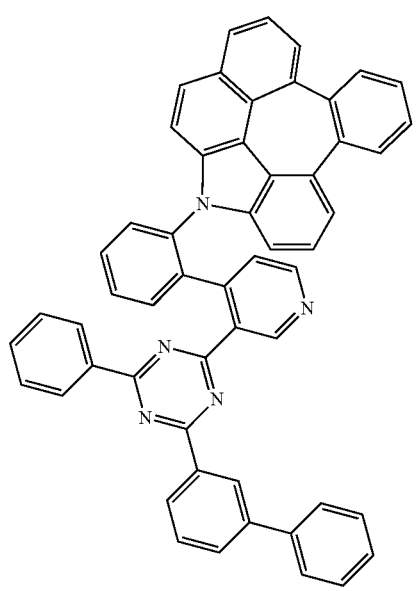
A-91
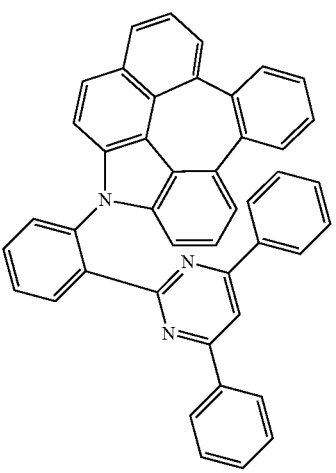
A-89
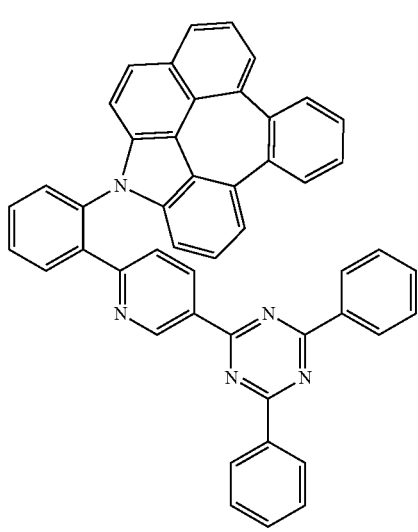
A-92
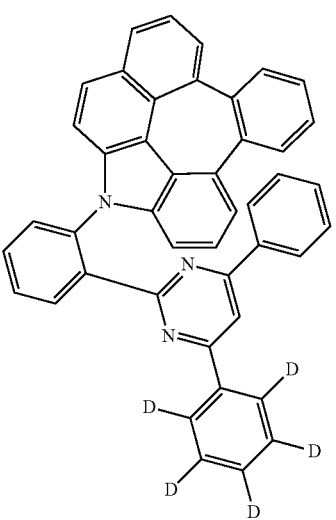

-continued
A-93
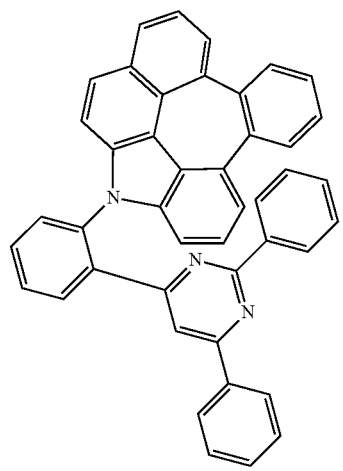
A-96
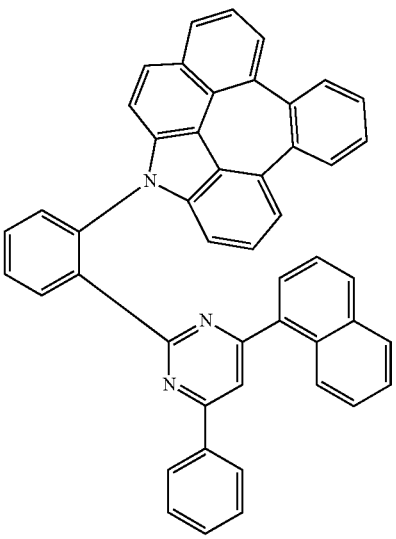
A-94
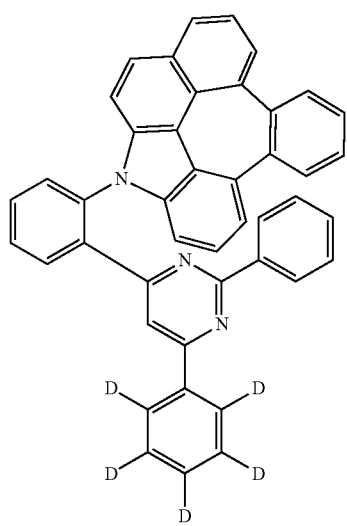
A-95
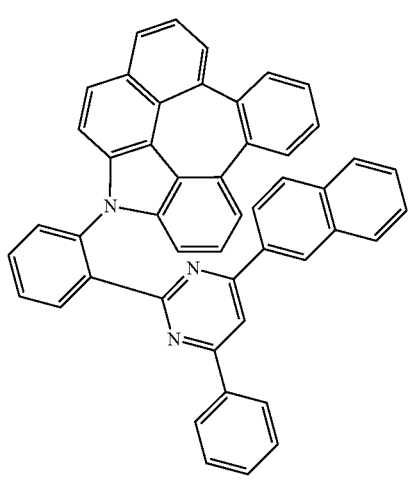
A-97
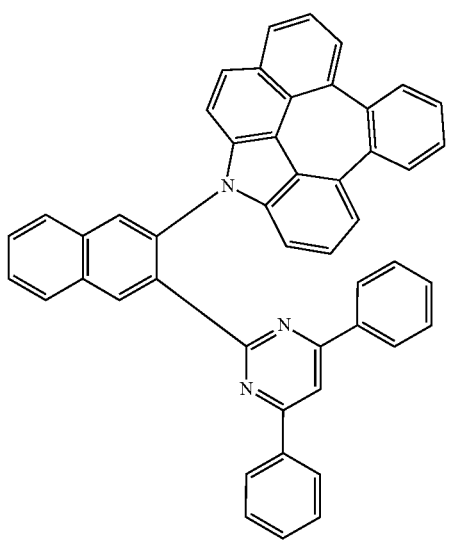

-continued
A-98
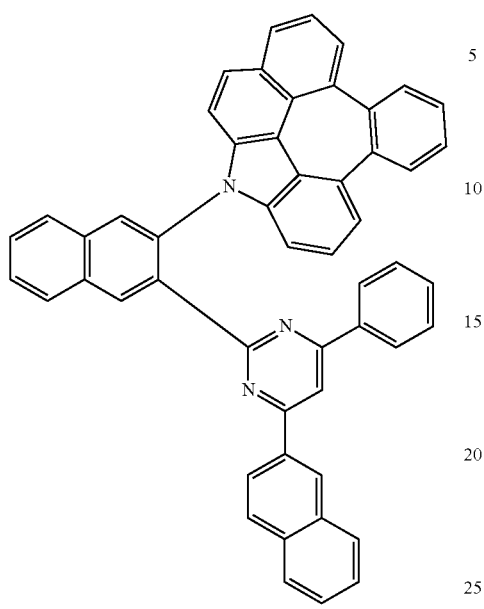
A-100
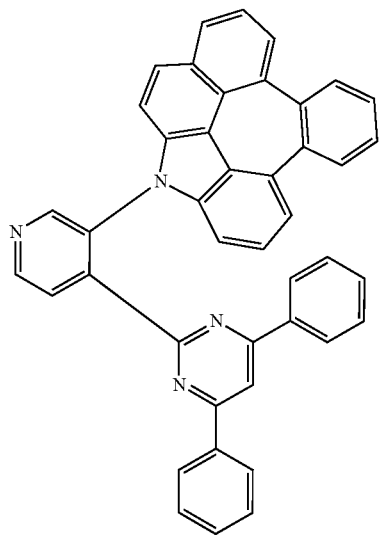
A-99
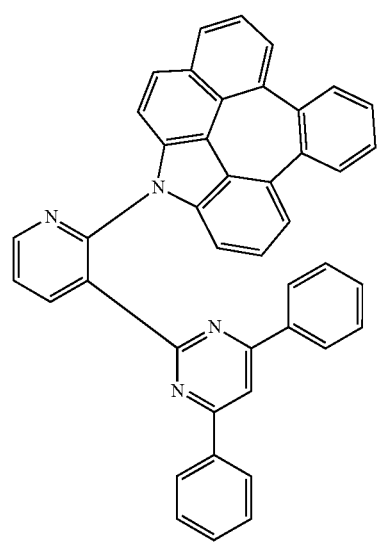
A-101
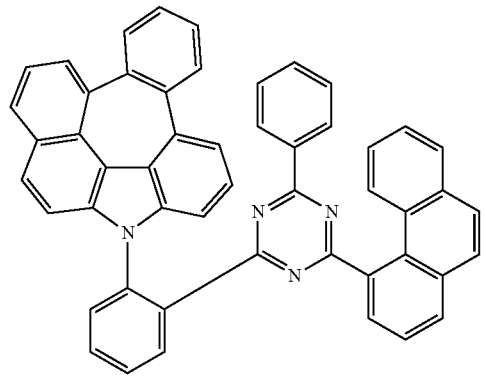

A-102

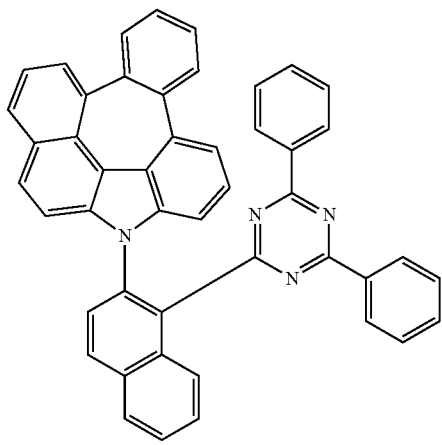

A-103

A-104

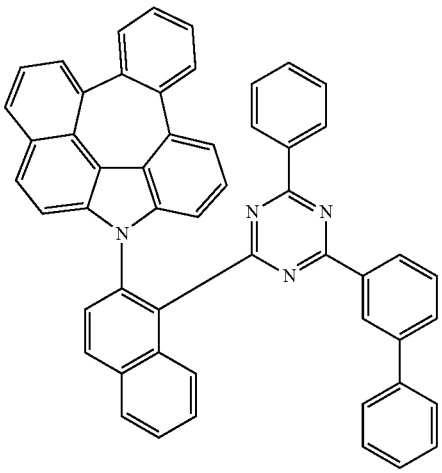

and

A-105

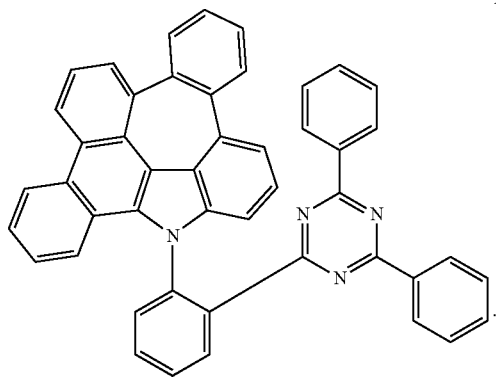

7. An organic electroluminescent material comprising the organic electroluminescent compound according to claim 1.

8. An organic electroluminescent device comprising the organic electroluminescent compound according to claim 1.

9. An organic electroluminescent device according to claim 8, wherein the organic electroluminescent compound is comprised in a light-emitting layer.

* * * * *